US011197937B2

(12) United States Patent
Tretiakova et al.

(10) Patent No.: US 11,197,937 B2
(45) Date of Patent: Dec. 14, 2021

(54) COMPOSITIONS FOR TREATMENT OF WET AGE-RELATED MACULAR DEGENERATION

(71) Applicant: The Trustees of the University of Pennsylvania, Philadelphia, PA (US)

(72) Inventors: Anna P. Tretiakova, Woburn, MA (US); James M. Wilson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 221 days.

(21) Appl. No.: 16/093,420

(22) PCT Filed: Apr. 14, 2017

(86) PCT No.: PCT/US2017/027529
§ 371 (c)(1),
(2) Date: Oct. 12, 2018

(87) PCT Pub. No.: WO2017/180936
PCT Pub. Date: Oct. 19, 2017

(65) Prior Publication Data

US 2019/0381194 A1 Dec. 19, 2019

Related U.S. Application Data

(60) Provisional application No. 62/466,721, filed on Mar. 3, 2017, provisional application No. 62/460,515, filed on Feb. 17, 2017, provisional application No. 62/442,946, filed on Jan. 5, 2017, provisional application No. 62/331,100, filed on May 3, 2016, provisional application No. 62/323,184, filed on Apr. 15, 2016.

(51) Int. Cl.

| | |
|---|---|
| ***A61K 48/00*** | (2006.01) |
| ***A61K 35/761*** | (2015.01) |
| ***A61K 9/00*** | (2006.01) |
| ***A61K 9/10*** | (2006.01) |
| ***C07K 16/22*** | (2006.01) |
| ***C12N 15/86*** | (2006.01) |

(52) U.S. Cl.
CPC ........ *A61K 48/0075* (2013.01); *A61K 9/0019* (2013.01); *A61K 9/0048* (2013.01); *A61K 9/10* (2013.01); *A61K 35/761* (2013.01); *A61K 48/005* (2013.01); *C07K 16/22* (2013.01); *C12N 15/86* (2013.01); *C07K 2317/55* (2013.01); *C07K 2319/33* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 6,596,535 | B1 | 7/2003 | Carter |
| 6,884,879 | B1 | 4/2005 | Baca et al. |
| 7,067,526 | B1 | 6/2006 | Yang et al. |
| 7,125,717 | B2 | 10/2006 | Carter |
| 7,282,199 | B2 | 10/2007 | Gao et al. |
| 7,456,683 | B2 | 11/2008 | Takano et al. |
| 7,790,449 | B2 | 9/2010 | Gao et al. |
| 7,906,111 | B2 | 3/2011 | Wilson et al. |
| 8,318,480 | B2 | 11/2012 | Gao et al. |
| 8,319,480 | B2 | 11/2012 | Ko et al. |
| 8,524,446 | B2 | 9/2013 | Gao et al. |
| 8,628,966 | B2 | 1/2014 | Chatterjee et al. |
| 8,734,809 | B2 | 5/2014 | Gao et al. |
| 8,927,514 | B2 | 1/2015 | Chatterjee et al. |
| 8,962,330 | B2 | 2/2015 | Gao et al. |
| 8,962,332 | B2 | 2/2015 | Gao et al. |
| 8,999,678 | B2 | 4/2015 | Vandeberghe et al. |
| 9,169,299 | B2 | 10/2015 | Lisowski et al. |
| 9,193,956 | B2 | 11/2015 | Schaffer et al. |
| 9,284,357 | B2 | 3/2016 | Gao et al. |
| 9,409,953 | B2 | 8/2016 | Asokan et al. |
| 9,458,517 | B2 | 10/2016 | Schaffer et al. |
| 9,585,971 | B2 | 3/2017 | Deverman et al. |

(Continued)

FOREIGN PATENT DOCUMENTS

| | | |
|---|---|---|
| JP | 2015-523060 | 8/2015 |
| WO | WO 1994/018317 | 8/1994 |

(Continued)

OTHER PUBLICATIONS

Limberis et al Mol. Therapy, 20, 1, S31 (Year: 2012).*
Limberis et al (Molecular Therapy vol. 20, Supplement 1, S31 (Year: 2012).*
Lucentis Product description, pp. 1-35 (Year: 2014).*
Zhang et al The Journal of Gene Medicine, 7, 354-365 (Year: 2005).*
Vandenberghe et al Sci Transl Med.Jun. 22; 3(88):88ra54, 1-9 (Year: 2011).*
Fang et al (Nature Biotechnology, 23(5), 584-590, IDS) (Year: 2005).*

(Continued)

*Primary Examiner* — Anoop K Singh
(74) *Attorney, Agent, or Firm* — Howson and Howson LLP; Cathy Kodroff

(57) ABSTRACT

A recombinant adeno-associated virus (rAAV) having an AAV8 capsid which is suitable for intra-retinal injection is provided herein. The rAAV comprises a vector genome packaged within the capsid which contains, operably linked to regulatory elements which direct expression of anti-human vascular endothelial growth factor (VEGF) antigen binding antibody fragment (aVEGF), a coding sequence for aVEGF, wherein the coding sequence is operably linked to regulatory elements which direct expression of the anti-VEGF Fab in the eye. Also provided herein are liquid suspensions containing these rAAV8.aVEGF and methods of using same for treatment of wet AMD and other ocular conditions.

5 Claims, 10 Drawing Sheets

Specification includes a Sequence Listing.

(56) References Cited

U.S. PATENT DOCUMENTS

| | | | | |
|---|---|---|---|---|
| 9,587,282 | B2 | 3/2017 | Schaffer et al. | |
| 9,840,553 | B2 * | 12/2017 | Perlroth | C07K 16/2863 |
| 2009/0142343 | A1 | 6/2009 | Fuh et al. | |
| 2010/0322931 | A1 | 12/2010 | Harding et al. | |
| 2012/0137379 | A1 * | 5/2012 | Gao | C07K 14/005 800/8 |
| 2012/0164106 | A1 | 6/2012 | Schaffer et al. | |
| 2012/0232133 | A1 * | 9/2012 | Balazs | C12N 7/00 514/44 R |
| 2013/0045186 | A1 | 2/2013 | Gao et al. | |
| 2013/0090375 | A1 | 4/2013 | Crystal et al. | |
| 2013/0224836 | A1 | 8/2013 | Muramatsu | |
| 2014/0309613 | A1 | 10/2014 | Behar-Cohen et al. | |
| 2015/0004101 | A1 | 1/2015 | Constable et al. | |
| 2015/0126588 | A1 | 5/2015 | Nakai et al. | |
| 2015/0182638 | A1 | 7/2015 | Crystal et al. | |
| 2015/0258120 | A1 | 9/2015 | Zamitsyn et al. | |
| 2015/0374803 | A1 | 12/2015 | Wolfe | |
| 2016/0074217 | A1 | 3/2016 | Price et al. | |
| 2016/0215024 | A1 | 7/2016 | Vandenberghe et al. | |
| 2016/0376323 | A1 | 12/2016 | Schaffer et al. | |
| 2017/0051257 | A1 | 2/2017 | Vandenberghe et al. | |
| 2017/0067908 | A1 | 3/2017 | Nakai et al. | |
| 2018/0155412 | A1 * | 6/2018 | Limberis | A61K 39/12 |
| 2020/0277364 | A1 | 9/2020 | Yoo et al. | |

FOREIGN PATENT DOCUMENTS

| | | | | |
|---|---|---|---|---|
| WO | WO 1996/020951 | | 7/1996 | |
| WO | WO 1996/041865 | | 12/1996 | |
| WO | WO 1999/010508 | | 3/1999 | |
| WO | WO 1999/010510 | | 3/1999 | |
| WO | WO 1999/036553 | | 7/1999 | |
| WO | WO 1999/041258 | | 8/1999 | |
| WO | WO 2001/029242 | | 4/2001 | |
| WO | WO-2001/091800 | | 12/2001 | |
| WO | WO 2002/007514 | | 1/2002 | |
| WO | WO 2003/068801 | | 8/2003 | |
| WO | WO 2004/084951 | | 10/2004 | |
| WO | WO 2009/058812 | | 5/2009 | |
| WO | WO 2010/054010 | | 5/2010 | |
| WO | WO-2010054010 | A1 * | 5/2010 | A61P 15/00 |
| WO | WO 2013/173129 | | 11/2013 | |
| WO | WO-2014/124282 | | 8/2014 | |
| WO | WO 2014/151341 | | 9/2014 | |
| WO | WO 2015/082570 | | 6/2015 | |
| WO | WO 2015/121501 | | 8/2015 | |
| WO | WO 2015/164778 | | 10/2015 | |
| WO | WO 2015/175639 | | 11/2015 | |
| WO | WO-2015175639 | A1 * | 11/2015 | A61P 43/00 |
| WO | WO 2015/191508 | | 12/2015 | |
| WO | WO 2016/040635 | | 3/2016 | |
| WO | WO 2016/134375 | | 8/2016 | |
| WO | WO 2017/040528 | | 3/2017 | |
| WO | WO-2017/040528 | | 3/2017 | |
| WO | WO 2017/072515 | | 5/2017 | |
| WO | WO 2017/120601 | | 7/2017 | |
| WO | WO 2017/181021 | | 10/2017 | |
| WO | WO-2017181021 | A1 * | 10/2017 | A61K 48/0075 |
| WO | WO 2019/067540 | | 9/2018 | |
| WO | WO 2020/206098 | | 4/2020 | |

OTHER PUBLICATIONS

Earley et al Human Gene Therapy, 31, 3, 151-162 (Year: 2020).*

Vandenberghe et al Cold Spring Harbor Perspect Med, , 5, 1017442 (Year: 2015).*

Moore et al Expert. Opinion Biol. Therp, 1235-1244 (Year: 2017).*

Constable Asia-Pacific Journal of Ophthalmology, 5(4), 300-303 (Year: 2016).*

Aleman, Inner retinal abnormalities in X-linked retinitis pigmentosa with RPGR mutations, Invest Ophthalmol Vis Sci., vol. 48(10):4759-65, Oct. 2007.

American Academy of Ophthalmology, Age Related Macular Degeneration, Preferred Practice Pattern, Jan. 2015.

Askou, Development of Gene Therapy for Treatment of Age-related Macular Degeneration, Acta Ophthalmologica Thesis, pp. 1-38, Jan. 2014.

Brown et al., Ranibizumab versus Verteporfin for Neovascular Age-Related Macular Degeneration, N Engl J Med, vol. 355:1432-1444, Oct. 2006.

Boning et al., Recent developments in adeno-associated virus vector technology, J. Gene Med., vol. 10(7):717-733, Jul. 2008.

Calcedo et al., Worldwide Epidemiology of Neutralizing Antibodies to Adeno-Associated Viruses, Journal of Infectious Diseases, vol. 199(3):381-390, Feb. 2009.

Daghestani et al., Theory and Applications of Surface Plasmon Resonance, Resonant Mirror, Resonant Waveguide Grating, and Dual Polarization Interferometry Biosensors, Sensors (Basel). vol. 10(11):9630-46, Jun. 2010.

Gao et al., Adeno-associated viruses undergo substantial evolution in primates during natural infections, Proc. Natl. Acad. Sci. U.S.A., vol. 100 (10):6081-6086, May 2003.

GenBank Accession No. K03104.1, Human cytomegalovirus major immediate-early gene, enhancer, Aug. 1993.

GenBank Accession No. V00882.1, Rabbit (*O. cuniculus*) gene for beta-globin, Nov. 2006.

GenBank Accession No. X00182.1, Gallus gallus cytoplasmic beta-actin gene, Nov. 2006.

GenBank Accession No. YP_077180, capsid protein [Adeno-associated virus—8], Aug. 2018.

GenBank Accession No. AF232305, Rattus norvegicus ubiquitin gene, promoter and partial sequence, Aug. 2000.

GenBank Accession No. D63791, *Homo sapiens* UbC gene for polyubiquitin, exon 1-2, partial cds, Jul. 2016.

Grieger & Samulski, Adeno-associated virus as a gene therapy vector: Vector development, production and clinical applications, Adv. Biochem. Engin/Biotechnol., vol. 99:119-145, Oct. 2005.

Grimm el al., Titration of AAV-2 particles via a novel capsid ELISA: packaging of genomes can limit production of recombinant AAV-2, Gene Therapy, vol. 6(7):1322-1330, Jul. 1999.

Kay et al., Targeting Photoreceptors via Intravitreal Delivery Using Novel, Capsid-Mutated AAV Vectors, PLoS One, vol. 8(4):e62097, Apr. 2013.

Limberis et al., 75: AAV8-Mediated Expression of VEGF Antagonist Ranibizumab in Macaque Eye: Comparison of Subretinal vs. Intravitreal Delivery of Vector, Molecular Therapy, $15^{th}$ Annual Meeting of the American Society of Gene and Cell Therapy, vol. 20(1):S31, May 2012.

Lock et al., Absolute determination of single-stranded and self-complementary adeno-associated viral vector genome titers by droplet digital PCR, Hum Gene Ther Methods, vol. 25(2):115-25, Apr. 2014 (ePubl Feb. 2014).

McCarty et al., Self-complementary recombinant adeno-associated virus (scAAV) vectors promote efficient transduction independently of DNA synthesis, Gene Therapy, vol. 8(16):1248-1254, Aug. 2001.

McCulloch, ISCEV Standard for full-field clinical electroretinography (2015 update), Doc Ophthalmol. vol. 130(1):1-12, Feb. 2015.

Mitchell and Bradley, Quality of life in age-related macular degeneration: a review of the literature, Health Qual Life Outcomes, vol. vol. 4:97, Dec. 2006.

Mowat et al., Tyrosine capsid-mutant AAV vectors for gene delivery to the canine retina from a subretinal or intravitreal approach, Gene Therapy, vol. 21:96-105, Jan. 2014.

Nanbru et al., Alternative Translation of the Proto-oncogene c-mycby an Internal Ribosome Entry Site, J. Biol. Chem., vol. 272:32061-32066, Dec. 1997.

NIH, Leading cause of blindness, NIH Medline Plus, vol. 3(2): 14-15, Jun. 2008.

Ohno-Matsui et al., Inducible expression of vascular endothelial growth factor in adult mice causes severe proliferative retinopathy and retinal detachment, The American journal of pathology, vol. 160(2):711-719, Feb. 2002.

Pennesi et al., Animal models of age related macular degeneration, Molecular aspects of medicine vol. 33(4):487-509, Aug. 2012.

Rosenfeld et al., Ranibizumab for Neovascular Age-Related Macular Degeneration, N Engl J Med, vol. 355:1419-1431, Oct. 2006.

(56) References Cited

OTHER PUBLICATIONS

Schmidt-Erfurth et al., Guidelines for the management of neovascular age-related macular degeneration by the European Society of Retina Specialists (EURETINA), Br J Ophthalmol, vol. 98:1144-1167, Jun. 2014.
Sommer et al., Quantification of adeno-associated virus particles and empty capsids by optical density measurement, Molec. Ther., vol. 7(1):122-128, Jan. 2003.
Stoneley et al., C-Myc 5' untranslated region contains an internal ribosome entry segment, Oncogene, vol. 16(3):423-428, Jan. 1998.
Thomson et al., A comprehensive comparison of multiple sequence alignments, Nucl. Acids. Res, vol. 27(13):2682-2690, May 1999.
Winter, Using the Student's t-test with extremely small sample sizes. Practical Assessment, Research and Evaluation, vol. 18 (10), Aug. 2013.
Wobus et al., Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection, J. Viral., vol. 74(19):9281-9293, Oct. 2000.
Xu, Pharmacokinetics of ranibizumab in patients with neovascular age-related macular degeneration: a population approach, Invest Ophthalmol Vis Sci, vol. 54(3):1616-24, Mar. 2013.
International Search Report and Written Opinion issued on International Patent Application No. PCT/US2017/027529, dated Sep. 15, 2017.
U.S. Appl. No. 62/466,721, filed Mar. 3, 2017.
U.S. Appl. No. 62/460,515, filed Feb. 17, 2017.
U.S. Appl. No. 62/442,946, filed Jan. 5, 2017.
U.S. Appl. No. 62/331,100, filed May 3, 2016.
U.S. Appl. No. 62/323,184, filed Apr. 15, 2016.
U.S. Appl. No. 62/322,098, filed Apr. 13, 2016.
U.S. Appl. No. 62/266,341, filed Dec. 11, 2015.
International Patent Application No. PCT/US16/65976, filed Dec. 9, 2016.
Search Report, dated Sep. 15, 2017, WO, PCT/US2017/0275299.
Limberis, Molecular Therapy, 75: AAV8-Mediated Expression of VEGF Antagonist Ranibizumab in Macaque Eye: Comparison of Subretinal vs. Intravitreal Delivery of Vector, vol. 20(1):S31, May 2012.
Schmidt-Erfurth, British Journal of Ophthalmology, Guidelines for the management of neovascular age-related macular degeneration by Euretina, vol. 98(9):1144-1167, Aug. 2014.
Askou, Acta Ophthalmologica Thesis, Development of Gene Therapy for Treatment of Age-related Macular Degeneration, pp. 1-38, Jan. 2014.
"Additional Positive Long-term and Interim Phase I/Ila Trial Update for RGX-314 for the Treatment of Wet AMD," Conference Call Presentation Apr. 22, 2002 (Exhibit B to the response filed Jul. 21, 2020).
Adamis et al., 1993, "Synthesis and secretion of vascular permeability factor/vascular endothelial growth factor by human retinal pigment epithelial cells", BBRC, 193(2):631-638, Jun. 15, 1993.
Adverum Biotechnologies, Inc., 2020, "Advemm Biotechnologies Reports Positive Interim Data from Cohorts 1-3 of OPTIC Phase 1 Trial of ADVM-022 Intravitreal Gene Therapy for Wet AMD", Advemm Biotechnologies, Inc., retrieved from the Internet at<https://www .globenewswire.com/news-release/2020/05/04/2027l31/0/en/Advemm- Biotechnologies-Reports-Positive-Interim-Data-from-Cohorts-1-3-of-OPTIC-Phase- 1-Trial-of- ADVM-022-Intravitreal-Gene-Therapy-for-Wet-AMD.html> on Jul. 19, 2020 (7 pages) (Exhibit D to the response filed Jul. 21, 2020).
Adverum Biotechnologies, Inc., ClinicalTrials.gov Identifier: NCT01494805, "Safety and Efficacy Study of rAAV.sFlt-1 in Patients With Exudative Age-Related Macular Degeneration (AMD)," last updated Sep. 1, 2017 (7 pages).
Ahmed and Rahi, 1985, "Physiological and pathobiological significance of ocular glycoproteins. I. Studies using fluorescein labelled glycine max", British Journal of Opthalmology, 69:162-170, Mar. 1, 1985.
Alba et al., 2005, "Gutless adenovims: last-generation adenovims for gene therapy", Gene Therapy, 12:S18-S27, Oct. 12, 2005.
Asensio-Sanchez, 2009, "Avastin is not the same that Lucentis", Arch Soc Esp Oftalmol, 84:417-428, Sep. 2009.
Ausubel et al, 2012, "Production of CGMP-Grade Lentiviral Vectors", Biopress Int., 10(2):32-43; Jun. 13, 2012.
Avastin—Scientific Discussion, 2005, EMEA:1-61.
Ayoub et al., 2013, "Correct primary structure assessment and extensive glyco-profiling of cetuximab by a combination of intact, middle-up, middle-down and bottom-up ESI and MALDI mass spectrometry techniques", Landes Bioscience, 5(5):699-710, Epub Jun. 20, 2013.
Bainbridge et al., 2002, "Inhibition of retinal neovascularisation by gene transfer of soluble VEGF receptor sFlt-1", Gene Ther, 9:320-326, Mar. 25, 2002.
Bainbridge et al., 2008, "Effect of gene therapy on visual function in Leber's congenital amaurosis", N Eng J of Med, 358(21):2231-2239, Epub Apr. 27, 2008.
Baldassare et al., 2017, "Subretinal Delivery of Cells via the suprachoroidal space: Janssen Trial", In: Schwartz et al. (eds), Cellular Therapies for Retinal Disease, Spring, Cham:95-104, Jun. 21, 2017.
Baumeister and Goletz et al., "Novel glycosylation technologies for the development of biosimilars and biobetters", Innovations in Pharmaceutical Technology:52-58, Dec. 2009.
Bennett et al., 2012, "AAV2 Gene Therapy Readministration in Three Adults with Congenital Blindness" Sci Transl Med., 4:120ra15 (12 pages), Feb. 8, 2012.
Bennett et al., 2016, "Safety and durability of effect of contralateral-eye administration of AAV2 gene therapy in patients with childhood-onset blindness caused by RPE65 mutations: a follow-on phase 1 trial", Lancet, 388(10045):661-672, Jun. 30, 2016.
Bondt et al., 2014, "Immunoglobulin G (IgG) Fab glycosylation analysis using a new massspectrometric high-throughput profiling method reveals pregnancy-associated changes", Mol. & Cell. Proteomics, 13(11):3029-3039 and Supplemental Tables, Epub Jul. 8, 2014.
Bosques et al., 2010, "Chinese hamster ovary cells can produce galactose-a-1,3-galactose antigens on proteins", Nat Biotech, 28:1153-1156, Nov. 2010.
Brown et al., 2006, "Ranibizumab versus verteporfin for neovascular age-related macular degeneration", N Eng J Med, 355(14):1432-1444, Oct. 5, 2006.
Cairns, 2015, "Avalanche crashes down as gene therapy disappoints," Vantage Kickstarting ideas, Jun. 16, 2015, retrieved from internet: https://www.evaluate.com/node/7407/pdf (2 pages).
Campochiario et al., 2016, "Lentiviral Vector Gene Transfer ofEndostatin/Angiostatin for Macular Degeneration (GEM) Study", Hum Gen Ther, 28:99-111, Epub, Sep. 26, 2016.
Campochiaro et al., 2006, "Adenoviral vector-delivered pigment epithelium-derived factor for neovascular age-related macular degeneration: results of a phase I clinical trial", Hum Gen Ther, 17(2):167-176, Feb. 2006.
Chen et al., 1999, "Selection and analysis of an optimized anti-VEGF antibody: crystal structure of an affinity-matured Fabin complex with antigen," J Mol Biol., 293(4):865-881, Nov. 5, 1999.
Chen et al., 2006, "Pharmacology/Toxicology Review and Evaluation", Center for Drug Evaluation and Research, BLA No. 125156 (62 pages).
Chen et al., 2015, "Safety and pharmacodynamics of suprachoroidal injection of triamcinolone acetonide as a controlled ocular drug release model", J Control Rel, 203:109-117, Epub Feb. 17, 2015.
Chen etal. J. Mol. Bio. 293, 865-881 (Year: 1999), Nov. 5, 1999.
Choe et al., 2003, "Tyrosine sulfation of human antibodies contributes to recognition of the CCR5 binding region ofHIV-1 gp120", Cell, 114:161-170, Jul. 25, 2003.
Chowdhury et al., 2010, "Proteome analysis of human aqueous humor," Invest Ophthalmol Vis Sci., 51(10):4921-4931, Epub May 12, 2010.
Comparison of Age-Related Macular Degeneration Treatments Trials (CATT) Research Group et al., 2016, "Five-Year Outcomes with Anti-Vascular Endothelial Growth Factor Treatment of Neovascular Age-Related Macular Degeneration: The Comparison of Age-

(56) References Cited

OTHER PUBLICATIONS

Related Macular Degeneration Treatments Trials," Ophthalmology, 123(8):1751-1761 and Supplemental materials, Mar. 2017.
Constable et al., 2016, "Phase 2a randomized clinical trial: safety and post hoc analysis of subretinal rAAV.xFLT-1 for wet age-related macular degeneration", EBioMedicine 14:167-175, Epub Nov. 10, 2016.
Courtois et al., 2016, "Rational design of therapeutic mAbs against aggregation through protein engineering and incorporation of glycosylation motifs applied to bevacizum", abmAbs 8(1):99-112, Oct. 29, 2015.
Dalton et al., 2014, "Over-expression of secreted proteins from mammalian cell lines", Protein Science, 23(5):517-525, Epub Mar. 11, 2014.
Deverman et al., 2016, "Cre-dependent selection yields AAV variants for widespread gene transfer to the adult brain", Nature Biotechnology, 34(2):204-209 plus supplement, Epub Feb. 1, 2016.
Dinculescu et al., 2005, "Adeno-associated virus-vectored gene therapy for retinal disease", Hum Gene Ther, 16(6):649-663, Jun. 2005.
Dumont et al., 2015, "Human cell lines for biopharmaceutical manufacturing: history, status, and future perspectives", Crit Rev Biotechnol (published online Sep. 18, 2015):1-13, Sep. 18, 2015.
Eter et al., 2006, "New pharmacologic approaches to therapy for age-related macular degeneration", BioDrugs, 20(3):167-179, Dec. 31, 2005.
Fang et al., 2005, "Stable antibody expression at therapeutic levels using the 2A peptide", Nature Biotechnology, 23:584-590, Apr. 17, 2020.
Faridmoayer et al., 2007, "Functional characterization of bacterial oligosaccharyltransferases involved in O-linked protein glycosylation", J. Bacterial., 1 89(22):8088-8098, Epub Sep. 21, 2007.
Fierce Biotech, 2020, "Avalanche hits the brakes on its gene therapy program after a Phase II misstep", retrieved from the internet at <www.fiercebiotech.com/r-d/avalanche-hits-brakes-on-its- gene-therapy-program-after-a-phase-ii-misstep> on Jul. 19, 2020, (1 page) (Exhibit C to the response filed Jul. 21, 2020.).
Finger et al., 2013, "Treatement patterns, visual acuity and quality-of-life outcomes of the WAVE study—a noninterventional study of ranibizumab treatment for neovascular age-related macular degeration in Germany", Acta Ophtalmol:540-546, Epub Nov. 22, 2012.
Fortmann et al., 2018, "Mousetap, a Novel Technique to Collect Uncontaminated Vitreous or Aqueous and Expand Usefulness of Mouse Models", Sci Rep, 8(1):6371, Apr. 23, 2018.
Furling et al., 2001, "Recombinant AAV vectors containing the foot and mouth disease virus 2A sequence confer efficient ibcistronic gene expression in cultured cells and rat substantia nigra neurons", Gene Ther, 8(11):854-873, Jun. 2001.
Gaffen et al., 2004, "Overview of interleukin-2 function, production and clinical applications," Cytokine, 28:109-123, Nov. 2004.
Galili et al., 1998, "A sensitive assay for measuring alpha-Gal epitope expression on cells by a monoclonal anti-Gal antibody", Transplantation, 65(8):1129-1132, Apr. 27, 1998.
Gao et al., 2002, "Novel adeno-associated viruses from rhesus monkeys as vectors for human gene therapy", Natl Acad Sci USA, 99:11854-11859, Epub Sep. 2002.
Gasset et al., Biohem Biophys Res Commun, 307, 198-205, Jul. 18, 2003.
Gehlbach et al., 2003, "Periocular injection of an adenoviral vector encoding pigment epithelium-derived factor inhibits choroidal neovascularization", Gene Ther, 10:637-646, Apr. 11, 2003.
Genvec, ClinicalTrials.gov Identifier: NCT00109499, "Study of AdGVPEDF.11D in Neovascular Age-related Macular Degeneration (AMD)," first posted Apr. 29, 2005, last updated May 12, 2011.
Genzyme, ClinicalTrials.gov Identifier: NCT01024998, "Safety and Tolerability Study of AAV2-sFLTO1 in Patients With Neovascular Age-Related Macular Degeneration (AMD)," last updated Aug. 22, 2018 (8 pages).
Goldstein, 2014, "Achieving drug delivery via the suprachoroidal space", Retina Today, 9(5):82-87, Jul./Aug. 2014.
Griffey et al., 2005, "AAV2-mediated ocular gene therapy for infantile neuronal ceroid lipofuscinosis", Molecular Therapy, 12(3):413-421, Sep. 2005.
Gurtu et al., 1996, "IRES bicistronic expression vectors for efficient creation of stable mammalian cell lines", Biochem Biophys Res Comm, 229(1):295-298, Dec. 4, 1999.
Hansson et al., 2015, "Efficient delivery and functional expression of transfected modified mRNA in human embryonic stem cell-derived retinal pigmented epithelial cells", J Biol Chem, 290(9):5661-5672, Epub Jan. 2, 2015.
Hara et al., 1989, "Highly sensitive determination of N-acetyl- and N-glycolylneuraminic acids in human serum and urine and rat serum by reversed-phase liquid chromatography with fluorescence detection", J Chromatogr. Biomed, 377:111-119, Apr. 25, 1986.
Hariprasad, 2016, "Suprachoroidal administration for retinal drug delivery", Retinal Physician, 13:20-23, Apr. 1, 2016.
Hauswirth et al., 2008, "Treatment of leber congenital amaurosis due to RPE65 mutations by ocular subretinal injection of adeno-associated virus gene vector: short-term results of a phase I trial", Hum Gen Ther, 19(10):979-990, Oct. 2008.
Heier et al., 2017, "Intravitreous injection of AAV2-sFLT0 1 in patients with advanced neovascular age-related macular degeneration: a phase 1, open-label trial", Lancet, 389:50-61, Epub May 17, 2017.
Holash et al., 2002, "VEGF-Trap: a VEGF blocker with potent antitumor effects," Proc Natl Acad Sci USA, 99(17):11393-11398, Epub Aug. 2002.
Holz et al., 2015, "Multi-country real-life experience of anti-vascular endothelial growth factor therapy for wet age-related macular degeneration", Br J Opthalmol, 99:220-226, Epub Sep. 5, 2014.
Honda et al., 2000, "Experimental subretinal neovascularization is inhibited by adenovirus- mediated soluble VEGF/flt-1 receptor gene transfection: a role of VEGF and possible treatment for SRN in age-related macular degeneration", Gene Ther, 7:978-985, May 25, 2000.
Huang et al., 2006, "Impact of variable domain glycosylation on antibody clearance: an LC/MS characterization", Anal Biochem, 349(2): 197-207, Epub Nov. 28, 2005.
Iwase et al., 2013, "Sustained delivery of a HIF-1 antagonist for ocular neovascularization", J Control Release, 172(3):625-633, Dec. 28, 2013.
Jacobson et al., 2015, "Improvement and decline in vision with gene therapy in childhood blindness", N Eng J Med, 372(20):1920-1926, May 14, 2015.
Jang et al., The structural basis for DNA binding by anti-DNA autoantibody, Molec. Immunol. 35:1207-1217, Dec. 1998.
Kanan and Al-Ubaidi, "Protein tyrosine-O-sulfation in the retina", Exp. Eye Res., 89(4):559-567, Jun. 10, 2009.
Kanan et al., 2009, "Protein tyrosine-O-sulfation in the retina", Exper. Eye Research, 89:559-567, Mar. 31, 2015.
Kenneth and Rocha, 2008, "Regulation of gene expression by hypoxia", Biochem J, 414:19-29, Aug. 15, 2008.
Kozarsky, K., 2012, "Novel adeno-associated viral therapy for wet age-related macular degeneration", SBIR STTR America's Seed Fund, available online at https://www.sbir.gov/print/sbirsearch/detail/400408 (3 pages).
Kumar et al., Molecular cloning and expression of the Fabs of human autoantibodies in *Escherichia coli.* Determination of the heavy or light chain contribution to the anti-DNA/-cardiolipin activity of the Fab, J. Biol. Chem. 275:35129-35136, Nov. 10, 2000.
Lai et al., 2001, "Suppression of choroidal neovascularization by adeno-associated virus vector expressing angiostatin", Invest Opthalmol Vis Sci, 42(10):2401-2407, Sep. 2001.
Lai et al., 2005, "Long-term evaluation of AAV-mediated sFlt-1 gene therapy for ocular neovascularization in mice and monkeys", Mol Ther, 12:659-658, Oct. 2005.
Leibiger et al., 1999, "Variable domain-linked oligosaccharides of a human monoclonal IgG:structure and influence on antigen binding", Biochem J, 338:529-538, Apr. 1999.
Lesch et al., 2011, "Production and purification of lentiviral vectors generated in 293T suspension cells with baculoviral vectors", Gene Therapy, 18(6):531-538, Epub Jan. 20, 2011.

(56) References Cited

OTHER PUBLICATIONS

Lien and Lowman, 2008, "Therapeutic Anti-VEGF Antibodies", Therapeutic Antibodies, Handbook of Experimental Pharmacology, 181:131-150.
Liu et al., 2014, "In vitro and in vivo modifications of recombinant and human IgG antibodies", mABs, 6(5):1145-1154, Epub Oct. 30, 2014.
Liu et al., 2018, "AAV8-antiVEGFfab Ocular Gene Transfer for Neovascular Age-Related Macular Degeneration", Mol Ther, 26:542-549, Epub Dec. 8, 2017.
Loos et al., 2015, "Glycan modulation and sulfoengineering of anti-HIV-I monoclonal antibody PG9 in plants", PNAS 112:12675-12680, Sep. 28, 2015.
Luke et al., 2012, "Translating 2A research into practice", Innovations in Biotechnology, Chapter 8:161-186, Feb. 17, 2012.
Magdelaine-Beuzelin, 2010, "Therapeutic antibodies in opthalmology", mAbs 2(2):17-180, Mar.-Apr. 2010.
Maguire et al., 2008, "Safety and efficacy of gene transfer for Leber's congenital amaurosis", N Eng J Med, 358(21):2240-2248, May 22, 2008.
Maguire et al., 2016, "Five-Year Outcomes with Anti-Vascular Endothelial Growth Factor Treatment of Neovascular Age-Related Macular Degeneration: The Comparison of Age-Related Macular Degeneration Treatments Trials", Opthamology, 123:1751-1761, Aug. 2016.
Mao et al., 2011, "Persistent suppression of ocular neovascularization with intravitreal administration of AAVrh. 10 coding for bevacizumab," Hum Gene Ther., 22(12):1525-1535, Epub Jul. 29, 2011.
Martin et al., 2011, "Ranibizumab and bevacizumab for neovascular age-related macular degeneration", N Eng J Med, 364:1897-1908, Epub Apr. 28, 2011.
McCarty et al., 2001, "Self-complementary recombinant adeno-associated vims (scAAV) vectors promote efficient transduction independently of DNA synthesis", Gene Therapy, 8(16):1248-1254, Aug. 15, 2001.
Miki et al., 2010, "Prolonged blockade of VEGF receptors does not damage retinal photoreceptors or ganglion cells," J Cell Physiol., 224(1):262-272, Apr. 23, 2010.
Mikkelsen and Ezban, 1991, "Heterogeneity in the tyrosine sulfation of Chinese hamster ovary cell produced recombinant FV111", Biochemistry, 30(6):1533-1537, Feb. 12, 1991.
Moore et al., 2003, "The biology and enzymology of protein tyrosine O-sulfation". Journal of Biological Chemistry, 278(27):24243-24246, Epub May 2, 2003.
Moore et al., 2017, "Gene therapy for age-related macular degeneration," Expert Opin Biol Ther., 17(10):1235-1244, Epub Jul. 20, 2017.
Mori et al., 2001, "Pigment epithelium-derived factor inhibits retinal and choroidal neovascularization", J Cell Physiol, 188(2):253-263, Jun. 11, 2001.
Muller et al., 1998, "VEGF and the Fab fragment of a humanized neutralizing antibody: crystal structure of the complex at 2.4, A resolution and mutational analysis of the interface", Structure 15, 6:1153-1167, Sep. 15, 1998.
Nishijima et al., 2007, "Vascular endothelial growth factor-A is a survival factor for retinal neurons and a critical neuroprotectant during the adaptive response to ischemic injury," Am J Pathol., 171(1):53-67, Jul. 1, 2007.
Novartis Pharmaceuticals Australia Pty Ltd, 2014, "Lucentis ranibizumab (rbe)", Australian Register of Therapeutic Goods; 35 pages, Oct. 2014.
Ohno-Matsui, 2002, "Inducible expression of vascular endothelial growth factor in adult mice causes severe proliferative retinopathy and retinal detachment", Am J Pathol, 160(2):711-719, Feb. 1, 2002.
O'Reilly et al., 2013, "Gene therapy for rare diseases: summary of a National Institutes of Health workshop, Sep. 13, 2012," Hum Gene Ther., 24(4):355-362, Epub Mar. 21, 2013.
Oxford Biomedica, ClinicalTrials.gov Identifier: NCT01301443, "Phase I Dose Escalation Safety Study of RetinoStat in Advanced Age-Related Macular Degeneration (AMD) (GEM)," first posted Feb. 23, 2011, last updated Apr. 5, 2017(6 pages).
Patel et al., 2011, "Suprachoroidal drug delivery to the back of the eye using hollow microneedles", Pharm Res, 28(1):166-176, Epub Sep. 21, 2010.
Patel et al., 2012, "Targeted administration into the suprachoroidal space using a microneedle for drug delivery to the posterior segment of the eye", Invest Opthalmol Vis Sci, 53(12):4433-4441, Jul. 1, 2012.
Pechan et al., 2009, "Novel anti-VEGF chimeric molecules delivered by AAV vectors for inhibition of retinal neovascularization", Gene Therapy, 16(1):10-16, Epub Jul. 17, 2008.
Peden et al., 2011, "Ab-externo AAV-mediated gene delivery to the suprachoroidal space using a 250 micron flexible microcatheter", PLOS One, 6(2):el7140, Feb. 11, 2011.
Powell and Rivera-Soto, 2015, "Viral expression cassette elements to enhance transgene target specificity and expression in gene therapy", Discov. Med., 19(102):49-57, Jan. 2015.
Prata et al., 2007, "Aqueous humor protein concentration in patients with primary open-angle glaucoma under clinical treatment," Arq Bras Oftalmol., 70(2):217-220 (inch English abstract), Mar.-Apr. 2007.
Quax et al., 2015, "Codon Bias as a Means to Fine-Tune Gene Expression", Mol Cell, 59(2):149-161, Jul. 16, 2015.
Rakoczy et al., 2015, "Gene therapy with recombinant adeno-associated vectors for neovascular age-related macular degeneration: 1 year follow-up of a phase 1 randomised clinical trial", Lancet 386(10011):2395-403, Dec. 12, 2015.
Raymond et al., 2012, "Production of highly sialylated monoclonal antibodies", Intech, ed. Durocher et al.:397-418, Sep. 26, 2012.
Regenxbio Inc., ClinicalTrials.gov Identifier: NCT03066258, "RGX-314 Gene Therapy for Neovascular AMD Trial," first posted Feb. 28, 2017, last updated Dec. 12, 2019 (7 pages).
REGENXBIO Press Release, Apr. 22, 2020, "REGENXBIO Announces Additional Positive Long- term and Interim Phase I/Ila Trial Update forRGX-314 for the Treatment of Wet AMD", retrieved from the internet at <https://regenxbio.gcs-web.com/news-releases/news-release-details/regenxbio-announces-additional-positive-long-term-and-interim> on Jul. 19, 2020 (8 pages).
Rosenfeld et al., 2006, "Ranibizumab for neovascular age-related macular degeneration", N Eng J Med, 355(14):1419-1431, Oct. 5, 2006.
Rota et al., 2004, "Marked inhibition ofretinal neovascularization in rats following soluble-flt-1 gene transfer", J Gene Med, 6:992-1002, Mar. 30, 2004.
Royle et al., 2002, "An analytical and structural database provides a strategy for sequencing O-glycans from microgram quantities of glycoproteins", Anal Biochem, 304(1):70-90, May 1, 2002.
Saint-Gentiez et al., 2008, "Endogenous VEGF is required for visual function: evidence for a survival role on muller cells and photoreceptors," PLoS One, 3(11):e3554 (13 pages), Nov. 3, 2008.
Salvi et al., 2017, "Expression of N-WASP is regulated by HiFla through the hypoxia response element in the N-WASP promoter", Biochemistry and Biophysics Reports, 9:13-21, Epub Mar. 2017.
Santiago-Ortiz et al., 2011, "AAV ancestral reconstruction library enables selection of broadly infectious viral variants", Gene Ther, 22(12):934-946, Jul. 17, 2015.
Scaria et al., 2006, "AAV-2 based gene therapy using novel anti-VEGF molecules for inhibition of angiogenesis in the eye," Molecular Therapy, J of the Amer Society of Gene Therapy, Cell Press, US, vol. 13:S340, Jan. 1, 2006.
Schodel et al., 2011, "High-resolution genome-wide mapping ofHIF-binding sites by ChIP-seq", Blood, 11 7(23):e207-e217, Jun. 9, 2011.
Schuman et al., 2008, "Spectral domain optical coherence tomography for glaucoma (an AOS thesis)", Trans. Am. Opthamol. Soc., 106:426-458, Dec. 2008.
Singer et al., 2012, "Horizon: An open-label extension trial ofranibizumab for choroidal neovascularization seconda to age-related macular degeneration", Opthamology, 119:1175-1183, Epub Feb. 4, 2012.

(56) References Cited

OTHER PUBLICATIONS

Sola and Griebenow, 2009, “Effects of glycosylation on the stability of protein pharmaceuticals”, J Pharm Sci, 98(4):1223-1245, Apr. 1, 2009.
Solinis et al., 2015, “Treatment of ocular disorder by gene therapy”, EP J of Pharmaceutics and Biopharmaceutics, Elsevier Sciene Publishers B.V., Amsterdam, NL., vol. 95:331-342, Epub Dec. 20, 2014.
Song et al. Light chain of natural antibody plays a dominant role in protein antigen binding, Biochem Biophys Res Comm 268:390-394, Feb. 16, 2000.
Stern et al., 2007, “Improving mammalian cell factories: the selection of signal peptide has a major impact on recombinant protein synthesis and secretion in mammalian cells” Trends Cell Mol Biol., 2:1-17.
Stone et al., 2009, “Tyrosine sulfation: an increasingly recognised post-translational modification of secreted proteins”, 25(5): 299-317, Jun. 2009.
Takahashi et al., 2003, “Intraocular expression of endostatin reduces VEGF-induced tetinal vascular permeability, neovascularization, and retinal detachment”, FASEB J, 17:896-898, Epub Mar. 28, 2003.
Tobe, 1998, “Evolution ofneovascularization in mice with overexpression of vascular endothelial growth factor in photoreceptors”, IOVS, 39(1):180-188, Jan. 1998.
Transcript of REGENXBIO Inc. Special Call dated Wednesday, Apr. 22, 2020 1:30 pm GMT, published by S&P Global Market Intelligence, retrieved from the internet at <Spglobal.com/marketintelligence.com> on Jul. 17, 2020 (18 pages) (Exhibit A to the response filed Jul. 21, 2020.).
Tripathi et al., 1989, “Protein composition of human aqueous humor: SDS-PAGE analysis of surgical and post-mortem samples,” Exp Eye Res., 48(1):117-130, Jan. 1989.
Tsuchiya et al., 1993, “Erythropoietin 5'-flanking sequence-binding protein induced during hypoxia and cobalt exposure”, J Biochem, 113(3):395, Mar. 1993.
Ueno et al., “Prolonged blockade of VEGF family members does not cause identifiable damage to retinal neurons or vessels,” J Cell Physiol., 217(1):13-22, Oct. 2008.
Valliere-Douglass et al., 2009, “Asparagine-linked oligosaccharides present on a non-consensus amino acid sequence in the CHI domain of human antibodies”, J Biol Chem, 284(32493-32506), Epub Sep. 18, 2009.
Valliere-Douglass et al., 2010,“Glutamine-linked and non-consensus asparagine-linked oligosacccharides present in human recombinant antibodies define novel protein glycosylation motifs”, J Biological Chemistry, 285(21):16012-16022, Epub Mar. 16, 2010.
Van De Bovenkamp et al., 2016, “The Emerging Importance of IgG Fab Glycosylation in Immunity”, Journal of Immunology, 196(4):1435-1441, Feb. 15, 2016.
Vandenberghe et al., 2011, “Dosage thresholds for AAV2 and AAV8 photoreceptor gene therapy in monkey”, Sci Trans Med, 3(88):88ra54, 1-9, Jun. 22, 2011.
Vandenberghe et al., 2013, “AAV9 targets cone photoreceptors in the nonhuman primate retina,” PLoS ONE, 8(1):e53463 , Jan. 30, 2013.
Vandenberghe, 2015, “What Is Next for Retinal Gene Therapy?” Cold Spring Harb Perspect Med., 5:a017442, Apr. 15, 2015.
Wang et al., 2013, “Glutamine-linked and non-consensus asparagine-linked oligosaccharides present in human recombinant antibodies define novel protein glycosylation motifs”, Analytical Biochem, 427:20-28, EPub Mar. 16, 2010.
Wang et al., 2013, “Structural characterization of recombinant alpha-1-antitrypsin expressed in a human cell line”, Analytical Biochemisliy, 437:20-28, Jun. 2013.
Wiley et al., 2016, “Using Patient-Specific Induced Pluripotent Stem Cells and Wild-Type Mice to Develop a Gene Augmentation-Based Strategy to Treat CLN3-Associated Retinal Degeneration”, Human Gene Therapy, 27(10):83 5-846, Epub Jun. 11, 2016.
Wimmer et al., 2015, “Functional characterization of AAV-Expressed recombinant anti- VEGF single-chain variable fragments in vitro”, J. of Ocular Pharmacology and Therapeutics, 31(5):269-276, Jun. 2015.
Wright et al., “Antibody variable region glycosylation: position effects on antigen binding and carbohydrate structure”, EMBO J, 10:2717-2723, Oct. 1991.
Wu et al. J. Mol. Biol. 294, 151-162, Nov. 19, 1999.
Wu et al., 2007, “Self-complementary recombinant adeno-associated viral vectors: packaging capacity and the role of rep proteins in vector purity”, Human Gene Therapy, 18(2):171-182, Feb. 2007.
Yan et al., 2005, “Inverted terminal repeat sequences are important for intermolecular recombination and circularization of adeno-associated virus genomes”, J Virol, 79(1):364-379, Jan. 2005.
Yang et al., 2015, “Tyrosine sulfation as a protein post-translational modification”, Molecules, 20(2):213 8-2164, Epub Jan. 28, 2015.
Yannuzzi et al., 2001, “Retinal angiomatous proliferation in age-related macular degeneration”, Retina, 21(5):416-434, Jul.-Sep. 2015.
Yeh et al., 2018, “Suprachoroidal injection of triamcinolone acetonide, CLS-TA, for macular edema due to noninfectious uveitis”, Retina, 00:1-9, Oct. 2015.
Yip et al., 2014, “Retinal Stem Cells and Regeneration of Vision System,” The Anatomical Record, 297:137-160, Dec. 2, 2013.
Zhang et al, 2005, The Journal of Gene Medicine, 7, 354-365. Dec. 23, 2004.
Zhang et al., 2015, “The proteome of human retina”, Proteomics, 15(4):836-740, and Supplemental Materials, Epub Jan. 14, 2015.
Zhang et al., 2016, “Defining the proteome of human iris, ciliary body, retinal pigment epithelium, and choroid”, Proteomics, 16(7):1146-1153 and Supplemental Material, Epub Mar. 11, 2016.
Zhong et al., 2008, “Next generation of adeno-associated virus 2 vectors: point mutations in tyrosines lead to high-efficiency transduction at lower doses”, Proc Natl Acad Sci USA, 105:7827-7832, Jun. 3, 2008.
Zinn et al., 2015, “In Silico Reconstruction of the Viral Evolutionary Lineage Yields a Potent Gene Therapy Vector,” Cell Rep., 12(6):1056-1068, Epub Jul. 30, 2015.
Zou et al., 2011, “Lasting controversy on ranibizumab and bevacizumab”, Theranostics, 1:395-202, Epub Dec. 12, 2011.
Cohen et al., 2013, “Changes in visual acuity in patients with wet age-related macular degeneration treated with intravitreal ranibizumab in daily clinical practice: the LUMIERE study”, Retina, 33:474-481, Mar. 2013.
Vajdos et al., Comprehensive functional maps of the antigen-binding site of an anti-ErbB2 antibody obtained with shotgun scanning mutagenesis, J. Mol. Biol. 320, 415-428, Jul. 5, 2002.
Fang et al., “An antibody delivery system for regulated expression of therapeutic levels of monoclonal antibodies in vivo”, Mol Ther, 15(6):1153-1159, epub Mar. 20, 2007.
Gelfand et al., 2016, “A Revised Hemodynamic Theory of Age-Related Macular Degeneration,” Trends Mol Med., 22(8):656-670, epub Jul. 13, 2016.
Heier et al., 2019, “Key Takeaways from the RGX-314 Phase I/IIa Clinical Trial for Wet AMD (Cohorts 1-5),” presented at the American Academy of Ophthalmology 2019 Retina Subspecialty Day meeting on Oct. 11, 2019.
Kotterman et al., 2014, “Antibody neutralization poses a barrier to intravitreal adeno-associated viral vector gene delivery to non-human primates”, Gene Ther, 22(2):116-126, Epub Dec. 11, 2014.
Magdelaine-Beuzelin, 2007, “Structure-function relationships of the variable domains of monoclonal antibodies approved for cancer treatment”, Critical Reviews in Oncology/Hematology, 64:210-225, Epub Jul. 12, 2007.
Lai et al., “Suppression of choroidal neovascularization by adeno-associated virus vector expressing angiostatin”, Invest Opthalmol Vis Sci, 42:2401-2407, Sep. 2001.
Platts-Mills et al., 2015, “Anaphylaxis to the carbohydrate side chain alpha-gal”, Immunol Allergy Clin North Am, 3 5(2):247-260, Epub Mar. 6, 2015.
Rudikoff et al. Proc Natl Acad Sci USA vol. 79 1979-1983, Mar. 1982.

(56) References Cited

OTHER PUBLICATIONS

Song et al., 2014, "In-depth method for the characterization of glycosylation in manufactured recombinant monoclonal antibody drugs", Anal Chem, 86(12):5661-5666 and Supplemental Data, Mach 18, 2016.
Maclaren et al., "Retinal gene therapy in patients with choroideremia: initial findings from a phase 1/2 clinical trial", Lancet, 383:1129-1137, Epub Mar. 29, 2014.
MacCallum et al. Antibody-antigen interactions: contact analysis and binding site topography, J. Mol. Biol. 262:732-7 45, Oct. 11, 1996.
Pechan et al., Novel anti-VEGF chimeric molecules delivered by AAV vectors for inhibition of retinal neovascularization, Gene therapy 16, 10-16, Epub Jul. 17, 2008.
Communication issued in corresponding European Patent Application No. 17734161.7, dated Jun. 19, 2020.
Extended European Search report dated Feb. 26, 2020 for European Pat. App. No. 17783242.5 (12 pages).
International Search Report and Written Opinion dated Nov. 29, 2018 for PCT/US18/52855; 11 pages.
International Search Report and Written Opinion dated Oct. 19, 2017 for PCT/US17/27650; 10 pages.
LUCENTIS ™ Pharmacology Review, Application No. 125156, Center for Drug Evaluation and Research, dated May 15, 2006.
Deverman et al., Cre-dependent selection yields AAV variants for widespread gene transfer to the adult brain, Nature Biology, vol. 34(2):204-211, Feb. 2016.
Gaffen et al., Overview of interleukin-2 function, production and clinical applications, Cytokine, vol. 28(3):109-23, Nov. 2004.
Griffey et al., AAV2-mediated ocular gene therapy for infantile neuronal ceroid lipofuscinosis, Molecular Therapy, vol. 12(3):413-21, Sep. 2005.
Kozarsky, K., Novel Adeno-Associated Viral Therapy for Wet Age-Related Macular Degeneration, SBIR/STTR America's Seed Fund, Awarded 2012.
Muller et al., VEGF and the Fab fragment of a humanized neutralizing antibody: crystal structure of the complex at 2.4 A resolution and mutational analysis of the interface, Structure, vol. 6(9):1153-67, Sep. 1998.
Penden et al., Ab-Externo AAV-Mediated Gene Delivery to the Suprachoroidal Space Using a 250 Micron Flexible Microcatheter, PLOS One, vol. 6(2):el7140, Feb. 2011.
Solinis et al., Treatment of ocular disorders by gene therapy, European Journal of Pharmaceutics and Biopharmaceutics, vol. 95(Pt B):331-42, Sep. 2015.
Wiley et al., Using Patient-Specific Induced Pluripotent Stem Cells and Wild-Type Mice to Develop a Gene Augmentation-Based Strategy to Treat CLN3-Associated Retinal Degeneration, Human Gene Therapy, vol. 27(10):83 5-846, Oct. 2016.
Wimmer et al., Functional Characterization of AAV-Expressed Recombinant Anti-VEGF Single-Chain Variable Fragments In Vitro, Journal of Ocular Pharmacology and Therapeutics, vol. 3.1(5):269-76, Jun. 2015.
Yip, H., Retinal Stem Cells and Regeneration of Vision System, The Anatomical Record, vol. 297(1):137-60, Jan. 2014.
Zhang et al., The proteome of human retina, Proteomics, vol. 15(4):836-840, Feb. 2015.
Zhang et al., The proteome of human retina, Proteomics, vol. 15(4):836-740, Supplemental Materials (331 pages), Feb. 2015.
Zhang et al., Defining the proteome of human iris, ciliary body, retinal pigment epithelium, and choroid, Proteomics, vol. 163(7):1146-1153, Apr. 2016.
Zhang et al., Defining the proteome of human iris, ciliary body, retinal pigment epithelium, and choroid, Proteomics, vol. 16(7):1146-1153, Supplemental Materials (1808 pages), Apr. 2016.
Zhang et al., Supplemental Materials (1748 pages).
Zinn et al., In Silico Reconstruction of the Viral Evolutionary Lineage Yields a Potent Gene Therapy Vector, Cell Reports, vol. 12(6):1056-68, Aug. 2015.
Office Action issued in corresponding Japanese Patent Application No. 2018-554334, dated Apr. 7, 2021, with translation provided by local Agent.

* cited by examiner

Animal ID: C62442; Group 2;
1.00 x $10^{11}$ GC/eye; right eye

Animal ID: C63116; Group 2;
1.00 x $10^{11}$ GC/eye; right eye

Animal ID: C66122; Group 3;
1.00 x $10^{11}$ GC/eye; right eye

Animal ID: C71941; Group 3;
1.00 x $10^{11}$ GC/eye; right eye

Animal ID: C74420; Group 5;
1.00 x $10^{11}$ GC/eye; right eye

Animal ID: C65873; Group 5;
1.00 x $10^{11}$ GC/eye; right eye

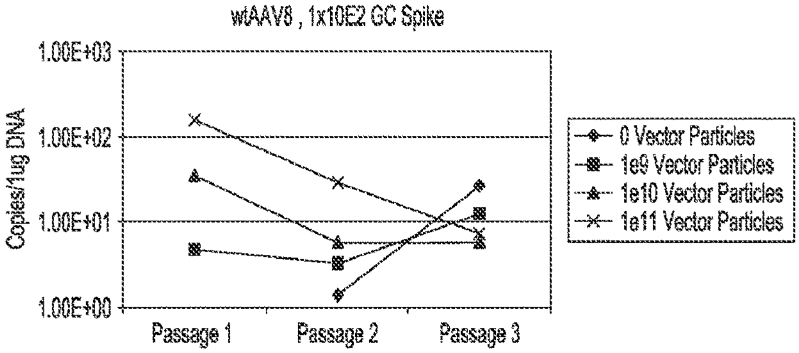
FIG. 10A
Controls
| Spike copies | Vector Copies | Passage 1 | Passage 2 | Passage 3 |
|---|---|---|---|---|
| blank | blank | 7.78E+00 | 7.47E+00 | 2.7E+01 |
| 0 | 0 | 0.00E+00 | 1.03E+01 | 5.5E+00 |
| 0 | 1.E+11 | 1.23E+02 | 7.91E+00 | 1.5E+01 |
Sensitivity : $1x10^4$ wt AAV8 GC
(~1 TCID50 IU) in $1x10^{11}$ GC
FIG. 10B
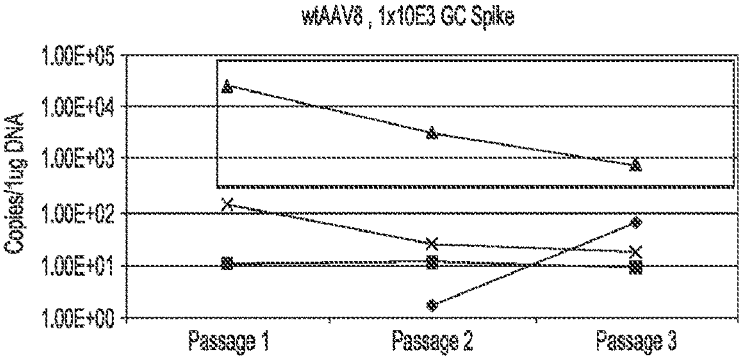
FIG. 10C
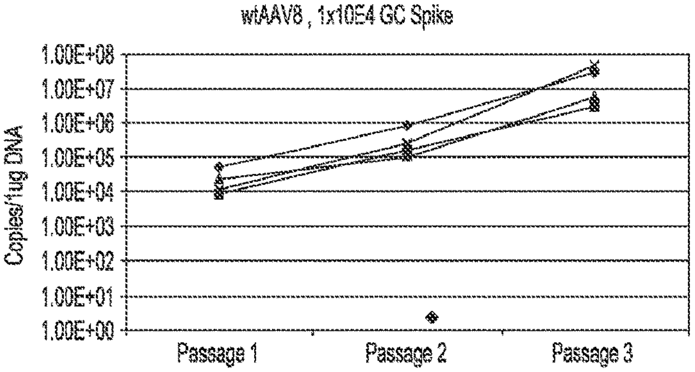
FIG. 10D

COMPOSITIONS FOR TREATMENT OF WET AGE-RELATED MACULAR DEGENERATION

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-16-7683PCT_ST25.txt".

BACKGROUND OF THE INVENTION

Age-related macular degeneration (AMD) is a progressive degenerative macular disease attacking the region of highest visual acuity (VA), the macula, and is the leading cause of blindness in Americans 60 years or older (NIH Medline Plus (2008), Leading cause of blindness, NIH Medline Plus 3(2) 14-15. www.nlm.nih.gov/medlineplus/magazine/issues/summer08/articles/summer08pg14-15.html). The neovascular "wet" form of the disease (nAMD or wet AMD) is characterized by choroidal neovascularization which is marked by proliferation of blood vessels and cells including those of the retinal pigment epithelium (RPE) (Carmeliet (2005) Nature 438: 932-936). Ultimately, photoreceptor death and scar formation result in a severe loss of central vision and the inability to read, write, and recognize faces or drive. Many patients can no longer maintain gainful employment, carry out daily activities and consequently report a diminished quality of life (Mitchell and Bradley (2006), Health Qual Life Outcomes 4: 97). Preventative therapies have demonstrated little effect and therapeutic strategies have focused primarily on treating the neovascular lesion.

Some currently available treatments for wet AMD include laser photocoagulation, photodynamic therapy with verteporfin, and intravitreal (IVT) injections with the vascular endothelial growth factor (VEGF) inhibitors such as pegaptanib, ranibizumab, bevacizumab or aflibercept (Schmidt-Erfurth, (2014) Guidelines for the management of neovascular age-related macular degeneration by the European Society of Retina Specialists (EURETINA) Br J Ophthalmol 98:1144-1167). While these therapies have some effect on best-corrected visual acuity (BCVA), their effects may be limited in restoring visual acuity and in duration (Schmidt-Erfurth, cited above, 2014, AAO PPP (2015) Preferred Practice Patterns: Age Related Macular Degeneration. American Academy of Ophthalmology). Several drugs in market that are used to treat wet AMD rely on a mechanism that inhibits VEGF and must be injected intravitreally. While these treatments are reported to succeed in prohibiting the disease from progressing, they require frequent injections of the drug.

Of specific note, ranibizumab, a recombinant, humanized monoclonal IgG1 antigen-binding fragment (Fab) is designed to bind and inhibit all active forms of human (VEGF). Ranibizumab is a humanized monoclonal antibody fragment produced in *Escherichia coli* cells by recombinant DNA technology. The binding of ranibizumab to VEGF-A prevents the interaction of VEGF-A with its receptors VEGFR-1 and VEGFR-2 on the surface of endothelial cells. This binding inhibits endothelial cell proliferation and neovascularization, as well as vascular leakage, all of which are thought to contribute to the progression of the neovascular (wet) form of age-related macular degeneration (Wet AMD). The safety and efficacy of ranibizumab (Lucentis®) has been established, and ranibizumab is United States (US) Food & Drug Administration (FDA) approved for IVT injection treatment in patients with neovascular AMD, as well as other retinal diseases (initially approved FDA 2006). While long term therapy with either monthly ranibizumab or monthly/every 8 week aflibercept may slow the progression of vision loss and improve vision, none of these treatments prevent neovascularization from recurring (Brown et al (2006) N Engl J Med, 355:1432-44; Rosenfeld et al., (2006) N Engl J Med 355:1419-31; Schmidt-Erfurth, 2014, cited above). Each has to be re-administered to prevent the disease from worsening. The need for repeat treatments can incur additional risk to patients and is inconvenient for both patients and treating physicians.

SUMMARY OF THE INVENTION

In one aspect, the invention provides a recombinant adeno-associated virus (rAAV) having an AAV8 capsid which is suitable for sub-retinal and/or intra-retinal injection. The AAV8 capsid packages a vector genome that provides for the production of a soluble antigen-binding fragment (Fab) of a human monoclonal antibody (MAb) that binds and inhibits human vascular endothelial growth factor (hVEGF)—the expression product is sometimes referred to herein as "anti-hVEGF Fab" or "aVEGF".

The vector genome packaged within the rAAV8 capsid, comprises:

(a) an AAV inverted terminal repeat(s) (ITR(s)) flanking an expression construct for the anti-VEGF Fab; (b) the expression construct having regulatory elements comprising a chicken beta-actin promoter or a ubiquitin C promoter that direct expression in the eye of a transgene encoding anti-hVEGF Fab; and (c) the transgene which encodes the heavy and light chains of the anti-hVEGF Fab, each chain having a heterologous leader sequence added to its amino terminus, and wherein the coding sequences for the heavy and light chains are separated by a coding sequence for a "cleavable" peptide linker or an IRES (internal ribosome entry site) to ensure production of separate heavy and light chain polypeptides, and a polyadenylation signal. The resulting transgene expression products may contain an amino acid residue in addition to those normally found in Fab heavy chains.

In particular embodiments, codon sequences for the heavy and light chains optimized for expression in human cells are used. As illustrated by the examples, these can include but are not limited to AAV2/8.CB7.CI.aVEGFv1.rBG; AAV2/8.CB7.CI.aVEGFv2.rBG; AAV2/8.CB7.CI.aVEGFv3.rBG; AAV2/8.CB7.CI.aVEGFv4.rBG; AAV2/8.CB7.CI.aVEGFv5.rBG; AAV2/8.CB7.CI.aVEGFv6.rBG; AAV2/8.CB7.CI.aVEGFv7.rBG; AAV2/8.CB7.CI.aVEGFv8.rBG; AAV2/8.CB7.CI.VEGFv9.rBG; AAV2/8.CB7.CI.aVEGFv10.rBG; AAV2/8.CB7.CI.aVEGFv11.rBG; AAV2/8.CB7.CI.aVEGFv12.rBG; AAV2/8.CB7.CI.aVEGFv13.rBG.

As used herein, "AAV2/8" and "AAV8" are used interchangeably to refer to a recombinant AAV having an AAV8 capsid and vector genome flanked by AAV2 ITRs.

In yet another aspect, a liquid suspension of any of the foregoing rAAV8.aVEGF for sub-retinal and/or intra-retinal injection is provided. The composition comprises an aqueous liquid and rAAV8.aVEGF as described herein, and optionally one or more excipients, preservatives, and/or surfactants.

In still a further aspect, a method for delivering an anti-hVEGF Fab to a patient having wet age-related related macular degeneration is provided. The method involves subretinally injecting the patient's eye with the liquid suspension comprising the rAAV8 vector carrying the expression construct for the anti-hVEGF Fab.

In certain embodiments, the invention provides a rAAV as described herein, or a liquid suspension, administrable subretinally to a patient. In certain embodiments, use of a rAAV or a liquid suspension, for subretinal administration to a patient is provided. The patient may have been previously diagnosed with wet age-related macular degeneration, or another ocular condition as defined herein.

In still a further embodiment, a product comprising: (a) a first container comprising an rAAV8.anti-hVEGF Fab and an aqueous liquid, (b) optionally a second container comprising a diluent, and (c) a needle for injection. In certain embodiments, the product is an injection kit.

The invention is illustrated by the examples below which demonstrate that subretinal administration of an rAAV8.aVEGF vector results in gene transfer throughout the retina, and expression of anti-VEGF Fab throughout the retina and in the vitreous and anterior chamber fluids. This result is surprising in view of prior art gene therapy studies that demonstrated that gene transfer spreads laterally outside of the original injection bleb but remains confined to those expanded boundaries and did not achieve gene transfer and transgene expression outside this expanded area of injection (the "bleb" formed in the retina at the injection site); and offers an advantage over standard of care treatment for nAMD in that a single administration of the rAAV8.aVEGF vector should result in (i) continuous delivery of the effective amounts of the VEGF inhibitor throughout the retina which may in turn improve performance as compared to repeated IVT administrations of high dose boluses of the VEGF inhibitor that dissipate over time; and (ii) avoidance of repeated ocular injections which pose additional risks and inconvenience to patients. Each aspect may improve therapeutic outcome.

Still other aspects and advantages of the invention will be apparent from the following detailed description of the invention.

BRIEF DESCRIPTION OF THE FIGURES

In FIGS. 3A and 3B, the results for animals in Group 2. In FIGS. 3C and 3D, the results for Group 3 are presented. In FIGS. 3B and 3D, the gray area in the panel presenting the results in serum denotes baseline levels. Circles denote females and squares denote males. Samples were analyzed in duplicate. The results are presented as mean±standard deviation. Abbreviations: Fab=fragment antigen-binding; GC=genome copies; OD=right eye; OS=left eye; VEGF=vascular endothelial growth factor.

In FIGS. 4B and 4D, the gray area in the panel presenting the results in serum denotes baseline levels. Circles denote females and squares denote males. Samples were analyzed in duplicate. The results are presented as mean±standard deviation. Abbreviations: Fab=fragment antigen-binding; GC=genome copies; OD=right eye; OS=left eye; VEGF=vascular endothelial growth factor.

In FIGS. 6A and 6C, infrared spectral domain optical coherence tomography images of the retinas with boundaries of injection site are depicted. In FIGS. 6B and 6D, graphs of concentrations of anti-VEGF Fab are presented. In this figure, the results for animals in Group 2 in Example 6 are presented. Abbreviations: ACF=anterior chamber fluid; BV=major blood vessel;

F=fovea; Fab=fragment antigen-binding; FOV=middle section containing fovea; GC=genome copies; IB=injection bleb; ID=identification; INF=inferior retinal section; O=optic disk; ODI=middle section containing optic disk; SUP=superior retinal section; VEGF=vascular endothelial growth factor; VIT=vitreous.

Figure 7A:
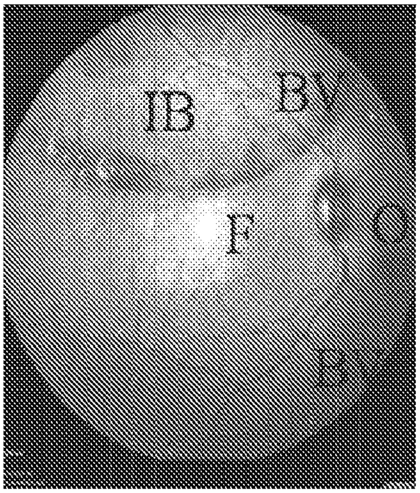
Figure 7B:
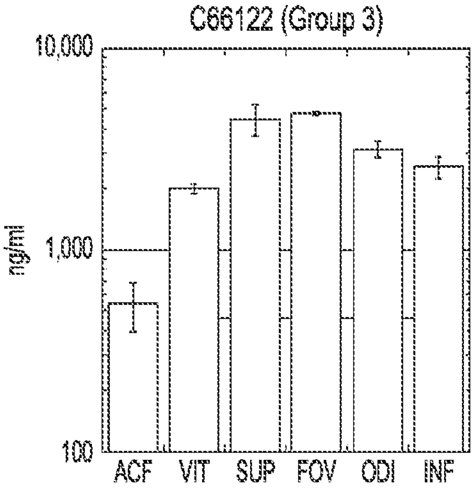
Figure 7C:
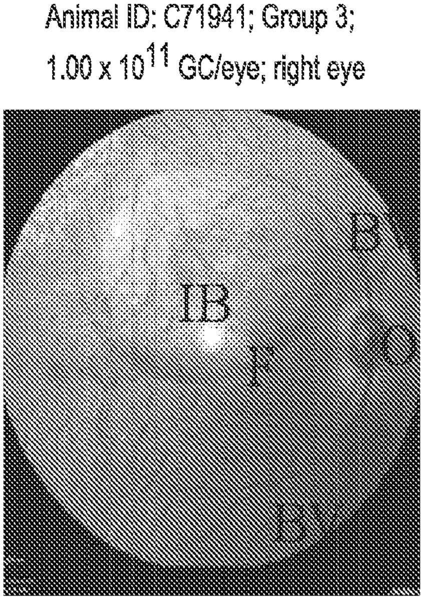
Figure 7D:
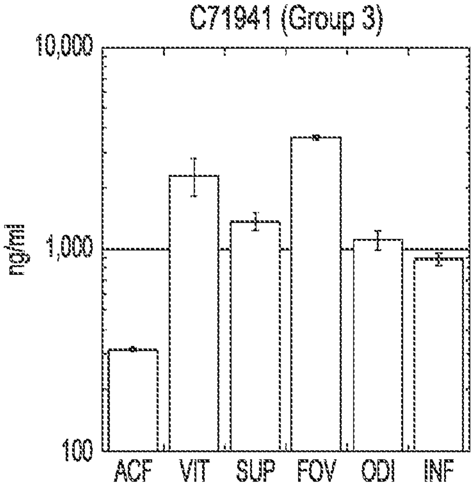

FIGS. 7A-7D provide results of expression of anti-VEGF Fab in anterior chamber fluid, vitreous, and retina (Group 3, Example 6). Cynomolgus monkeys were administered a single dose of $1.00\times10^{11}$ GC/eye of AAV2/8 vector subretinally. These data represent results from different AAV8.aVEGF vectors than shown in FIGS. 5A-5D. Concentrations of anti-VEGF Fab were determined in anterior chamber fluid, vitreous, and 4 different parts of retina. Eyes were dissected as described in FIGS. 5A-5D. In FIGS. 7A and 7C, infrared spectral domain optical coherence tomography images of the retinas with boundaries of injection site are depicted. In the graphs of FIGS. 7B and 7D, concentrations of anti-VEGF Fab are presented. In this figure, the results for animals in Group 3 in Example 6 are presented. Abbreviations: ACF=anterior chamber fluid; BV=major blood vessel; F=fovea; Fab=fragment antigen-binding; FOV=middle section containing fovea; GC=genome copies; IB=injection bleb; ID=identification; INF=inferior retinal section; O=optic disk; ODI=middle section containing optic disk; SUP=superior retinal section; VEGF=vascular endothelial growth factor; VIT=vitreous.

Figure 8A:
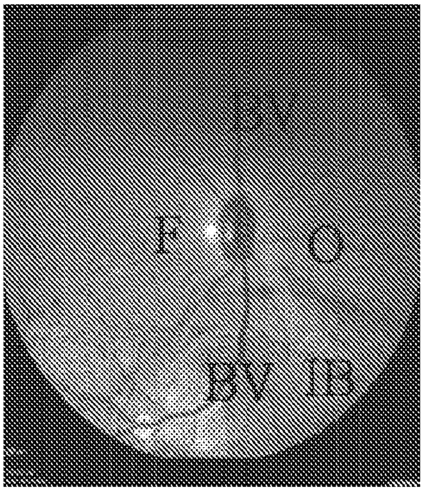
Figure 8B:
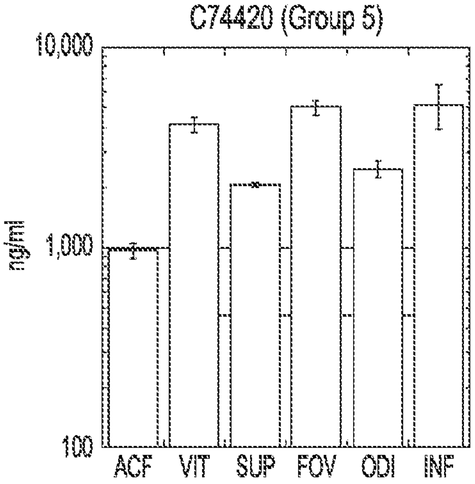
Figure 8C:
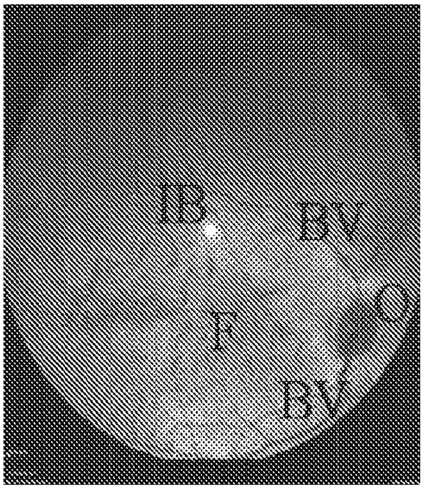
Figure 8D:
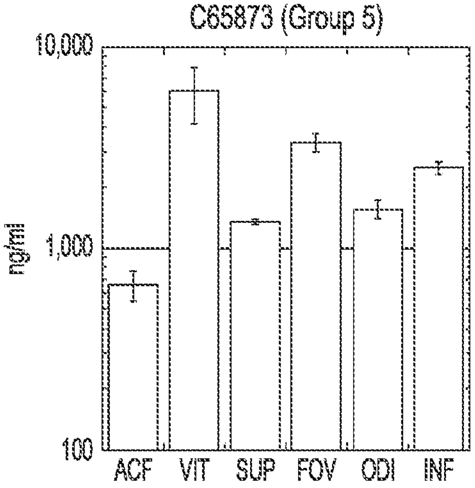

FIGS. 8A-8D provide results of expression of anti-VEGF Fab in anterior chamber fluid, vitreous, and retina (Group 5, Example 6). Cynomolgus monkeys were administered a single dose of $1.00\times10^{11}$ GC/eye of AAV2/8 vector subretinally. These data represent results from different AAV8.aVEGF vectors than shown in FIGS. 5A-5D. Concentrations of anti-VEGF Fab were determined in anterior chamber fluid, vitreous, and 4 different parts of retina. Eyes were dissected as described in FIGS. 5A-5D. In FIGS. 8A and 8C, infrared spectral domain optical coherence tomography images of the retinas with boundaries of injection site are depicted. In the graphs of FIGS. 8B and 8D, concentrations of anti-VEGF Fab are presented. In this figure, the results for animals in Group 5 in Example 6 are presented. Abbreviations: ACF=anterior chamber fluid; BV=major blood vessel; F=fovea; Fab=fragment antigen-binding; FOV=middle section containing fovea; GC=genome copies; IB=injection bleb; ID=identification; INF=inferior retinal section; O=optic disk; ODI=middle section containing optic disk; SUP=superior retinal section; VEGF=vascular endothelial growth factor; VIT=vitreous.

Figure 9:
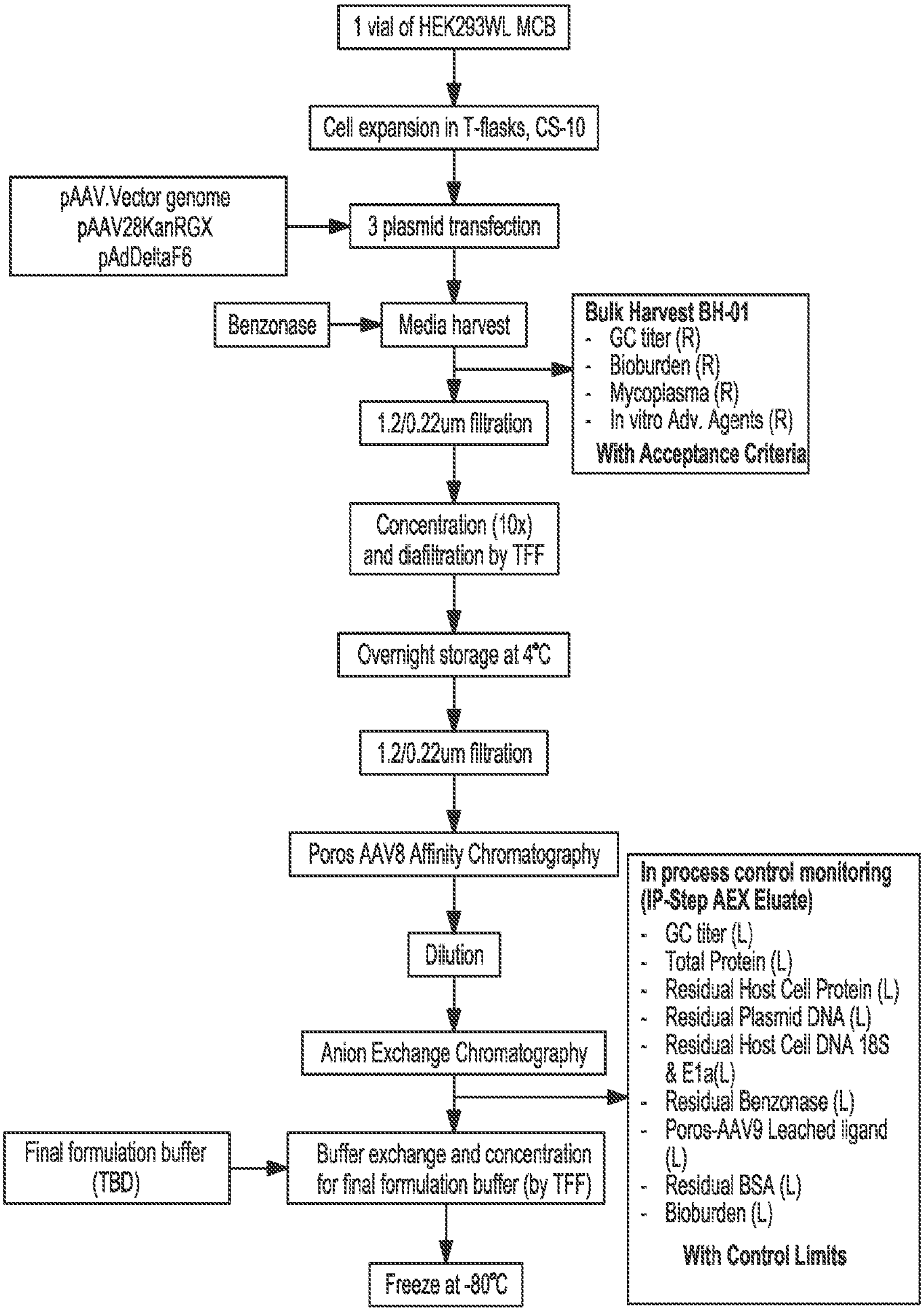

FIG. 9 provides a flow diagram of the manufacturing process.

FIGS. 10A-10D illustrate the results of an rcAAV assay for AAV8. wtAAV8 is spiked into different GC amounts of AAV vector and the cap gene copy number per 1 μg of 293 cell DNA is determined after three successive passages of the cell lysate onto fresh cells. 3 different spike levels of wtAAV8 [one level per panel: $1\times10^2$ GC, $1\times10^3$ GC and $1\times10^4$ GC] 4 different vector amounts [0 GC (dark square), $1\times10^9$ GC (gray square) $1\times10^{10}$ GC (triangle) and $1\times10^{11}$ GC (marked with X)] are shown and background levels are indicated (controls).

DETAILED DESCRIPTION OF THE INVENTION

Recombinant, replication-defective adeno-associated virus (rAAV) vectors having an AAV8 capsid and compositions containing same which are suitable for subretinal injections to deliver an anti-VEFG antibody binding fragment (Fab). Also provided are compositions containing same, and in particularly, liquid aqueous suspension. Uses of these compositions are also provided.

The rAAV8 vectors are designed to express an anti-VEGF antibody binding fragment (Fab) in mammalian, and more particularly, human cells. These anti-VEGF Fabs are particularly well suited for treatment of age-related macular degeneration (AMD). For convenience, these vectors are terms rAAV8.AMD. As described herein, a series of novel AAV8.aVEGF constructs have been developed which have demonstrated high yield, expression levels, and/or activity.

The invention is illustrated by the examples below which demonstrate that subretinal administration of an rAAV8.aVEGF vector results in gene transfer throughout the retina, and expression of anti-VEGF Fab throughout the retina and in the vitreous and anterior chamber fluids. This result is surprising in view of prior art gene therapy studies that demonstrated that gene transfer spreads laterally outside of the original injection bleb but remains confined to those expanded boundaries and did not achieve gene transfer and transgene expression outside this expanded area of injection (the "bleb" formed in the retina at the injection site); and offers an advantage over standard of care treatment for nAMD in that a single administration of the rAAV8.aVEGF vector should result in (i) continuous delivery of the effective amounts of the VEGF inhibitor throughout the retina which may in turn improve performance as compared to repeated IVT administrations of high dose boluses of the VEGF inhibitor that dissipate over time; and (ii) avoidance of repeated ocular injections which pose additional risks and inconvenience to patients. Each aspect may improve therapeutic outcome.

The present invention provides constructs encoding a novel anti-VEGF Fab having, at a minimum, a heavy chain amino acid sequence of SEQ ID NO: 1 and a light chain amino acid sequence of SEQ ID NO:2, each of which has been engineered to have an exogenous leader sequence for each the heavy chain and light chain. In certain constructs illustrated herein, the leader sequence is derived from a human IL2 leader. Further, in certain constructs illustrated in the working examples, the heavy and light chains are separated by a furin/F2a linker, which may result may result in one or more extra amino acids being added to the heavy chain [SEQ ID NO:1]. In one embodiment, a single arginine [R] is added to the heavy chain. However, in certain embodiments, another linker may be selected and/or a different system may result in no additional amino acid, or one or more extra amino acids [e.g., R, Lys (K), RK, RKR, RKRR among others]. In prior provisional applications, the resulting constructs were termed herein, aVEGF-R. However, for clarity, these constructs encoding the anti-VEGF Fab transgene product described herein, are referred to as: anti-VEGF Fab, aVEGF, anti-hVEGF, anti-human VEGF, or anti-VEGF Fab transgene product. In the constructs encoding this transgene product, a numerical designation following the term aVEGF, e.g., aVEGFv1, aVEGFv2, aVEGFv3, through aVEGFv13, refers to different nucleic acid coding sequences for the open reading frame of the immunoglobulin heavy chain and light chains.

In certain embodiments, the amino acid sequence of the anti-VEGF Fab has 513 amino acids, including anti-VEGF is heavy and light chain separated by extra amino acids as a result of the linker. For example, while each of the following expression cassettes encodes the same anti-VEGF heavy chain and light chain, in one embodiment, there may be one amino acid added to the last position of the heavy chain. In still other embodiments, there may be two, three, four or more extra amino acids attached to the heavy chain. For example, in certain embodiments, the nucleic acid sequences coding for the heavy and light chains of anti-VEGF Fab are separated by a self-cleaving furin (F)/F2A linker. A furin recognition site that consists of arginine-lysine-arginine-arginine amino acid sequence may be used. Due to the mechanism of furin-mediated cleavage, vector-expressed anti-VEGF Fab may contain an additional arginine (R) residue added to the last position of the heavy chain [SEQ ID NO: 1]. In other embodiments, the vector-expressed anti-VEGF Fab may contain the dipeptide arginine-lysine at the end of the heavy chain, the tripeptide arginine-lysine-arginine at the end of the heavy chain, or the polypeptide arginine-lysine-arginine-arginine at the end of the heavy chain. In certain embodiments, the vector expressed anti-VEGF Fab are a heterogeneous mixture of two or more of these Fab products. Other furin cleavage sites can be used (arginine-X-X-arginine, or arginine-X-lysine or arginine-arginine), which can also generate C-terminal heterogeneity. In other words, other vector expressed anti-VEGF Fabs may be a heterogeneous population of the Fab in which the heavy chain has 0, 1, 2, 3, or 4 amino acids at its C-terminus as a result of the linker processing. In addition, the light and heavy chain each contain a heterologous leader peptide which directs nascent peptide into appropriate cellular compartment where leader peptide is processed away from the mature protein by the host cellular machinery. In certain embodiments, the anti-VEGF Fab contains no HC or LC leader sequences. See, e.g., SEQ ID NO: 33.

In certain embodiments, the anti-VEGF Fab heavy chain has the amino acid sequence of residues 21-252 of SEQ ID NO: 33 with a leader sequence. In other embodiments, the anti-VEGF Fab light chain has the amino acid sequence of residues 300-513 of SEQ ID NO: 33 with a leader sequence. For example, the leader sequence may be from about 15 to about 25 amino acids, preferably about 20 amino acids. In some embodiments, the leader has the sequence of amino acids 1-20 of SEQ ID NO: 33.

In one embodiment, the coding sequences for the heavy chain and light chain of anti-VEGFv1 are provided in SEQ ID NO: 24. More particularly, the heavy chain variable region open reading frame (ORF) is provided in nucleotides (nt) 1843 to 2211 and the heavy chain constant region (CH1) ORF is provided in nt 2212-2532, with reference to SEQ ID NO: 24. Thus, the aVEGFv1 heavy chain, without the leader, has the nucleic acid sequence of nt 1843 to 2532. The light chain variable region (VL) ORF is provided in nt 2680 to 3000 and the light chain constant region (CL) is provided in nt 3001 to 3321 of SEQ ID NO: 24. Thus, the aVEGFv2 light chain, without the leader, has the nucleic acid sequence of nt 2680 to 3321 of SEQ ID NO: 24.

In another embodiment, the coding sequences for the heavy chain and light chain of anti-VEGFv2 are provided in SEQ ID NO: 3. More particularly, the VH ORF is provided in nt 2059 to 2427 and the CH1 is provided in 2428 to 2748 of SEQ ID NO: 3; the heavy chain without the leader has the nucleic acid sequence of nt 2059 to 2748 of SEQ ID NO: 3. The VL ORF is provided in nt 2896 to 3216 and CL is provided in nt 3217 to 3536 of SEQ ID NO: 3; the light chain without the leader sequence has the nucleic acid sequence of nt 2896 to 3536 of SEQ ID NO: 3.

In yet another embodiment, the coding sequences for the heavy chain and light chain of aVEGFv3 are provided in SEQ ID NO: 19. The VH ORF is provided in nt 1842 to 2210 and the CH1 is provided in nt 2211 to 2531 of SEQ ID NO: 19; the heavy chain without the leader has the nucleic acid sequence of nt 1842 to 2531 of SEQ ID NO: 19. The VL ORF is provided in nt 2679 to 2999 and CL is provided in nt 3000 to 3320 of SEQ ID NO: 19; the light chain without the leader has the nucleic acid sequence of nt 2670 to 3320 of SEQ ID NO: 19.

In a further embodiment, the coding sequences for the heavy and light chain of aVEGFv4 are provided in SEQ ID NO: 35. The heavy chain leader sequence is encoded by nt 1993-2052, the VH ORF is at nt 2053-2421 and the CH1 is at nt 2422-2742 of SEQ ID NO: 35. As in the other constructs described herein, as a result of the location of the F2A cleavage site, sequences encoding additional amino acids may be retained on the VH chain. The light chain leader sequence is encoded by nt 2830-2889; the VL ORF is provided in nt 2890-3210; the CL ORF is located at nt 3211-3531 of SEQ ID NO: 35.

In a further embodiment, the coding sequences for the heavy and light chain of aVEGFv5 is provided within SEQ ID NO: 36. The heavy chain leader sequence is encoded by nt 1993-2052, the VH ORF is encoded by nt 2053-2421, and the CH1 is encoded by nt 2422-2742 of SEQ ID NO: 36. As in the other constructs described herein, as a result of the location of the F2A cleavage site, sequences encoding additional amino acids may be retained on the VH chain. The light chain leader sequence is encoded by nt 2830-2889; the VL ORF is provided in nt 2890-3210; the CL ORF is located at nt 3211-3531 of SEQ ID NO: 36.

In a further embodiment, the coding sequences for the heavy and light chain of aVEGFv6 is provided within SEQ ID NO: 37. The heavy chain leader sequence is encoded by nt 1993-2051, the VH ORF is encoded by nt 2053-2421, and the CH1 is encoded by nt 2422-2742 of SEQ ID NO: 37. As in the other constructs described herein, as a result of the location of the F2A cleavage site, sequences encoding additional amino acids may be retained on the VH chain. The light chain leader sequence is encoded by nt 2830-2889; the VL ORF is provided in nt 2890-3210; the CL ORF is located at nt 3211-3531 of SEQ ID NO: 37.

In a further embodiment, the coding sequences for the heavy and light chain of aVEGFv7 is provided within SEQ ID NO: 38. The heavy chain leader sequence is encoded by nt 1993-2052, the VH ORF is encoded by nt 2053-2421, and the CH1 is encoded by nt 2422-2742 of SEQ ID NO: 38. As in the other constructs described herein, as a result of the location of the F2A cleavage site, an additional Arg codon is retained on the VH chain. The light chain leader sequence is encoded by nt 2830-2889; the VL ORF is provided in nt 2890-3210; the CL ORF is located at nt 3211-3531 of SEQ ID NO: 38.

In a further embodiment, the coding sequences for the heavy and light chain of aVEGFv8 is provided within SEQ ID NO: 39. The heavy chain leader sequence is encoded by nt 1993-2052, the VH ORF is encoded by nt 205-2421, and the CH1 is encoded by nt 2422-2742 of SEQ ID NO: 39. As in the other constructs described herein, as a result of the location of the F2A cleavage site, an additional Arg codon is retained on the VH chain. The light chain leader sequence is encoded by nt 2830-2889; the VL ORF is provided in 2890-3210; the CL ORF is located at nt 3211-3531 of SEQ ID NO: 39.

In a further embodiment, the coding sequences for the heavy and light chain of aVEGFv9 is provided within SEQ ID NO: 40. The heavy chain leader sequence is encoded by nt 1999-2058, the VH ORF is encoded by nt 2059-2427, and the CH1 is encoded by nt 2428-2748 of SEQ ID NO: 40. As in the other constructs described herein, as a result of the location of the F2A cleavage site, an additional Arg codon is retained on the VH chain. The light chain leader sequence is encoded by nt 2836-2895; the VL ORF is provided in nt 2896-3216; the CL ORF is located at nt 3217-3637 of SEQ ID NO: 40.

In a further embodiment, the coding sequences for the heavy and light chain of aVEGFv10 is provided within SEQ ID NO: 41. The heavy chain leader sequence is encoded by nt 1993-2052, the VH ORF is encoded by nt 2053-2421, and the CH1 is encoded by nt 2422-2742 of SEQ ID NO: 41. As in the other constructs described herein, as a result of the location of the F2A cleavage site, an additional Arg codon is retained on the VH chain. The light chain leader sequence is encoded by nt 2830-2889; the VL ORF is provided in nt 2890-3210; the CL ORF is located at nt 3211-3231 of SEQ ID NO: 41.

In a further embodiment, the coding sequences for the heavy and light chain of aVEGFv11 is provided within SEQ ID NO: 42. The heavy chain leader sequence is encoded by nt 1993-2052, the VH ORF is encoded by nt 2053-2421, and the CH1 is encoded by nt nt 2422-2742 of SEQ ID NO: 42. As in the other constructs described herein, an F2A cleavage site is located between the end of the heavy chain and the beginning of the light chain. The light chain leader sequence is encoded by nt 2830-2889; the VL ORF is provided in nt 2890-3210; the CL ORF is located at nt 3211-3531 of SEQ ID NO: 42.

In a further embodiment, the coding sequences for the heavy and light chain of aVEGFv12 is provided within SEQ ID NO: 43. The heavy chain leader sequence is encoded by nt 1993-2052, the VH ORF is encoded by nt 2053-2421, and the CH1 is encoded by nt 2422-2742 of SEQ ID NO: 43. The light chain leader sequence is encoded by nt 2830-2889; the VL ORF is provided in nt 2890-3210; the CL ORF is located at nt 3211-3531 of SEQ ID NO: 43.

In a further embodiment, the coding sequences for the heavy and light chain of aVEGFv13 is provided within SEQ ID NO: 44. The heavy chain leader sequence is encoded by nt 1993-2052, the VH ORF is encoded by nt 2053-2421, and the CH1 is encoded by nt 2422-2742 of SEQ ID NO: 44. The light chain leader sequence is encoded by nt 2830-2889; the VL ORF is nt 2890-3210; the CL ORF is located at nt 3211-3531 of SEQ ID NO: 44.

Ranibizumab is described herein as a positive control and is currently marketed under the brand name Lucentis®. It is described as a Fab moiety of a high affinity version of recombinant humanized monoclonal antibody rhuMAb vascular endothelial growth factor (VEGF). It consists of a 214-residue light chain linked by a disulfide bond at its C-terminus to the 231-residue N-terminal segment of the heavy chain. The expected amino acid sequences of the heavy and light chains are provided in SEQ ID NO: 1 and 2. CAS number 347396-82-1.

As used herein, an "immunoglobulin domain" refers to a domain of an antibody heavy chain or light chain as defined with reference to a conventional, full-length antibody.

More particularly, a full-length antibody contains a heavy (H) chain polypeptide which contains four domains: one N-terminal variable (VH) region and three C-terminal constant (CH1, CH2 and CH3) regions and a light (L) chain polypeptide which contains two domains: one N-terminal variable (VL) region and one C-terminal constant (CL) region. An Fc region may contain two domains (CH2-CH3). A Fab region contains one constant and one variable domain for each the heavy and light chains.

In one embodiment, rAAV.aVEGF vector has an AAV8 capsid and a vector genome packaged therein which comprises at least one element heterologous to AAV8. In one embodiment, the vector genome contains, from 5' to 3': (a) an AAV 5' ITR; (b) an enhancer; (c) a promoter; (d) an intron; (e) a leader sequence and the anti-VEGF heavy chain coding sequence; (f) a furin-F2a linker; (g) a leader sequence and the anti-VEFG light chain coding sequence; (h) a polyA signal; and (i) an AAV3' ITR.

In certain embodiments, the processing of anti-VEGF Fab heavy chain and light chains is directed by leader peptides that are derived from human IL2 protein. In one embodiment the leader sequence is an interleukin (IL) IL-2 leader sequence, which may be the wild-type human IL2, MYRMQLLSCIALSLALVTNS [SEQ ID NO: 29], or a mutated leader, such as MYRMQLLLLIALSLALVTNS [SEQ ID NO: 30] or MRMQLLLLIALSLALVTNS [SEQ ID NO: 31]. In another embodiment, a human serpinF1 secretion signal may be used as leader peptides. Other leader sequences can be used, or other leaders exogenous to the heavy and light chain.

As used in the following description of the vector genome unless otherwise specified as the light chain or heavy chain, reference to a coding sequence (e.g., aVEGFv2) encompasses the anti-VEGF heavy chain—furin/F2a linker—anti-VEGF light chain. In one embodiment, a nucleic acid sequence encoding the furin recognition site Arginine-Lysine-Arginine-Arginine is selected. In certain embodiments, nucleic acids encoding a F2A linker which is a 24 amino acid peptide derived from FMDV (GenBank #CAA2436.1) is selected. However, if desired, an IRES sequence, e.g., such as derived from encephalomycarditis virus (EMCV): SEQ ID NO: 32: [TATGCTAGTACGTCTCTCAAGGATAAGTAAGTAATATTAAGGTACGGGAGGTAT TGGACAGGCCGCAATAAAATATCTTTATTTTCATTACATCTGTGTGTTGGTTTTTT GTGTGAATCGATAGTACTAACATACGCTCTCCATCAAAACAAAACGAAACAAAA CAAACTAGCAAAATAGGCTGTCCCCAGTGCAAGTGCAGGTGCCAGAACATTTCT CTGGCCTAACTGGCCGGTACCTGAGCTCTAGTTTCACTTTCCCTAGTTTCACTTTC CCTAGTTTCACTTTCCCTAGTTTCACTTTCCCTAGTTTCACTTTCCCCTCGAGGAT ATCAAGATCTGGCCTCGGCGGCCAG], cMyc [Nanbru C, et al (1997). J. Biol. Chem. 272, 32061-32066; Stoneley M, et al., (1998). Oncogene 16, 423-428.1, or foot and mouth disease (FMD) may be selected.

Inverted terminal repeats (ITR) from AAV2 may be selected. Vectors having ITRs from a different source than its capsid are termed "pseudotyped". In certain embodiments, ITRs from a source other than AAV2 may be selected for this construct to generate another pseudotyped AAV. Alternatively, ITRs from the same source as the capsid may be selected. In certain embodiments, ITRs may be selected to generate a self-complementary AAV, such as defined infra.

In certain embodiments, the promoter is CB7, a hybrid between a cytomegalovirus (CMV) immediate early enhancer (C4) and the chicken beta actin promoter. In other embodiments, the promoter is a ubiquitin C (UbC) promoter. See, e.g., WO 2001/091800. See, e.g., GenBank® accession numbers AF232305 (rat) and D63791 (human), respectively. Still other promoters and/or enhancers may be selected. See, e.g., cytomegalovirus (CMV) immediate early enhancer (260 bp, C4; GenBank #K03104.1). Chicken beta-actin promoter (281 bp; CB; GenBank #X00182.1). In still other embodiments, multiple enhancers and/or promoters may be included.

In certain embodiments, an intron is included. One suitable intron is a chicken beta-actin intron. In one embodiment, the intron is 875 bp (GenBank #X00182.1). In another embodiment, a chimeric intron available from Promega is used. However, other suitable introns may be selected.

The vector genomes described herein include a polyadenylation signal (polyA). A variety of suitable polyA are known. In one example, the polyA is rabbit beta globin, such as the 127 bp rabbit beta-globin polyadenylation signal (GenBank #V00882.1). In other embodiments, an SV40 polyA signal is selected. Still other suitable polyA sequences may be selected.

Optionally, other suitable vector elements may be selected which may include, e.g., a UTR sequence or a Kozak sequence.

In one embodiment, the vector genome contains, ITR-CB7-CI-aVEGFv2-rBG-ITR, [SEQ ID NO: 3]. In another embodiment, the vector genome contains: ITR-UbC-CI-aVEGFv2-SV40-ITR.[SEQ ID NO: 9]. In one embodiment, the vector genome contains, ITR-CB7-CI-aVEGFv3-rBG-ITR [SEQ ID NO: 14]. In another embodiment, the vector genome contains: ITR-UbC-PI-aVEGFv3-SV40-ITR [SEQ ID NO: 19]. In another embodiment, the vector genome contains: ITR-UbC-PI-aVEGFv1-SV40-ITR [SEQ ID NO: 24]. In a further embodiment, the vector genome contains AAV2-ITR-CB7.CI.aVEGFv4.rBG-AAV2 ITR [SEQ ID NO: 35]. In a further embodiment, the vector genome contains AAV2-ITR-CB7.CI.aVEGFv5.rBG-AAV2 ITR [SEQ ID NO: 36]. In a further embodiment, the vector genome contains AAV2-ITR-CB7.CI.aVEGFv6.rBG-AAV2 ITR [SEQ ID NO: 37]. In a further embodiment, the vector genome contains AAV2-ITR-CB7.CI.aVEGFv7.rBG-AAV2 ITR [SEQ ID NO: 38]. In a further embodiment, the vector genome contains AAV2-ITR-CB7.CI.aVEGFv8.rBG-AAV2 ITR [SEQ ID NO: 39]. In a further embodiment, the vector genome contains AAV2-ITR-CB7.CI.aVEGFv9.rBG-AAV2 ITR [SEQ ID NO: 40]. In a further embodiment, the vector genome contains AAV2-ITR-CB7.CI.aVEGFv10.rBG-AAV2 ITR [SEQ ID NO: 41]. In a further embodiment, the vector genome contains AAV2-ITR-CB7.CI.aVEGFv11.rBG-AAV2 ITR [SEQ ID NO: 42]. In a further embodiment, the vector genome contains AAV2-ITR-CB7.CI.aVEGFv12.rBG-AAV2 ITR [SEQ ID NO: 43]. In a further embodiment, the vector genome contains AAV2 ITR-CB7.CI.aVEGFv13.rBG-AAV2 ITR [see, SEQ ID NO: 44]. In a further embodiment, the vector genome contains AAV2 ITR-CMV.PI.aVEGFv7.eCMVIres.aVEGF.SV40-AAV2 ITR [SEQ ID NO: 45]. In another embodiment, the vector genome contains AAV2 ITR.CMV.PI.aVEGF.FMDV1IRES.SV40-ITR [SEQ ID NO: 46]. In still a further embodiment, the vector genome contains AAV2 ITR.CMV.PI.aVEGF.cMycIRES.Fab.SV40-ITR [SEQ ID NO: 47].

For use in producing an AAV viral vector (e.g., a recombinant (r) AAV), the expression cassettes can be carried on any suitable vector, e.g., a plasmid, which is delivered to a packaging host cell. The plasmids useful in this invention may be engineered such that they are suitable for replication and packaging in prokaryotic cells, mammalian cells, or both. Suitable transfection techniques and packaging host cells are known and/or can be readily designed by one of skill in the art.

Methods for generating and isolating AAVs suitable for use as vectors are known in the art. See generally, e.g., Grieger & Samulski, 2005, "Adeno-associated virus as a gene therapy vector: Vector development, production and clinical applications," *Adv. Biochem. Engin/Biotechnol.* 99: 119-145; Buning et al., 2008, "Recent developments in adeno-associated virus vector technology," *J. Gene Med.* 10:717-733; and the references cited below, each of which is incorporated herein by reference in its entirety. For packaging a transgene into virions, the ITRs are the only AAV components required in cis in the same construct as the nucleic acid molecule containing the expression cassettes. The cap and rep genes can be supplied in trans.

In one embodiment, the expression cassettes described herein are engineered into a genetic element (e.g., a shuttle plasmid) which transfers the immunoglobulin construct sequences carried thereon into a packaging host cell for production of a viral vector. In one embodiment, the selected genetic element may be delivered to an AAV packaging cell by any suitable method, including transfection, electroporation, liposome delivery, membrane fusion techniques, high velocity DNA-coated pellets, viral infection and protoplast fusion. Stable AAV packaging cells can also be made. Alternatively, the expression cassettes may be used to generate a viral vector other than AAV, or for production of mixtures of antibodies in vitro. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, N.Y. (2012).

As used herein, "AAV8 capsid" refers to the AAV8 capsid having the amino acid sequence of GenBank accession: YP_077180 (SEQ ID NO: 48) encoded by nucleic acid sequence of NCBI Reference Sequence: NC_006261.1 (SEQ ID NO: 49), both of which are incorporated by reference herein. Some variation from this encoded sequence is encompassed by the present invention, which may include sequences having about 99% identity to the referenced amino acid sequence in GenBank accession: YP_077180; U.S. Pat. Nos. 7,282,199, 7,790,449; 8,319,480; 8,962,330; 8,962,332, (i.e., less than about 1% variation from the referenced sequence). In another embodiment, the AAV8 capsid may have the VP1 sequence of the AAV8 variant described in WO2014/124282, which is incorporated by reference herein. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003), US 2013/0045186A1, and WO 2014/124282. In certain embodiments, an AAV8 variant which shows tropism for the desired target cell, e.g., photoreceptors, RPE or other ocular cells is selected. For example, an AAV8 capsid may have Y447F, Y733F and T494V mutations (also called "AAV8 (C&G+T494V)" and "rep2-cap8(Y447F+733F+T494V)"), as described by Kay et al, Targeting Photoreceptors via Intravitreal Delivery Using Novel, Capsid-Mutated AAV Vectors, PLoS One. 2013; 8(4): e62097. Published online 2013 Apr. 26, which is incorporated herein by reference. See, e.g., Mowat et al, Tyrosine capsid-mutant AAV vectors for gene delivery to the canine retina from a subretinal or intravitreal approach, Gene Therapy 21, 96-105 (January 2014), which is incorporated herein by reference. In another embodiment, the AAV capsid is an AAV8 capsid, which preferentially targets bipolar cells. See, WO 2014/024282, which is incorporated herein by reference.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

The terms “percent (%) identity”, “sequence identity”, “percent sequence identity”, or “percent identical” in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to “identity”, “homology”, or “similarity” between two different sequences, “identity”, “homology” or “similarity” is determined in reference to “aligned” sequences. “Aligned” sequences or “alignments” refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the “Clustal Omega”, “Clustal X”, “MAP”, “PIMA”, “MSA”, “BLOCKMAKER”, “MEME”, and “Match-Box” programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., “A comprehensive comparison of multiple sequence alignments”, 27(13):2682-2690 (1999). As used herein, the term “operably linked” refers to both expression control sequences that are contiguous with the gene of interest and expression control sequences that act in trans or at a distance to control the gene of interest.

A “replication-defective virus” or “viral vector” refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be “gutless”—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

The abbreviation “sc” refers to self-complementary. “Self-complementary AAV” refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, “Self-complementary recombinant adeno-associated virus (scAAV) vectors promote efficient transduction independently of DNA synthesis”, Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

The term “heterologous” when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

The term “exogenous” when used with reference to a protein or nucleic acid sequences indicates two or more sequences or subsequences which are from different sources, e.g., an AAV and a human protein.

It is to be noted that the term “a” or “an” refers to one or more. As such, the terms “a” (or “an”), “one or more,” and “at least one” are used interchangeably herein.

The words “comprise”, “comprises”, and “comprising” are to be interpreted inclusively rather than exclusively. The words “consist”, “consisting”, and its variants, are to be interpreted exclusively, rather than inclusively. While various embodiments in the specification are presented using “comprising” language, under other circumstances, a related embodiment is also intended to be interpreted and described using “consisting of” or “consisting essentially of” language.

As used herein, the term “about” means a variability of 10% from the reference given, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

rAAV8.aVEGF Formulation

The rAAV8.aVEGF formulation is a suspension containing an effective amount of rAAV8.aVEGF vector suspended in an aqueous solution. In certain embodiments, the suspension contains buffered saline, optionally with a surfactant and/or other excipients. A buffered saline typically contains a physiologically compatible salt or mixture of salts, e.g. phosphate buffered saline, sodium chloride, or a mixture thereof.

In one embodiment, the formulation may contain, e.g., about $1\times10^{8}$ GC/eye to about $7\times10^{12}$ GC/eye, or about $5\times10^{9}$ GC/eye to about $1\times10^{11}$ GC/eye, or about $10^{10}$ GC/eye, or about as measured by oqPCR or digital droplet PCR (ddPCR) as described in, e.g., M. Lock et al, Hu Gene Therapy Methods, Hum Gene Ther Methods. 2014 April; 25(2):115-25. doi: 10.1089/hgtb.2013.131. Epub 2014 Feb. 14, which is incorporated herein by reference.

For example, a suspension as provided herein may contain both NaCl and KCl. The pH may be in the range of 6.5 to 8, or 7.2 to 7.6. pH may be assessed using any suitable method, e.g., USP <791> [US Pharmacopeial Convention, reference standards]. A suitable surfactant, or combination of surfactants, may be selected from among a Poloxamers, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension. In one embodiment, the rAAV8.aVEGF formulation is a suspension containing at least $1\times10^{11}$ genome copies (GC)/mL, or greater, e.g., about $1\times10^{13}$ GC/mL as measured by oqPCR or digital droplet PCR (ddPCR) as described in, e.g., M. Lock et al, Hu Gene Therapy Methods, Hum Gene Ther Methods. 2014 April; 25(2):115-25. doi: 10.1089/hgtb.2013.131. Epub 2014 Feb. 14, which is incorporated herein by reference. In one embodiment, the vector is suspended in an aqueous solution containing 180 mM sodium chloride, 10 mM sodium phosphate, 0.001% Poloxamer 188, pH 7.3. The formulation is suitable for use in human subjects and is administered subretinally.

In order to ensure that empty capsids are removed from the dose of AAV8.aVEGF that is administered to patients, empty capsids are separated from vector particles during the vector purification process. In one embodiment, the vector particles containing packaged genomes are purified from empty capsids using the process described in International Patent Application No. PCT/US16/65976, filed Dec. 9, 2016 and its priority documents, U.S. Patent Appln No. 62/322,098, filed Apr. 13, 2016 and 62/266,341, filed on Dec. 11, 2015, and entitled "Scalable Purification Method for AAV8", which is incorporated by reference herein. Briefly, a two-step purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates.

In one embodiment, the pH used is from 10 to 10.4 (about 10.2) and the rAAV particles are at least about 50% to about 90% purified from AAV8 intermediates, or a pH of 10.2 and about 90% to about 99% purified from AAV8 intermediates. In one embodiment, this is determined by genome copies. A stock or preparation of rAAV8 particles (packaged genomes) is "substantially free" of AAV empty capsids (and other intermediates) when the rAAV8 particles in the stock are at least about 75% to about 100%, at least about 80%, at least about 85%, at least about 90%, at least about 95%, or at least 99% of the rAAV8 in the stock and "empty capsids" are less than about 1%, less than about 5%, less than about 10%, less than about 15% of the rAAV8 in the stock or preparation. In one embodiment, the formulation is be characterized by an rAAV stock having a ratio of "empty" to "full" of 1 or less, preferably less than 0.75, more preferably, 0.5, preferably less than 0.3.

In a further embodiment, the average yield of rAAV particles is at least about 70%. This may be calculated by determining titer (genome copies) in the mixture loaded onto the column and the amount presence in the final elutions. Further, these may be determined based on q-PCR analysis and/or SDS-PAGE techniques such as those described herein or those which have been described in the art.

For example, to calculate empty and full particle content, VP3 band volumes for a selected sample (e.g., an iodixanol gradient-purified preparation where # of GC=# of particles) are plotted against GC particles loaded. The resulting linear equation (y=mx+c) is used to calculate the number of particles in the band volumes of the test article peaks. The number of particles (pt) per 20 μL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., *Gene Therapy* (1999) 6:1322-4330; Sommer et al., *Molec. Ther*. (2003) 7:122428. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., *J. Viral*. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent DTT), and capsid proteins were resolved on pre-cast gradient polyacylamide gels (e.g., Novex). Silver staining may be performed using SilverXpress (Invitrogen, CA) according to the manufacturer's instructions. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes), Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

Manufacturing

The rAAV8.aVEGF vector can be manufactured as shown in the flow diagram shown in FIG. 9. Briefly, cells (e.g. HEK 293 cells) are propagated in a suitable cell culture system and transfected for vector generation. The rAAV8.aVEGF vector can then be harvested, concentrated and purified to prepare bulk vector which is then filled and finished in a downstream process. Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest.

The crude cell harvest may thereafter be subject method steps such as concentration of the vector harvest, diafiltration of the vector harvest, microfluidization of the vector harvest, nuclease digestion of the vector harvest, filtration of microfluidized intermediate, purification by chromatography, purification by ultracentrifugation, buffer exchange by tangential flow filtration, and formulation and filtration to prepare bulk vector.

In a specific embodiment, the methods used for manufacturing the gene therapy vectors are described in the examples herein.

Patient Population

Patients who are candidates for treatment include those with neovascular age-related macular degeneration, macular edema following retinal vein occlusion (RVO), diabetic macular edema (DME), diabetic retinopathy (non-proliferative diabetic retinopathy (NPDR), proliferative diabetic retinopathy (PDR) in patients with DME, diabetic retinopathy in patients with diabetic macular edema. These patients are particularly well suited for subretinal treatment with an AAV8.aVEGF composition as described herein.

Patients who are candidates for intraocular, including, e.g., subretinal and/or intravitreal administration, with an AAV8.aVEGF as described herein include those with macular degeneration, neovascular/wet/exudative age-related macular degeneration, macular edema following retinal vein occlusion (RVO) (including central retinal vein occlusion (CRVO) and branch retinal vein occlusion (BRVO)) central/hemi/branch retinal vein occlusion, retinal artery occlusion; retinal neovascularization; diabetic macular edema (DME), diabetic retinopathy (non-proliferative diabetic retinopathy (NPDR), proliferative diabetic retinopathy (PDR)) in patients with DME, diabetic retinopathy without macular edema (including pre-treatment of vitrectomy for proliferative diabetic retinopathy); active photocoagulated diabetic retinopathy; choroidal neovascularization, rare causes of choroidal neovascularization (angioid streaks, choroiditis [including choroiditis secondary to ocular histoplasmosis], idiopathic degenerative myopia, retinal dystrophies, rubeosis iridis, and trauma), idiopathic choroidal neovascularization, corneal neovascularization; retinopathy of prematurity, optic nerve head perfusion, retrolental fibroplasia; retinal degeneration; vitreomacular traction syndrome; retinal detachment, diabetic traction retinal detachment, submacular vascularized pigment epithelial detachments, Vogt Koyanagi Harada Disease, pigment epithelial detachment, pigment epithelium rip; vitreoretinopathy proliferative; vitreoretinal surgery in diabetic tractional retinal detachment, polypoidal choroidal vasculopathy; punctate inner choroidopathy (PIC); multifocal choroiditis; central serous chorioretinopathy (CSC), serpiginous choroiditis, vitreous hemorrhage, pars plana vitrectomy for vitreous hemorrhage, diabetic premacular hemorrhage with active fibrovascular proliferation; Choroidal hemorrhage amblyopia; myopia, myopic choroidal neovascularization, choroidal subfoveal/juxtafoveal neovascularization in high myopia; choroidal melanoma; ocular histoplasmosis syndrome, tecalcitrant inflammatory ocular neovascularization (neovascularization, tuberculosis, multifocal serpiginous choroiditis, harada toxoplasmosis); Pseudoxanthoma elasticum; hereditary eye diseases; corneal endothelial cell loss; Vogt Koyanagi Harada Disease, non-arteritic anterior ischemic optic neuropathy; cystoid macular edema; refractory cystoid macular oedema; idiopathic macular telangiectasia; Coat's disease (Coates' disease, also known as exudative retinitis or retinal telangiectasis); glaucoma, neovascular glaucoma, steroid-induced glaucoma, ocular hypertension, Glaucoma surgery; control of wound healing; uveal melanoma; uveitis; radiation maculopathy, pattern dystrophy, radiation retinopathy, radiation necrosis; Hippel-Lindau Disease; Von Hippel-Lindau Syndrome; endophthalmitis; neuromyelitis optica spectrum disorder; pterygium, primary pterygium (including as adjunctive therapy for primary pterygium surgery), recurrent pterygium; retinal drusen; eye neoplasms; intraocular melanoma; cataract; corneal graft failure; trabeculectomy; lipid keratopathy, penetrating keratoplasty, herpetic keratopathy, rosacea; retinal angioma; retinovascular disease; vision disorders, vitreoretinopathy proliferative; iris neovascularization (NV); corneal NV, including pannus, pars planitis sarcoid or Eale's disease.

Patients who are candidates for treatment with an AAV8.aVEGF (the anti-VEGF transgene product) in a regimen which involves a combination with, but not limited to 24GyE proton, 16GyE, Xylocaine, Proparacaine Hydrochloride, Tetravisc, Acuvail, Zimura, Triamcinolone acetonide, Ranibizumab, or Ozurdex. Examples of suitable indications include those in the preceding paragraph. For example, a combination regimen involving an AAV8.aVEGF with one or more of the drugs listed above, may be used for treatment of exudative age-related macular degeneration, central retinal vein occlusion, idiopathic polypoidal choroidal vasculopathy, and/or diabetic macular edema.

The AAV8.aVEGF composition described herein are also useful in preventing vascularization in a number of cancers, neoplasms and other diseases associated with VEGF. Such compositions may be administered for any suitable route, including, e.g., intravenous, intralesional, direct delivery to a tumor or organ, among others. Such patients may include those with Acute Lymphoblastic Leukemia (ALL), Acute Myeloid Leukemia (AML), Adrenocortical Carcinoma, Adrenocortical Carcinoma, AIDS-Related Cancers, Kaposi Sarcoma, AIDS-Related Lymphoma, Primary CNS Lymphoma, Anal Cancer, Appendix Cancer, Astrocytomas, Atypical Teratoid/Rhabdoid Tumor, Basal Cell Carcinoma of the Skin, Bladder Cancer, Bone Cancer (includes Ewing Sarcoma and Osteosarcoma and Malignant Fibrous Histiocytoma), Brain Tumors, Breast Cancer, Bronchial Tumors, Burkitt Lymphoma, Non-Hodgkin Lymphoma, Carcinoid Tumors, Carcinoma of Unknown Primary, Cardiac Tumors, Central Nervous System Atypical Teratoid/Rhabdoid Tumor, Embryonal Tumors, Germ Cell Tumor, Primary CNS Lymphoma, Cervical Cancer, Unusual Cancers of Childhood, Cholangiocarcinoma, Bile Duct Cancer, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma, Ductal Carcinoma In Situ (DCIS), Central Nervous System Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Malignant, Osteosarcoma, Gallbladder Cancer, Gastric Cancer, Childhood Gastric Cancer, Gastrointestinal Stromal Tumors (GIST), Germ Cell Tumors, Childhood Central Nervous System Germ Cell Tumors, Childhood Extracranial Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular Cancer, Histiocytosis, Langerhans Cell, Hodgkin Lymphoma, Hypopharyngeal Cancer, Intraocular Melanoma, Islet Cell Tumors, Pancreatic Neuroendocrine Tumors, Kaposi Sarcoma, Kidney Cancer, Langerhans Cell Histiocytosis, Laryngeal Cancer, Childhood Laryngeal Cancer and Papillomatosis, Leukemia, Lip and Oral Cavity Cancer, Liver Cancer, Lung Cancer (Non-Small Cell and Small Cell), Childhood Lung Cancer, Lymphoma, Male Breast Cancer, Malignant Fibrous Histiocytoma of Bone and Osteosarcoma, Melanoma, Intraocular Melanoma, Merkel Cell Carcinoma, Malignant Mesothelioma, Metastatic Cancer, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasms, Mycosis Fungoides, Myelodysplastic Syndromes, Myelodysplastic, Myeloproliferative Neoplasms, Myelogenous Leukemia, Chronic (CML), Acute Myeloid Leukemia (AML), Chronic Myeloproliferative Neoplasms, Nasal Cavity and Paranasal Sinus Cancer; Nasopharyngeal Cancer, Neuroblastoma, Non-Hodgkin Lymphoma, Oral Cancer, Lip and Oral Cavity Cancer and Oropharyngeal Cancer, Osteosarcoma and Malignant Fibrous Histiocytoma of Bone, Ovarian Cancer, Pancreatic Cancer, Pancreatic Neuroendocrine Tumors, Papillomatosis, Paraganglioma, Paranasal Sinus and Nasal Cavity Cancer, Parathyroid Cancer, Penile Cancer, Pharyngeal Cancer, Pheochromocytoma, Plasma Cell Neoplasm/Multiple Myeloma, Pleuropulmonary Blastoma; Pregnancy and Breast Cancer, Primary Central Nervous System (CNS) Lymphoma, Primary Peritoneal Cancer, Prostate Cancer, Rectal Cancer, Recurrent Cancer, Renal Cell Cancer, Retinoblastoma, Salivary Gland Cancer, Sarcoma, Childhood Rhabdomyosarcoma, Childhood Vascular Tumors, Ewing Sarcoma, Osteosarcoma, Uterine Sarcoma, Sézary Syndrome, Skin Cancer, Small Cell Lung Cancer, Small Intestine Cancer, Soft Tissue Sarcoma, Squamous Cell Carcinoma of the Skin, Squamous Neck Cancer with Occult Primary, Metastatic, Stomach Cancer, Cutaneous T-Cell Lymphoma, Testicular Cancer, Throat Cancer, Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter (Kidney (Renal Cell) Cancer), Carcinoma of Unknown Primary, Childhood Cancer of Unknown Primary, Unusual Cancers of Childhood, Ureter and Renal Pelvis, Urethral Cancer; Endometrial Uterine Cancer, Uterine Sarcoma, Uterine Leiomyosarcomas, Vaginal Cancer, Vascular Tumors, Vulvar Cancer, Wilms Tumor and Other Childhood Kidney Tumors, abdominal neoplasms (adenocarcinoma; hepatocellular, papillary serous mullerian, Lapatinib, colorectal, ovarian, fallopian tube, peritoneal ncer/neoplasms/carcinoma/tumors); lymphoproliferative disorder; small intestine cancer; acoustic neuroma (e.g. vestibular Schwannoma, Neurofibromatosis Type 2); acute myeloid leukemia, acute respiratory distress syndrome (ARDS), head and neck cancer; squamous cell carcinoma, multiple myeloma, non-hodgkin's lymphoma; B-cell lymphoma, sarcoma, neuroblastoma, advanced cancer, alignant neoplasms of female genital organs; metastatic or unresectable solid tumor, anaplastic astrocytoma, Colon Cancer, Metastatic Melanoma, Malignant Ascites, Renal Cell Carcinoma, Glioblastoma, Gliosarcoma, Colorectal Liver Metastases, Advanced Malignancy, Myeloma, Gestational Trophoblastic Neoplasia, Choriocarcinoma, Placental Site Trophoblastic Tumor, Epithelioid Trophoblastic Tumor, Biliary Tract Cancer, Malignant Glioma, Cervical Cancer, Uterine Cancer, Mesothelioma. Candidates thereof are treated with said composition alone or in combination with anti-cancer treatments, for example but not limited to paclitaxel, carboplatin, oxaliplatin, radiation, capecitabine, irinotecan, fluorouracil, doxorubin hydrochloride liposome, erlotinib hydrochloride, irinotecan hydrochloride, Irinotecan hydrochloride hydrate (CPT-11), gemcitabine hydrochloride, Pazopanib Hydrochloride, topotecan hydrochloride, Trifluridine/tipiracil hydrochloride, Pegylated Liposomal Doxorubicin Hydrochloride, enzastaurin hydrochloride, mitoxantrone hydrochloride; epirubicin hydrochloride, docetaxel, gemcitabine, erlotinib, cisplatin, chemotherapy, cetuximab, FOLFIRI-Cetuximab, 5-Fluorouracil (5-FU), LV5FU2, cyclophosphamide, temozolomide, pemetrexed, levofolinate calcium (l-LV), Leucovorin Calcium, FOLFOX, FOLFOX6, mFOLFOX, FOLFOXIRI, FOLFIRI, doxorubicin, Liposomal Doxorubicin, doxorubicin HCL liposome, Sorafenib Tosylate, sorafenib, triamcinolone, Triamcinolone acetonide, trastuzumab, everolimus, sunitinib, dexamethasone, conventional surgery, xeloda, radiotherapy, temsirolimus, pazopanib, Leucovorin (LV), l-LV, anitumumab, epirubicin, verteporfin, AMG 655, Amgen 386, AMG 479, AMG 706, AMG 951, AMG 102, Folinic Acid, levo-folinic acid, etoposide, BAY 43-9006, atezolizumab, Interferon Alfa-2b, Interferon alpha-2a, interferon alfa, Gamma-Interferon-1b, Photodynamic Therapy, vinorelbine tartrate, vinorelbine, topotecan, tarceva, pemetrexed disodium, estramustine phosphate sodium, Imetelstat sodium, XELOX, RAD001, pegfilgrastim, paclitaxel albumin-stabilized nanoparticle formulation, ipilimumab, Stereotactic Radiosurgery (SRS), Stereotactic Radiation, ozurdex, letrozole, AG-013736 (axitinib), filgrastim, crizotinib, cediranib maleate, cediranib, bortezomib, abraxane, vorinostat, vincristine, TRC105, rituximab, regorafenib, pembrolizumab, methotrexate, imatinib, Herceptin, tecentriq, oxaliplatin (OXA), lomustine, ixabepilone, CPT-11, CGC-11047, vinorelbine tartrat, tartrate, prednisone, nivolumab, fulvestrant, enzastaurin, doxil, AZD2014, AZD2281, AZD2171, AZD4547, AZD5363, AZD8931, Vitamin B12, Vitamin C, Vitamin D, Valproic acid, mitomycin C, Cediranib Maleate, lenalidomide, lapatinib, HAI Abraxane, HAI Irinotecan, GDC-0941, GDC-0449, GDC-0980, bicalutamide, xeliri, vandetanib, thalidomide, rapamycin, olaparib, NovoTTF100A, Navelbine, metmab, Imatinib Mesylate (Gleevec), ifosfamide, hydroxychloroquine, and GM-CSF.

Still other suitable conditions for treatment may include, e.g., Hemophilia, Synovitis, Hypertension, keloid, inflammation, Radiation Necrosis, and Neoplastic Meningitis. These and the conditions described above may be delivered by any suitable route, except where subretinal or another type of administration to the eye is specified.

In certain embodiments, patients receive a single dose of rAAV8.aVEGF administered subretinally. For example, this is particularly well suited for treatment of neovascular age-related macular degeneration, macular edema following retinal vein occlusion (RVO), diabetic macular edema (DME), diabetic retinophathy (non-proliferative diabetic retinopathy (NPDR), proliferative diabetic retinopathy (PDR) in patients with DME, diabetic retinopathy in patients with diabetic macular edema.

The dose of rAAV8.aVEGF administered to a patient is at least $1\times10^{9}$ GC/eye to $1\times10^{13}$ GC/eye, or at least $1\times10^{10}$ GC/eye to about $7.5\times10^{12}$ GC/eye (as measured by oqPCR or ddPCR). However, other doses may be selected. For example, therapeutically effective subretinal doses of the rAAV8.aVEGF for patients may range from about $6.6\times10^{9}$ GC/eye to about $6.6\times10^{11}$ GC/eye, most preferably, $6.6\times10^{10}$ GC/eye, in an injection volume ranging from about 0.1 mL to about 0.5 mL, preferably in 0.1 to 0.15 mL (100-150 μl). In still other embodiments, therapeutically effective concentrations may be about $1\times10^{5}$ concentration can be $1\times10^{5}$ GC/μL to $1\times10^{9}$ GC/μL, and the volume of injection for any GC concentration in that range can be from 10 μL to 300 μL.

In certain embodiments, patients may receive an rAAV8.aVEGF by subretinal administration by a retinal surgeon under local anesthesia. The procedure may involve standard 3 port pars plana vitrectomy with a core vitrectomy followed by subretinal delivery into the subretinal space by a subretinal cannula (36 to 41 gauge). In certain embodiments, 100 to 150 microliters of rAAV8.aVEGF will be delivered.

In some embodiments, rAAV8.aVEGF is administered in combination with one or more therapies for the treatment of wetAMD or another selected disorder. In some embodiments, rAAV.aVEGF is administered in combination with laser coagulation, photodynamic therapy with verteporfin, and intravitreal with anti-VEGF agent, including but not limited to pegaptanib, ranibizumab, aflibercept, or bevacizumab.

In certain embodiments, patients for rAAV8.aVEGF therapy may include those which have previously responded to conventional anti-VEGF antibody (Fab) treatment.

The goal of the gene therapy treatment of the invention is to slow or arrest the progression of retinal degeneration, and to slow or prevent loss of vision with minimal intervention/invasive procedures. In certain embodiments, the efficacy of the gene therapy treatment may be indicated by the elimination of or reduction in the number of rescue treatments using standard of care, for example, intravitreal injections with anti-VEGF agents, including but not limited to pegaptanib, ranibizumab, aflibercept, or bevacizumab.

In certain embodiments, efficacy by measured by one or more of the following: Vision change, visual acuity, including best corrected visual acuity measured by (BCVA) score, Snellen chard or Early Treatment Diabetic Retinopathy (ETDRS) visual acuity score, percentage of subjects losing or gaining measured by ETDRS, distance best corrected visual acuity, reading best corrected visual acuity, change in NEI Visual Functioning Questionnaire-25 (VFQ-25) score, questionnaire of vision-related quality of life, contrast sensitivity measured by Pelli-Robson charts; low-contrast visual acuity on Electronic Visual Acuity Tester; peripheral visual field as measured by Goldmann visual field, mean angle opening distance and trabecular-iris spur area measured by Heidelberg Slit-Lamp Optical Coherence Tomography, Preferential-Hyperacuity-Perimeter (PHP) testing of Age Related Macular Degeneration (AMD) by characterizing central and paracentral metamorphopsia, retinal sensitivity (mfERG, Nidek MP-1 microperimetry), Visual Analog Scale (VAS), Macular Mapping Test, electrophysiological changes, including electroretinogram (ERG), pattern electroretinography (PERG) and full field (or flash) electroretinography (ffERG), multifocal electroretinography (mfERG), mfERG central ring amplitude density; mean retinal sensitivity (dB) in three concentric rings (4°, 8° & 12°), visual evoked potential (VEP): ECG parameters included PR interval, QRS interval, and corrected QT interval using Fridericia's formula (QTcF). Anatomical changes, including regression of NVE (retinal neovascularization), CNVM (Choroidal Neovascular Membranes), changes measured using optical coherence topography (OCT), including macular volume, macular thickness, central macular subfield thickness, retinal volume (inner retinal volume and outer retinal volume), retinal thickness, central retinal thickness, central subfield retinal thickness (CSRT), subfoveal retinal thickness (SRT), foveal thickness, maximum diameter of foveal avascular zone, integrity of retinal layers, external limiting membrane (ELM) integrity, ellipsoidal line/band integrity, lens status, lens opacity, neovascular membrane regression percentage measured by Optical coherence tomography angiography (OCTA), degree of integrity of the photoreceptors in the inner/outer segments layer in the 1 mm centered in the fovea. Optionally, during trial, AMD lesion size and leakage may be by fluorescein angiography, change in total lesion size and CNV (choroidal neovascularization) size by fluorescein angiography (FA) and Indocyanine green angiography (ICG), active CNV leakage which may include subretinal fluid or hemorrhage, area of leakage, area of macular leakage, change in percentage of lesion hemorrhage, change in drusen size, amount of fluid, intra-retinal cystoid changes (IRCs) volume, vessel density, presence of intra/sub-retinal fluid, sub-retinal fluid (SRF) height and diameter, intraretinal fluid volume, anterior chamber reaction, chorioretinal perfusion (ICG), development of geographic atrophy (GA) as detected by fundus photography (FP) and/or fundus autofluorescence (AF), presence and extension of capillary occlusion, peripheral retinal ischemia, macular sensitivity using microperimetry, neovascularization of the iris, neovascularization of the angle, diabetic retinopathy.

In certain embodiments, subretinal and/or intra-retinal injection of the AAV8.aVEGF results in plasma and serum levels free of the aVEGF.

In certain embodiments, efficacy may be monitored by measuring BCVA (Best-Corrected Visual Acuity), intraocular pressure, slit lamp biomicroscopy, indirect ophthalmoscopy, SD-OCT (SD-Optical Coherence Tomography). Signs of vision loss, infection, inflammation and other safety events, including retinal detachment may also be monitored.

SD-OCT is a useful non-invasive, in vivo cross-sectional retinal microscopy technique. Suitable equipment is commercially available. See, e.g., Spectralis OCT, Heidelberg Engineering, Carlsbad, Calif. In brief, this technique may be performed by dilating pupils. En face retinal imaging can be performed with near infrared (NIR) reflectance (REF) and/or with NIR fundus autofluorescence (FAF) using the scanning laser ophthalmoscope of this imaging system. Spectral domain optical coherence tomography scanning can be performed with 9 mm long horizontal and vertical cross-sections through the fovea and overlapping 30×25 mm raster scans extending into the near midperiphery. The parameters may be modified as needed, or other suitable parameters determined comparable.

Retinal function can be evaluated by a full-field electroretinogram (ERG). An ERG is a mass electrical potential generated by the retina in response to light stimulus. Usually, it is recorded by an electrode in contact with the corneal surface. Electroretinograms can be conducted in accordance with the recommendations set by the International Society for Clinical Electrophysiology of Vision (ISCEV; McCulloch, Doc Ophthalmol. 2015 February; 130(1):1-12. 2015). In summary, an electroretinogram (ERG) is usually generated when all retinal cells actively respond to a flash stimulation (a dark-adapted animal, moderate to intense flash). The 2 components are the following: •a-wave: cornea-negative signal, first after the flash. Origin: photoreceptor photocurrent, the most direct signature of photoreceptor function. •b-wave: cornea-positive signal following the a-wave generated mostly by on-bipolar cells (second order neurons downstream from photoreceptors). In the examples described below, the following International Society for Clinical Electrophysiology of Vision (ISCEV) standard and additional protocols were used. However, these parameters may be adjusted as needed or required. Dark-adapted rod ERG: Stimulus intensity: 0.01 to 0.02 cd s $m^{-2}$. Response: b-wave only, no a-wave. Source: rod "on" bipolar cells (second order neurons driven by input from rods). Meaning: a measure of rod function. Dark-adapted standard flash ERG: Stimulus intensity: 3 cd s $m^{-2}$. Response: combined rod-cone a- and b-waves; 60% to 70% of the signal being generated by the rod-driven pathway. Source: photoreceptors, both rods and cones (a-wave); higher order neurons driven by both rods and cones. Meaning: a measure of mostly rod function; less sensitive to the state of dark adaptation and less variable than the "dim flash" response. Dark-adapted bright flash ERG: Stimulus intensity: 10 cd s $m^{-2}$. Response and meaning: same as for the "standard flash" response, but bright flash response is larger in magnitude and may be less variable. Light-adapted standard flash cone ERG: Stimulus intensity: 3 cd s $m^{-2}$, delivered in presence of 30 cd $m^{-2}$ background light after 5 minutes of light adaptation. Response: a- and b-waves generated by cone-driven pathways. Meaning: in presence of background light which completely desensitizes rods the ERG is produced exclusively by cones and cone-driven secondary retinal neurons and is a measure of the cone function. Light-adapted bright flash cone ERG (in addition to the ISCEV standard): Stimulus intensity: 10 cd s $m^{-2}$, delivered in presence of 30 cd $m^{-2}$ background light after 5 minutes of light adaptation. Response and meaning: cone-driven ERG as in case of the "Standard cone ERG", but of greater magnitude and potentially less variable. ERG measures (a-wave amplitude, a-wave implicit time, b-wave amplitude, b-wave implicit time) were summarized using mean and standard deviation (SD) for treated eyes and control eye.

Another measure of efficacy may include a lack of thickening of the retina.

As illustrated in the examples below, administration of $1\times10^{10}$ GC/eye of an AAV8.aVEFG vector causes no impairment to retinal function. This dose is not a limitation on the therapeutically effective amounts which can be administered.

Measuring Clinical Objectives

Safety of the gene therapy vector after administration can be assessed by the number of adverse events, changes noted on physical examination, and/or clinical laboratory parameters assessed at multiple time points up to about 36 months post vector administration. Although physiological effect may be observed earlier, e.g., in about 1 day to one week, in one embodiment, steady state levels expression levels are reached by about 12 weeks.

Improvement/efficacy resulting from rAAV.aVEGF administration can be assessed as a defined mean change in baseline in visual acuity at about 12 weeks, 12 months, 24 months, 36 months, or at other desired time points. Other improvements/efficacy can be assessed as mean change from baseline in central retinal thickness as measured by spectral domain optical coherence tomography (SD-OCT) at 12, 24 and 36 months. In some embodiments, treatment with rAAV.aVEGF results in a 5%, 10%, 15%, 20%, 30%, 40%, 50% or more increase in visual acuity from baseline. In some embodiments, treatment with rAAV.aVEGF results in a decrease, e.g., about 5%, about 10%, about 15%, about 20%, about 30%, about 40%, about 50% or more decrease in central retinal thickness. In other embodiments, the central retinal thickness is stable, i.e., no increase in central retinal thickness. In certain embodiments, a measure of efficacy includes stabilizing retinal thickness, and/or stabilizing/decreasing) exudate and/or drusen.

In one embodiment, expression may be observed as early as about 8 hours to about 24 hours post-dosing. One or more of the desired clinical effects described above may be observed within several days to several weeks post-dosing.

The invention is illustrated by the examples below which demonstrate that subretinal administration of an rAAV8.aVEGF vector results in gene transfer throughout the retina, and expression of anti-VEGF Fab throughout the retina and in the vitreous and anterior chamber fluids. This result is surprising in view of prior art gene therapy studies that demonstrated that gene transfer spreads laterally outside of the original injection bleb but remains confined to those expanded boundaries and did not achieve gene transfer and transgene expression outside this expanded area of injection (the "bleb" formed in the retina at the injection site); and offers an advantage over standard of care treatment for nAMD in that a single administration of the rAAV8.aVEGF vector should result in (i) continuous delivery of the effective amounts of the VEGF inhibitor throughout the retina which may in turn improve performance as compared to repeated IVT administrations of high dose boluses of the VEGF inhibitor that dissipate over time; and (ii) avoidance of repeated ocular injections which pose additional risks and inconvenience to patients. Each aspect may improve therapeutic outcome.

EXAMPLES

The following abbreviations are used in the specification: AAV refers to Adeno-Associated Virus. ACF refers to Anterior Chamber Fluid. Ad5 refers to Adenovirus type 5. AE refers to Adverse Event. AMD refers to Age-Related Macular Degeneration. BCA refers to Bicinchoninic Acid. BCVA refers to Best-Corrected Visual Acuity. BH refers to Bulk Harvest. BI refers to Bulk Drug Substance Intermediate. BP refers to Base pairs. CB refers to Chicken Beta Actin Promoter. CB7 refers to a hybrid CMV Enhancer (C4) and Chicken β-Actin Promoter. CBC refers to Complete Blood Count. CI refers to chicken β-Actin Intron. CMC refers to Chemistry, Manufacturing and Control. CMO refers to Contract Manufacturing Organization. CMV refers to Cytomegalovirus. CNV refers to Choroidal Neovascularization. CS-10 refers to Corning 10-layer CellSTACKs® plates. ddPCR refers to Droplet Digital Polymerase Chain Reaction. DLS refers to Dynamic Light Scattering. DMEM refers to Dulbecco's Modified Eagle Medium. DNA refers to deoxyribonucleic Acid. DP refers to Drug Product. ELISA refers to Enzyme-Linked Immunosorbent Assay. ERG refers to electroretinogram. ELISPOT refers to Enzyme Linked Immunospot. Fab refers to Antigen-Binding Fragment. FBS refers to Fetal Bovine Serum. GC refers to Genome Copies. g refers to gram. GLP refers to Good Laboratory Practices. GMP refers to Good Manufacturing Practices. HEK293 refers to Human Embryonic Kidney Cells. HCP refers to Host Cell Protein. HS-36 refers to Corning 36-layer HYPERStacks®. ICH refers to International Conference on Harmonization. IND refers to Investigational New Drug. IP refers to In-Process. ITR refers to Inverted Terminal Repeat. IU refers to Infectious Unit. IV refers to Intravenous. IVT refers to Intravitreal. KDa refers to KiloDalton. Kg refers to Kilogram. LOQ refers to Limit of Quantification. Lucentis® is a brand name Ranibizumab. MCB refers to Master Cell Bank. MED refers to Minimally Effective Dose. μl refers to microliter. mL refers to milliliter. Mm refers to millimeter. mRNA refers to Messenger RNA. MS refers to Mass Spectrometry. Ng refers to Nanogram. NHP refers to Non-Human Primate. OCT refers to Optical Coherence Tomography. oqPCR refers to Optimized Quantitative Polymerase Chain Reaction. PCR refers to Polymerase Chain Reaction. PD refers to Pharmacodynamics popPK refers to Population Pharmacokinetics. PEI refers to Polyethylenimine PK refers to Pharmacokinetics. POC refers to Proof-Of-Concept. PRN refers to pro re nata (as needed). QA refers to Quality Assurance. qPCR refers to Quantitative Polymerase Chain Reaction. rAAV refers to Recombinant Adeno-Associated Virus. RBG refers to Rabbit Beta-Globin. RPE refers to Retinal Pigment Epithelium. S-36 refers to HYPERstack®36-layer. SEND refers to Standards for Exchange of Nonclinical Data. SOC refers to Standard of Care. SOP refers to Standard Operating Procedure. TCID50 refers to Tissue Culture Infectious Dose 50%. TFF refers to Tangential Flow Filtration. μL refers to Microliter. VA refers to Visual Acuity. VEGF refers to Vascular Endothelial Growth Factor. WAMD refers to Wet Age-Related Macular Degeneration. YAG refers to Yttrium-aluminum-garnet.

Example 1

Treating Human Subjects

This Example relates to a gene therapy treatment for patients with neovascular (wet) age-related macular degeneration (nAMD). In this example, the gene therapy vector, rAAV8.aVEGF, a replication deficient adeno-associated viral vector 8 (AAV8) carrying a coding sequence for a soluble anti-VEGF Fab protein is administered to patients with nAMD. The goal of the gene therapy treatment is to slow or arrest the progression of retinal degeneration and to slow or prevent loss of vision with minimal intervention/invasive procedures.

A. Gene Therapy Vector

Figure 1:
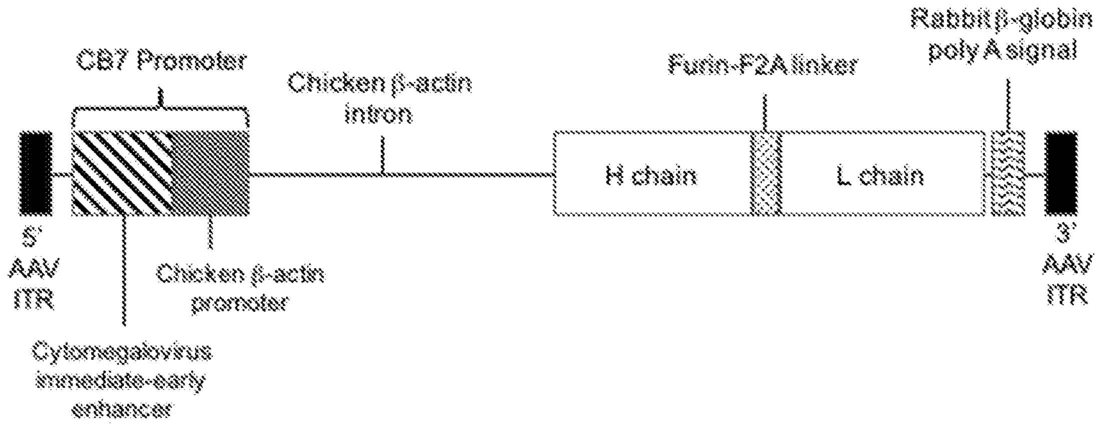
FIG. 1 provides a schematic representation of an AAV8 vector genome containing a gene cassette flanked by the AAV2 inverted terminal repeat (ITRs) and expressing human anti-vascular endothelial growth factor (anti-VEGF) antigen binding antibody fragment (Fab). Control elements include the CB7 promoter consisting of the chicken β-actin promoter and CMV enhancer, chicken β-actin and a rabbit β-globin poly A signal. The nucleic acid sequences coding for the heavy and light chains of anti-VEGF Fab are separated by a self-cleaving furin (F)/F2A linker. A furin recognition site that consists of arginine-lysine-arginine-arginine amino acid sequence was used. In addition, the light and heavy chain each contain a heterologous leader peptide which directs nascent peptide into appropriate cellular compartment where leader peptide is processed away from the mature protein by the host cellular machinery. These and the other synthetic anti-VEGF constructs are termed herein, AAV.aVEGF.
Figure 2:
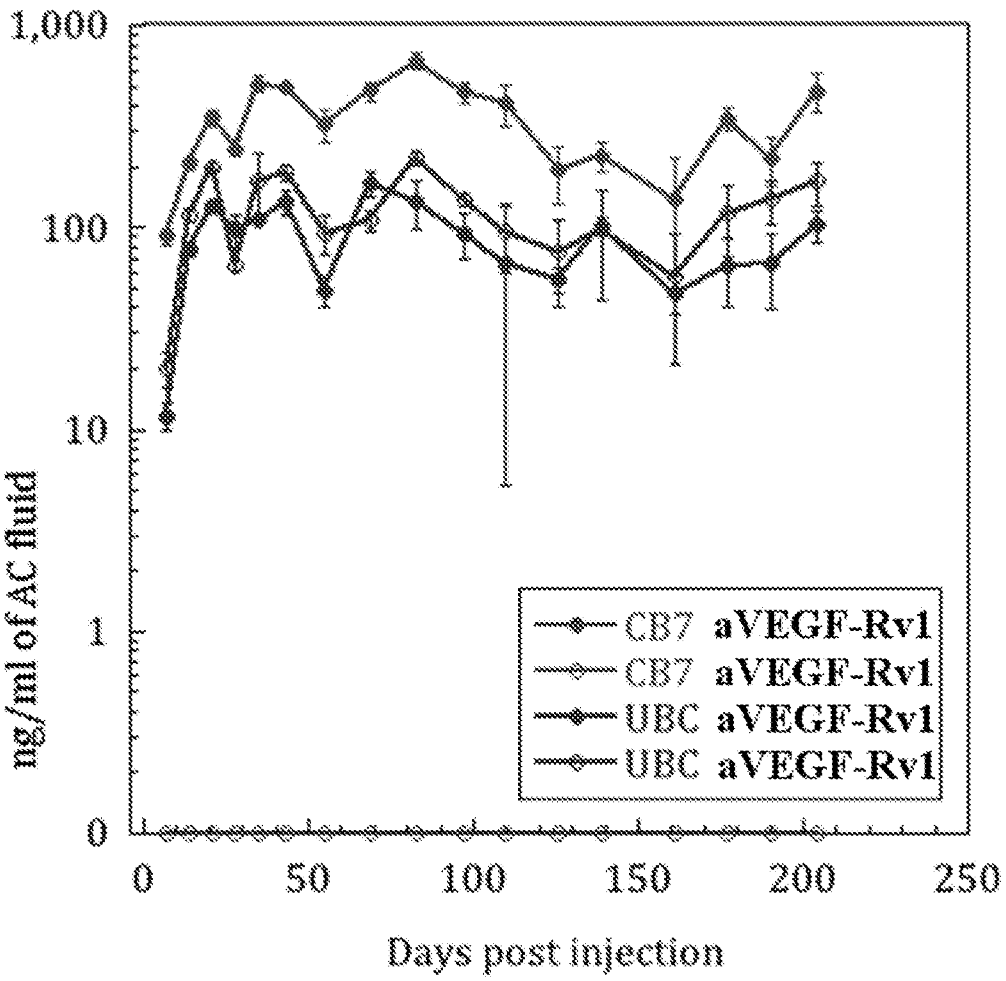
FIG. 2 provides the expression levels and kinetics of AAV8.CB7.aVEGFv1 or rAAV8.UbC.aVEGFv1 at various time points post-injection of the left eye (os) or right eye (od).AAV8.CB7.aVEGF-Rv1 is the top line with the closed circle. AAV8.UBC.aVEGF-Rv1 is the bottom line with the closed circle. The middle line with the open circles is AAV8.UBC.aVEGF-Rv1.
Figure 3A:
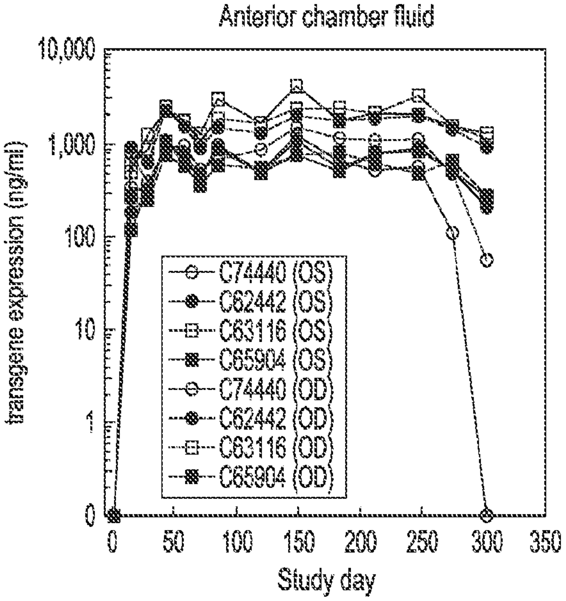
FIGS. 3A-3D show expression of anti-VEGF Fab in anterior chamber fluid and blood for animals in Groups 2 and 3 as described in Example 3 in which Cynomolgus monkeys were administered a single dose of $1.00\times10^{11}$ GC/eye of AAV2/8 vectors into each eye subretinally. Anterior chamber fluid and blood were collected at prespecified timepoints. Expression of the anti-VEGF Fab was determined using enzyme-linked immunosorbent assay.
Figure 3B:
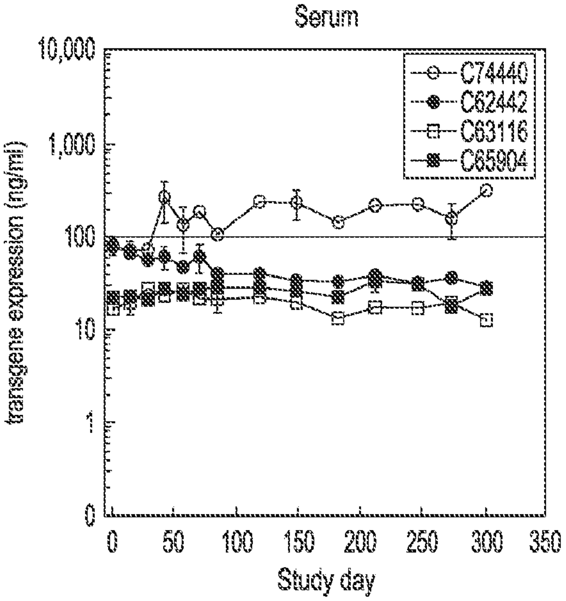
Figure 3C:
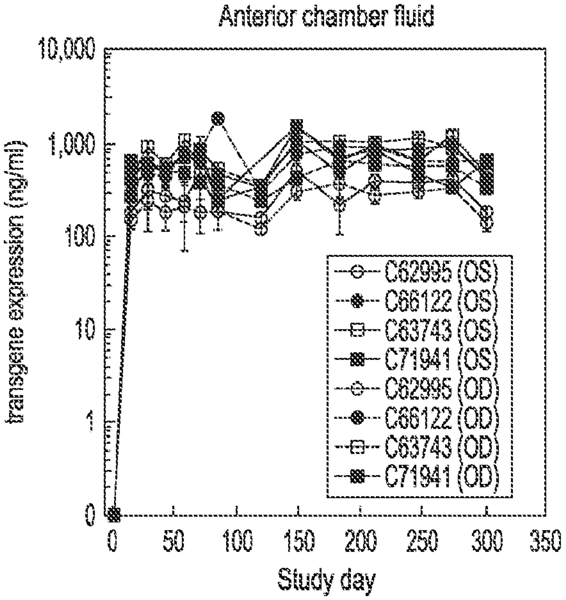
Figure 3D:
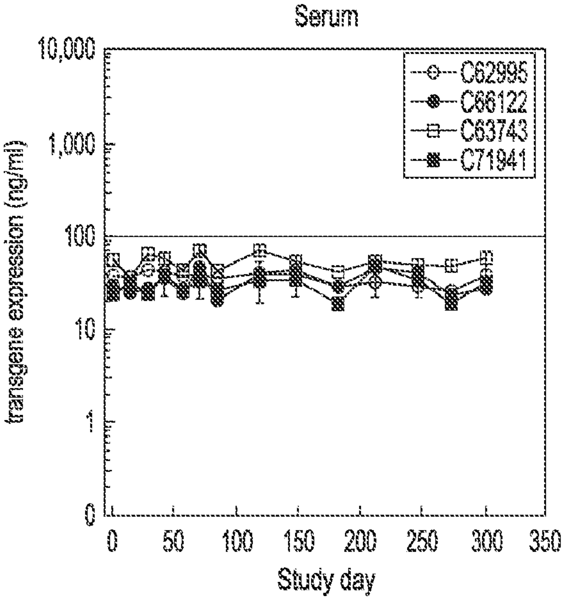
Figure 4A:
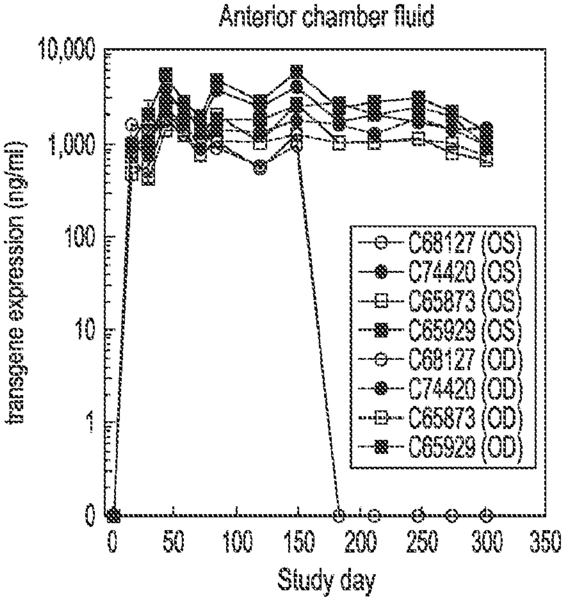
FIGS. 4A-4D show expression of anti-VEGF Fab in anterior chamber fluid and blood for animals in Groups 5 and 6 as described in Example 3 in which cynomolgus monkeys were administered a single dose of $1.00\times10^{11}$ GC/eye of AAV2/8 vectors into each eye subretinally. Anterior chamber fluid and blood were collected at prespecified timepoints. Expression of the anti-VEGF Fab was determined using enzyme-linked immunosorbent assay. The results for Group 5 are presented in FIGS. 4A and 4B and the results for Group 6 is presented in FIGS. 4C and 4D.
Figure 4B:
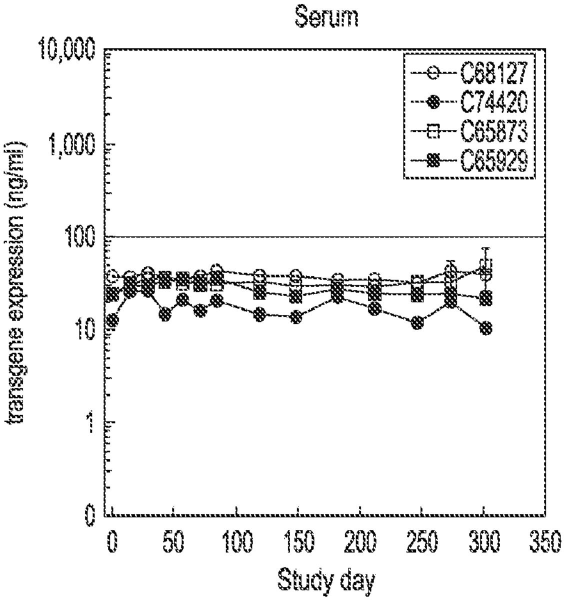
Figure 4C:
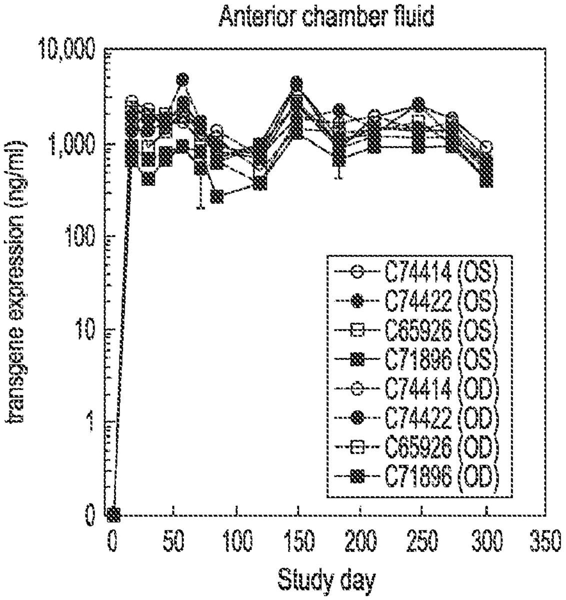
Figure 4D:
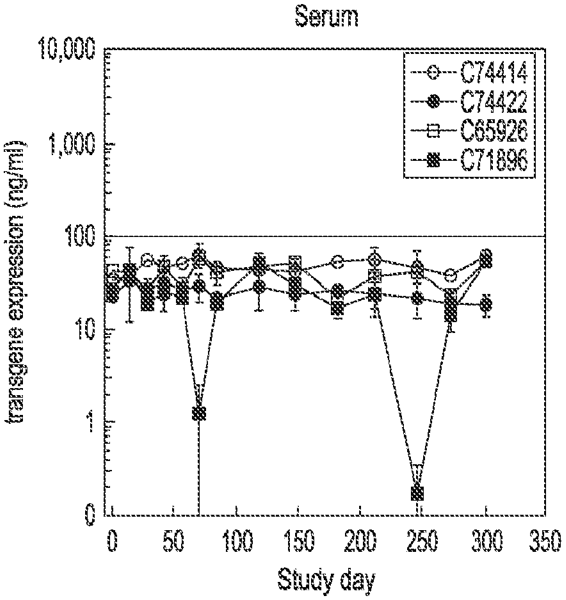
Figure 5A:
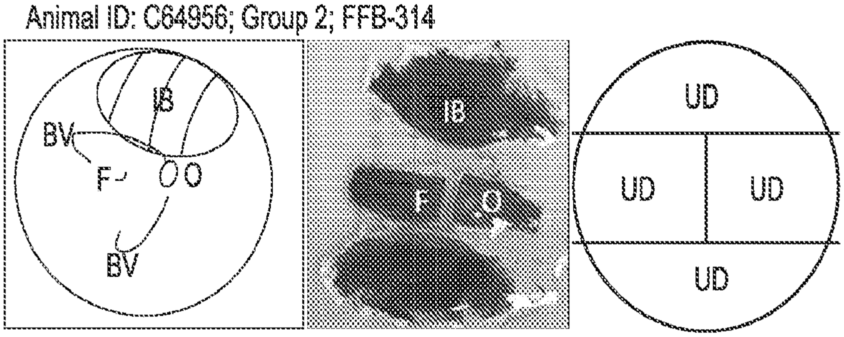
FIGS. 5A-5D provide levels of mRNA for AAV8.aVEGF test vector in retina determined by RT-qPCR. Cynomolgus monkeys were administered a single dose of $1.00\times10^{12}$ GC/eye of a AAV8.aVEGF test vector or FFB-314 into the right eye subretinally. Levels of mRNA for the AAV8.aVEGF test vector were determined in different portions of the dissected retinas by quantitative reverse transcription polymerase chain reaction (RT-qPCR). In left panels, schematics of injection sites are depicted. In middle panels, retinal dissections are presented. In right panels, levels of mRNA for AAV8.aVEGF test vector mRNA (GC per 100 ng of RNA) in 4 sections of retina are depicted. Abbreviations: BV=major blood vessel; F=fovea; GC=genome copies; IB=injection bleb; ID=identification; O=optic disk; UD=undetected.
Figure 5B:
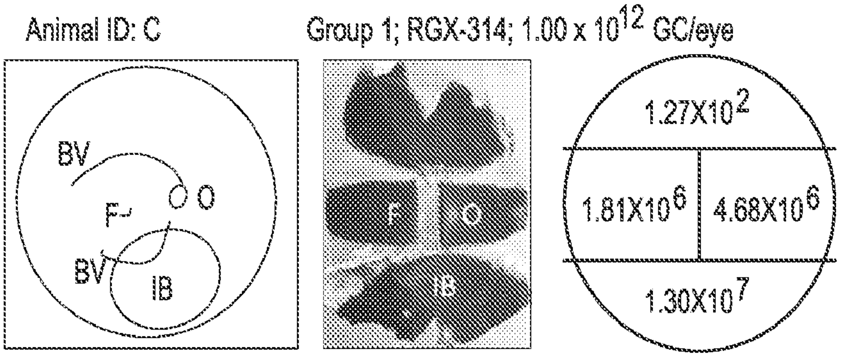
Figure 5C:
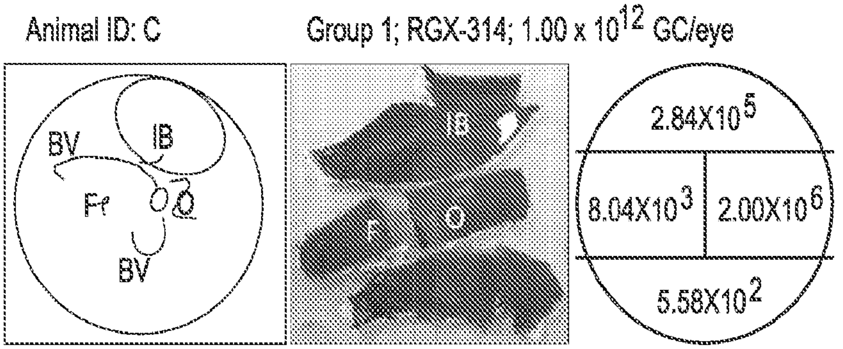
Figure 5D:
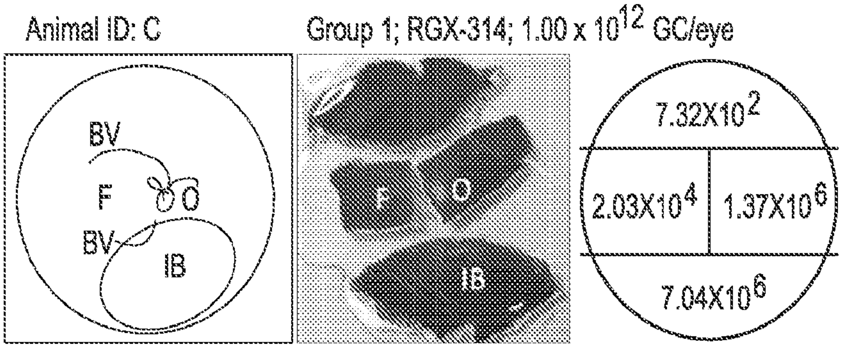
Figure 6A:
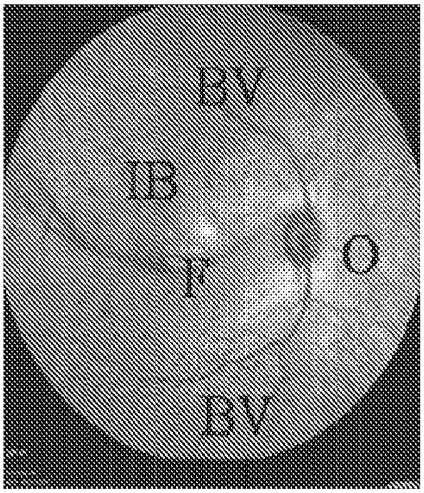
FIGS. 6A-6D provide results of expression of anti-VEGF Fab in anterior chamber fluid, vitreous, and retina (Group 2, Example 6). Cynomolgus monkeys were administered a single dose of $1.00\times10^{11}$ GC/eye of AAV2/8 vector subretinally. These data represent results from different AAV8.aVEGF vectors than shown in FIGS. 5A-5D. Concentrations of anti-VEGF Fab were determined in anterior chamber fluid, vitreous, and 4 different parts of retina. Eyes were dissected as described in FIGS. 5A-5D.
Figure 6B:
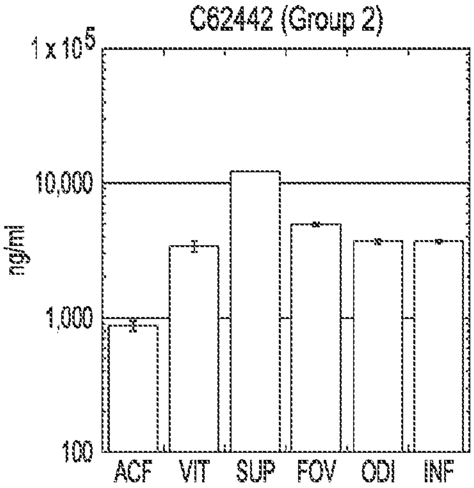
Figure 6C:
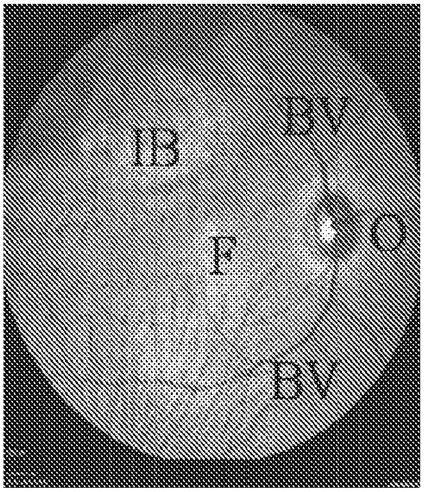
Figure 6D:
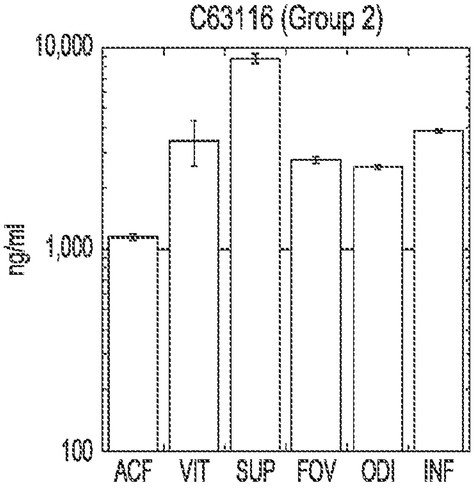

The generation of several rAAV8.aVEGF gene therapy vectors is described in Example 2 herein. Moreover, a schematic representation of the rAAV8.aVEGF vector genome is shown in FIG. 1. rAAV8.aVEGF is a non-replicating recombinant AAV8 viral vector containing a transgene that leads to the production of a human anti-vascular endothelial growth factor (anti-VEGF) antigen binding antibody fragment (Fab). The gene cassette is flanked by the AAV2 inverted terminal repeats (ITRs). Expression from the cassette is driven by a CB7 promoter, a hybrid of a cytomegalovirus immediate-early enhancer and the chicken β-actin promoter. Transcription from this promoter is enhanced by the presence of the chicken β-actin intron. The polyadenylation signal for the expression cassette is from the rabbit β-globin gene. The nucleic acid sequences coding for the heavy and light chains of anti-VEGF Fab are separated by a self-cleaving furin (F)/F2A linker. The incorporation of the furin-F2A linker ensures expression of about equal amounts of the heavy and the light chain polypeptides.

The final product is supplied as a frozen solution of the AAV vector active ingredient in a formulation buffer in Crystal Zenith® vials sealed with latex-free rubber stoppers and aluminum flip-off seals. Vials are stored at ≤−60° C.

B. Dosing & Route of Administration

A volume of 250 μL of rAAV8.aVEGF is administered as a single dose via subretinal delivery in the eye of a subject in need of treatment. The subject receives a dose of $3\times10^9$ GC/eye, $1\times10^{10}$ GC/eye, or $6\times10^{10}$ GC/eye.

rAAV8.aVEGF is administered by a single subretinal delivery by a retinal surgeon with the subject under local anesthesia. The procedure involves a standard 3-port pars plana vitrectomy with a core vitrectomy followed by subretinal delivery of rAAV8.aVEGF into the subretinal space by a subretinal cannula (38 gauge). The delivery is automated via the vitrectomy machine to deliver 250 μL to the subretinal space.

rAAV8.aVEGF can be administered in combination with one or more therapies for the treatment of wet AMD. For example, rAAV8.aVEGF is administered in combination with laser coagulation, photodynamic therapy with verteporfin, and intravitreal with anti-VEGF agent, including but not limited to pegaptanib, ranibizumab, aflibercept, or bevacizumab.

Starting at about 4 weeks post-rAAV8.aVEGF administration, a patient may receive intravitreal ranibizumab rescue therapy in the affected eye.

C. Patient Subpopulations

Suitable patients may include those:

Having a diagnosis of nAMD;

Responsive to anti-VEGF therapy;

Requiring frequent injections of anti-VEGF therapy;

Males or females aged 50 years or above;

Having a BCVA≤20/100 and ≥20/400 (≤65 and ≥35 ETDRS letters) in the affected eye;

Having a BCVA between ≤20/63 and ≥20/400 (≤75 and ≥35 ETDRS letters);

Having a documented diagnosis of subfoveal CNV secondary to AMD in the affected eye;

Having CNV lesion characteristics as follows: lesion size less than 10 disc areas (typical disc area is 2.54 $mm^2$), blood and/or scar <50% of the lesion size;

Having received at least 4 intravitreal injections of an anti-VEGF agent for treatment of nAMD in the affected eye in the 8 months (or less) prior to treatment, with anatomical response documented on SD-OCT; and/or Having subretinal or intraretinal fluid present in the affected eye, evidenced on SD-OCT.

Prior to treatment, patients are screened and one or more of the following criteria may indicate this therapy is not suitable for the patient:

- CNV or macular edema in the affected eye secondary to any causes other than AMD;
- Blood occupying ≥50% of the AMD lesion or blood >1.0 $mm^2$ underlying the fovea in the affected eye;
- Any condition preventing VA improvement in the affected eye, e.g., fibrosis, atrophy, or retinal epithelial tear in the center of the fovea;
- Active or history of retinal detachment in the affected eye;
- Advanced glaucoma in the affected eye;
- Any condition in the affected eye that may increase the risk to the subject, require either medical or surgical intervention to prevent or treat vision loss, or interfere with study procedures or assessments;
- History of intraocular surgery in the affected eye within 12 weeks prior to screening (Yttrium aluminum garnet capsulotomy may be permitted if performed >10 weeks prior to the screening visit);
- History of intravitreal therapy in the affected eye, such as intravitreal steroid injection or investigational product, other than anti-VEGF therapy, in the 6 months prior to screening;
- Presence of an implant in the affected eye at screening (excluding intraocular lens).
- History of malignancy requiring chemotherapy and/or radiation in the 5 years prior to screening (Localized basal cell carcinoma may be permitted);
- History of therapy known to have caused retinal toxicity, or concominant therapy with any drug that may affect visual acuity or with known retinal toxicity, e.g, chloroquine or hydroxychloroquine;
- Ocular or periocular infection in the affected eye that may interfere with the surgical procedure;
- Myocardial infarction, cerebrovascular accident, or transient ischemic attacks within the past 6 months of treatment;
- Uncontrolled hypertension (systolic blood pressure [BP] >180 mmHg, diastolic BP>100 mmHg) despite maximal medical treatment;
- Any concomitant treatment that may interfere with ocular surgical procedure or healing process;
- Known hypersensitivity to ranibizumab or any of its components or past hypersensitivity to agents like rAAV8.aVEGF;
- Any serious or unstable medical or psychological condition that, in the opinion of the Investigator, would compromise the subject's safety or successful participation in the study.
- Aspartate aminotransferase (AST)/alanine aminotransferase (ALT)>2.5×upper limit of normal (ULN)
- Total bilirubin>1.5×ULN unless the subject has a previously known history of Gilbert's syndrome and a fractionated bilirubin that shows conjugated bilirubin <35% of total bilirubin
- Prothrombin time (PT)>1.5×ULN
- Hemoglobin<10 g/dL for male subjects and <9 g/dL for female subjects
- Platelets<100×$10^3$/μL
- Estimated glomerular filtration rate (GFR)<30 mL/min/1.73 $m^2$ Starting at about 4 weeks post-rAAV8.aVEGF administration, a patient may receive intravitreal ranibizumab rescue therapy in the affected eye for disease activity if 1 or more of the following rescue criteria apply:

- Vision loss of ≥5 letters (per Best Corrected Visual Acuity [BCVA]) associated with accumulation of retinal fluid on Spectral Domain Optical Coherence Tomography (SD-OCT)
- Choroidal neovascularization (CNV)-related increased, new, or persistent subretinal or intraretinal fluid on SD-OCT
- New ocular hemorrhage Further rescue injections may be deferred per the Investigator's discretion if one of the following sets of findings occur:

- Visual acuity is 20/20 or better and central retinal thickness is "normal" as assessed by SD-OCT, or
- Visual acuity and SD-OCT are stable after 2 consecutive injections.

If injections are deferred, they are resumed if visual acuity or SD-OCT get worse per the criteria above.

D. Measuring Clinical Objectives

Primary clinical objectives include slowing or arresting the progression of retinal degeneration and slowing or preventing loss of vision. Clinical objectives are indicated by the elimination of or reduction in the number of rescue treatments using standard of care, for example, intravitreal injections with anti-VEGF agents, including but not limited to pegaptanib, ranibizumab, aflibercept, or bevacizumab. Clinical objectives are also indicated by a decrease or prevention of vision loss and/or a decrease or prevention of retinal detachment.

Clinical objectives are determined by measuring BCVA (Best-Corrected Visual Acuity), intraocular pressure, slit lamp biomicroscopy, indirect ophthalmoscopy, and/or SD-OCT (SD-Optical Coherence Tomography). In particular, clinical objectives are determined by measuring mean change from baseline in BCVA over time, measuring the gain or loss of ≥15 letters compared to baseline as per BCVA, measuring mean change from baseline in CRT as measured by SD-OCT over time, measuring mean number of ranibizumab rescue injections over time, measuring time to $1^{st}$ rescue ranibizumab injection, measuring mean change from baseline in CNV and lesion size and leakage area based on FA over time, measuring mean change from baseline in aqueous aVEGF protein over time, performing vector shedding analysis in serum and urine, and/or measuring immunogenicity to rAAV.aVEGF, i.e., measuring Nabs to AAV, measuring binding antibodies to AAV, measuring antibodies to aVEGF, and/or performing ELISpot.

Clinical objectives are also determined by measuring the mean change from baseline over time in area of geographic atrophy per fundus autofluorescence (FAF), measuring the incidence of new area of geographic atrophy by FAF (in subjects with no geographic atrophy at baseline, measuring the proportion of subjects gaining or losing ≥5 and ≥10 letters, respectively, compared with baseline as per BCVA, measuring the proportion of subjects who have a reduction of 50% in rescue injections compared with previous year, measuring the proportion of subjects with no fluid on SD-OCT.

Improvement/efficacy resulting from rAAV.aVEGF administration can be assessed as a defined mean change in baseline in visual acuity at about 4 weeks, 12 weeks, 6 months, 12 months, 24 months, 36 months, or at other desired timepoints. Treatment with rAAV.aVEGF can result in a 5%, 10%, 15%, 20%, 30%, 40%, 50% or more increase in visual acuity from baseline. Improvements/efficacy can be assessed as mean change from baseline in central retinal thickness (CRT) as measured by spectral domain optical coherence tomography (SD-OCT) at 4 weeks, 12 weeks, 6 months, 12 months, 24 months and 36 months. Treatment with rAAV.aVEGF can result in a 5%, 10%, 15%, 20%, 30%, 40%, 50% or more increase central retinal thickness from baseline.

Example 2

Generation of AAV8.CMV.aVEGF

Each of the aVEGF vectors described herein include an expression cassette including apromoter which drives expression of the anti-VEGF Fab heavy chain and light chain, each of which has an IL2 leader sequence. The Fab coding sequence in the vector genomes carried by the rAAV in the tested composition (suspension) were designed to be identical. The expression cassette is flanked by a 5' AAV2 ITR and a 3' AAV2 ITR. Each of the tested vector genomes contains a coding sequence variant for the same anti-VEGF Fab (previously designated aVEGF-Arg or aVEGF-R). In certain embodiments, the expressed aVEGF Fab is a homogenous population. In certain embodiments, the expressed aVEGF Fab has heterogeneity at the heavy chain carboxy terminus. The open reading frames for the IL2-aVEGF heavy chain and IL2-aVEGF light chain were separated by an encoded furin cleavage site/F2A linker to promote equal molar expression of both, heavy and light chains. This results in expression of an aVEGF heavy chain which optionally further contains 0, 1, 2, 3 or 4 amino acids at its carboxy terminus. an arginine, arginine-lysine, arginine-lysine-arginine, or arginine-lysine-arginine-arginine at its carboxy terminus.

Various coding sequences are designated aVEGFv1, v2, etc. These vector genomes are provided in the Sequence Listing, which is incorporated by reference.

The following elements to be included in the transgene cassette in AAV2/8 vector for expression of anti-VEGF Fab in mice were evaluated.

7 different promoters (98 male C57BL/6 mice; Jackson Laboratories) were assessed using a convenient antibody (F16) expressed from AAV2/8. Expression of F16 mAb was measured by ELISA against hemagglutinin (HA) protein;

2 different leader peptides (28 male C57BL/6 mice; Jackson Laboratories). Expression of anti-VEGF Fab was measured by ELISA against VEGF;

3 different light-heavy chain separators (42 male C57BL/6 mice; Jackson Laboratories) were evaluated using the following vectors.

| | | No. of animals Dose (GC/eye) | | |
|---|---|---|---|---|
| Group | Treatment | $1.00 \times 10^9$ | $5.00 \times 10^9$ | ROA |
| 1 | AAV2/8.CMV.PI.aVEGFv7.EMCVIRES.Fab. SV40; the sequence of the expression cassette is provided in SEQ ID NO: 45 | 7 | 7 | Subretinal |
| 2 | AAV2/8.CMV.PI.aVEGFv7.FMDV1IRES.Fab. SV40; the sequence of the expression cassette is provided in SEQ ID NO: 46 | 7 | 7 | Subretinal |
| 3 | AAV2/8.CMV.PI.aVEGFv7.cMycIRES.Fab.SV40; the sequence of the expression cassette is provided in SEQ ID NO: 47 | 7 | 7 | Subretinal |

Abbreviation:
GC = genome copies;
No. = number;
ROA = route of administration.

13 different coding sequences (182 male C57BL/6 mice; Jackson Laboratories). Expression of anti-VEGF Fab was measured by ELISA against VEGF.

Vectors were delivered into subretinal space of the mouse eye. Expression of reporter genes was determined by enzyme-linked immunosorbent assay (ELISA).

Seven different promoters were evaluated in another study: 3 viral (cytomegalovirus [CMV], thymidine kinase [TK], simian virus [SV40]), 3 non-viral (phosphoglycerate kinase [PGK], human elongation factor-1α [EF1a], ubiquitin C [UbC]), and 1 hybrid (chicken β-actin [CB7]) promoters.

Two different leader peptides were also evaluated using rAAV8 vectors having identical vector elements and the same coding sequence, i.e., v3, with the exception of the leader sequence (interleukin-2 vs the serpin leader). AAV2/8=adeno associated virus (AAV) capsid type 8 with AAV2 inverted terminal repeats flanking the transgene; amd201Lead=anti-VEGF Fab with IL2 leader sequence and Furin F2A as light-heavy chain separator; amd201altLead=anti-VEGF Fab with SF1 leader sequence and Furin F2A as light-heavy chain separator; CB7=chicken β actin promoter; CI=chimeric intron; rBG=rabbit β globin polyadenylation sequence.

Three different internal ribosome entry site (IRES) sequences separating heavy and light chains of anti-VEGF Fab were evaluated in another study. These IRES sequences were derived from encephalomyocarditis virus (EMCV), cMyc, and foot-and-mouth disease virus 1 (FMDV1). In this study, the vectors were identical except for the light and heavy chain separators (EMC, FMDV1 and cMyc). AAV2/8=adeno associated virus (AAV) capsid type 8 with AAV2 inverted terminal repeats flanking the transgene; amd201=codon variant of anti-VEGF Fab with IL2 leader sequence; CMV=cytomegalovirus promoter; EMCV=encephalomyocarditis virus; Fab=fragment antigen-binding region; FMDV1=foot and mouth disease virus 1; IRES=internal ribosome entry site; PI=Promega intron; SV40=simian virus polyadenylation sequence In another study, thirteen different coding sequences for the anti-VEGF Fab were evaluated. The overall coding sequence variance was between approximately 20% and 30%. The vectors are described in the following Table.

Vectors with Different Coding Sequences Used. The SEQ ID NO for the expression cassettes is provided in the following table:

| Vector | SEQ ID NO: (vector genome) |
|---|---|
| AAV2/8.CB7.CI.aVEGFv4.rBG | 35 |
| AAV2/8.CB7.CI.aVEGFv5.rBG | 36 |
| AAV2/8.CB7.CI.aVEGFv1.rBG | 34 |
| AAV2/8.CB7.CI.aVEGFv2.rBG: | 3 |
| AAV2/8.CB7.CI.aVEGFv6.rBG | 37 |
| AAV2/8.CB7.CI.aVEGFv7.rBG | 38 |
| AAV2/8.CB7.CI.aVEGFv8.rBG | 39 |
| AAV2/8.CB7.CI.aVEGFv9.rBG | 40 |
| AAV2/8.CB7.CI.aVEGFv10.rBG | 41 |
| AAV2/8.CB7.CI.aVEGFv11.rBG | 42 |
| AAV2/8.CB7.CI.aVEGFv12.rBG | 43 |
| AAV2/8.CB7.CI.aVEGFv3.rBG | 14 |
| AAV2/8.CB7.CI.aVEGFv13.rBG | 44 |

Vectors in all studies were diluted in Dulbecco's phosphate-buffered saline (DPBS).

Animals were assigned into treatment groups and administered $1.00\times10^9$ or $5.00\times10^9$ genome copies (GC)/eye of AAV2/8 vectors into the right eye. The left eye was used as an untreated control. Vectors were administered subretinally in a total volume of 1 μL.

A. Subretinal Injections

Subretinal injections were conducted using aseptic technique and sterile dissecting instruments. Animals were anesthetized with ketamine/xylazine or 3% to 5% isoflurane and administered meloxicam Animals were then placed under a dissection microscope with the eye to be injected under view (using a 15× magnification). The temporal conjunctiva was grasped with jeweler's forceps and carefully cut down to the sclera using the tip of Vannas iridotomy scissors. Conjunctival peritomy was conducted by introducing the lower lip of the scissors through the incision and extending circumferentially both superiorly and inferiorly of the conjunctiva. Any conjunctival debris was carefully removed from the surface of the sclera. The conjunctiva adjacent to the cornea was grasped with the forceps, providing traction to rotate the globe and allow optimal surgical exposure. Using a 30½-gauge needle, a small incision, large enough to allow the blunt-tip needle to pass through, was made.

The tip of a 33-gauge blunt-tip needle mounted on a Hamilton auto-injector syringe was introduced into the incision tangentially to the surface of the globe. The needle was passed along the inner surface of the sclera with the tip entering approximately 1 mm. The 33-gauge needle passed through the sclera and choroid and then terminated in the subretinal space. Up to 1 μL of vector was delivered. Once the procedure was completed, antibiotic ophthalmic ointment was applied to the eye.

B. Assay Methods

The collected eyes were homogenized by placing entire eyeball into a conical tube with stainless steel beads and 200 μL of cocktail containing protein lysis and extraction buffer (RIPA) and cOmplete™, Mini Protease Inhibitor Cocktail tablets (1 tablet/10 mL of RIPA buffer). The eyes were homogenized for at least 2 minutes in a TissueLyser (Qiagen, USA) or until fully homogenized. Homogenate was centrifuged for 20 minutes at 12000 RPM at 4° C. in a cold room. The supernatants were transferred into fresh tubes and used in analytical assays.

Determination of Protein Concentrations in Eye Homogenates

Protein concentration in eye homogenate was determined using Pierce™ BCA Protein Assay Kit (Thermo Fisher Scientific) per the manufacturer's instructions. Equal amounts of protein in all samples were used in ELISA.

Enzyme-Linked Immunosorbent Assay

Ninety-six-well, round-bottom plates were coated with 2 μg/mL of HA A-Beijing or 1 μg/mL VEGF overnight at 4° C. After coating, the plates were washed 5 times with 200 μL of phosphate-buffered saline (PBS) with 0.05% Tween-20 (PBS-T) using a 405 TS Washer (BioTek Instruments, Winooski, Vt.). Plates were then blocked with 200 μL/well of 1% bovine serum albumin (BSA) at room temperature (RT) for 1 hour. After washing (as described), 100 μL/well of sample was loaded into duplicate wells and incubated at 37° C. for 1 hour. Following incubation, the plates were washed (as described) and then blocked with 1% BSA at RT for 1 hour. After washing (as described), 100 μL/well of the primary antibody was added and incubated at RT for 1 hour. Wells were then washed (as described) and incubated with 100 μL/well of the secondary antibody at RT for 1 hour. Following a final wash (as described), 150 μL/well of 3,3',5,5'-tetramethylbenzidine, a detection substrate, was added and incubated at RT for 30 minutes protected from light. The reaction was stopped with 50 μL/well of 2N $H_2SO_4$. The plates were then read at the excitation/emission of 450 nm/540 nm using spectrophotometer SpectraMax® M3 (Molecular Devices, Sunnyvale, Calif.).

The following primary antibodies were used: 1.0 mg/mL Goat Anti-Human IgG H&L (Biotin) preadsorbed at a 1:10000 dilution in PBS (Abcam 0.5 mg/mL); 0.5 mg/mL Goat Anti-Human IgG H&L (Biotin) preadsorbed at a 1:5000 dilution in PBS (Abcam, 1 mg/mL). The following secondary antibody was used: 1 mg/mL Streptavidin (HRP) at a 1:30000 dilution in PBS.

Statistical Analyses

Average and standard deviation values for concentration of reporter genes for ELISA were calculated using Microsoft Office Excel 2010.

C. Results

AAV2/8 vectors with 7 different promoters were evaluated for expression of FI6 mAb. Expression of FI6 mAb was not observed in any animal when promoter EF 1-α was used. Expression of FI6 mAb was low when promoters SV40.PI, PGK.PI and TK.PI were used. Promoters CMV.PI, CB7.CI, and UbC.PI demonstrated the highest expression of FI6 mAb. No expression was observed in the untreated left eye in any animal (data on file). AAV2/8 vectors with 2 different leader peptides were evaluated for expression of anti-VEGF Fab. Compared to aVEGFv7 with an IL2 leader, expression of anti-VEGF Fab at low dose was greater when leader peptide aVEGFv7 with SF2 leader was used. At high dose, the expression of anti-VEGF Fab was similar for both leader peptides. No expression was observed in the untreated left eye in any animal (data on file). AAV2/8 vectors with 3 different light-heavy chain separators were evaluated for expression of anti-VEGF Fab. Expression of anti-VEGF Fab was not observed in any animal when cMyc light-heavy chain separator was used. With EMCV and FMDV1 light-heavy chain separators, anti-VEGF Fab was expressed at low levels. No expression was observed in the untreated left eye in any animal (data on file).

AAV2/8 vectors with 13 different coding sequences were evaluated for expression of anti-VEGF Fab transgene product. When coding sequences aVEGFv4, aVEGFv5, aVEGFv6, aVEGFv7, aVEGFv8, and aVEGFv9 were used, expression of anti-VEGF Fab was low. Expression was higher with coding sequences aVEGFv13, aVEGFv10, aVEGFv11, and aVEGFv12. When coding sequences aVEGFv1, aVEGFv2, and aVEGFv3 were used, expression of anti-VEGF Fab was the highest. No expression was observed in the untreated left eye in any animal (data on file).

Each of the vectors encodes the same anti-VEGF transgene product. Based in part on these results, a single replication-defective, recombinant AAV8.aVEGF was selected for further development. This tert vector has an AAV8 capsid and a vector genome in which AAV2 ITRs flank a CB7 promoter, an intron, an anti-VEGF coding sequence selected from the coding sequence as described earlier and a rBG poly A sequence. This is termed the test vector (alternatively AAV2/8.aVEGF test vector or AAV8.aVEGF test vector) in the following examples, except where specifically specified otherwise.

Example 3

Pharmacokinetic (PK) Study in Non-Human Primates

Macaques were used in this study because they are the closest species to humans for studying retinal diseases. Cynomolgus monkeys and humans have similar eye anatomy, including fovea. The dimensions of the eyes are comparable, which allows determination of the human dose based on relative retinal areas.

This study was conducted to select AAV2/8 vector for clinical development and to evaluate toxicity and immunogenicity of AAV2/8 vector and anti-VEGF Fab in cynomolgus monkeys. The study is ongoing. The results presented are based on the data collected at Month 10. Evaluation of toxicity of AAV2/8 vector and anti-VEGF Fab is described. Animals were administered AAV2/8 vectors subretinally. Toxicity was evaluated based on clinical observations, body weights, indirect ophthalmoscopy, spectral domain optical coherence tomography, hematology, coagulation, clinical chemistry, and gross pathologic findings. The only adverse finding related to AAV2/8 vector or anti-VEGF Fab was some thinning in outer nuclear layer localized to the injection site observed by spectral domain optical coherence tomography in several eyes of animals administered 1.00× $10^{11}$ GC/eye of AAV2/8 vectors.

Animals were assigned into 4 treatment groups. Animals were administered a single dose of 1.00×$10^{11}$ genome copies (GC)/eye of AAV2/8 vectors into each eye in a total volume of 100 μL. Vectors were administered subretinally (confirmed visually by appearance of a dome shaped retinal detachment/retinal bleb under microscope) into both eyes. The following table lists the tested vectors.

| Group | Treatment | Dose (GC/eye) | No. of animals | ROA OD OS |
|---|---|---|---|---|
| 2 | AAV2/8.UbC.PI.aVEGFv2.SV40 | 1.00 × $10^{11}$ | 2 M, 2 F | Subretinal |
| 3 | AAV2/8.UbC.PI.aVEGFv3.SV40 | 1.00 × $10^{11}$ | 2 M, 2 F | Subretinal |
| 5 | AAV2/8.CB7.CI.aVEGFv2aVEGFv2.rBG | 1.00 × $10^{11}$ | 2 M, 2 F | Subretinal |
| 6 | AAV2/8.CB7.CI.aVEGFv3.rBG | 1.00 × $10^{11}$ | 2 M, 2 F | Subretinal |

Abbreviation:
F = female;
GC = genome copies;
M = male;
No. = number;
OD = right eye;
OS = left eye;
ROA = route of administration.

Subretinal Injections

For subretinal injections, a needle was inserted through a trocar, introduced by sclerotomy, at the 2 or 10 o'clock position. The needle was advanced through the vitreous to penetrate the retina in the posterior pole. Under the microscopic control, 100 μL of test article was injected into the subretinal space. This was confirmed by appearance of a dome shaped retinal detachment/retinal bleb. If the first injection attempt did not result in retinal detachment, the cannula was moved to another site in the retina. The injection site may have resulted in a temporary scotoma. The injected solution was reabsorbed within a few hours by the retina. The retinal detachment was made in the peripheral retina and did not result in permanent blindness. The site of sclerotomy was sutured with absorbable suture and the eye dressed with PredG ointment or equivalent. Subconjunctival kenalog or equivalent was administered. Animals were observed daily and administered parenteral analgesics as needed. If vitreal inflammation appeared, animals were treated with topical atropine and PredG ointment or equivalent daily until symptoms resolved.

Collection of Anterior Chamber Fluid

Animals were anesthetized and their head stabilized. Betadine 5% antiseptic solution and Proparacaine or equivalent were applied to each eye. An eye speculum was placed to allow access to the anterior chamber. The procedure was performed with a tuberculin syringe attached to a 27- to 30-gauge hypodermic needle. The eye was held steady with forceps or a cotton tip applicator on the nasal conjunctiva.

The needle was inserted bevel up through the paralimbal peripheral clear cornea, anterior to the iris plane. Once the eye was entered, a sampler slowly withdrew the plunger of the syringe to aspirate the aqueous fluid. A maximum of 100 μL of anterior chamber fluid was collected. Once anterior chamber fluid was drained, the needle was withdrawn from the eye. The anterior chamber fluid was placed on wet ice until use or storage. After the procedure, topical flurbiprofen, PredG ointment, and antibiotic drops were applied to each eye. Anterior chamber fluid was collected on the following Study days (occasionally adjusted due to weekends, holidays or scheduling issues)

0, 15, 29, 43, 57, 71, 85, 120, 149, 183, 212, 247, 274, and 302.

Spectral Domain Optical Coherence Tomography

Retinal structure (at a micron-level resolution) was evaluated by in vivo, non-invasive, cross-sectional retinal microscopy with SD-OCT (Spectralis OCT, Heidelberg Engineering, Carlsbad, Calif.). Pupils were dilated with phenylephrine 2.5% and tropicamide 1%. En-face retinal imaging was performed with near infrared (NIR) reflectance (REF) and in a subset of animals with NIR fundus autofluorescence (FAF) using the scanning laser ophthalmoscope of this imaging system. Spectral domain optical coherence tomography scanning was performed with 9 mm long horizontal and vertical cross-sections through the fovea and overlapping 30×25 mm raster scans extending into the near midperiphery. See, Aleman, Invest Ophthalmol Vis Sci. 2007 October; 48(10):4759-65.

Enzyme-Linked Immunosorbent Assay (ELISA)

The ELISA was performed essentially as described for the mouse studies above. Ninety-six-well, round-bottom plates were coated with 1 μg/mL of VEGF for expression of anti-VEGF Fab. Plates were coated overnight at 4° C. After coating, the plates were washed 5 times with 200 μL of phosphate-buffered saline (PBS) with 0.05% Tween-20 (PBS-T) using a 405 TS Washer (BioTek Instruments, Winooski, Vt.). Plates were then blocked with 200 μL/well of 1% bovine serum albumin (BSA) at room temperature (RT) for 1 hour. After washing (as described), 100 μL/well of sample was loaded into duplicate wells and incubated at 37° C. for 1 hour. Following incubation, the plates were washed (as described) and then blocked with 1% BSA at RT for 1 hour. After washing (as described), 100 μL/well of the primary antibody was added and incubated at RT for 1 hour. Wells were then washed (as described) and incubated with 100 μL/well of the secondary antibody at RT for 1 hour.

Following a final wash (as described), 150 μL/well of 3,3',5,5'-tetramethylbenzidine, a detection substrate, was added and incubated at RT for 30 minutes protected from light. The reaction was stopped with 50 μL/well of 2N $H_2SO_4$. The plates were then read at the excitation/emission of 450 nm/540 nm using spectrophotometer SpectraMax® M3 (Molecular Devices, Sunnyvale, Calif.). The following primary antibodies were used: 1.0 mg/mL Goat Anti-Human IgG H&L (Biotin) preadsorbed at a 1:10000 dilution in PBS; 0.5 mg/mL Goat Anti-Human IgG H&L (Biotin) preadsorbed at a 1:5000 dilution in PBS. The following secondary antibody was used: 1 mg/mL Streptavidin (HRP) at a 1:30000 dilution in PBS.

Average and standard deviation values for concentrations of the anti-VEGF Fab in anterior chamber fluid and blood were calculated using Microsoft Office Excel 2010.

A Pharmacology Results

Four AAV vectors with different promoters and coding sequences were evaluated as described earlier in this example Vectors were administered subretinally. Expression of anti-VEGF Fab was determined by enzyme-linked immunosorbent assay.

Expression of Anti-VEGF Fab in Anterior Chamber Fluid

In anterior chamber fluid of animals in all groups, similar expression kinetics was observed (FIG. 3A-3D; FIG. 4A-4D). Onset of expression of the anti-VEGF Fab was rapid, generally within 7 days. Steady-state expression levels were achieved within 1 month. All except 2 animals continued to express the anti-VEGF Fab at steady-state levels until the last evaluated timepoint.

One animal in Group 2 (FIG. 3B) and 1 animal in Group 5 (FIG. 4A) lost expression of the anti-VEGF Fab. Loss of expression coincided with appearance of antibodies against the anti-VEGF Fab. No difference in expression of the anti-VEGF Fab between males and females and between the right and the left eye was observed.

Generally, vectors controlled by the CB7.CI promoter (FIG. 4A-4D) expressed the anti-VEGF Fab at higher levels than vectors controlled by the UbC.PI promoter (FIG. 3). Vector AAV2/8.CB7.CI.aVEGFv3aVEGFv3.rBG was selected as a primary vector for clinical development. This selection was based on expression level of transgene, better translatability of relative expression levels from mice to cynomolgus monkeys for aVEGFv3 coding sequence, and greater level of experience with CB7.CI promoter.

Expression of Anti-VEGF Fab in Blood

In some patients administered a single IVT injection of Lucentis, ranibizumab was observed in serum (Xu, 2013). To determine if subretinal administration of AAV2/8 vector results in systemic exposure to the anti-VEGF Fab, its concentrations were measured in serum.

Expression of the anti-VEGF Fab was around the baseline levels in blood of all animals (FIGS. 3A-3D, FIGS. 4A-3D).

B. Toxicology

Evaluation of toxicity of AAV2/8 vector and anti-VEGF Fab is described in this subpart B. Animals were administered AAV2/8 vectors subretinally. Toxicity was evaluated based on clinical observations, body weights, indirect ophthalmoscopy, spectral domain optical coherence tomography (SD-OCT), hematology, coagulation, clinical chemistry, and gross pathologic findings.

For each variable in each treatment group, the measurements at each time point were compared to the corresponding baseline values using Wilcoxon rank-sum test. The Wilcoxon rank-sum test is a nonparametric alternative to the two-sample t-test, which is based solely on the order in which the observations from the 2 samples fall. It is a preferable test for dataset with small sample size. Statistical significance was declared at the 0.05 level without the adjustment for multiple testing. The analysis was done using R program (version 3.3.1; cran.r-project.org/) with function "wilcox.test".

The study is ongoing. The results presented are based on the data collected by Month 10. There were no mortalities in this study. No adverse clinical observations related to AAV2/8 vector or anti-VEGF Fab were noted in any animal. No clinically meaningful changes in body weight during the study were observed for any animal. No adverse observations related to AAV2/8 vector or anti-VEGF Fab were noted during indirect ophthalmoscopy in any animal Spectral Domain Optical Coherence Tomography All 4 animals (8 eyes) in Group 6 were imaged by SD OCT. Injected regions in the eyes that received the intermediate dose level of AAV8.aVEGF test vector ($1.00\times10^{11}$ GC/eye) showed intermediate outcomes as compared to $1.00\times10^{10}$ and $1.00\times10^{12}$ dose levels described in Example 7 (esp., subpart B). In two animals (Animal C71896 and Animal C65936), some thinning of ONL was observed (data on file). In addition, in 2 animals (Animal C74422 and Animal C74414), minimal changes were observed (data on file). No clinically significant changes in hematology, coagulation, or clinical chemistry parameters were observed in any animal.

No findings related to AAV2/8 vector or anti-VEGF Fab were observed in 2 animals sacrificed at Month 10. In Animal C65936, a liver mass was observed, which microscopically was focal chronic grade 3 inflammation. In Animal C74414, bilateral grade 3 lymphoid hyperplasia was observed. These finding were not related to AAV2/8 vector or anti-VEGF Fab. At a dose level of $1.00\times10^{11}$ GC/eye of AAV2/8 vector, the only findings related to AAV2/8 vector or anti-VEGF Fab were minimal vacuolation of the lens of the right eye of Animal C65926 Minimal perivascular mononuclear cell infiltrates around the vasculature of the right optic nerve in Animal C74414 were observed. In the same animal, a minimal mononuclear cell infiltrate in the subconjunctiva of the left eye and a minimal perivascular exocular mononuclear cell infiltrate in right eye were also noted.

The only adverse finding related to AAV2/8 vector or anti-VEGF Fab was some thinning in ONL localized to the injection site observed by SD OCT in several eyes of animals administered $1.00\times10^{11}$ GC/eye of AAV2/8 vectors.

C. Immunology

In this section, evaluation of immunogenicity of AAV2/8 vector and anti-VEGF Fab is described. Vectors were administered subretinally as described earlier in this example. Immunogenicity was assessed by the presence of IgM and IgG antibodies against anti-VEGF Fab, neutralizing antibodies against AAV8 capsid, and cellular immune response against AAV2/8 vector and anti VEGF Fab.

To summarize, one animal each in Groups 2 and 5 had antibodies against anti-VEGF Fab, high levels of NAbs to AAV8 capsid, and T-cell responses. Both animals lost expression of anti-VEGF Fab. Animals with pre-existing NAbs to AAV8 capsid generally had increased response after administration of AAV2/8 vector when compared to animals without pre-existing NAbs. In some animals sacrificed at approximately Study day 300, NAbs to AAV8 capsid were observed in vitreous fluid. No antibodies against anti-VEGF Fab and no T-cell responses were observed in animals in Group 6. Only mild fluctuations in the levels of NAbs were observed in animals in Group 6 after administration of AAV2/8 vector.

Anti-VEGF Fab was expressed in all animals administered AAV2/8 vectors (Part A of this Example). Two animals (Animal C74440 and Animal C68127) lost expression of the anti-VEGF Fab. Loss of expression coincided with appearance of antibodies against the anti-VEGF Fab.

Overall, levels of IgM and IgG against anti-VEGF Fab were below baseline levels in anterior chamber fluid and serum. Increases above the baseline levels at some timepoints were observed in some animals. In 1 animal each in Groups 2 (Animal C74440) and 5 (Animal C68127), levels of IgG against anti-VEGF Fab in anterior chamber fluid increased above baseline levels approximately at approximately 6 months. The levels generally increased thereafter. In both animals, IgG against anti-VEGF Fab increased above the baseline levels in serum. These increases in IgG coincided with loss of expression of anti-VEGF Fab. Importantly, IgM and IgG against anti-VEGF Fab in animals in Group 6 were not detected or were below the baseline levels for the duration of the study.

In brief, the animal immune system permitted continued localized expression of anti-VEGF transgene product, despite the fact that the transgene product is a human antibody.

Presence of Neutralizing Antibodies Against AAV8 Capsid

Baseline levels of NAbs against AAV8 capsid were determined in serum from blood samples collected on Study day 0. The limit of detection was a 1:5 dilution; titers of <5 were considered undetectable. In 2 of 16 animals (Animal C63116 and Animal C66122), pre-existing NAbs in serum were not observed. The levels of NAbs in these 2 animals following administration of AAV2/8 vectors remained below the limit detection or were low. In 14 of 16 animals, pre-existing NAbs were observed. In 11 of these animals, levels of NAbs fluctuated throughout the study. In 1 animal each in Groups 2 (Animal C74440) and 5 (Animal C68127), levels of NAbs following administration of AAV2/8 vector increased up to 256 and 128 two-fold dilutions respectively at two months. These increases in NAbs coincided with loss of expression of anti-VEGF Fab. In 6 sacrificed animals from Groups 2, 3 and 5, the presence of NAbs was evaluated in vitreous fluid. In 2 animals (Animal C63116 and Animal C66122), with undetectable NAb in serum time of sacrifice, NAbs were not present in vitreous fluid at sacrifice. In the remaining animals, levels of NAbs at sacrifice did not correlate with levels in serum at time of sacrifice. In all animals in Group 6, pre-existing NAbs were observed. The levels of NAbs in these animals fluctuated mildly throughout the study.

T-Cell Responses to AAV2/8 Vector and Anti-VEGF Fab

In 1 animal (Animal C74440) in Group 2, elevated T-cell responses were observed at a single time point. In this animal, antibodies against anti-VEGF Fab and NAbs against AAV8 capsid were also observed. This animal lost expression of anti-VEGF Fab. In 1 animal (Animal C65873) in Group 5, displayed sustained T-cell responses to the pool B peptides of AAV8 capsid were observed including preinjection baseline sample. The same animal had the highest levels of NAbs after administration of AAV2/8 vector. Another animal (Animal C68127) in the same group developed T-cells to all peptide pools of AAV8 capsid which were not sustained over time. This animal had antibodies against anti-VEGF Fab and the second highest level of NAbs. The animal lost expression of anti-VEGF Fab.

No other sustained T-cell responses to the transgene product were observed. No sustained T-cell responses were observed in animals in Group 6.

Example 4

Animal Models Useful for Evaluating AAV2/8.aVEGF and Anti-VEGF Transgene Product VEGF transgenic mice are used as animal models of Wet AMD. Two such models include the Rho/VEGF mouse model and the Tet/opsin/VEGF model.

A. Rho/VEGF Mouse Model

Rho/VEGF mice are transgenic mice in which the rhodopsin promoter drives expression of human vascular endothelial growth factor (VEGF165) in photoreceptors, causing new vessels to sprout from the deep capillary bed of the retina and grow into the subretinal space, starting at postnatal Day 10. The production of VEGF is sustained and therefore the new vessels continue to grow and enlarge and form large nets in the subretinal space similar to those seen in humans with neovascular age-related macular degeneration. See Tobe, Takao, et al. "Evolution of neovascularization in mice with overexpression of vascular endothelial growth factor in photoreceptors." Investigative ophthalmology & visual science 39.1 (1998): 180-188.

An enzyme-linked immunosorbent assay (ELISA) can be performed as follows. Briefly, plates are coated with 1 μg/mL of VEGF overnight at 4° C. 1% BSA is used as blocking buffer and is allowed to incubate at room temperature for 1 hour at 200 μL per well. Samples are loaded in duplicate at 100 μL per well and incubated for 1 hour at 37° C., followed by a second blocking buffer incubation. The primary antibody is a goat Anti-Human IgG H&L conjugated with Biotin which is left to incubate for 1 hour at room temperature at 100 μL per well. Secondary antibody is a 1:30,000 dilution of Streptavidin, loaded at 100 μL per well and incubated at room temperature for 1 hour. TMB solution is used as detection substrate (0.1M NaOAc Citric Buffer (pH 6.0), Hydrogen Peroxide, 100× TMB Stock), loaded at 150 μL per well and incubated at room temperature for 30 minutes without exposure to light. 50 μL of stop solution (2N $H_2SO_4$) is added to each well, and each plate was then read at 450 nm-540 nm.

In one study performed using this model and a test AAV8.aVEGF as described in the preceding examples, the ELISA results were as follows:

| | Dose (GC/eye) | Eye 1R | Eye 1L | Eye 2R | Eye 2L | Eye 3R | Eye 3L |
|---|---|---|---|---|---|---|---|
| AAV8.aVEGF | 1.00E+10 | 0.00 | 0.00 | 0.00 | 0.00 | 0.00 | 0.00 |
| AAV8.aVEGF | 1.00E+08 | 0.00 | 0.00 | 0.00 | 0.00 | 0.00 | 313.58 |
| AAV8.aVEGF | 3.00E+08 | 0.00 | 0.00 | 0.00 | 0.00 | 0.00 | 0.00 |
| AAV8.aVEGF | 1.00E+09 | 0.00 | 530.45 | 0.00 | 0.00 | 324.01 | 0.00 |
| AAV8.aVEGF | 3.00E+09 | 0.00 | 0.00 | 0.00 | 0.00 | 208.71 | 0.00 |
| AAV8.aVEGF | 1.00E+10 | 232.23 | 239.19 | 139.30 | 0.00 | 0.00 | 0.00 |

| Vector | Dose (GC/eye) | Eye 4R | Eye 4L | Eye 5R | Eye 5L |
|---|---|---|---|---|---|
| Empty | 1.00E+10 | 0.00 | 0.00 | 0.00 | 0.00 |
| AAV8.aVEGF | 1.00E+08 | 0.00 | 251.56 | 0.00 | 0.00 |
| AAV8.aVEGF | 3.00E+08 | 0.00 | 0.00 | 0.00 | 0.00 |
| AAV8.aVEGF | 1.00E+09 | 0.00 | 564.75 | 0.00 | 0.00 |
| AAV8.aVEGF | 3.00E+09 | 355.31 | 207.95 | | |
| AAV8.aVEGF | 1.00E+10 | 134.53 | 0.00 | 214.05 | 167.79 |

Anti-VEGF FAb levels are shown in ng/eye.

B. Tet/Opsin/VEGF Mouse Model

Tet/opsin/VEGF mice are transgenic mice that are normal until given doxycycline in drinking water. Doxycycline induces very high photoreceptor expression of vascular endothelial growth facto r(VEGF), leading to massive vascular leakage, culminating in total exudative retinal detachment in 80-90% of mice within 4 days of induction. See, Ohno-Matsui, Kyoko, et al. "Inducible expression of vascular endothelial growth factor in adult mice causes severe proliferative retinopathy and retinal detachment." The American journal of pathology 160.2 (2002): 711-719.

The ELISA can be performed as described in Part A of this Example. In one study performed using this model and a test AAV8.aVEGF as described in the preceding examples, the ELISA results were as follows. Results are shown in the tables below as the average±standard deviation (Std).

| | | | Mouse Eye ID's | | | |
|---|---|---|---|---|---|---|
| Sample | Vector | Dose (GC/eye) | 1R Avg ± Std | 1L Avg ± Std | 2R Avg ± Std | 2L Avg ± Std |
| Empty | Empty | 1.00E+10 | 0.00 ± 0.00 | 0.00 ± 0.00 | 0.00 ± 0.00 | 0.00 ± 0.00 |
| 1.00E+11 | AAV8.aVEGF | 1.00E+08 | 0.00 ± 0.00 | 216.34 ± 14.85 | 0.00 ± 0.00 | 0.00 ± 0.00 |
| 3.00E+11 | AAV8.aVEGF | 3.00E+08 | 88.23 ± 0.10 | 106.54 ± 1.01 | 0.00 ± 0.00 | 0.00 ± 0.00 |
| 1.00E+12 | AAV8.aVEGF | 1.00E+09 | 424.07 ± 19.26 | 0.00 ± 0.00 | 344.51 ± 30.67 | 0.00 ± 0.00 |
| 3.00E+12 | AAV8.aVEGF | 3.00E+09 | 581.28 ± 50.45 | 175.23 ± 20.45 | 254.13 ± 21.33 | 477.85 ± 34.54 |
| 1.00E+13 | AAV8.aVEGF | 1.00E+10 | 366.10 ± 20.76 | 309.06 ± 2.45 | 234.42 ± 4.78 | 173.46 ± 1.86 |

| | | | Mouse Eye ID's | | | | | |
|---|---|---|---|---|---|---|---|---|
| Sample | Vector | Dose (GC/eye) | 3R Avg ± Std | 3R Avg ± Std | 4R Avg ± Std | 4L Avg ± Std | 5R Avg ± Std | 5L Avg ± Std |
| Empty | Empty | 1.00E+10 | 0.00 ± 0.00 | 0.00 ± 0.00 | 0.00 ± 0.00 | 0.00 ± 0.00 | 0.00 ± 0.00 | 0.00 0.00 |
| 1.00E+11 | AAV8.aVEGF | 1.00E+08 | 0.00 ± 0.00 | 0.00 ± 0.00 | 0.00 ± 0.00 | 0.00 ± 0.00 | 0.00 ± 0.00 | 322.39 ± 23.43 |
| 3.00E+11 | AAV8.aVEGF | 3.00E+08 | 0.00 ± 0.00 | 0.00 ± 0.00 | 88.25 ± 1.96 | 0.00 ± 0.00 | 150.83 ± 26.63 | 444.96 ± 54.45 |
| 1.00E+12 | AAV8.aVEGF | 1.00E+09 | 0.00 ± 0.00 | 0.00 ± 0.00 | 537.61 ± 17.07 | 0.00 ± 0.00 | 0.00 ± 0.00 | 0.00 ± 0.00 |
| 3.00E+12 | AAV8.aVEGF | 3.00E+09 | 366.10 ± 23.68 | 285.85 ± 27.94 | 456.01 ± 27.81 | 155.71 ± 12.75 | 778.20 ± 143.25 | 270.15 ± 10.85 |
| 1.00E+13 | AAV8.aVEGF | 1.00E+10 | 498.95 ± 26.64 | 289.96 ± 8.95 | 291.74 ± 7.96 | 338.82 ± 6.03 | 165.10 ± 4.85 | 301.23 ± 21.10 |

C. Other Animal Models

Other animal models of Wet AMD are utilized. In the laser trauma model, high-powered, focused laser energy is used to induce a break in Bruch's membrane. Subretinal injection of matrigel, VEGF, macrophages, lipid hydroperoxide, and/or polyethylene glycol induces choroidal neovascularization (CNV), a wet AMD pathology. See Pennesi, Mark E., Martha Neuringer, and Robert J. Courtney. "Animal models of age related macular degeneration." Molecular aspects of medicine 33.4 (2012): 487-509.

Optimized rAAV.aVEGF vectors are generated, diluted and delivered into subretinal space of the transgenic mice eye with dosage described in the previous examples. Expressions of reporter genes, VEGF and anti-VEGF antibodies in the eye and/or plasma are determined by PCR, qPCR, ddPCR, oqPCR, Western Blot and ELISA as described in previous Examples. Electron Microscopy and Immunohistochemical analysis are also performed to evaluate the retinal neovascularization. The number of lesions per retina, area per lesion, neovascularization area per retina and traction retinal detachment Histopathological Evaluation of Retinas are quantified.

Example 5

Assessment of Expression of Anti-VEGF Fab (Transgene Product) in Cynomolgus Monkeys This study was conducted to assess the expression of the anti-VEGF Fab (transgene product) and to evaluate toxicity, immunogenicity, and biodistribution of an AAV8 vector expressing the anti-VEGF Fab following its administration in cynomolgus monkeys. In this report, expression of the transgene product and immunogenicity of the vector are described. Animals were administered an AAV2/8.aVEGF vector as described in these Examples or FFB-314 (control article) subretinally. Expression of transgene product in anterior chamber fluid and blood was determined by enzyme linked immunosorbent assay (ELISA). Immunogenicity was assessed by the presence of neutralizing antibodies (NAbs) against AAV8 capsid before and after administration. The transgene product is expressed in anterior chamber fluid of all animals administered the vector. The transgene product is not expressed in blood. Increase in levels of NAbs was observed in 1 animal (C73723) administered AAV8.aVEGF; this animal had pre-existing NAbs.

Animals in this study were administered a single dose of $1.00\times10^{12}$ genome copies (GC)/eye of AAV8.CB7.CI.aVEGFv3.rBG or formulation buffer, FFB-314.

AAV8.CB7.CI.aVEGFv3.RBG and FFB-314 were administered subretinally into the right eye (confirmed visually by appearance of a dome shaped retinal detachment/retinal bleb under microscope) in a total volume of 100 μL.

Animals were randomized using www.jamestease.co.uk/team-generator. One of 4 animals was selected using www.randomizer.org/ by random and assigned to Group 2. The remaining 3 animals were assigned to Group 1. Group designation and dose levels for this study are presented in the following Table.

| Group | Treatment[a] | Dose (GC/eye) | No. of animals | Follow-up |
|---|---|---|---|---|
| 1 | AAV8.aVEGF | $1.00 \times 10^{12}$ | 1 M, 2 F | 7 days |
| 2 | FFB-314 | NA | 1 M | |

Abbreviation:
F = female;
GC = genome copies;
M = male;
NA = not applicable;
No. = number.
[a]Test and control articles were administered subretinally into the right eye.

Animals were euthanized on Study day 7. Samples of anterior chamber fluid and blood were collected for determination of expression of the anti-VEGF FAb transgene product and/or the presence of NAbs against AAV8 capsid.

Subretinal injections were performed as described in the earlier examples. Collection of anterior chamber fluid was as described in earlier examples. For the ELISA, ninety-six-well, round-bottom plates were coated with 1 μg/mL of VEGF for expression of the anti-VEGF Fab transgene product, or 0.5 μg/mL of a commercial anti-VEGF Fab for expression of IgM and IgG against the Anti-VEGF Fab transgene product. The ELISA methods were as described in the earlier examples.

The following primary antibodies were used: 1.0 mg/mL Goat Anti-Human IgG H&L (Biotin) preadsorbed at a 1:10000 dilution in PBS; 0.5 mg/mL Goat Anti-Human IgG H&L (Biotin) preadsorbed at a 1:5000 dilution in PBS. The following secondary antibody was used: 1 mg/mL Streptavidin (HRP) at a 1:30000 dilution in PBS.

Neutralizing Antibody Assay

Neutralizing antibody responses to AAV8 capsid were analyzed as follows. A Poly D lysine-coated 96-well black-walled/clear-bottom plate was seeded with human embryonic kidney 293 (HEK293) cells at $1\times10^5$ cells/well (referred to as a cell plate); the plate was incubated at 37° C. overnight. The following day, the serum sample was heat-inactivated at 56° C. for 35 minutes. The heat-inactivated sample and a recombinant vector (AAV8.CMV.LacZ at $1\times10^9$ GC/well; provided by the Penn Vector Core at the University of Pennsylvania) were used to formulate a serum-vector plate. The recombinant vector was diluted in serum-free Dulbecco's Modified Eagle Medium (DMEM) and incubated with 2-fold serial dilutions (starting at 1:5) of the heat inactivated samples at 37° C. for 1 hour. Prior to combining the serum vector plate with the cell plate, the HEK293 cells (now at $2\times10^5$ cells/well) were infected with wild type HAdV5 (90 particles/cell) and incubated at 37° C. for 2 hours. After the incubation, the serum-vector plate and the cell plate were combined and incubated at 37° C. for 1 hour. Following the incubation, an equal volume of 20% fetal bovine serum (FBS) with DMEM was added to each well and the combined plate was incubated at 37° C. for additional 18 to 22 hours. The next day, the combined plate was washed with PBS and the HEK293 cells were lysed, and the lysate was developed using a mammalian β-galactosidase bioluminescence assay kit per the manufacturer's instructions. As a control, mouse serum was used instead of serum sample. The resulting luminescence was measured using a SpectraMax® M3 microplate luminometer. The resulting NAb titer was reported as the serum dilution that inhibits transduction of vector by at least 50% compared to the mouse serum.

Statistical Analyses

Average and standard deviation values for concentrations of the Anti-VEGF Fab transgene product in anterior chamber fluid and blood were calculated using Microsoft Office Excel 2010.

Results

Expression of Anti-VEGF Fab Transgene Product in Anterior Chamber Fluid

The Anti-VEGF Fab transgene product was not expressed in anterior chamber fluid of the animal administered FFB-314. The anti-VEGF Fab transgene product was expressed in anterior chamber fluid collected from the right eye of all animals administered AAV8. aVEGF test vector. No expression was observed in the left eye. No difference in expression of the Anti-VEGF Fab transgene product between males and females was observed.

Expression of Anti-VEGF Fab Transgene Product in Blood

In some patients administered a single IVT injection of Lucentis, ranibizumab was observed in serum (Xu, Invest Ophthalmol Vis Sci, 54: 1616-24(2013)). To determine if subretinal administration of AAV8.aVEGF test vector results in systemic exposure to the Anti-VEGF Fab transgene product, its concentrations were measured in serum.

Expression of the Anti-VEGF Fab transgene product was below nonspecific background levels in blood of the animal administered FFB-314 and all animals administered the AAV8.aVEGF vector as compared to matched pre-injection level.

Presence of Neutralizing Antibodies Against AAV8 Capsid

Baseline levels of NAbs against AAV8 capsid were determined in serum from blood samples collected on Study day 0. The limit of detection was a 1:5 dilution; titers of <5 were considered undetectable.

| | Animal | NAb titer | |
|---|---|---|---|
| Treatment | Identification | Baseline | Study day 7 |
| FFB-314 | C64956 | 5 | 40 |
| AAV2/8.aVEGF | C73723 | 10 | 320 |
| $1.00\times10^{12}$ GC/eye | C74431 | <5 | <5 |
| | C65027 | 40 | 10 |

Abbreviations:
GC = genome copies;
NAb = neutralizing antibody.
Note:
the NAb titer values reported are the reciprocal dilutions of serum at which the relative luminescence units (RLUs) were reduced for 50% comparted to control wells (without sample). The limit of detection was 1:5 dilution of sample.

Animal administered FFB-314 had pre-existing NAbs against AAV8 capsid (see preceding Table). One animal (C74431) administered AAV8.aVEGF test vector did not have detectable NAbs to AAV8 capsid. In 2 animals (C73723, C65027) administered AAV8.aVEGF test vector, pre-existing NAbs against AAV8 capsid were observed, which persisted on Day 7 (see preceding Table).

Toxicity was evaluated based on clinical observations, body weights, indirect ophthalmoscopy, hematology, coagulation, clinical chemistry, and gross pathologic findings. There were no mortalities or unscheduled sacrifices in this study. No adverse clinical observations related to AAV8.aVEGF test vector or the Anti-VEGF Fab transgene product were noted for any animal Several animals exhibited intermittent transient bouts of diarrhea with no impact to the welfare of the animals because body weights remained stable. No clinically meaningful changes in body weight during the study were observed for any animal. No adverse observations related to AAV8.aVEGF Test vector or the Anti-VEGF Fab transgene product were noted during indirect ophthalmoscopy in any animal No clinically significant changes in hematology, coagulation, or clinical chemistry parameters were observed in any animal. All clinical pathology parameters were within normal ranges in all animals. There were no gross finding in animals C64956 and C74431. The surfaces of the right and left kidney of C73723 were pale. There was a focal lesion on the liver in C65027. In conclusion, there were no major toxicology findings.

The test vector in Examples 6-11 is rAAV8.CB7.CI.aVEGFrv3.rBG.

Example 6

Expression of AAV2/8.aVEGF Vector in Cynomolgus Monkeys

This study was conducted to assess expression of the anti-VEGF transgene product and to evaluate toxicity, immunogenicity, and effect on normal retinal function of AAV2/8.aVEGF and the anti-VEGF transgene product, and shedding of AAV8.aVEGFin cynomolgus monkeys. The study is ongoing.

An AAV2/8.aVEGF described earlier in the examples is used this study. The vector is diluted in Dulbecco's phosphate-buffered saline (DPBS) with 0.001% Pluronic F-68. As a control article, FFB-314 (DPBS with 0.001% Pluronic F-68) was used. The study is ongoing. The results presented are based on the data collected at Month 3.

Macaques were used because they are the closest species to humans for studying retinal diseases. These monkeys and humans have similar eye anatomy, including fovea. The dimensions of the eyes are comparable, which allows determination of the human dose based on relative retinal areas.

Animals in this Example were administered a single dose of $1.00\times10^{10}$ genome copies (GC)/eye of AAV8.aVEGF, or $1.00\times10^{12}$ GC/eye of AAV8.aVEGF, or FFB-314. AAV8.aVEGF and FFB-314 were administered subretinally into the right eye (confirmed visually by appearance of a dome-shaped retinal detachment/retinal bleb under microscope) in a total volume of 100 µL.

Animals were randomly assigned to 6 sets of 4 animals per set using www.jamestease.co.uk/team-generator. After assigning the sets, 1 of 4 animals from each of the 6 sets was selected using www.randomizer.org/ at random and assigned to groups administered FFB-314 for each given administration date (Groups 2, 4, 6, 8, 10, and 12). The remaining 3 animals were assigned to groups administered $1\times10^{12}$ GC/eye or $1\times10^{10}$ GC/eye AAV8.aVEGF (Groups 1, 3, 5, 7, 9, and 11). Group designation and dose levels for Examples 6 and 7 are presented below.

Group Designation and Dose Levels

| Group | Treatment[a] | Dose (GC/eye) | Number (#) of animals | Follow-up |
|---|---|---|---|---|
| 1 | AAV8.aVEGF test vector | $1.00 \times 10^{12}$ | 1 M, 2 F | 3 months |
| 2 | FFB-314 | NA | 1 M | |
| 3 | AAV8.aVEGF test vector | $1.00 \times 10^{10}$ | 2 M, 1 F | |
| 4 | FFB-314 | NA | 1 M | |
| 5 | AAV8.aVEGF test vector | $1.00 \times 10^{12}$ | 2 M, 2 F[b] | 1 year |
| 6 | FFB-314 | NA | 1 F | |
| 7 | AAV8.aVEGF test vector | $1.00 \times 10^{10}$ | 1 M, 2 F | |
| 8 | FFB-314 | NA | 1 F | |
| 9 | AAV8.aVEGF test vector | $1.00 \times 10^{12}$ | 2 M, 1F | 7 days |
| 10 | FFB-314 | NA | 1 M | |
| 11 | AAV8.aVEGF test vector | $1.00 \times 10^{10}$ | 2 M, 1 F | |
| 12 | FFB-314 | NA | 1 F | |

Abbreviation:
F = female;
GC = genome copies;
M = male;
NA = not applicable;
No. = number.
[a]Test and control articles were administered subretinally into the right eye.
[b]One female animal was euthanized during the study because of severe eye infection. The animal was replaced.

Samples of anterior chamber fluid and blood were collected for determination of expression of the Anti-VEGF Fab transgene product Subretinal injections were performed as described in earlier examples.

A. Pharmacology

The results presented are based on the data collected at Month 3. In this report, expression of the anti-VEGF Fab transgene product is described.

1. Methods

Animals were administered AAV8.aVEGF test vector or FFB-314 (control article) subretinally. Expression of anti-VEGF transgene product in anterior chamber fluid and blood was determined by enzyme linked immunosorbent assay (ELISA) which was performed as described in previous examples.

2. Pharmacology Results (a) Expression of Transgene Product in Anterior Chamber Fluid:

The transgene product was not expressed in anterior chamber fluid of any animal administered FFB-314. The transgene product was expressed in anterior chamber fluid of all animals administered AAV8.aVEGF test vector. Onset of expression was rapid, generally within 7 days. Steady-state expression levels were achieved within 1 month. All animals continued to express the transgene product at steady-state levels until the last evaluated timepoint. However, overall expression levels of the anti-transgene product were greater in animals administered $1.00\times10^{12}$ GC/eye of AAV8.aVEGF test vector. No difference in expression of the transgene product between males and females was observed.

(b) Expression of Transgene Product in Blood

In some patients administered a single IVT injection of Lucentis, ranibizumab was observed in serum (Xu, Invest Ophthalmol Vis Sci. 2013 Mar. 5, 54(3):1616-24). To determine if subretinal administration of an AAV2/8.aVEGF test vector described in these examples results in systemic exposure to the anti-VEGF Fab transgene product, its concentrations were measured in serum. Expression of the anti-VEGF Fab transgene product was below nonspecific background levels in blood of all animals administered AAV8.aVEGF test vector compared to matched pre-injection levels.

3. Conclusion:

Anti-VEGF Fab transgene product is expressed in anterior chamber fluid of all animals administered AAV8.aVEGF test vector.

Anti-VEGF Fab transgene product is not expressed in blood of any animal administered AAV8.aVEGF test vector.

B. Toxicology

In this report, evaluation of toxicity of an AAV2/8.aVEGF test vector is described. Animals were administered AAV8.aVEGF test vector or FFB-314 (control article) subretinally. Toxicity was evaluated based on clinical observations, body weights, ocular pressure, indirect ophthalmoscopy, spectral domain optical coherence tomography, hematology, coagulation, clinical chemistry, and gross pathologic findings, and histopathologic findings.

Ocular pressure was evaluated via rebound tonometry (TonoVet). This method is easy to use and does not require topical anesthesia. Rebound tonometry estimates OP by using an induction coil to magnetize a small, plastic-tipped metal probe that is launched against the cornea. As the probe rebounds back to the instrument, it creates an induction current from which the OP is calculated. Up to 2 readings were taken, from which an average OP was determined, and accuracy of the results was indicated. Application with the device was performed according to the manufacturer's instructions.

Retinal structure (at a micron-level resolution) was evaluated by in vivo, non-invasive, cross-sectional retinal microscopy with SD-OCT (Spectralis OCT, Heidelberg Engineering, Carlsbad, Calif.). Pupils were dilated with phenylephrine 2.5% and tropicamide 1%. En-face retinal imaging was performed with near infrared (NIR) reflectance (REF) and in a subset of animals with NIR fundus autofluorescence (FAF) using the scanning laser ophthalmoscope of this imaging system. Spectral domain optical coherence tomography scanning was performed with 9 mm long horizontal and vertical cross-sections through the fovea and overlapping 30×25 mm raster scans extending into the near midperiphery.

The only adverse AAV8.aVEGF test vector—related finding was significant retinal thinning and loss of photoreceptors observed by spectral domain optical coherence tomography in animals administered $1.00\times10^{12}$ GC/eye of test vector.

C. Electroretinogram (ERG)

In this subpart, assessment of effects of AAV8.aVEGF test vector and the anti-VEGF Fab transgene product on normal retinal function is described. Animals were administered AAV8.aVEGF test vector or FFB-314 (control article) subretinally. Retinal function was evaluated by the full-field electroretinogram (ERG). The full-field ERG is a widely used electrophysiologic test of retinal function. Electroretinogram is a mass electrical potential generated by the retina in response to light stimulus. Usually, it is recorded by an electrode in contact with the corneal surface. Electroretinograms in this study were conducted in accord with the recommendations set by the International Society for Clinical Electrophysiology of Vision (ISCEV; McCulloch, Doc Ophthalmol. 2015 February; 130(1):1-12. 2015). The results presented are based on the data collected at Month 3. In this report, assessment of effects of AAV8.aVEGF test vector and the anti-VEGF Fab transgene product on normal retinal function is described. Animals were administered AAV8.aVEGF test vector or FFB-314 (control article) subretinally. Retinal function was evaluated by the full-field electroretinogram. In summary, administration of $1.00\times10^{10}$ genome copies (GC)/eye of AAV8.aVEGF test vector do not impair retinal function. In contrast, administration of $1.00\times10^{12}$ GC/eye of AAV8.aVEGF test vector impairs retinal function.

1. Electroretinogram (ERG) Parameters

An electroretinogram (ERG) generated usually when all retinal cells are active respond to a flash stimulation (a dark-adapted animal, moderate to intense flash). The 2 components are the following:

- a-wave: cornea-negative signal, first after the flash. Origin: photoreceptor photocurrent, the most direct signature of photoreceptor function.
- b-wave: cornea-positive signal following the a-wave generated mostly by on-bipolar cells (second order neurons downstream from photoreceptors).

In this study, the following International Society for Clinical Electrophysiology of Vision (ISCEV) standard and additional protocols were used:

- Dark-adapted rod ERG: Stimulus intensity: 0.01 to 0.02 cd s $m^{-2}$. Response: b-wave only, no a-wave. Source: rod "on" bipolar cells (second order neurons driven by input from rods). Meaning: a measure of rod function. Designation in data sheets: "Dim flash".
- Dark-adapted standard flash ERG: Stimulus intensity: 3 cd s $m^{-2}$. Response: combined rod-cone a- and b-waves; 60% to 70% of the signal being generated by the rod-driven pathway. Source: photoreceptors, both rods and cones (a-wave); higher order neurons driven by both rods and cones. Meaning: a measure of mostly rod function; less sensitive to the state of dark adaptation and less variable than the "dim flash" response. Designation in data sheets: "Standard flash".
- Dark-adapted bright flash ERG: Stimulus intensity: 10 cd s $m^{-2}$. Response and meaning: same as for the "standard flash" response, but bright flash response is larger in magnitude and may be less variable. Designation in data sheets: "Bright flash".
- Light-adapted standard flash cone ERG: Stimulus intensity: 3 cd s $m^{-2}$, delivered in presence of 30 cd $m^{-2}$ background light after 5 minutes of light adaptation. Response: a- and b-waves generated by cone-driven pathways. Meaning: in presence of background light which completely desensitizes rods the ERG is produced exclusively by cones and cone-driven secondary retinal neurons and is a measure of the cone function. Designation in data sheets: "Standard cone ERG".
- Light-adapted bright flash cone ERG (in addition to the ISCEV standard): Stimulus intensity: 10 cd s $m^{-2}$, delivered in presence of 30 cd $m^{-2}$ background light after 5 minutes of light adaptation. Response and meaning: cone-driven ERG as in case of the "Standard cone ERG", but of greater magnitude and potentially less variable.

ERG measures (a-wave amplitude, a-wave implicit time, b-wave amplitude, b-wave implicit time) were summarized using mean and standard deviation (SD) for treated eyes and control eye, and for each treatment (FFB-314 (vehicle) groups, AAV8.aVEGF test vector $1.00\times10^{10}$ GC/eye groups, AAV8.aVEGF test vector $1.00\times10^{12}$ GC/eye groups). The paired t-test was used for comparing the ERG measures between AAV8.aVEGF test vector (treated) eye and FFB-314 (control eye), and for comparison between post-injection vs. pre-injection. The two-sample t-test was used for comparing the ERG measures between AAV8.aVEGF test vector $1.00\times10^{10}$ GC/eye groups vs. FFB-314 (vehicle) groups, AAV8.aVEGF test vector $1.00\times10^{12}$ GC/eye groups vs. FFB-314 (vehicle) groups, and AAV8.aVEGF test vector $1.00\times10^{12}$ GC/eye groups vs. AAV8.aVEGF test vector $1.00\times10^{10}$ GC/eye groups. The t-test is appropriate even when the sample size is small [Winter J C F. Using the Student's t-test with extremely small sample sizes. Practical Assessment, Research and Evaluation. 2013; 18 (10). Available online: pareonline.net/-getvn.asp?v=18&n=10] 1 or the data are not normally distributed. See, Shuster J J. Diagnostic for assumptions in moderate to large simple clinical trials: do they really help? Statist. Med. 2005; 24:2431-2438; Ganju J. D. Comment on "Diagnostic for assumptions in moderate to large simple clinical trials: do they really help?" Statist. Med. 2006; 25:1798-1800.] All the statistical analyses were performed in SAS v9.4 (SAS Institute Inc., Cary, N.C.), and two-sided p-value≤0.05 is considered as statistically significant.

2. Results

Anti-VEGF Fab transgene product was expressed in all animals administered AAV8.aVEGF test vector (see pharmacology results in Part A of this Example). Retinal function 3 months following administration of AAV8.aVEGF test vector or FFB-314 (post-injection) was compared to retinal function before administration (pre-injection) for treated and untreated eyes. An animal in Group 8 was excluded from data analyses due to an unobtainable ERG following administration of FFB-314.

| ERG test | Parameter | Stimulus intensity ($cd \cdot s \cdot m^{-2}$) | FFB-314 Mean (SD) | Low dose Mean (SD) | High dose Mean (SD) | p-value Low dose vs. FFB-314 | High dose vs. FFB-314 | High dose vs. Low dose |
|---|---|---|---|---|---|---|---|---|
| Dark-adapted | a-wave amplitude (uv) | 3 | 68.2 (10.0) | 58.4 (17.4) | 31.3 (12.4) | 0.4 | 0.003 | 0.01 |
| | | 10 | 113.8 (0.9) | 109.8 (25.6) | 54.1 (21.0) | 0.8 | 0.002 | 0.002 |
| Light-adapted | a-wave amplitude (uv) | 3 | 19.9 (4.1) | 18.7 (3.5) | 9.8 (3.7) | 0.65 | 0.007 | 0.002 |
| | | 10 | 36.1 (7.1) | 33.3 (7.4) | 19.5 (8.6) | 0.61 | 0.02 | 0.01 |

Abbreviations:
ERG = electroretinogram;
GC = genome copies;
SD = standard deviation.
Low dose: $1.00 \times 10^{10}$ GC/eye of AAV8.aVEGF test vector
High dose: $1.00 \times 10^{12}$ GC/eye of AAV8.aVEGF test vector.

a. Comparison of Retinal Function Between Treatment Groups

For treated eyes, retinal function post-injection was comparable between animals in low-dose group ($1.00\times10^{10}$ GC/eye of AAV8.aVEGF test vector) and FFB-314 group (see preceding Table). For treated eyes, retinal function post-injection in animals in high-dose group ($1.00\times10^{12}$ GC/eye of AAV8.aVEGF test vector) was significantly reduced compared to animals in FFB-314 group (see preceding Table). For treated eyes, retinal function post-injection in animals in high-dose group was significantly reduced compared to animals in low-dose group (see preceding Table). For untreated eyes, retinal function post-injection was comparable to pre-injection for all groups.

b. Comparison of Retinal Function Within Treatment Groups

For treated eyes, in animals in low-dose and FFB-314 groups, retinal function post-injection was comparable to matched pre-injection baseline. For treated eyes, in animals in high-dose group, retinal function post-injection was significantly reduced compared to matched pre-injection baseline. For untreated eye, retinal function post-injection was comparable to matched pre-injection baseline.

E. Virus Shedding

Shedding of AAV8.aVEGF test vector was determined by quantitative PCR analysis targeting transgene-specific sequence in samples of tears, nasal secretion, serum, saliva, urine, and feces. Samples were collected before and after administration of AAV8.aVEGF test vector or FFB-314. AAV8.aVEGF test vector DNA was readily detectable in most samples collected from animals administered AAV8.aVEGF test vector. The presence of AAV8.aVEGF DNA was dose-dependent, transient, and decreased over time.

F. Immunogenicity

In this study, immunogenicity of AAV8.aVEGF test vector and the anti-VEGF Fab transgene product is described. Immunogenicity was assessed by the following:

The presence of IgM and IgG antibodies against the anti-VEGF Fab transgene product using enzyme linked immunosorbent assay (ELISA);

The presence of neutralizing antibodies (NAbs) against AAV8 capsid using NAb assay;

T-cell responses to AAV8.aVEGF test vector and the anti-VEGF Fab transgene product using enzyme linked immunospot (ELISPOT) assay.

Animals were administered AAV8.aVEGF test vector or FFB-314 (control article) subretinally as described earlier in this Example. No sustained IgM, IgG, or T-cell responses to the anti-VEGF Fab transgene product were observed in any animal Animals administered $1.00\times10^{12}$ GC/eye AAV8.aVEGF test vector developed a higher neutralizing antibody (Nab) response to AAV8 capsid than animals administered $1.00\times10^{10}$ GC/eye AAV8.aVEGF test vector. The NAb response was higher in animals with pre-existing NAbs. Slightly increased T-cell responses against AAV8 capsid were observed in 2 of 6 animals administered $1.00\times10^{12}$ GC/eye test vector.

Results

Anti-VEGF Fab transgene product was expressed in all animals administered AAV8.aVEGF test vector (Example 6). There was no significant IgM against the Anti-VEGF Fab transgene product in serum or in anterior chamber fluid of animals administered FFB-314. IgG against the Anti-VEGF Fab transgene product above baseline level was not observed in animals administered FFB-314.

IgM against the anti-VEGF Fab transgene product was elevated above the baseline level in anterior chamber fluid of 1 animal administered $1.00\times10^{10}$ GC/eye of AAV8.aVEGF test vector. However, as there was no corresponding elevation in the serum, therefore this observation was not clinically significant. IgG against the anti-VEGF Fab transgene product above baseline level was not observed in this treatment group.

IgM against the anti-VEGF Fab transgene product above baseline level was observed in anterior chamber fluid of 1 animal administered $1.00\times10^{12}$ GC/eye of AAV8.aVEGF test vector. However, as there was no corresponding elevation in the serum, this observation was not clinically meaningful. IgG against the anti-VEGF Fab transgene product above baseline level was observed in serum and anterior chamber fluid from another animal and in anterior chamber fluid only of a third animal in this treatment group. However, as neither was preceded by any detectable IgM, these observations were not clinically meaningful. The presence of IgG in these animals was not associated with loss of expression of the anti-VEGF Fab transgene product.

Baseline levels of NAbs against AAV8 capsid were determined in serum from blood samples collected on Study day 0. The limit of detection was a 1:5 dilution; titers of <5 were considered undetectable.

In 4 of 6 animals administered FFB-314, pre-existing NAbs were not observed. Two animals that were followed by Study day 90 did not develop NAbs. In 2 animals administered FFB-314, pre-existing NAbs were observed. The levels of NAbs in these 2 animals fluctuated no more than 2 two-fold serial dilutions during the study.

In 2 of 9 animals administered $1.00\times10^{10}$ GC/eye of AAV8.aVEGF test vector, pre-existing NAbs were not observed. In 1 animal that was followed by Study day 90, NAbs were not observed following administration of AAV8.aVEGF test vector. In animals with pre-existing NAbs, their levels increased by no more than 4 two-fold serial dilutions following administration of AAV8.aVEGF test vector.

In 4 of 9 animals administered $1.00\times10^{12}$ GC/eye of AAV8.aVEGF test vector, pre-existing NAbs were not observed. Regardless of status of pre-existing NAbs, in most animals, an increase in NAb response of up to 9 two-fold serial dilutions was observed following administration of AAV8.aVEGF. This response was sustained through the Study day 90.

T-cell responses to AAV8.aVEGF test vector were observed in 1 animal administered FFB-314 at a single timepoint. In 1 animal, non-specific T cell responses were observed at all timepoints.

Sustained T-cell responses to AAV8.aVEGF test vector were not observed in animals administered $1.00\times10^{10}$ GC/eye of test vector.

In 4 of 6 animals administered $1.00\times10^{12}$ GC/eye of AAV8.aVEGF test vector, low-level immune response against AAV8.aVEGF test vector was observed. In 2 of 4 animals with low-level immune response, a sustained (more than 2 consecutive time points) response was observed. Sustained T-cell responses to the anti-VEGF Fab transgene product were not observed in any animal.

No sustained IgM, IgG, or T-cell responses to the Anti-VEGF Fab transgene product were observed in any animal.

Animals administered $1.00\times10^{12}$ GC/eye AAV8.aVEGF test vector developed a higher NAb response to AAV8.aVEGF test vector than animals administered $1.00\times10^{10}$ GC/eye of the same test vector. The NAb response was higher in animals with pre-existing NAbs. Slightly increased T-cell responses against this AAV8.aVEGF test vector were observed in 2 of 6 animals administered $1.00\times10^{12}$ GC/eye the AAV8.aVEGF test vector.

Example 7

Evaluation of Distribution of AAV2/8 Vector mRNA and Anti-VEFG Fragment Antigen-Binding Following Subretinal Administration of AAV2/8 Vectors in Cynomolgus Monkeys This study was conducted to evaluate retinal distribution of AAV2/8 vector mRNA and distribution of anti-VEGF Fab throughout the eye following subretinal administration of AAV2/8 vector utilizing tissues from Example 3, Example 5 and Example 6. Levels of mRNA in different parts of retina were assessed by quantitative reverse transcription-polymerase chain reaction and by in situ hybridization. Concentrations of anti-VEGF Fab were determined in retinal sections, anterior chamber fluid and vitreous humor by enzyme-linked immunosorbent assay.

mRNA for AAV2/8 vector is distributed throughout the entire retina following subretinal administration. Similarly, anti-VEGF Fab is distributed throughout the entire retina and is detected in both, vitreous and anterior chamber fluid.

| Vector |
|---|
| AAV2/8.UbC.PI.aVEGFv2.SV40 |
| AAV2/8.UbC.PI.aVEGFv3.SV40 |
| AAV2/8.CB7.CI.aVEGFv2.rBG |
| AAV2/8.CB7.CI.aVEGFv3.rBG |

Site of subretinal administration is denoted by a retinal bleb, which can be visualized by SD OCT. In all SD OCT images, retinal blebs are visible.

Levels of mRNA for AAV2/8.aVEGF Test Vector in Retina Determined by RT-qPCR mRNA for AAV8.aVEGF test vector was not detected in the retina of the animal administered FFB-314. mRNA for the AAV8.aVEGF test vector was detected in retinas of all animals administered the AAV8.aVEGF test vector. The highest level of mRNA was detected in the retinal sections that incorporated the site of the subretinal injection. However, mRNA for the AAV8.aVEGF test vector was also detected in sections outside of the injection bleb. mRNA levels in these sections were lower than those in the bleb. The levels were up to 4 logs lower in sections most peripheral to the injection blebs. In sections immediately adjacent to the injection bleb, the levels of mRNA were intermediate.

Expression of mRNA for AAV2/8 Vectors in Retina Determined by In Situ Hybridization (ISH)

Expression of mRNA for the AAV2/8 vector determined by ISH was high at the injection site. The transduced cells within retinal layers included RPE cells, photoreceptors, and ganglion cells. Expression of mRNA was lower when moving away from the injection site, disappearing almost completely in the areas most distal to the injection site.

Concentrations of Anti-VEGF Fab in Anterior Chamber Fluid, Vitreous, and Retina

Anti-VEGF Fab was expressed in retinas, vitreous, and anterior chamber fluid of eyes of all animals administered AAV2/8 vector (FIGS. 6-8). Expression in the vitreous was 3- to 9-fold higher than in the anterior chamber fluid. With the exception of 1 animal (C65873) in Group 5 (FIG. 8), maximal expression in the retinal segments was 1.2- to 3.6-fold higher than in the vitreous. This concentration gradient is likely a reflection of the mechanism of distribution of anti-VEGF Fab. Anti-VEGF Fab is secreted into vitreous by transduced retina and then diffuses form vitreous to the anterior chamber fluid. Of note, expression of anti-VEGF Fab throughout the retina is more uniform than expression of mRNA.

Overall, functional AAV2/8 vector is surprisingly distributed throughout the entire retina following subretinal administration as evidenced by the expression of the vector mRNA by the transduced cells, instead of being limited to the injection bleb. Anti-VEGF Fab is also surprisingly distributed throughout the entire retina including retinal segments that are peripheral to the injection bleb, and is detected in both, vitreous and anterior chamber fluid.

Example 8

Determination of Affinity for Binding of Anti-VEGF Transgene Product to Recombinant Human VEGF This study was conducted to determine affinity for binding of the Anti-VEGF Fab heavy and line chains product to recombinant human VEGF. Binding affinity was determined using Biacore 3000 system, based on surface plasmon resonance (SPR) technique. This technique is based on the plane-polarized light hitting a sensor chip under the conditions of total internal reflection. Interaction between immobilized ligands (e.g., VEGF) and interacting molecules (e.g., Anti-VEGF Fab transgene product) on the sensor chip causes a change in angle of reflectivity of plane-polarized light. This change is immediately detected by sensogram in real time as response units (Daghestani, Theory and applications of surface plasmon resonance, resonant mirror, resonant waveguide grating, and dual polarization interferometry biosensors. Sensors (Basel). 2010; 10(11): 9630-46.). The equilibrium binding affinity constant for binding of the Anti-VEGF Fab transgene product is consistent with published range for ranibizumab.

Example 9

Tissue Cross-Reactivity Study

The objective of this study was to assess using immunohistochemical techniques, the potential cross-reactivity of the Sponsor supplied antibody Fab fragment aVEGF transgene product with histologically prepared cryo-sections from a selected panel of human tissues.

Anti-VEGF Fab transgene product (1 mg/mL) ("Test product") and ranibizumab (0.97 mg/mL) were used for this study. Natural Human IgG Fab Fragment Protein (the "Control Article") was supplied at a protein concentration of 14.64 mg/mL. To facilitate immunohistochemical detection the Test transgene product, natural human IgG Fab fragment protein and ranibizumab were conjugated with biotin. The respective protein concentrations were 2.79 mg/mL, 2.88 mg/mL and 2.89 mg/mL. Cryo-sections from the control material and the human tissues for examination were prepared. The assessment of tissue viability indicated that the panel of human tissues was viable. Following slide evaluation of the control titration the following three concentrations of Test transgene product-Biotin: 5, 2.5 and 1.25 μg/mL, and the following concentration of ranibizumab-Biotin: 2.5 μg/mL, were selected for use in the tissue titration. In the tissue titration no specific positive staining was observed with anti-VEGF transgene product-Biotin or ranibizumab-Biotin in any of the tissues examined. All other observed staining was variable and considered to be non-specific.

Under the conditions of this study, antigen-specific binding of Test transgene product-Biotin and ranibizumab-Biotin was demonstrated in the positive control materials (human glioblastoma and VEGF protein spots). No similar staining was observed with Natural human IgG Fab fragment protein-Biotin or the antibody diluent at the concentrations examined in the tissue titration.

Example 10

Clinical Study

A rAAV8.aVEGF vector was selected for further study which provides the advantage of single sub-retinal administration, thereby reducing the burden of repeated injections. Continued expression of anti-VEGF Fab in NHP for over 6 months and reduction in neovascularization in an animal model of WAMD treated with an rAAV8.aVEGF vector have been demonstrated in pre-clinical studies, and safety of sub-retinal injection is evaluated in non-human primates. The initial clinical study evaluates the safety and transgene expression after a single sub-retinal injection of an rAAV8.aVEGF test vector as described above. Once injected sub-retinally, these vectors are expected to continue to release an anti-VEGF Fab transgene product and block the angiogenic signal thereby protecting the retina from further damage.

Each dosing cohort includes 3 subjects. The first 3 subjects enrolled start with the lowest dose and each group escalates. After each first rAAV8.aVEGF dose, there is a 4 week observation period for safety prior to the next patient being dosed. The primary safety endpoint is at 6 weeks post administration of rAAV8.aVEGF.

Primary Endpoints

Ocular and non-ocular safety assessment at 6 weeks, 24 weeks, 6 and 12 months post procedure.

Secondary Endpoints

Ocular and non-ocular safety over 106 weeks

Mean change from baseline in aqueous rAAV8.aVEGF protein over time

Mean change from baseline in BCVA over time

Proportion of subjects gaining or losing ≥15 letters compared to baseline as per BCVA at Week 26, Week 54, and Week 106

Mean change from baseline in CRT as measured by SD-OCT over time

Mean number of ranibizumab rescue injections over time

Time to 1st rescue ranibizumab injection

Mean change from baseline in CNV and lesion size and leakage area based on FA over time Immunogenicity measurements (NAb to AAV8, binding antibodies to AAV8, antibodies to aVEGF protein, and Enzyme-Linked ImmunoSpot [ELISpot]).

Vector shedding analysis in serum and urine.

Exploratory Endpoints:

Mean change from baseline over time in area geographic atrophy per fundus autoflorescence (FAF) Incidence of new area of geographic atrophy by FAF (in subjects with no geographic atrophy at baseline)

Proportion of subjects gaining or losing ≥ and ≥10 letters, respectively, compared with baseline as per BCVA Proportion of subjects who have a reduction of 50% in rescue injections compared with previous year Proportion of subjects with no fluid on SD-OCT For the present study, patients must have a diagnosis of neovascular age-related macular degeneration (wet AMD) and meet the following criteria.

Inclusion Criteria:

In order to be eligible to participate in this study, a subject must meet all of the following criteria. It is understood that one or more of these criteria may not be required for further studies and for treatment of other populations.

1. Males or females aged 50 years or above.
2. Sentinel subject for each dose cohort must have a BCVA≤20/100 and ≥20/400 (≤65 and ≥35 ETDRS letters) in the study eye.
   a. Following the sentinel subject evaluation, the rest of the subjects in the dose cohort must have a BCVA between ≤20/63 and ≥20/400 (≤75 and ≥35 ETDRS letters).
3. In the case both eyes are eligible, study eye must be the subject's worse-seeing eye, as determined by the Investigator.
4. Must have a documented diagnosis of subfoveal CNV secondary to AMD in the study eye.
   a. CNV lesion characteristics: lesion size needs to be less than 10 disc areas (typical disc area is 2.54 mm2), blood and/or scar <50% of the lesion size.
5. Must have received at least 4 intravitreal injections of an anti-VEGF agent for treatment of nAMD in the study eye in the 8 months (or less) prior to Visit 1, with anatomical response documented on SD-OCT.

6. Must have subretinal or intraretinal fluid present at Visit 1 in the study eye, evidenced on SD-OCT.

7. Must be pseudophakic (status post cataract surgery) in the study eye.

8. Must be willing and able to comply with all study procedures and be available for the duration of the study.

9. Females of childbearing potential must have a negative urine pregnancy test at the screening visit, have negative serum results by Day 8, and be willing to have additional pregnancy tests during the study.

10. Sexually active subjects (both female and male) must be willing to use a medically accepted method of barrier contraception (e.g., condom, diaphragm, or abstinence) from screening visit until 24 weeks after vector administration. Cessation of birth control after this point should be discussed with a responsible physician.

11. Must be willing and able to provide written, signed informed consent.

Exclusion Criteria:

Subjects who meet any of the following exclusion criteria are not eligible to participate in the study. It is understood that future studies and treatment of other patient populations may not include any or all of these criteria.

1. CNV or macular edema in the study eye secondary to any causes other than AMD.

2. Blood occupying ≥50% of the AMD lesion or blood>1.0 mm2 underlying the fovea in the study eye.

3. Any condition preventing VA improvement in the study eye, eg, fibrosis, atrophy, or retinal epithelial tear in the center of the fovea.

4. Active or history of retinal detachment in the study eye.

5. Advanced glaucoma in the study eye.

6. Any condition in the study eye that, in the opinion of the Investigator, may increase the risk to the subject, require either medical or surgical intervention during the course of the study to prevent or treat vision loss, or interfere with study procedures or assessments.

7. History of intraocular surgery in the study eye within 12 weeks prior to the screening visit. Yttrium aluminum garnet capsulotomy is permitted if performed >10 weeks prior to the screening visit.

8. History of intravitreal therapy in the study eye, such as intravitreal steroid injection or investigational product, other than anti-VEGF therapy, in the 6 months prior to screening.

9. Presence of an implant in the study eye at screening (excluding intraocular lens).

10. History of malignancy requiring chemotherapy and/or radiation in the 5 years prior to screening. Localized basal cell carcinoma is permitted.

11. Receipt of any investigational product within the 30 days of enrollment or 5 half-lives of the investigational product, whichever is longer.

12. Participation in any other gene therapy study.

13. History of therapy known to have caused retinal toxicity, or concominant therapy with any drug that may affect visual acuit or with known retinal toxicity, eg, chloroquine or hydroxychloroquine.

14. Ocular or periocular infection in the study eye that may interfere with the surgical procedure.

15. Myocardial infarction, cerebrovascular accident, or transient ischemic attacks within the past 6 months.

16. Uncontrolled hypertension (systolic blood pressure [BP]>180 mmHg, diastolic BP>100 mmHg) despite maximal medical treatment.

17. Any concomitant treatment that, in the opinion of the Investigator, may interfere with ocular surgical procedure or healing process.

18. Known hypersensitivity to ranibizumab or any of its components or past hypersensitivity (in the Investigator's opinion) to agents like rAAV8.aVEFG test vector.

19. Any serious or unstable medical or psychological condition that, in the opinion of the Investigator, would compromise the subject's safety or successful participation in the study.

Criteria for Continuing Study After Receiving Ranibizumab

At Visit 2, subjects are assessed for initial anti-VEGF response to ranibizumab. Subjects undergo both SD-OCT and BCVA, which are compared by the Investigator with the Visit 1 values:

1. Responsive (subjects continue in the study): Response is defined as reduction in CRT>50 microns or >30% improvement in fluid by SD-OCT.

2. Non-responsive (subjects exit the study as early withdrawals): Non-response is defined as not meeting the criteria above. Additional subjects continue to be enrolled until up to 6 subjects in each cohort receive a single dose of rAAV8.aVEFG test vector.

At this visit central lab results are reviewed. Any subjects with the following values are withdrawn:

3. Aspartate aminotransferase (AST)/alanine aminotransferase (ALT)>2.5×upper limit of normal (ULN)

4. Total bilirubin>1.5×ULN unless the subject has a previously known history of Gilbert's syndrome and a fractionated bilirubin that shows conjugated bilirubin<35% of total bilirubin 5. Prothrombin time (PT)>1.5×ULN 6. Hemoglobin<10 g/dL for male subjects and <9 g/dL for female subjects 7. Platelets<100×103/μL 8. Estimated glomerular filtration rate (GFR)<30 mL/min/1.73 m2

In the initial study, ranibizumab (LUCENTIS, Genentech) 0.5 mg is administered by intravitreal injection on Visit 1, 14 days prior to rAAV8.aVEGF test vector subretinal delivery. The rAAV8.aVEGF is given by subretinal administration by a retinal surgeon under local anesthesia. The procedure involves standard 3 port pars plana vitrectomy with a core vitrectomy followed by a single subretinal administration into the subretinal space by a subretinal cannula (36 to 41 gauge). 100-150 microliters of rAAV8.aVEGF is delivered. Patients receive one of 3, 4 or 5 doses. Three dose levels: $3\times10^9$ genome copies (GC)/eye, $1\times10^{10}$ GC/eye, and $6\times10^{10}$ GC/eye. Starting at 4 weeks post-rAAV8.aVEGF test vector administration, the subject may receive intravitreal ranibizumab rescue therapy in the study eye for disease activity if 1 or more of the following rescue criteria apply: Vision loss of ≥5 letters (per Best Corrected Visual Acuity [BCVA]) associated with accumulation of retinal fluid on Spectral Domain Optical Coherence Tomography (SD-OCT). Choroidal neovascularization (CNV)-related increased, new, or persistent subretinal or intraretinal fluid on SD-OCT. New ocular hemorrhage.

Further rescue injections may be deferred per the clinician's discretion if one of the following sets of findings occur: Visual acuity is 20/20 or better and central retinal thickness is "normal" as assessed by SD-OCT, or Visual acuity and SD-OCT are stable after 2 consecutive injections.

If injections are deferred, they are resumed if visual acuity or SD-OCT get worse per the criteria above.

Example 11

Dose Escalation Study

This Phase I, open-label, multiple-cohort, dose-escalation study is designed to evaluate the safety and tolerability of rAAV8.aVEGF gene therapy in subjects with previously treated neovascular AMD (nAMD). Three doses are studied in approximately 18 subjects. Subjects who meet the inclusion/exclusion criteria and have an anatomic response to an initial anti VEGF injection receive a single dose of rAAV8.aVEGF administered by subretinal delivery. rAAV8.aVEGF uses an AAV8 vector that contains a gene that encodes for a monoclonal antibody fragment which binds to and neutralizes VEGF activity. Safety is the primary focus for the initial 24 weeks after rAAV8.aVEGF administration (primary study period). In certain embodiments, the study includes administering an anti-VEGF antibody, e.g., ranibizumab, and response is measured at week 1 (Visit 2) by SD-OCT. For patients responsive to this treatment, rAAV8.aVEGF may be administered at Visit 3 (week 2), post-anti-VEGF antibody administration and safety is then assessed through week 26 (24 weeks post-rAAV8.aVEGF administration). Following completion of the primary study period, subjects continue to be assessed until 104 weeks following treatment with rAAV8.aVEGF.

Subjects who meet the inclusion/exclusion criteria are enrolled and receive a 0.5 mg intravitreal injection of ranibizumab in the study eye (Visit 1). At Visit 2 (7 days after ranibizumab injection), subjects are evaluated by SD-OCT to confirm anatomic response to the initial anti-VEGF activity associated with the ranibizumab injection compared with their baseline assessment. Subjects who do not have an anatomic response are withdrawn from the study. For withdrawn subjects, anyone who has an AE associated with the ranibizumab injections on Visit 1 is followed until the AE resolves (up to 30 days post-injection). At Visit 3 (Week 2), subjects receive a single dose of rAAV8.aVEGF Fab administered in an operating room by subretinal delivery. The sentinel subject in each cohort has vision of ≤20/100 and ≥20/400 (≤65 and ≥35 ETDRS letters). After rAAV8.aVEGF Fab administration to the sentinel subject, there is a 4-week observation period for safety. Up to 5 additional subjects (with expanded vision criteria of ≤20/63 and ≥20/400 [≤75 and ≥35 ETDRS letters]) may be enrolled in parallel with a minimum of 1 day between each enrollment. If no safety review triggers (SRTs) are observed, then 4 weeks after the last subject is dosed. Subjects have 3 visits within the first 4 weeks after treatment with rAAV8.aVEGF Fab. Starting 4 weeks after rAAV8.aVEGF Fab administration, subjects may receive intravitreal ranibizumab rescue therapy if they meet predefined rescue injection criteria. Immunogenicity to the vector and transgene of rAAV8.aVEGF Fab is assessed throughout the study.

Safety is the primary focus for the initial 24 weeks after rAAV8.aVEGF administration (primary study period). Following completion of the primary study period, subjects continue to be assessed until 104 weeks following treatment with rAAV8.aVEGF (Week 106). At the end of the study, subjects are invited to participate in a long-term follow-up study. The safety and tolerability of rAAV8.aVEGF are assessed in each dosed subject and are monitored through assessment of ocular and non-ocular AEs and SAEs, chemistry, hematology, coagulation, urinalysis, immunogenicity, ocular examinations and imaging (BCVA, intraocular pressure, slit lamp biomicroscopy, indirect ophthalmoscopy, and SD-OCT), and vital signs.

A. Arms and Interventions

| Arms | Assigned Intervention |
|---|---|
| Dose 1 3 × $10^9$ GC of rAAV8.aVEGF | Biological/Vaccine: rAAV8.aVEGF is a recombinant adeno-associated virus (AAV) gene therapy vector carrying a coding sequence for a soluble anti-VEGF protein |
| Experimental: Dose 2 1 × $10^{10}$ GC of rAAV8.aVEGF | Biological/Vaccine: rAAV8.aVEGF is a recombinant adeno-associated virus (AAV) gene therapy vector carrying a coding sequence for a soluble anti-VEGF protein |
| Experimental: Dose 3 6 × $10^{10}$ GC of rAAV8.aVEGF | Biological/Vaccine: rAAV8.aVEGF is a recombinant adeno-associated virus (AAV) gene therapy vector carrying a coding sequence for a soluble anti-VEGF protein |

B. Endpoints:

Primary Outcome Measure:

1. Safety: Incidence of ocular adverse events (AE) and non-ocular serious adverse events (SAE) over 26 weeks Secondary Outcome Measure:

2. Safety: Incidence of ocular and non-ocular AEs and SAEs over 106 weeks

3. Change in best corrected visual acuity (BCVA) over 106 weeks

4. Change in central retinal thickness (CRT) as measured by SD-OCT over 106 weeks.

5. Rescue injections: mean number of rescue injections over 106 weeks

6. Change in choroidal neovascularization and lesion size and leakage area CNV changes as measured by FA over 106 weeks Criteria: Inclusion Criteria:

1. Patients≥50 years with a diagnosis of subfoveal CNV secondary to AMD in the study eye receiving prior intravitreal anti-VEGF therapy. Selected patient population is not gender based (males and females included).

2. BCVA between ≤20/100 and ≥20/400 (≤65 and ≥35 Early Treatment Diabetic Retinopathy Study [ETDRS] letters) for the first patient in each cohort followed by BCVA between ≤20/63 and ≥20/400 (≤75 and ≥35 ETDRS letters) for the rest of the cohort.

3. History of need for and response to anti-VEGF therapy.

4. Response to anti-VEGF at trial entry (assessed by SD-OCT at week 1 (Visit 2)

5. Must be pseudophakic (status post cataract surgery) in the study eye.

6. Aspartate aminotransferase (AST)/Alanine aminotransferase (ALT)<2.5×upper limit of normal (ULN); Total Bilirubin (TB)<1.5×ULN; Prothrombin time (PT)<1.5×ULN; Hemoglobin (Hb)>10 g/dL (males) and >9 g/dL (females); Platelets>100×$10^3$/μL; estimated glomerular filtration rate (eGFR)>30 mL/min/1.73 $m^2$ 7. Must be willing and able to provide written, signed informed consent.

Exclusion Criteria:

1. CNV or macular edema in the study eye secondary to any causes other than AMD.

2. Any condition preventing visual acuity improvement in the study eye, eg, fibrosis, atrophy, or retinal epithelial tear in the center of the fovea.

3. Active or history of retinal detachment in the study eye.

4. Advanced glaucoma in the study eye.

5. History of intravitreal therapy in the study eye, such as intravitreal steroid injection or investigational product, other than anti-VEGF therapy, in the 6 months prior to screening.

6. Presence of an implant in the study eye at screening (excluding intraocular lens).

7. Myocardial infarction, cerebrovascular accident, or transient ischemic attacks within the past 6 months.

8. Uncontrolled hypertension (systolic blood pressure [BP]>180 mmHg, diastolic BP>100 mmHg) despite maximal medical treatment.

Example 12

Vector Production and Manufacturing

A. Description of the Manufacturing Process

Cell Seeding: A qualified human embryonic kidney 293 cell line is used for the production process. Cell culture used for vector production is initiated from a single thawed MCB vial, and expanded per a Master Batch Record Document (MBR). Cells are expanded to $5\times10^9$-$5\times10^{10}$ cells using Corning T-flasks and CS-10, which allow sufficient cell mass to be generated for seeding up to 50 HS-36 for vector production per BDS lot. Cells are cultivated in medium composed of Dulbecco's Modified Eagle Medium (DMEM), supplemented with 10% gamma irradiated, US-sourced, Fetal Bovine Serum (FBS). The cells are anchorage dependent and cell disassociation is accomplished using TrypLE™ Select, an animal product-free cell dissociation reagent. Cell seeding is accomplished using sterile, single-use disposable bioprocess bags and tubing sets. The cells are maintained at 37° C. (±2° C.), in 5% (±0.5%) $CO_2$ atmosphere.

Transient Transfection: Following approximately 3 days of growth (DMEM media+10% FBS), HS-36 cell culture media are replaced with fresh, serum free DMEM media and transfected with the 3 production plasmids using an optimized PEI-based transfection method. All plasmids used in the production process are produced in the context of a CMO quality system and infrastructure utilizing controls to ensure traceability, document control, and materials segregation.

Sufficient DNA plasmid transfection complex are prepared in the BSC to transfect 50 HS-36 (per BDS batch). Initially a DNA/PEI mixture is prepared containing 7.5 mg of the relevant vector genome plasmid), 150 mg of pAdDeltaF6(Kan), 75 mg of pAAV2/8Kan AAV helper plasmid and GMP grade PEI (PEIPro, PolyPlus Transfection SA). This plasmid ratio is determined to be optimal for AAV production in small scale optimization studies. After mixing well, the solution is allowed to sit at room temperature for 25 min. and then added to serum-free media to quench the reaction and then added to the HS-36's. The transfection mixture is equalized between all 36 layers of the HS-36 and the cells are incubated at 37° C. (±2° C.) in a 5% (±0.5%) $CO_2$ atmosphere for 5 days.

Cell Media Harvesting: Transfected cells and media are harvested from each HS-36 using disposable bioprocess bags by aseptically draining the medium out of the units. Following the harvest of media, the ~200 liter volume is supplemented with $MgCl_2$ to a final concentration of 2 mM (co-factor for Benzonase) and Benzonase nuclease (Cat #: 1.016797.0001, Merck Group) is added to a final concentration of 25 units/mL. The product (in a disposable bioprocess bag) is incubated at 37° C. for 2 hr in an incubator to provide sufficient time for enzymatic digestion of residual cellular and plasmid DNA present in the harvest as a result of the transfection procedure. This step is performed to minimize the amount of residual DNA in the final vector DP. After the incubation period, NaCl is added to a final concentration of 500 mM to aid in the recovery of the product during filtration and downstream tangential flow filtration.

Clarification: Cells and cellular debris is removed from the product using a depth filter capsule (1.2/0.22 μm) connected in series as a sterile, closed tubing and bag set that is driven by a peristaltic pump. Clarification assures that downstream filters and chromatography columns are protected from fouling and bioburden reduction filtration ensures that at the end of the filter train, any bioburden potentially introduced during the upstream production process is removed before downstream purification. The harvest material is passed through a Sartorius Sartoguard PES capsule filter (1.2/0.22 μm) (Sartorius Stedim Biotech Inc.).

Large-scale Tangential Flow Filtration: Volume reduction (10-fold) of the clarified product is achieved by Tangential Flow Filtration (TFF) using a custom sterile, closed bioprocessing tubing, bag and membrane set. The principle of TFF is to flow a solution under pressure parallel to a membrane of suitable porosity (100 kDa). The pressure differential drives molecules of smaller size through the membrane and effectively into the waste stream while retaining molecules larger than the membrane pores. By recirculating the solution, the parallel flow sweeps the membrane surface preventing membrane pore fouling. By choosing an appropriate membrane pore size and surface area, a liquid sample may be rapidly reduced in volume while retaining and concentrating the desired molecule. Diafiltration in TFF applications involves addition of a fresh buffer to the recirculating sample at the same rate that liquid is passing through the membrane and to the waste stream. With increasing volumes of diafiltration, increasing amounts of the small molecules are removed from the recirculating sample. This results in a modest purification of the clarified product, but also achieves buffer exchange compatible with the subsequent affinity column chromatography step. Accordingly, a 100 kDa, PES membrane is used for concentration that is then diafiltered with a minimum of 4 diavolumes of a buffer composed of: 20 mM Tris pH 7.5 and 400 mM NaCl. The diafiltered product is stored overnight at 4° C. and then further clarified with a 1.2/0.22 μm depth filter capsule to remove any precipitated material.

Affinity Chromatography: The diafiltered product is applied to a Poros™ Capture Select™ AAV8 affinity resin (Life Technologies) that efficiently captures the AAV8 serotype. Under these ionic conditions, a significant percentage of residual cellular DNA and proteins flow through the column, while AAV particles are efficiently captured. Following application, the column is washed to remove additional feed impurities followed by a low pH step elution (400 mM NaCl, 20 mM Sodium Citrate; pH 2.5) that is immediately neutralized by collection into a $1/10^{th}$ volume of a neutralization buffer (Bis Tris Propane, 200 mM, pH 10.2).

Anion Exchange Chromatography: To achieve further reduction of in-process impurities including empty AAV particles, the Poros-AAV8 elution pool is diluted 50-fold (20 mM Bis Tris Propane, 0.001% Pluronic F68; pH 10.2) to reduce ionic strength to enable binding to a CIMultus™ QA monolith matrix (BIA Separations). Following a low-salt wash, vector product is eluted using a 60 CV NaCl linear salt gradient (10-180 mM NaCl). This shallow salt gradient effectively separates capsid particles without a vector genome (empty particles) from particles containing vector genome (full particles) and results in a preparation enriched for full capsids. Fractions are collected into tubes containing 1/100th volume of 0.1% pluronic F68 and 1/27$^{th}$ volume of Bis Tris pH 6.3 to minimize non-specific binding to tubes and the length of exposure to high pH respectively. The appropriate peak fraction is collected, and the peak area assessed and compared to previous data for determination of the approximate vector yield.

Final Formulation and Bioburden Reduction Filtration to yield the BDS: TFF is used to achieve final formulation on the pooled AEX fractions with a 100 kDa membrane. This is accomplished by diafiltration of formulation buffer (PBS with NaCl and 0.001% Pluronic or PBS with 0.001% Pluronic to be selected following completion of stability studies) and concentrated to yield the BDS Intermediate at a desired target Samples are removed for BDS Intermediate testing (described in the section below). The BDS Intermediate is stored in sterile polypropylene tubes and frozen at ≤−60° C. in a quarantine location until release for Final Fill. Stability studies are underway to assess stability following storage at <−60° C.

Final Fill: The frozen BDS is thawed, pooled, adjusted to the target concentration (dilution or concentrating step via TFF) using the final formulation buffer (PBS with NaCl and 0.001% Pluronic or PBS with 0.001% Pluronic to be selected following completion of stability studies). The product is then be terminally filtered through a 0.22 μm filter and filled into either West Pharmaceutical's "Ready-to-Use" (pre-sterilized) glass vials or Crystal Zenith (polymer) vials (vial type pending the outcome of comparability studies) and stoppers with crimp seals at a fill volume ≥0.1 mL to ≤0.5 mL per vial. Vials are individually labeled according to the specifications below. Labeled vials are stored at ≤−60° C. All doses require dilution in the formulation buffer prior to administration. The dilution is conducted by the pharmacy at the time of dosing.

B. Assay Methods

Sterility and Bacteriostasis/Fungistasis: This procedure is performed once according to United States Pharmacopeia (USP) <71>, to ensure that the sample matrix does not cause inhibition of the assay. Included in the test is the suitability test.

Particle Aggregation: Drug product particle aggregation is assessed using a dynamic light scattering (DLS) assay. DLS measures fluctuations in scattered light intensity due to diffusing particles and is used to characterize the size of various particles in the sample. DLS instrument software typically displays the particle population at different diameters. If the system is monodisperse, only one population is detected and the mean effective diameter of the particles can be determined. In a polydisperse system, such as in the case of aggregation, multiple particle populations are detected and sized using CONTIN analysis.

Residual plasmid DNA: Detection of plasmid DNA sequences is accomplished using qPCR and primer probe sets specific for the kanamycin gene present in the plasmid backbone but not in vector genomes. The assay is performed in both the presence and absence of DNase digestion such that the amount of free plasmid and the amount packaged into vector particles can be determined.

E1 DNA: Adenoviral E1 DNA is a host cell contaminant and is detected by qPCR specific for the gene. The assay is performed in both the presence and absence of DNase digestion such that both free and packaged E1 DNA can be quantified.

Residual Host Cell DNA: Levels of residual host cell DNA (HCDNA) are quantified using qPCR directed against the human 18s rDNA gene which is a high copy number DNA sequence and thus confers sensitivity. In addition to total residual HCDNA levels, the amount of DNA at various size ranges is also determined.

Residual Host Cell Protein: Residual 293 host cell protein (HCP) is detected using commercially available ELISA kits such as that sold by Cygnus Technologies.

Poros-AAV8 Leachable Ligand: An Enzyme-Linked Immunosorbent Assay (ELISA) kit supplied by Life Technologies, the maker of the Poros-AAV8 resin, is used to detect leached camelid antibody in the drug product.

Mycoplasma Detection: Mycoplasma testing is performed according to USP <63>.

Bioburden Testing: This test is performed according to USP <61>.

Endotoxin Testing: This assay is performed according to USP <85>.

In vitro Assay for Adventitious Agents: The purpose of the in vitro assay for viral contaminants is to detect possible adventitious viruses introduced during AAV8.AMD vector production and is based upon CBER's 1993 Points to Consider and ICH Q5A. The in vitro assays use 3 indicator cell lines—human diploid lung (MRC-5) cells, African green monkey kidney (Vero) cells, and human foreskin fibroblast (Hs68) cells. Assay endpoints are observation of cytopathic effects (CPE) over a course of at least 28 days as well as hemadsorption at the end of the assay period, which facilitates the detection of a broad range of viruses.

Vector Genome Identity: DNA Sequencing: Viral Vector genomic DNA is isolated and the sequence determined by 2-fold sequencing coverage using primer walking. Sequence alignment is performed and compared to the expected sequence.

Vector Capsid Identity: AAV Capsid Mass spectrometry of VP1: Confirmation of the AAV2/8 serotype of the drug product is achieved by an assay based upon analysis of peptides of the AAV capsid protein.

Genomic Copy (GC) Titer: A droplet digital PCR (ddPCR)-based technique for determining the genome copy (GC) titer for AAV vectors is described in Lock et al. Human Gene Therapy Methods 25:115-125. The assay utilized involves digestion with DNase I, followed by digital PCR analysis to measure encapsulated vector genomic copies. DNA detection is accomplished using sequence specific primers targeting the RBG polyA region in combination with a fluorescently tagged probe hybridizing to this same region. A number of standards, validation samples and controls (for background and DNA contamination) have been introduced into the assay.

Empty to Full Particle Ratio: The total particle content of the drug product is determined by SDS-PAGE analysis. A reference vector preparation purified on an iodixanol gradient is analyzed by various methods (analytical ultracentrifugation, electron microscopy and absorbance at 260/280 nm) to established percentage of full particles in the preparation. This reference material is serially diluted to known genome copy numbers (and thus by extension, particle numbers) and each dilution is run on an SDS PAGE gel along with a similar dilution series of the drug product. Peak area volumes of both the reference material and drug product VP3 protein bands are determined by densitometry and the reference material volumes are plotted versus particle number. The total particle concentration of the drug product is determined by extrapolation from this curve and the genome copy (GC) titer is then subtracted to obtain the empty particle titer. The empty to full particle ratio is the ratio of the empty particle titer to the GC titer.

Infectious Titer: The infectious unit (IU) assay is used to determine the productive uptake and replication of AAV8.AMD vector in RC32 cells (rep2 expressing HeLa cells). A 96-well end-point format has been employed similar to that previously published. Briefly, RC32 cells are co-infected by serial dilutions of AAV8.AMD BDS and a uniform dilution of Ad5 with 12 replicates at each dilution of rAAV. Seventy-two hours after infection the cells are lysed, and qPCR performed to detect rAAV vector amplification over input. An end-point dilution Tissue Culture Infectious Dose 50% ($TCID_{50}$) calculation (Spearman-Karber) is performed to determine a replicative titer expressed as IU/mL. Since "infectivity" values are dependent on particles coming into contact with cells, receptor binding, internalization, transport to the nucleus and genome replication, they are influenced by assay geometry and the presence of appropriate receptors and post-binding pathways in the cell line used. Receptors and post-binding pathways are not usually maintained in immortalized cell lines and thus infectivity assay titers are not an absolute measure of the number of "infectious" particles present. However, the ratio of encapsidated GC to "infectious units" (described as GC/IU ratio) can be used as a measure of product consistency from lot to lot.

Host Cell DNA: A qPCR assay is used to detect residual human 293 DNA. After spiking with a "non-relevant DNA", total DNA (non-relevant, vector and residual genomic) is extracted from ~1 mL of product. The Host Cell DNA is quantified using qPCR targeting the 18S rDNA gene. The quantities of DNA detected are normalized based on the recovery of the spiked non-relevant DNA.

Host Cell Protein: An ELISA is performed to measure levels of contaminating host HEK293 cell proteins. The Cygnus Technologies HEK293 Host Cell Proteins 2$^{nd}$ Generation ELISA kit is used according to instructions.

Replication-competent AAV (rcAAV) Assay: A sample is analyzed for the presence of replication competent AAV2/8 (rcAAV) that can potentially arise during the production process.

An example of this type of assay is shown in (FIGS. 10A-10D), where wtAAV8 is spiked into different GC amounts of AAV8 vector and the cap gene copy number per 1 μg of 293 cell DNA is determined after 3 successive passages of the cell lysate onto fresh cells. The details of the assay development are included in the CTA submission. These results indicate that the minimum detectable amount of wtAAV8 using this assay is $10^4$ GC. This number is equivalent to approximately 1 $TCID_{50}$ IU and reflects the lack of infectivity of AAV8 for 293 cells as evidenced by the high GC:IU ratios obtained compared to AAV2. The low sensitivity appears unavoidable with the current assay system but might be overcome in future by engineering a cell line with a yet to be discovered AAV8 cellular receptor or other protein important in post-entry pathways. Spiking the wtAAV8 into AAV8 vector concentrations of up to $10^{11}$ GC had little effect on detection and indicates a lack of interference of the vector on wtAAV8 replication at this vector level. While wildtype AAV has been used extensively as a surrogate in the past for rcAAV2 and in our own rcAAV assay development efforts for AAV8, the best surrogate is a AAV8 capsid containing AAV2 ITRs, an AAV2 rep gene and an AAV8 cap gene.

| Sample Steps | Test | Analytical Method | Acceptance Criteria[1] |
|---|---|---|---|
| Final Drug Product in vials | Appearance | Visual Inspection | Clear to slightly Opaque, colorless to faint white solution, free of non-product related foreign particulates |
| | pH | USP <791> | 7.4 +/− 0.2 |
| | GC Titer | ddPCR | ≥1 × $10^{11}$ GC/mL** |
| | AAV Vector Genome Identity | Sequencing (Sanger) | Confirm expected sequence |
| Final Drug Product in vials | Total Protein Content | Micro BCA | Report result |
| | Osmolality Content | USP <785> | <400 mOsm |
| | Empty/Full Particle ratio Purity | PT (by SDS-PAGE)/GC Ratio | Report result |
| | Empty:Full particle ratio Purity | OD260/280 | Report result |
| | Viral Capsid Purity Purity | SDS-PAGE | Report result |
| | Aggregation Characterization Purity | Dynamic Light Scattering | Report result |
| | In vitro potency Potency | HEK293transduction/ ranibizumab ELISA | Conforms to reference standard |
| | Transgene expression Characterization Identity | In vitro expression and ELISA | Positive for ranibizumab |
| | Infectious Titer Characterization Potency | TCID50/qPCR | Report results |
| | rcAAV by triple passage HEK293 + Ad5 Characterization Safety | Cell Culture/qPCR | Report results |

-continued

| Sample Steps | Test | Analytical Method | Acceptance Criteria[1] |
|---|---|---|---|
| | Capsid Identity Characterization | UPLC/Mass Spectrometry | AAV-8 signature peptide detected. Signature peptides for AAV1, 2, 6, 9 hu37 and Rh10 not detected |
| | Endotoxin Safety | USP <85> Kinetic Chromogenic | <0.80 EU/mg* or (≤ the safety limit based on dose calculations, pending the verification of total protein) |
| | Sterility Safety | USP <71> | No Growth |
| | Container Closure Integrity (for stability study only and not for lot release) | Dye Ingress Test | Container is Integral |

[1]The acceptance criteria is determined upon completion of the first GMP campaign.
*Endotoxin limit calculation is based on dose in Mass. Once the total protein concentration is confirmed from the GMP run, the limit can be recalculated. The current limit is based on the protein concentration from the Tox materials in relation to GC titer. The value is an approximation and not a definitive value. The dual acceptance criteria presented here.
**DP GC Titer criteria may change depending on the final selected dose levels for the study The clinically suitable surfactant Pluronic F68 is added to the final formulation buffer of AAV8.AMD and is anticipated to minimize this type of loss. The interaction of the drug product with both the storage vial and the clinical delivery device is investigated to determine the amount of vector loss through binding to surfaces. GC titers (oqPCR) of the engineering run drug product are determined before and after vialling and storage at ≤−60° C. For the delivery device, the DP is thawed, diluted in the appropriate clinical diluent to the correct dosing concentration and passed through the device. GC titrations are performed on the DP directly after thaw, after dilution and after passage through the device, and the appropriate number of replicates is included to assure statistical significance. Comparison of GC titers in this manner enables an assessment of DP loss during storage and administration to the patient. Parallel studies are also performed in a similar way to assess the activity of the drug product after passing through the delivery device. For this purpose the in vitro ranibizumab expression-based potency assay is employed.

Sequence Listing Free Text

The following information is provided for sequences containing free text under numeric identifier <223>.

| SEQ ID NO: (containing free text) | Free text under <223> |
|---|---|
| 1 | <223> Humanized anti-VEGF Fab heavy chain<br><220><br><221> MISC_FEATURE<br><222> (28) . . . (39)<br><223> complementarity determining region<br><220><br><221> MISC_FEATURE<br><222> (54) . . . (83)<br><223> complementarity determining region |
| 2 | <223> Humanized anti-VEGF Fab<br><220><br><221> MISC_FEATURE<br><222> (26) . . . (37) |

-continued

| SEQ ID NO: (containing free text) | Free text under <223> |
|---|---|
| | <223> complementarity determining region<br><220><br><221> MISC_FEATURE<br><222> (107) . . . (117)<br><223> complementarity determining region |
| 3 | <223> 5'ITR.CB7.CI.aVEGFv2.rBG.3'ITR<br><220><br><221> repeat_region<br><222> (1) . . . (130)<br><223> 5' ITR<br><220><br><221> promoter<br><222> (198) . . . (579)<br><223> CMV IE promoter<br><220><br><221> enhancer<br><222> (279) . . . (538)<br><223> C4 enhancer with 2 mismatches<br><220><br><221> misc_feature<br><222> (279) . . . (538)<br><223> C4 enhancer<br><220><br><221> promoter<br><222> (582) . . . (862)<br><223> CB promoter<br><220><br><221> TATA_signal<br><222> (836) . . . (839)<br><220><br><221> misc_feature<br><222> (955) . . . (1829)<br><223> chicken beta-actin intron<br><220><br><221> Intron<br><222> (956) . . . (1928)<br><223> chicken beta-actin intron<br><220><br><221> Intron<br><222> (956) . . . (1928)<br><223> chicken beta-actin promoter<br><220><br><221> 5'UTR<br><222> (1946) . . . (1993) |

-continued

| SEQ ID NO: (containing free text) | Free text under <223> |
|---|---|
| | <223> c-myc 5' UTR |
| | <220> |
| | <221> misc__feature |
| | <222> (1994) . . . (1999) |
| | <223> kozak sequnce |
| | <220> |
| | <221> transit__peptide |
| | <222> (1999) . . . (2058) |
| | <220> |
| | <221> CDS |
| | <222> (2059) . . . (2427) |
| | <223> aVEGFv2 VH |
| | <220> |
| | <221> CDS |
| | <222> (2428) . . . (2748) |
| | <223> CH1 |
| | <220> |
| | <221> misc__feature |
| | <222> (2752) . . . (2763) |
| | <223> Furin cleavage site |
| | <220> |
| | <221> CDS |
| | <222> (2764) . . . (2835) |
| | <223> F2A linker |
| | <220> |
| | <221> transit__peptide |
| | <222> (2836) . . . (2895) |
| | <220> |
| | <221> CDS |
| | <222> (2896) . . . (3216) |
| | <223> aVEGFv2 VL |
| | <220> |
| | <221> CDS |
| | <222> (3217) . . . (3537) |
| | <223> CL |
| | <220> |
| | <221> polyA__signal |
| | <222> (3613) . . . (3739) |
| | <223> rabbit globin polyA |
| | <220> |
| | <221> repeat__region |
| | <222> (3828) . . . (3957) |
| | <223> 3' ITR |
| 4 | <223> Synthetic Construct |
| 5 | <223> Synthetic Construct |
| 6 | <223> Synthetic Construct |
| 7 | <223> Synthetic Construct |
| 8 | <223> Synthetic Construct |
| 9 | <213> Artificial Sequence |
| | <220> |
| | <223> AAV25'ITR.UbC.Ci.aVEGFv2.rBG.AAV23'ITR |
| | <220> |
| | <221> repeat__region |
| | <222> (17) . . . (146) |
| | <223> 5' ITR |
| | <220> |
| | <221> promoter |
| | <222> (207) . . . (1435) |
| | <223> UbC with C insertion at 289 and G insertion at 990 |
| | <220> |
| | <221> Intron |
| | <222> (1529) . . . (1661) |
| | <223> chimeric intron |
| | <220> |
| | <221> 5'UTR |
| | <222> (1736) . . . (1783) |
| | <223> c-myc 5'UTR |
| | <220> |
| | <221> misc__feature |
| | <222> (1784) . . . (1789) |
| | <223> kozak |
| | <220> |
| | <221> misc__feature |
| | <222> (1789) . . . (1848) |
| | <223> kozak |
| | <220> |
| | <221> CDS |
| | <222> (1849) . . . (2217) |
| | <223> aVEGFv2 VH |
| | <220> |
| | <221> CDS |
| | <222> (2218) . . . (2538) |
| | <223> CH1 |
| | <220> |
| | <221> misc__feature |
| | <222> (2542) . . . (2553) |
| | <223> furin cleavage site |
| | <220> |
| | <221> misc__feature |
| | <222> (2554) . . . (2625) |
| | <223> F2a linker |
| | <220> |
| | <221> misc__feature |
| | <222> (2626) . . . (2685) |
| | <223> Leader |
| | <220> |
| | <221> CDS |
| | <222> (2686) . . . (3006) |
| | <223> aVEGFv2 VL |
| | <220> |
| | <221> CDS |
| | <222> (3007) . . . (3327) |
| | <223> CL |
| | <220> |
| | <221> polyA__signal |
| | <222> (3345) . . . (3576) |
| | <223> SV40 late polyadenylation signal |
| | <220> |
| | <221> repeat__region |
| | <222> (3641) . . . (3770) |
| | <223> 3' ITR |
| 10 | <223> Synthetic Construct |
| 11 | <223> Synthetic Construct |
| 12 | <223> Synthetic Construct |
| 13 | <223> Synthetic Construct |
| 14 | <223> ITR.CB7.CI.aVEGRv3.rBG.ITR |
| | <220> |
| | <221> repeat__region |
| | <222> (1) . . . (130) |
| | <223> 5'ITR |
| | <220> |
| | <221> promoter |
| | <222> (198) . . . (579) |
| | <223> CMV IE promoter |
| | <220> |
| | <221> enhancer |
| | <222> (279) . . . (538) |
| | <223> C4 enhancer with 2 mismatches |
| | <220> |
| | <221> promoter |
| | <222> (582) . . . (862) |
| | <223> CB promoter |
| | <220> |
| | <221> TATA__signal |
| | <222> (836) . . . (839) |
| | <220> |
| | <221> Intron |
| | <222> (956) . . . (1928) |
| | <223> chicken beta-actin intron |
| | <220> |
| | <221> 5'UTR |
| | <222> (1940) . . . (1987) |
| | <220> |
| | <221> misc__feature |
| | <222> (1988) . . . (1993) |
| | <223> Kozak |
| | <220> |
| | <221> misc__feature |

-continued

| SEQ ID NO: (containing free text) | Free text under <223> |
| --- | --- |
| | <222> (1993) . . . (2052)<br><223> leader<br><220><br><221> CDS<br><222> (2053) . . . (2421)<br><223> aVEGFv3 VH<br><220><br><221> CDS<br><222> (2422) . . . (2742)<br><223> CH1<br><220><br><221> misc_feature<br><222> (2746) . . . (2757)<br><223> furin cleavage site<br><220><br><221> misc_feature<br><222> (2758) . . . (2829)<br><223> F2a linker<br><220><br><221> misc_feature<br><222> (2830) . . . (2889)<br><223> leader<br><220><br><221> CDS<br><222> (2890) . . . (3210)<br><223> aVEGFv3 VL<br><220><br><221> CDS<br><222> (3211) . . . (3531)<br><223> CL<br><220><br><221> polyA_signal<br><222> (3607) . . . (3733)<br><223> rabbit globin polyA<br><220><br><221> repeat_region<br><222> (3822) . . . (3951)<br><223> 3' ITR |
| 15 | <223> Synthetic Construct |
| 16 | <223> Synthetic Construct |
| 17 | <223> Synthetic Construct |
| 18 | <223> Synthetic Construct |
| 19 | <223> ITR.UbC.PI.aVEGFv3.SV40.ITR<br><220><br><221> repeat_region<br><222> (17) . . . (146)<br><223> AAV2 5' ITR<br><220><br><221> promoter<br><222> (207) . . . (1434)<br><223> UbC, with C insert at 289 and G insert at 990<br><220><br><221> Intron<br><222> (1528) . . . (1660)<br><223> chimeric intron<br><220><br><221> 5'UTR<br><222> (1729) . . . (1776)<br><223> c-myc 5'UTR<br><220><br><221> misc_feature<br><222> (1777) . . . (1782)<br><223> kozak<br><220><br><221> misc_feature<br><222> (1782) . . . (1841)<br><223> leader<br><220><br><221> CDS<br><222> (1842) . . . (2210)<br><223> aVEGFv3 VH<br><220><br><221> CDS<br><222> (2211) . . . (2531)<br><223> CH1<br><220><br><221> misc_feature<br><222> (2535) . . . (2546)<br><223> furin cleavage site<br><220><br><221> misc_feature<br><222> (2547) . . . (2618)<br><223> F2a linker<br><220><br><221> misc_feature<br><222> (2619) . . . (2678)<br><223> leader<br><220><br><221> CDS<br><222> (2679) . . . (2999)<br><223> aVEGFv3 VL<br><220><br><221> CDS<br><222> (3000) . . . (3320)<br><223> CL<br><220><br><221> polyA_signal<br><222> (3338) . . . (3569)<br><223> SV40 late polyA<br><220><br><221> repeat_region<br><222> (3634) . . . (3763)<br><223> AAV2 3'ITR |
| 20 | <223> Synthetic Construct |
| 21 | <223> Synthetic Construct |
| 22 | <223> Synthetic Construct |
| 23 | <223> Synthetic Construct |
| 24 | <223> ITR.UbC.PI.aVEGFv1.SV40.ITR<br><220><br><221> repeat_region<br><222> (17) . . . (146)<br><223> ITR<br><220><br><221> promoter<br><222> (207) . . . (1435)<br><223> UbC<br><220><br><221> Intron<br><222> (1529) . . . (1661)<br><223> Promoga chimeric intron<br><220><br><221> 5'UTR<br><222> (1730) . . . (1777)<br><223> c-myc 5'UTR<br><220><br><221> misc_feature<br><222> (1778) . . . (1783)<br><223> kozak<br><220><br><221> misc_feature<br><222> (1783) . . . (1842)<br><223> leader<br><220><br><221> CDS<br><222> (1843) . . . (2211)<br><223> aVEGFv1 VH<br><220><br><221> CDS<br><222> (2212) . . . (2532)<br><223> CH1<br><220><br><221> misc_feature<br><222> (2536) . . . (2547)<br><223> furin cleavage site<br><220><br><221> misc_feature<br><222> (2548) . . . (2619)<br><223> F2A linker<br><220> |

-continued

| SEQ ID NO: (containing free text) | Free text under <223> |
| --- | --- |
| | <221> misc_feature |
| | <222> (2620) . . . (2679) |
| | <223> leader |
| | <220> |
| | <221> CDS |
| | <222> (2680) . . . (3000) |
| | <223> aVEGFv1 VL |
| | <220> |
| | <221> CDS |
| | <222> (3001) . . . (3321) |
| | <223> CL |
| | <220> |
| | <221> polyA_signal |
| | <222> (3339) . . . (3570) |
| | <223> SV40 polyadenylation signal |
| | <220> |
| | <221> repeat_region |
| | <222> (3635) . . . (3764) |
| | <223> ITR |
| 25 | <223> Synthetic Construct |
| 26 | <223> Synthetic Construct |
| 27 | <223> Synthetic Construct |
| 28 | <223> Synthetic Construct |
| 30 | <223> synthetic leader |
| 31 | <223> synthetic leader 2 |
| 32 | <223> derived from encephalomycarditts virus |
| 33 | <223> aVEGF |
| | <220> |
| | <221> MISC_FEATURE |
| | <222> (1) . . . (20) |
| | <223> leader |
| | <220> |
| | <221> MISC_FEATURE |
| | <222> (21) . . . (252) |
| | <223> aVEGF Heavy Chain |
| | <220> |
| | <221> MISC_FEATURE |
| | <222> (280) . . . (299) |
| | <223> leader |
| | <220> |
| | <221> MISC_FEATURE |
| | <222> (300) . . . (513) |
| | <223> aVEGF Light Chain |
| 34 | <223> ITR.CB7.CI.aVEGFv1.rBG.ITR |
| | <220> |
| | <221> repeat_region |
| | <222> (1) . . . (130) |
| | <223> 5' ITR |
| | <220> |
| | <221> promoter |
| | <222> (204) . . . (584) |
| | <223> CMV IE promoter |
| | <220> |
| | <221> promoter |
| | <222> (585) . . . (862) |
| | <223> CB promoter |
| | <220> |
| | <221> TATA_signal |
| | <222> (836) . . . (839) |
| | <220> |
| | <221> Intron |
| | <222> (956) . . . (1928) |
| | <223> chicken beta-actin intron |
| | <220> |
| | <221> 5'UTR |
| | <222> (1940) . . . (1987) |
| | <223> c-myc 5'UTR |
| | <220> |
| | <221> misc_feature |
| | <222> (1988) . . . (1993) |
| | <223> kozak |
| | <220> |
| | <221> misc_feature |
| | <222> (1993) . . . (2052) |
| | <223> leader |
| | <220> |
| | <221> misc_feature |
| | <222> (2053) . . . (2421) |
| | <223> aVEGFv1 VH |
| | <220> |
| | <221> misc_feature |
| | <222> (2422) . . . (2742) |
| | <223> CH1 |
| | <220> |
| | <221> misc_feature |
| | <222> (2746) . . . (2757) |
| | <223> furin cleavage site |
| | <220> |
| | <221> misc_feature |
| | <222> (2758) . . . (2829) |
| | <223> F2A linker |
| | <220> |
| | <221> misc_feature |
| | <222> (2830) . . . (2889) |
| | <223> leader |
| | <220> |
| | <221> misc_feature |
| | <222> (2890) . . . (3210) |
| | <223> aVEGFv1 VL |
| | <220> |
| | <221> misc_feature |
| | <222> (3211) . . . (3531) |
| | <223> CL |
| | <220> |
| | <221> misc_feature |
| | <222> (3532) . . . (3537) |
| | <223> stop cassette |
| | <220> |
| | <221> polyA_signal |
| | <222> (3607) . . . (3733) |
| | <223> Rabbit globin poly A |
| | <220> |
| | <221> misc_feature |
| | <222> (3785) . . . (3821) |
| | <223> part of AAV |
| | <220> |
| | <221> repeat_region |
| | <222> (3822) . . . (3951) |
| | <223> 3'ITR |
| 35 | <223> ITR.CB7.CI.aVEGFv4.rBG.ITR |
| | <220> |
| | <221> repeat_region |
| | <222> (1) . . . (130) |
| | <223> 5'ITR |
| | <220> |
| | <221> promoter |
| | <222> (198) . . . (579) |
| | <223> CMV IE promoter |
| | <220> |
| | <221> enhancer |
| | <222> (279) . . . (538) |
| | <223> C4 enhancer |
| | <220> |
| | <221> promoter |
| | <222> (582) . . . (862) |
| | <223> CB promoter |
| | <220> |
| | <221> Intron |
| | <222> (956) . . . (1928) |
| | <223> chicken beta-actin intron |
| | <220> |
| | <221> 5'UTR |
| | <222> (1940) . . . (1987) |
| | <223> c-myc 5'UTR |
| | <220> |
| | <221> misc_feature |
| | <222> (1988) . . . (1993) |
| | <223> kozak |
| | <220> |
| | <221> misc_feature |

-continued

| SEQ ID NO: (containing free text) | Free text under <223> |
|---|---|
| | <222> (1993) . . . (2052)<br><223> leader<br><220><br><221> misc_feature<br><222> (2053) . . . (2421)<br><223> aVEGFv4 VH<br><220><br><221> misc_feature<br><222> (2422) . . . (2742)<br><223> CH1<br><220><br><221> misc_feature<br><222> (2746) . . . (2757)<br><223> furin cleavage site<br><220><br><221> misc_feature<br><222> (2758) . . . (2829)<br><223> F2A linker<br><220><br><221> misc_feature<br><222> (2830) . . . (2889)<br><223> leader<br><220><br><221> misc_feature<br><222> (2890) . . . (3210)<br><223> aVEGFv4 VL<br><220><br><221> misc_feature<br><222> (3211) . . . (3531)<br><223> CL<br><220><br><221> misc_feature<br><222> (3532) . . . (3537)<br><223> stop cassette<br><220><br><221> polyA_signal<br><222> (3607) . . . (3733)<br><223> Rabbit globin poly A<br><220><br><221> repeat_region<br><222> (3822) . . . (3951)<br><223> 3'ITR |
| 36 | <223> ITR.CB7.CI.aVEGFv5.rBG.ITR<br><220><br><221> repeat_region<br><222> (1) . . . (130)<br><223> 5'ITR<br><220><br><221> promoter<br><222> (198) . . . (579)<br><223> CMV IE promoter<br><220><br><221> enhancer<br><222> (279) . . . (538)<br><223> C4 enhancer<br><220><br><221> promoter<br><222> (582) . . . (862)<br><223> CB promoter<br><220><br><221> Intron<br><222> (956) . . . (1928)<br><223> chicken beta-actin intron<br><220><br><221> 5'UTR<br><222> (1940) . . . (1987)<br><223> c-myc 5'UTR<br><220><br><221> misc_feature<br><222> (1988) . . . (1993)<br><223> kozak<br><220><br><221> misc_feature<br><222> (1993) . . . (2052)<br><223> leader<br><220><br><221> misc_feature<br><222> (2053) . . . (2421)<br><223> aVEGFv5 VH<br><220><br><221> misc_feature<br><222> (2422) . . . (2742)<br><223> CH1<br><220><br><221> misc_feature<br><222> (2746) . . . (2757)<br><223> furin cleavage site<br><220><br><221> misc_feature<br><222> (2758) . . . (2829)<br><223> F2A linker<br><220><br><221> misc_feature<br><222> (2830) . . . (2889)<br><223> leader<br><220><br><221> misc_feature<br><222> (2890) . . . (3210)<br><223> aVEGFv5 VL<br><220><br><221> misc_feature<br><222> (3211) . . . (3531)<br><223> CL<br><220><br><221> misc_feature<br><222> (3532) . . . (3537)<br><223> stop cassette<br><220><br><221> polyA_signal<br><222> (3607) . . . (3733)<br><223> rabbit globin poly A<br><220><br><221> repeat_region<br><222> (3822) . . . (3951)<br><223> 3'ITR |
| 37 | <223> ITR.CB7.CI.aVEGFv6.rBG.ITR<br><220><br><221> repeat_region<br><222> (1) . . . (130)<br><223> 5'ITR<br><220><br><221> promoter<br><222> (198) . . . (579)<br><223> CMV IE promoter<br><220><br><221> enhancer<br><222> (279) . . . (538)<br><223> C4 enhancer<br><220><br><221> promoter<br><222> (582) . . . (862)<br><223> CB promoter<br><220><br><221> Intron<br><222> (956) . . . (1928)<br><223> chicken beta-actin intron<br><220><br><221> 5'UTR<br><222> (1940) . . . (1987)<br><223> c-myc 5'UTR<br><220><br><221> misc_feature<br><222> (1993) . . . (2052)<br><223> leader<br><220><br><221> misc_feature<br><222> (2053) . . . (2421)<br><223> aVEGFv6 VH<br><220><br><221> misc_feature |

-continued

| SEQ ID NO: (containing free text) | Free text under <223> |
|---|---|
| | <222> (2422) . . . (2742) |
| | <223> CH1 |
| | <220> |
| | <221> misc_feature |
| | <222> (2746) . . . (2757) |
| | <223> furin cleavage site |
| | <220> |
| | <221> misc_feature |
| | <222> (2758) . . . (2829) |
| | <223> F2A linker |
| | <220> |
| | <221> misc_feature |
| | <222> (2830) . . . (2889) |
| | <223> leader |
| | <220> |
| | <221> misc_feature |
| | <222> (2890) . . . (3210) |
| | <223> aVEGFv6 VL |
| | <220> |
| | <221> misc_feature |
| | <222> (3211) . . . (3531) |
| | <223> CL |
| | <220> |
| | <221> misc_feature |
| | <222> (3532) . . . (3537) |
| | <223> stop cassette |
| | <220> |
| | <221> polyA_signal |
| | <222> (3607) . . . (3733) |
| | <223> Rabbit globin poly A |
| | <220> |
| | <221> repeat_region |
| | <222> (3822) . . . (3951) |
| | <223> 3'ITR |
| 38 | <223> ITR.CB7.CI.aVEGFv7.rBG.ITR |
| | <220> |
| | <221> repeat_region |
| | <222> (1) . . . (130) |
| | <223> 5'ITR |
| | <220> |
| | <221> promoter |
| | <222> (198) . . . (579) |
| | <223> CMV IE promoter |
| | <220> |
| | <221> enhancer |
| | <222> (279) . . . (538) |
| | <223> C4 enhancer |
| | <220> |
| | <221> promoter |
| | <222> (582) . . . (862) |
| | <223> CB promoter |
| | <220> |
| | <221> Intron |
| | <222> (956) . . . (1928) |
| | <223> chicken beta-actin intron |
| | <220> |
| | <221> 5'UTR |
| | <222> (1940) . . . (1987) |
| | <223> c-myc 5'UTR |
| | <220> |
| | <221> misc_feature |
| | <222> (1988) . . . (1993) |
| | <223> kozak |
| | <220> |
| | <221> misc_feature |
| | <222> (1993) . . . (2052) |
| | <223> leader |
| | <220> |
| | <221> misc_feature |
| | <222> (2053) . . . (2421) |
| | <223> aVEGFv7 VH |
| | <220> |
| | <221> misc_feature |
| | <222> (2422) . . . (2742) |
| | <223> CH1 |

-continued

| SEQ ID NO: (containing free text) | Free text under <223> |
|---|---|
| | <220> |
| | <221> misc_feature |
| | <222> (2746) . . . (2757) |
| | <223> furin cleavage site |
| | <220> |
| | <221> misc_feature |
| | <222> (2758) . . . (2829) |
| | <223> F2A linker |
| | <220> |
| | <221> misc_feature |
| | <222> (2830) . . . (2889) |
| | <223> leader |
| | <220> |
| | <221> misc_feature |
| | <222> (2890) . . . (3210) |
| | <223> aVEGFv7 VL |
| | <220> |
| | <221> misc_feature |
| | <222> (3211) . . . (3531) |
| | <223> CL |
| | <220> |
| | <221> misc_feature |
| | <222> (3532) . . . (3537) |
| | <223> stop cassette |
| | <220> |
| | <221> polyA_signal |
| | <222> (3607) . . . (3733) |
| | <223> rabbit globin poly A |
| | <220> |
| | <221> repeat_region |
| | <222> (3822) . . . (3951) |
| | <223> 3'ITR |
| 39 | <223> ITR.CB7.CI.aVEGFv8.rBG.ITR |
| | <220> |
| | <221> repeat_region |
| | <222> (1) . . . (130) |
| | <223> 5'ITR |
| | <220> |
| | <221> promoter |
| | <222> (198) . . . (579) |
| | <223> CMV IE promoter |
| | <220> |
| | <221> enhancer |
| | <222> (279) . . . (538) |
| | <223> C4 enhancer |
| | <220> |
| | <221> promoter |
| | <222> (582) . . . (862) |
| | <223> CB promoter |
| | <220> |
| | <221> Intron |
| | <222> (956) . . . (1928) |
| | <223> chicken beta-actin intron |
| | <220> |
| | <221> 5'UTR |
| | <222> (1940) . . . (1987) |
| | <223> c-myc 5'UTR |
| | <220> |
| | <221> misc_feature |
| | <222> (1988) . . . (1993) |
| | <223> kozak |
| | <220> |
| | <221> misc_feature |
| | <222> (1993) . . . (2052) |
| | <223> leader |
| | <220> |
| | <221> misc_feature |
| | <222> (2053) . . . (2421) |
| | <223> aVEGFv8 VH |
| | <220> |
| | <221> misc_feature |
| | <222> (2422) . . . (2742) |
| | <223> CH1 |
| | <220> |
| | <221> misc_feature |

-continued

| SEQ ID NO: (containing free text) | Free text under <223> |
|---|---|
| | <222> (2746) . . . (2757)<br><223> furin cleavage site<br><220><br><221> misc_feature<br><222> (2758) . . . (2829)<br><223> F2A linker<br><220><br><221> misc_feature<br><222> (2830) . . . (2889)<br><223> leader<br><220><br><221> misc_feature<br><222> (2890) . . . (3210)<br><223> aVEGFv8 VL<br><220><br><221> misc_feature<br><222> (3211) . . . (3531)<br><223> CL<br><220><br><221> misc_feature<br><222> (3532) . . . (3537)<br><223> stop cassette<br><220><br><221> polyA_signal<br><222> (3607) . . . (3733)<br><223> rabbit globin poly A<br><220><br><221> repeat_region<br><222> (3822) . . . (3951)<br><223> 3'ITR |
| 40 | <223> ITR.CB7.CI.aVEGFv9.rBG.ITR<br><220><br><221> repeat_region<br><222> (1) . . . (130)<br><223> 5'ITR<br><220><br><221> promoter<br><222> (198) . . . (579)<br><223> CMV IE promoter<br><220><br><221> enhancer<br><222> (279) . . . (538)<br><223> C4 enhancer<br><220><br><221> promoter<br><222> (582) . . . (862)<br><223> CB promoter<br><220><br><221> Intron<br><222> (956) . . . (1928)<br><223> chicken beta-actin intron<br><220><br><221> 5'UTR<br><222> (1946) . . . (1993)<br><223> c-myc 5'UTR<br><220><br><221> misc_feature<br><222> (1994) . . . (1999)<br><223> kozak<br><220><br><221> misc_feature<br><222> (1999) . . . (2058)<br><223> leader<br><220><br><221> misc_feature<br><222> (2059) . . . (2427)<br><223> aVEGFv9 VH<br><220><br><221> misc_feature<br><222> (2428) . . . (2748)<br><223> CH1<br><220><br><221> misc_feature<br><222> (2752) . . . (2763)<br><223> furin cleavage site<br><220><br><221> misc_feature<br><222> (2764) . . . (2835)<br><223> F2A linker<br><220><br><221> misc_feature<br><222> (2836) . . . (2895)<br><223> leader<br><220><br><221> misc_feature<br><222> (2896) . . . (3216)<br><223> aVEGFv9 VL<br><220><br><221> misc_feature<br><222> (3217) . . . (3537)<br><223> CL<br><220><br><221> misc_feature<br><222> (3538) . . . (3543)<br><223> Stop Cassette<br><220><br><221> polyA_signal<br><222> (3613) . . . (3739)<br><223> rabbit globin poly A<br><220><br><221> repeat_region<br><222> (3828) . . . (3957)<br><223> 3'ITR |
| 41 | <223> ITR.CB7.CI.aVEGFv10.rBG.ITR<br><220><br><221> repeat_region<br><222> (1) . . . (130)<br><223> 5'ITR<br><220><br><221> promoter<br><222> (198) . . . (579)<br><223> CMV IE promoter<br><220><br><221> enhancer<br><222> (279) . . . (538)<br><223> C4 enhancer<br><220><br><221> promoter<br><222> (582) . . . (862)<br><223> CB promoter<br><220><br><221> Intron<br><222> (956) . . . (1928)<br><223> chicken beta-actin intron<br><220><br><221> 5'UTR<br><222> (1940) . . . (1987)<br><223> c-myc 5'UTR<br><220><br><221> misc_feature<br><222> (1988) . . . (1993)<br><223> kozak<br><220><br><221> misc_feature<br><222> (1993) . . . (2052)<br><223> leader<br><220><br><221> misc_feature<br><222> (2053) . . . (2421)<br><223> aVEGFv10 VH<br><220><br><221> misc_feature<br><222> (2422) . . . (2742)<br><223> CH1<br><220><br><221> misc_feature<br><222> (2746) . . . (2757)<br><223> furin cleavage site<br><220><br><221> misc_feature |

-continued

| SEQ ID NO: (containing free text) | Free text under <223> |
|---|---|
| | <222> (2758) . . . (2829) |
| | <223> F2A linker |
| | <220> |
| | <221> misc_feature |
| | <222> (2830) . . . (2889) |
| | <223> leader |
| | <220> |
| | <221> misc_feature |
| | <222> (2890) . . . (3210) |
| | <223> aVEGFv10 VL |
| | <220> |
| | <221> misc_feature |
| | <222> (3211) . . . (3531) |
| | <223> CL |
| | <220> |
| | <221> misc_feature |
| | <222> (3532) . . . (3537) |
| | <223> stop cassette |
| | <220> |
| | <221> polyA_signal |
| | <222> (3607) . . . (3733) |
| | <223> rabbit globin poly A |
| | <220> |
| | <221> repeat_region |
| | <222> (3822) . . . (3951) |
| | <223> 3'ITR |
| 42 | <223> ITR.CB7.CI.aVEGFv11.rBG.ITR |
| | <220> |
| | <221> repeat_region |
| | <222> (1) . . . (130) |
| | <223> 5'ITR |
| | <220> |
| | <221> promoter |
| | <222> (198) . . . (579) |
| | <223> CMV IE promoter |
| | <220> |
| | <221> enhancer |
| | <222> (279) . . . (538) |
| | <223> C4 enhancer |
| | <220> |
| | <221> promoter |
| | <222> (582) . . . (862) |
| | <223> CB promoter |
| | <220> |
| | <221> Intron |
| | <222> (956) . . . (1928) |
| | <223> chicken beta-actin intron |
| | <220> |
| | <221> 5'UTR |
| | <222> (1940) . . . (1987) |
| | <223> c-myc 5' UTR |
| | <220> |
| | <221> misc_feature |
| | <222> (1988) . . . (1993) |
| | <223> kozak |
| | <220> |
| | <221> misc_feature |
| | <222> (1993) . . . (2052) |
| | <223> leader |
| | <220> |
| | <221> misc_feature |
| | <222> (2053) . . . (2421) |
| | <223> aVEGFv11 VH |
| | <220> |
| | <221> misc_feature |
| | <222> (2422) . . . (2742) |
| | <223> CH1 |
| | <220> |
| | <221> misc_feature |
| | <222> (2746) . . . (2754) |
| | <223> furing cleavage site |
| | <220> |
| | <221> misc_feature |
| | <222> (2755) . . . (2829) |
| | <223> F2A linker |
| | <220> |
| | <221> misc_feature |
| | <222> (2830) . . . (2889) |
| | <223> leader |
| | <220> |
| | <221> misc_feature |
| | <222> (2890) . . . (3210) |
| | <223> aVEGFv11 VL |
| | <220> |
| | <221> misc_feature |
| | <222> (3211) . . . (3531) |
| | <223> CL |
| | <220> |
| | <221> misc_feature |
| | <222> (3532) . . . (3537) |
| | <223> stop cassette |
| | <220> |
| | <221> polyA_signal |
| | <222> (3607) . . . (3733) |
| | <223> rabbit globin poly A |
| | <220> |
| | <221> repeat_region |
| | <222> (3822) . . . (3951) |
| | <223> 3' ITR |
| 43 | <223> ITR.CB7.CI.aVEGFv12.rBG.ITR |
| | <220> |
| | <221> repeat_region |
| | <222> (1) . . . (130) |
| | <223> 5'ITR |
| | <220> |
| | <221> promoter |
| | <222> (198) . . . (579) |
| | <223> CMV IE promoter |
| | <220> |
| | <221> enhancer |
| | <222> (279) . . . (538) |
| | <223> C4 enhancer |
| | <220> |
| | <221> promoter |
| | <222> (582) . . . (862) |
| | <223> CB promoter |
| | <220> |
| | <221> Intron |
| | <222> (956) . . . (1928) |
| | <223> chicken beta-actin intron |
| | <220> |
| | <221> 5'UTR |
| | <222> (1940) . . . (1987) |
| | <223> c-myc 5'UTR |
| | <220> |
| | <221> misc_feature |
| | <222> (1988) . . . (1993) |
| | <223> kozak |
| | <220> |
| | <221> misc_feature |
| | <222> (1993) . . . (2052) |
| | <223> leader |
| | <220> |
| | <221> misc_feature |
| | <222> (2053) . . . (2421) |
| | <223> aVEGFv12 VH |
| | <220> |
| | <221> misc_feature |
| | <222> (2422) . . . (2742) |
| | <223> CH1 |
| | <220> |
| | <221> misc_feature |
| | <222> (2746) . . . (2757) |
| | <223> furing cleavage site |
| | <220> |
| | <221> misc_feature |
| | <222> (2758) . . . (2829) |
| | <223> F2A linker |
| | <220> |
| | <221> misc_feature |

-continued

| SEQ ID NO: (containing free text) | Free text under <223> |
|---|---|
| | <222> (2830) . . . (2889) |
| | <223> leader |
| | <220> |
| | <221> misc_feature |
| | <222> (2890) . . . (3210) |
| | <223> aVEGFv12 VL |
| | <220> |
| | <221> misc_feature |
| | <222> (3211) . . . (3531) |
| | <223> CL |
| | <220> |
| | <221> misc_feature |
| | <222> (3532) . . . (3537) |
| | <223> stop cassette |
| | <220> |
| | <221> polyA_signal |
| | <222> (3607) . . . (3733) |
| | <223> rabbit globin poly A |
| | <220> |
| | <221> repeat_region |
| | <222> (3822) . . . (3951) |
| | <223> 3'ITR |
| 44 | <223> ITR.CB7.CI.aVEGFv13.rBG.ITR |
| | <220> |
| | <221> repeat_region |
| | <222> (1) . . . (130) |
| | <223> 5'ITR |
| | <220> |
| | <221> misc_feature |
| | <222> (131) . . . (167) |
| | <223> part of AAV |
| | <220> |
| | <221> promoter |
| | <222> (198) . . . (579) |
| | <223> CME IE promoter |
| | <220> |
| | <221> misc_feature |
| | <222> (204) . . . (233) |
| | <223> promoter start |
| | <220> |
| | <221> enhancer |
| | <222> (279) . . . (538) |
| | <223> C4 enhancer with 2 mismatches |
| | <220> |
| | <221> misc_feature |
| | <222> (561) . . . (584) |
| | <223> CMV promoter end |
| | <220> |
| | <221> promoter |
| | <222> (582) . . . (862) |
| | <223> CB promoter |
| | <220> |
| | <221> misc_feature |
| | <222> (585) . . . (615) |
| | <223> begin promoter |
| | <220> |
| | <221> TATA_signal |
| | <222> (836) . . . (839) |
| | <220> |
| | <221> Intron |
| | <222> (956) . . . (1928) |
| | <223> chichen beta-actin intron |
| | <220> |
| | <221> misc_feature |
| | <222> (1814) . . . (1830) |
| | <223> end of intron |
| | <220> |
| | <221> 5'UTR |
| | <222> (1940) . . . (1987) |
| | <223> c-myc 5'UTR |
| | <220> |
| | <221> misc_feature |
| | <222> (1988) . . . (1993) |
| | <223> kozak |
| | <220> |
| | <221> misc_feature |
| | <222> (1993) . . . (2052) |
| | <223> leader |
| | <220> |
| | <221> misc_feature |
| | <222> (2053) . . . (2421) |
| | <223> aVEGFv13 VH |
| | <220> |
| | <221> misc_feature |
| | <222> (2422) . . . (2742) |
| | <223> CH1 |
| | <220> |
| | <221> misc_feature |
| | <222> (2746) . . . (2757) |
| | <223> furin cleavage site |
| | <220> |
| | <221> misc_feature |
| | <222> (2758) . . . (2829) |
| | <223> F2A linker |
| | <220> |
| | <221> misc_feature |
| | <222> (2830) . . . (2889) |
| | <223> leader |
| | <220> |
| | <221> misc_feature |
| | <222> (2890) . . . (3210) |
| | <223> aVEGFv13 VL |
| | <220> |
| | <221> misc_feature |
| | <222> (3211) . . . (3531) |
| | <223> CL |
| | <220> |
| | <221> misc_feature |
| | <222> (3532) . . . (3537) |
| | <223> stop cassette |
| | <220> |
| | <221> polyA_signal |
| | <222> (3607) . . . (3733) |
| | <223> rabbit globin poly A |
| | <220> |
| | <221> misc_feature |
| | <222> (3785) . . . (3821) |
| | <223> part of AAV |
| | <220> |
| | <221> repeat_region |
| | <222> (3822) . . . (3951) |
| | <223> 3'ITR |
| 45 | <223> ITR.CMV.PI.aVEGFv7.eMCV.IRES.SV40.ITR |
| | <220> |
| | <221> repeat_region |
| | <222> (1) . . . (130) |
| | <223> ITR |
| | <220> |
| | <221> promoter |
| | <222> (191) . . . (932) |
| | <223> human CMV I.E. enhancer & promoter |
| | <220> |
| | <221> Intron |
| | <222> (1047) . . . (1179) |
| | <223> Promega chimeric intron |
| | <220> |
| | <221> 5'UTR |
| | <222> (1248) . . . (1295) |
| | <223> c-myc 5'UTR |
| | <220> |
| | <221> misc_feature |
| | <222> (1299) . . . (1307) |
| | <223> kozak |
| | <220> |
| | <221> misc_feature |
| | <222> (1305) . . . (1364) |
| | <223> leader |
| | <220> |
| | <221> misc_feature |

| SEQ ID NO: (containing free text) | Free text under <223> |
|---|---|
| | <222> (1365) . . . (1685)<br><223> aVEGFv7 VL<br><220><br><221> misc_feature<br><222> (1686) . . . (2006)<br><223> CL<br><220><br><221> enhancer<br><222> (2018) . . . (2608)<br><223> IRES<br><220><br><221> misc_feature<br><222> (2606) . . . (2665)<br><223> leader<br><220><br><221> misc_feature<br><222> (2666) . . . (3034)<br><223> aVEGFv7 VH<br><220><br><221> misc_feature<br><222> (3035) . . . (3355)<br><223> CH1<br><220><br><221> polyA_signal<br><222> (3384) . . . (3615)<br><223> SV40 late polyadenylation signal<br><220><br><221> repeat_region<br><222> (3680) . . . (3809)<br><223> ITR |
| 46 | <223> ITR.CMV.PI.aVEGFv7.fmdIRES.SV40.ITR<br><220><br><221> repeat_region<br><222> (1) . . . (130)<br><223> ITR<br><220><br><221> promoter<br><222> (191) . . . (932)<br><223> human CMV I.E. enhancer and promoter<br><220><br><221> TATA_signal<br><222> (897) . . . (901)<br><220><br><221> Intron<br><222> (1047) . . . (1179)<br><223> Promega chimeric intron<br><220><br><221> 5'UTR<br><222> (1248) . . . (1295)<br><223> c-myc 5'UTR<br><220><br><221> misc_feature<br><222> (1299) . . . (1307)<br><223> kozak<br><220><br><221> misc_feature<br><222> (1305) . . . (1313)<br><223> leader<br><220><br><221> misc_feature<br><222> (1314) . . . (1364)<br><223> leader<br><220><br><221> misc_feature<br><222> (1365) . . . (1685)<br><223> aVEGFv7 VL<br><220><br><221> misc_feature<br><222> (1686) . . . (2006)<br><223> CL<br><220><br><221> misc_feature<br><222> (2021) . . . (2482)<br><223> FMDV<br><220><br><221> misc_feature<br><222> (2501) . . . (2542)<br><223> leader<br><220><br><221> misc_feature<br><222> (2543) . . . (2911)<br><223> aVEGFv7 VH<br><220><br><221> misc_feature<br><222> (2912) . . . (3232)<br><223> CH1<br><220><br><221> polyA_signal<br><222> (3261) . . . (3492)<br><223> Sv40 late polyadenylation signal<br><220><br><221> repeat_region<br><222> (3557) . . . (3686)<br><223> ITR |
| 47 | <223> ITR.CMV.PI.aVEGFv7.cMycIRES.SV40.ITR<br><220><br><221> repeat_region<br><222> (1) . . . (130)<br><223> ITR<br><220><br><221> promoter<br><222> (191) . . . (932)<br><223> human CMV I.E. enhancer and promoter<br><220><br><221> TATA_signal<br><222> (897) . . . (901)<br><220><br><221> Intron<br><222> (1047) . . . (1179)<br><223> Promega chimeric intron<br><220><br><221> 5'UTR<br><222> (1248) . . . (1295)<br><223> c-myc 5'UTR<br><220><br><221> misc_feature<br><222> (1299) . . . (1307)<br><223> kozak<br><220><br><221> misc_feature<br><222> (1305) . . . (1313)<br><223> leader<br><220><br><221> misc_feature<br><222> (1314) . . . (1364)<br><223> leader<br><220><br><221> misc_feature<br><222> (1365) . . . (1685)<br><223> aVEGFv7 VL<br><220><br><221> misc_feature<br><222> (1686) . . . (2006)<br><223> CL<br><220><br><221> misc_feature<br><222> (2021) . . . (2415)<br><223> IRES c-myc<br><220><br><221> misc_feature<br><222> (2226) . . . (2273)<br><223> mini c-myc IRES<br><220><br><221> misc_feature<br><222> (2275) . . . (2275)<br><223> this C to T mutaion increases expression<br><220><br><221> misc_feature |

-continued

| SEQ ID NO: (containing free text) | Free text under <223> |
|---|---|
| | <222> (2434) . . . (2475)<br><223> leader<br><220><br><221> misc_feature<br><222> (2476) . . . (2844)<br><223> aVEGFv7 VH<br><220><br><221> misc_feature<br><222> (2845) . . . (3165)<br><223> CH1<br><220><br><221> polyA_signal<br><222> (3194) . . . (3425)<br><223> SV40 late polyadenylation signal<br><220><br><221> repeat_region<br><222> (3490) . . . (3619)<br><223> ITR |

-continued

| SEQ ID NO: (containing free text) | Free text under <223> |
|---|---|
| 48 | <223> AAV8 capsid |
| 49 | <223> Nucleic acid sequence of AAV8 capsid |

All publications cited in this specification are incorporated herein by reference in their entireties, as are U.S. Provisional Patent Application No. 62/466,721, filed Mar. 3, 2017, U.S. Provisional Patent Application No. 62/460,515, filed Feb. 17, 2017, U.S. Provisional Patent Application No. 62/442,946, filed Jan. 5, 2017, U.S. Provisional Patent Application No. 62/331,100, filed May 3, 2016 and U.S. Provisional Patent Application No. 62/323,184, filed Apr. 15, 2016. Similarly, the Sequence Listing filed herewith is hereby incorporated by reference. While the invention has been described with reference to particular embodiments, it will be appreciated that modifications can be made without departing from the spirit of the invention. Such modifications are intended to fall within the scope of the appended claims.

The invention claimed is:

1. A recombinant adeno-associated virus (rAAV) having an AAV8 capsid, wherein the rAAV comprises a vector genome packaged within the capsid, wherein the vector genome comprises a 5' AAV-2 inverted terminal repeat, an expression cassette consisting of the contiguous nucleotides 198 to 3733 of SEQ ID NO: 14, and a 3' AAV-2 inverted terminal repeat.

2. A liquid suspension suitable for sub-retinal and/or intra-retinal injection, said suspension comprising an aqueous liquid and the recombinant adeno-associated virus (rAAV) according to claim 1 and optionally one or more excipients, preservatives, and/or surfactants.

3. A product comprising: (a) a first container comprising the rAAV according to claim 1 and an aqueous liquid, (b) optionally a second container comprising a diluent, and (c) a needle for injection.

4. The suspension according to claim 2, wherein the suspension comprises about $1\times10^{11}$ genome copies (GC)/mL to about $1\times10^{13}$ GC/mL of the rAAV.

5. The suspension according to claim 2, wherein the suspension volume is about 10 μL to about 300 μL.

* * * * *

```
SEQUENCE LISTING


<160> NUMBER OF SEQ ID NOS: 49

<210> SEQ ID NO 1
<211> LENGTH: 231
<212> TYPE: PRT
<213> ORGANISM: Artificial Sequence
<220> FEATURE:
<223> OTHER INFORMATION: Humanized anti-VEGF Fab heavy chain
<220> FEATURE:
<221> NAME/KEY: MISC_FEATURE
<222> LOCATION: (28)..(39)
<223> OTHER INFORMATION: complementarity determining region
<220> FEATURE:
<221> NAME/KEY: MISC_FEATURE
<222> LOCATION: (54)..(83)
<223> OTHER INFORMATION: complementarity determining region

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu
225                 230


<210> SEQ ID NO 2
<211> LENGTH: 214
<212> TYPE: PRT
<213> ORGANISM: Artificial Sequence
<220> FEATURE:
<223> OTHER INFORMATION: Humanized anti-VEGF Fab
<220> FEATURE:
<221> NAME/KEY: MISC_FEATURE
<222> LOCATION: (26)..(37)
<223> OTHER INFORMATION: copmlementarity determining region
<220> FEATURE:
<221> NAME/KEY: MISC_FEATURE
<222> LOCATION: (107)..(117)
<223> OTHER INFORMATION: copmlementarity determining region

<400> SEQUENCE: 2

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 3
<211> LENGTH: 3957
<212> TYPE: DNA
```

<213> ORGANISM: Artificial Sequence
<220> FEATURE:
<223> OTHER INFORMATION: 5'ITR.CB7.CI.aVEGFv2.rBG.3'ITR
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer with 2 mismatches
<220> FEATURE:
<221> NAME/KEY: misc_feature
<222> LOCATION: (279)..(538)
<223> OTHER INFORMATION: C4 enhancer
<220> FEATURE:
<221> NAME/KEY: promoter
<222> LOCATION: (582)..(862)
<223> OTHER INFORMATION: CB promoter
<220> FEATURE:
<221> NAME/KEY: TATA_signal
<222> LOCATION: (836)..(839)
<220> FEATURE:
<221> NAME/KEY: misc_feature
<222> LOCATION: (955)..(1829)
<223> OTHER INFORMATION: chicken beta-actin intron
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: Intron
<222> LOCATION: (956)..(1928)
<223> OTHER INFORMATION: chicken beta-actin promoter
<220> FEATURE:
<221> NAME/KEY: 5'UTR
<222> LOCATION: (1946)..(1993)
<223> OTHER INFORMATION: c-myc 5' UTR
<220> FEATURE:
<221> NAME/KEY: misc_feature
<222> LOCATION: (1994)..(1999)
<223> OTHER INFORMATION: kozak sequnce
<220> FEATURE:
<221> NAME/KEY: transit_peptide
<222> LOCATION: (1999)..(2058)
<220> FEATURE:
<221> NAME/KEY: CDS
<222> LOCATION: (2059)..(2427)
<223> OTHER INFORMATION: aVEGFv2 VH
<220> FEATURE:
<221> NAME/KEY: CDS
<222> LOCATION: (2428)..(2748)
<223> OTHER INFORMATION: CH1
<220> FEATURE:
<221> NAME/KEY: misc_feature
<222> LOCATION: (2752)..(2763)
<223> OTHER INFORMATION: Furin cleavage site
<220> FEATURE:
<221> NAME/KEY: CDS
<222> LOCATION: (2764)..(2835)
<223> OTHER INFORMATION: F2A linker
<220> FEATURE:
<221> NAME/KEY: transit_peptide
<222> LOCATION: (2836)..(2895)
<220> FEATURE:
<221> NAME/KEY: CDS
<222> LOCATION: (2896)..(3216)
<223> OTHER INFORMATION: aVEGFv2 VL
<220> FEATURE:
<221> NAME/KEY: CDS
<222> LOCATION: (3217)..(3537)
<223> OTHER INFORMATION: CL
<220> FEATURE:
<221> NAME/KEY: polyA_signal
<222> LOCATION: (3613)..(3739)

-continued

```
<223> OTHER INFORMATION: rabbit globin polyA
<220> FEATURE:
<221> NAME/KEY: repeat_region
<222> LOCATION: (3828)..(3957)
<223> OTHER INFORMATION: 3' ITR

<400> SEQUENCE: 3

ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctaccag ggtaatgggg    180

atcctctaga actatagcta gtcgacattg attattgact agttattaat agtaatcaat    240

tacggggtca ttagttcata gcccatatat ggagttccgc gttacataac ttacggtaaa    300

tggcccgcct ggctgaccgc ccaacgaccc ccgcccattg acgtcaataa tgacgtatgt    360

tcccatagta acgccaatag ggactttcca ttgacgtcaa tgggtggagt atttacggta    420

aactgcccac ttggcagtac atcaagtgta tcatatgcca agtacgcccc ctattgacgt    480

caatgacggt aaatggcccg cctggcatta tgcccagtac atgaccttat gggactttcc    540

tacttggcag tacatctacg tattagtcat cgctattacc atggtcgagg tgagccccac    600

gttctgcttc actctcccca tctccccccc ctccccaccc ccaattttgt atttatttat    660

tttttaatta ttttgtgcag cgatgggggc gggggggggg ggggggcgcg cgccaggcgg    720

ggcggggcgg ggcgaggggc ggggcggggc gaggcggaga ggtgcggcgg cagccaatca    780

gagcggcgcg ctccgaaagt ttccttttat ggcgaggcgg cggcggcggc ggccctataa    840

aaagcgaagc gcgcggcggg cgggagtcgc tgcgcgctgc cttcgccccg tgccccgctc    900

cgccgccgcc tcgcgccgcc cgccccggct ctgactgacc gcgttactcc cacaggtgag    960

cgggcgggac ggcccttctc ctccgggctg taattagcgc ttggtttaat gacggcttgt   1020

ttcttttctg tggctgcgtg aaagccttga ggggctccgg gagggccctt tgtgcggggg   1080

gagcggctcg gggggtgcgt gcgtgtgtgt gtgcgtgggg agcgccgcgt gcggctccgc   1140

gctgcccggc ggctgtgagc gctgcgggcg cggcgcgggg ctttgtgcgc tccgcagtgt   1200

gcgcgagggg agcgcggccg gggccggtgc cccgcggtgc ggggggggct gcgaggggaa   1260

caaaggctgc gtgcggggtg tgtgcgtggg ggggtgagca gggggtgtgg gcgcgtcggt   1320

cgggctgcaa ccccccctgc acccccctcc ccgagttgct gagcacggcc cggcttcggg   1380

tgcggggctc cgtacggggc gtggcgcggg gctcgccgtg ccgggcgggg ggtggcggca   1440

ggtgggggtg ccgggcgggg cggggccgcc tcgggccggg gagggctcgg gggaggggcg   1500

cggcggcccc cggagcgccg gcggctgtcg aggcgcggcg agccgcagcc attgcctttt   1560

atggtaatcg tgcgagaggg cgcagggact tcctttgtcc caaatctgtg cggagccgaa   1620

atctgggagg cgccgccgca ccccctctag cgggcgcggg gcgaagcggt gcggcgccgg   1680

caggaaggaa atgggcgggg agggccttcg tgcgtcgccg cgccgccgtc cccttctccc   1740

tctccagcct cggggctgtc cgcgggggga cggctgcctt cggggggggac ggggcagggc   1800

ggggttcggc ttctggcgtg tgaccggcgg ctctagagcc tctgctaacc atgttcatgc   1860

cttcttcttt ttcctacagc tcctgggcaa cgtgctggtt attgtgctgt ctcatcattt   1920

tggcaaagaa ttcgctagag ctagcgggca ctttgcactg gaacttacaa cacccgagca   1980

aggacgcgac tctccaccat gtatcggatg cagctgctgc tgctgattgc tctgagcctg   2040

gctctggtga ccaacagc gaa gtg cag ctg gtg gaa agc ggc ggc ggc ctg     2091
                    Glu Val Gln Leu Val Glu Ser Gly Gly Gly Leu
                    1               5                   10
```

```
gtg cag ccc ggc ggc agc ctg cgg ctg agc tgt gct gct agc ggc tat      2139
Val Gln Pro Gly Gly Ser Leu Arg Leu Ser Cys Ala Ala Ser Gly Tyr
            15                  20                  25

gac ttt acc cat tat ggc atg aac tgg gtg cgg cag gct ccc ggc aag      2187
Asp Phe Thr His Tyr Gly Met Asn Trp Val Arg Gln Ala Pro Gly Lys
        30                  35                  40

ggc ctg gaa tgg gtg ggc tgg att aac acc tat acc ggc gaa ccc acc      2235
Gly Leu Glu Trp Val Gly Trp Ile Asn Thr Tyr Thr Gly Glu Pro Thr
    45                  50                  55

tat gct gct gac ttt aag cgg cgg ttt acc ttt agc ctg gac acc agc      2283
Tyr Ala Ala Asp Phe Lys Arg Arg Phe Thr Phe Ser Leu Asp Thr Ser
60                  65                  70                  75

aag agc acc gct tat ctg cag atg aac agc ctg cgg gct gaa gac acc      2331
Lys Ser Thr Ala Tyr Leu Gln Met Asn Ser Leu Arg Ala Glu Asp Thr
                80                  85                  90

gct gtg tat tat tgt gct aag tat ccc tat tat tat ggc acc agc cat      2379
Ala Val Tyr Tyr Cys Ala Lys Tyr Pro Tyr Tyr Tyr Gly Thr Ser His
            95                  100                 105

tgg tat ttt gac gtg tgg ggc cag ggc acc ctg gtg acc gtg agc agc      2427
Trp Tyr Phe Asp Val Trp Gly Gln Gly Thr Leu Val Thr Val Ser Ser
        110                 115                 120

gct agc acc aag ggc ccc agc gtg ttt ccc ctg gct ccc agc agc aag      2475
Ala Ser Thr Lys Gly Pro Ser Val Phe Pro Leu Ala Pro Ser Ser Lys
    125                 130                 135

agc acc agc ggc ggc acc gct gct ctg ggc tgt ctg gtg aag gac tat      2523
Ser Thr Ser Gly Gly Thr Ala Ala Leu Gly Cys Leu Val Lys Asp Tyr
140                 145                 150                 155

ttt ccc gaa ccc gtg acc gtg agc tgg aac agc ggc gct ctg acc agc      2571
Phe Pro Glu Pro Val Thr Val Ser Trp Asn Ser Gly Ala Leu Thr Ser
                160                 165                 170

ggc gtg cat acc ttt ccc gct gtg ctg cag agc agc ggc ctg tat agc      2619
Gly Val His Thr Phe Pro Ala Val Leu Gln Ser Ser Gly Leu Tyr Ser
            175                 180                 185

ctg agc agc gtg gtg acc gtg ccc agc agc agc ctg ggc acc cag acc      2667
Leu Ser Ser Val Val Thr Val Pro Ser Ser Ser Leu Gly Thr Gln Thr
        190                 195                 200

tat att tgt aac gtg aac cat aag ccc agc aac acc aag gtg gac aag      2715
Tyr Ile Cys Asn Val Asn His Lys Pro Ser Asn Thr Lys Val Asp Lys
    205                 210                 215

aag gtg gaa ccc aag agc tgt gac aag acc cat ctgcggaagc ggcgg gct     2766
Lys Val Glu Pro Lys Ser Cys Asp Lys Thr His                  Ala
220                 225                 230

ccc gtg aag cag acc ctg aac ttt gac ctg ctg aag ctg gct ggc gac      2814
Pro Val Lys Gln Thr Leu Asn Phe Asp Leu Leu Lys Leu Ala Gly Asp
            235                 240                 245

gtg gaa agc aac ccc ggc ccc atgtatcgga tgcagctgct gctgctgatt         2865
Val Glu Ser Asn Pro Gly Pro
        250

gctctgagcc tggctctggt gaccaacagc gac att cag ctg acc cag agc ccc     2919
                                 Asp Ile Gln Leu Thr Gln Ser Pro
                                 255                 260

agc agc ctg agc gct agc gtg ggc gac cgg gtg acc att acc tgt agc      2967
Ser Ser Leu Ser Ala Ser Val Gly Asp Arg Val Thr Ile Thr Cys Ser
        265                 270                 275

gct agc cag gac att agc aac tat ctg aac tgg tat cag cag aag ccc      3015
Ala Ser Gln Asp Ile Ser Asn Tyr Leu Asn Trp Tyr Gln Gln Lys Pro
    280                 285                 290

ggc aag gct ccc aag gtg ctg att tat ttt acc agc agc ctg cat agc      3063
Gly Lys Ala Pro Lys Val Leu Ile Tyr Phe Thr Ser Ser Leu His Ser
```

```
                      295                 300                 305                 310
ggc gtg ccc agc cgg ttt agc ggc agc ggc agc ggc acc gac ttt acc           3111
Gly Val Pro Ser Arg Phe Ser Gly Ser Gly Ser Gly Thr Asp Phe Thr
                          315                 320                 325

ctg acc att agc agc ctg cag ccc gaa gac ttt gct acc tat tat tgt           3159
Leu Thr Ile Ser Ser Leu Gln Pro Glu Asp Phe Ala Thr Tyr Tyr Cys
                330                 335                 340

cag cag tat agc acc gtg ccc tgg acc ttt ggc cag ggc acc aag gtg           3207
Gln Gln Tyr Ser Thr Val Pro Trp Thr Phe Gly Gln Gly Thr Lys Val
            345                 350                 355

gaa att aag cgg acc gtg gct gct ccc agc gtg ttt att ttt ccc ccc           3255
Glu Ile Lys Arg Thr Val Ala Ala Pro Ser Val Phe Ile Phe Pro Pro
        360                 365                 370

agc gac gaa cag ctg aag agc ggc acc gct agc gtg gtg tgt ctg ctg           3303
Ser Asp Glu Gln Leu Lys Ser Gly Thr Ala Ser Val Val Cys Leu Leu
375                 380                 385                 390

aac aac ttt tat ccc cgg gaa gct aag gtg cag tgg aag gtg gac aac           3351
Asn Asn Phe Tyr Pro Arg Glu Ala Lys Val Gln Trp Lys Val Asp Asn
                395                 400                 405

gct ctg cag agc ggc aac agc cag gaa agc gtg acc gaa cag gac agc           3399
Ala Leu Gln Ser Gly Asn Ser Gln Glu Ser Val Thr Glu Gln Asp Ser
            410                 415                 420

aag gac agc acc tat agc ctg agc agc acc ctg acc ctg agc aag gct           3447
Lys Asp Ser Thr Tyr Ser Leu Ser Ser Thr Leu Thr Leu Ser Lys Ala
        425                 430                 435

gac tat gaa aag cat aag gtg tat gct tgt gaa gtg acc cat cag ggc           3495
Asp Tyr Glu Lys His Lys Val Tyr Ala Cys Glu Val Thr His Gln Gly
    440                 445                 450

ctg agc agc ccc gtg acc aag agc ttt aac cgg ggc gaa tgt                   3537
Leu Ser Ser Pro Val Thr Lys Ser Phe Asn Arg Gly Glu Cys
455                 460                 465

tgataaagcg gccgcggtac tctagagtc gacccgggcg gcctcgagga cggggtgaac          3597

tacgcctgag gatccgatct ttttccctct gccaaaaatt atggggacat catgaagccc         3657

cttgagcatc tgacttctgg ctaataaagg aaatttattt tcattgcaat agtgtgttgg         3717

aattttttgt gtctctcact cggaagcaat tcgttgatct gaatttcgac cacccataat         3777

acccattacc ctggtagata agtagcatgg cgggttaatc attaactaca aggaacccct         3837

agtgatggag ttggccactc cctctctgcg cgctcgctcg ctcactgagg ccgggcgacc         3897

aaaggtcgcc cgacgcccgg gctttgcccg ggcggcctca gtgagcgagc gagcgcgcag         3957

<210> SEQ ID NO 4
<211> LENGTH: 123
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
```

```
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120


<210> SEQ ID NO 5
<211> LENGTH: 107
<212> TYPE: PRT
<213> ORGANISM: Artificial Sequence
<220> FEATURE:
<223> OTHER INFORMATION: Synthetic Construct

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105


<210> SEQ ID NO 6
<211> LENGTH: 24
<212> TYPE: PRT
<213> ORGANISM: Artificial Sequence
<220> FEATURE:
<223> OTHER INFORMATION: Synthetic Construct

<400> SEQUENCE: 6

Ala Pro Val Lys Gln Thr Leu Asn Phe Asp Leu Leu Lys Leu Ala Gly
1               5                   10                  15

Asp Val Glu Ser Asn Pro Gly Pro
            20


<210> SEQ ID NO 7
<211> LENGTH: 107
<212> TYPE: PRT
<213> ORGANISM: Artificial Sequence
<220> FEATURE:
<223> OTHER INFORMATION: Synthetic Construct

<400> SEQUENCE: 7

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105


<210> SEQ ID NO 8
<211> LENGTH: 107
<212> TYPE: PRT
<213> ORGANISM: Artificial Sequence
<220> FEATURE:
<223> OTHER INFORMATION: Synthetic Construct

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 9
<211> LENGTH: 3770
<212> TYPE: DNA
<213> ORGANISM: Artificial Sequence
<220> FEATURE:
<223> OTHER INFORMATION: AAV25'ITR.UbC.Ci.aVEGFv2.rBG.AAV23'ITR
<220> FEATURE:
<221> NAME/KEY: repeat_region
<222> LOCATION: (17)..(146)
<223> OTHER INFORMATION: 5' ITR
<220> FEATURE:
<221> NAME/KEY: promoter
<222> LOCATION: (207)..(1435)
<223> OTHER INFORMATION: UbC with C insertion at 289 and G insertion at
      990
<220> FEATURE:
<221> NAME/KEY: Intron
<222> LOCATION: (1529)..(1661)
<223> OTHER INFORMATION: chimeric intron
<220> FEATURE:
<221> NAME/KEY: 5'UTR
<222> LOCATION: (1736)..(1783)
<223> OTHER INFORMATION: c-myc 5'UTR
<220> FEATURE:
<221> NAME/KEY: misc_feature
<222> LOCATION: (1784)..(1789)
<223> OTHER INFORMATION: kozak
<220> FEATURE:
<221> NAME/KEY: misc_feature
<222> LOCATION: (1789)..(1848)
<223> OTHER INFORMATION: kozak
<220> FEATURE:
<221> NAME/KEY: CDS
<222> LOCATION: (1849)..(2217)
<223> OTHER INFORMATION: aVEGFv2 VH
<220> FEATURE:
<221> NAME/KEY: CDS
```

<222> LOCATION: (2218)..(2538)
<223> OTHER INFORMATION: CH1
<220> FEATURE:
<221> NAME/KEY: misc_feature
<222> LOCATION: (2542)..(2553)
<223> OTHER INFORMATION: furin cleavage site
<220> FEATURE:
<221> NAME/KEY: misc_feature
<222> LOCATION: (2554)..(2625)
<223> OTHER INFORMATION: F2a linker
<220> FEATURE:
<221> NAME/KEY: misc_feature
<222> LOCATION: (2626)..(2685)
<223> OTHER INFORMATION: Leader
<220> FEATURE:
<221> NAME/KEY: CDS
<222> LOCATION: (2686)..(3006)
<223> OTHER INFORMATION: aVEGFv2 VL
<220> FEATURE:
<221> NAME/KEY: CDS
<222> LOCATION: (3007)..(3327)
<223> OTHER INFORMATION: CL
<220> FEATURE:
<221> NAME/KEY: polyA_signal
<222> LOCATION: (3345)..(3576)
<223> OTHER INFORMATION: SV40 late polyadenylation signal
<220> FEATURE:
<221> NAME/KEY: repeat_region
<222> LOCATION: (3641)..(3770)
<223> OTHER INFORMATION: 3' ITR

<400> SEQUENCE: 9
taaggcctta attaggctgc gcgctcgctc gctcactgag gccgcccggg caaagcccgg 60
gcgtcgggcg acctttggtc gcccggcctc agtgagcgag cgagcgcgca gagagggagt 120
ggccaactcc atcactaggg gttccttgta gttaatgatt aacccgccat gctacttatc 180
tacgtagcca tgctctagga agatctggcc tccgcgccgg gttttggcgc ctcccgcggg 240
cgcccccctc ctcacggcga gcgctgccac gtcagacgaa gggcgcagcg agcgtcctga 300
tccttccgcc cggacgctca ggacagcggc ccgctgctca taagactcgg ccttagaacc 360
ccagtatcag cagaaggaca ttttaggacg ggacttgggt gactctaggg cactggtttt 420
ctttccagag agcggaacag gcgaggaaaa gtagtccctt ctcggcgatt ctgcggaggg 480
atctccgtgg ggcggtgaac gccgatgatt atataaggac gcgccgggtg tggcacagct 540
agttccgtcg cagccgggat ttgggtcgcg gttcttgttt gtggatcgct gtgatcgtca 600
cttggtgagt agcgggctgc tgggctggcc ggggctttcg tggccgccgg gccgctcggt 660
gggacggaag cgtgtggaga gaccgccaag ggctgtagtc tgggtccgcg agcaaggttg 720
ccctgaactg ggggttgggg ggagcgcagc aaaatggcgg ctgttcccga gtcttgaatg 780
gaagacgctt gtgaggcggg ctgtgaggtc gttgaaacaa ggtgggggc atggtgggcg 840 gcaagaaccc aaggtcttga ggccttcgct aatgcgggaa agctcttatt cgggtgagat 900
gggctggggc accatctggg gaccctgacg tgaagtttgt cactgactgg agaactcggt 960
ttgtcgtctg ttgcgggggc ggcagttatg gcggtgccgt tgggcagtgc acccgtacct 1020
ttgggagcgc gcgccctcgt cgtgtcgtga cgtcacccgt tctgttggct tataatgcag 1080
ggtggggcca cctgccggta ggtgtgcggt aggcttttct ccgtcgcagg acgcagggtt 1140
cgggcctagg gtaggctctc ctgaatcgac aggcgccgga cctctggtga ggggagggat 1200
aagtgaggcg tcagtttctt tggtcggttt tatgtaccta tcttcttaag tagctgaagc 1260
tccggttttg aactatgcgc tcggggttgg cgagtgtgtt ttgtgaagtt ttttaggcac 1320
cttttgaaat gtaatcattt gggtcaatat gtaattttca gtgttagact agtaaattgt 1380

```
ccgctaaatt ctggccgttt ttggcttttt tgttagacga agctttattg cggtagttta   1440

tcacagttaa attgctaacg cagtcagtgc ttctgacaca acagtctcga acttaagctg   1500

cagaagttgg tcgtgaggca ctgggcaggt aagtatcaag gttacaagac aggtttaagg   1560

agaccaatag aaactgggct tgtcgagaca gagaagactc ttgcgtttct gataggcacc   1620

tattggtctt actgacatcc actttgcctt tctctccaca ggtgtccact cccagttcaa   1680

ttacagctct taaggctaga gtacttaata cgactcacta taggctagag ctagcgggca   1740

ctttgcactg gaacttacaa cacccgagca aggacgcgac tctccaccat gtatcggatg   1800

cagctgctgc tgctgattgc tctgagcctg gctctggtga ccaacagc gaa gtg cag     1857
                                                     Glu Val Gln
                                                     1

ctg gtg gaa agc ggc ggc ggc ctg gtg cag ccc ggc ggc agc ctg cgg     1905
Leu Val Glu Ser Gly Gly Gly Leu Val Gln Pro Gly Gly Ser Leu Arg
    5                   10                  15

ctg agc tgt gct gct agc ggc tat gac ttt acc cat tat ggc atg aac     1953
Leu Ser Cys Ala Ala Ser Gly Tyr Asp Phe Thr His Tyr Gly Met Asn
20                  25                  30                  35

tgg gtg cgg cag gct ccc ggc aag ggc ctg gaa tgg gtg ggc tgg att     2001
Trp Val Arg Gln Ala Pro Gly Lys Gly Leu Glu Trp Val Gly Trp Ile
                40                  45                  50

aac acc tat acc ggc gaa ccc acc tat gct gct gac ttt aag cgg cgg     2049
Asn Thr Tyr Thr Gly Glu Pro Thr Tyr Ala Ala Asp Phe Lys Arg Arg
            55                  60                  65

ttt acc ttt agc ctg gac acc agc aag agc acc gct tat ctg cag atg     2097
Phe Thr Phe Ser Leu Asp Thr Ser Lys Ser Thr Ala Tyr Leu Gln Met
        70                  75                  80

aac agc ctg cgg gct gaa gac acc gct gtg tat tat tgt gct aag tat     2145
Asn Ser Leu Arg Ala Glu Asp Thr Ala Val Tyr Tyr Cys Ala Lys Tyr
    85                  90                  95

ccc tat tat tat ggc acc agc cat tgg tat ttt gac gtg tgg ggc cag     2193
Pro Tyr Tyr Tyr Gly Thr Ser His Trp Tyr Phe Asp Val Trp Gly Gln
100                 105                 110                 115

ggc acc ctg gtg acc gtg agc agc gct agc acc aag ggc ccc agc gtg     2241
Gly Thr Leu Val Thr Val Ser Ser Ala Ser Thr Lys Gly Pro Ser Val
                120                 125                 130

ttt ccc ctg gct ccc agc agc aag agc acc agc ggc ggc acc gct gct     2289
Phe Pro Leu Ala Pro Ser Ser Lys Ser Thr Ser Gly Gly Thr Ala Ala
            135                 140                 145

ctg ggc tgt ctg gtg aag gac tat ttt ccc gaa ccc gtg acc gtg agc     2337
Leu Gly Cys Leu Val Lys Asp Tyr Phe Pro Glu Pro Val Thr Val Ser
        150                 155                 160

tgg aac agc ggc gct ctg acc agc ggc gtg cat acc ttt ccc gct gtg     2385
Trp Asn Ser Gly Ala Leu Thr Ser Gly Val His Thr Phe Pro Ala Val
    165                 170                 175

ctg cag agc agc ggc ctg tat agc ctg agc agc gtg gtg acc gtg ccc     2433
Leu Gln Ser Ser Gly Leu Tyr Ser Leu Ser Ser Val Val Thr Val Pro
180                 185                 190                 195

agc agc agc ctg ggc acc cag acc tat att tgt aac gtg aac cat aag     2481
Ser Ser Ser Leu Gly Thr Gln Thr Tyr Ile Cys Asn Val Asn His Lys
                200                 205                 210

ccc agc aac acc aag gtg gac aag aag gtg gaa ccc aag agc tgt gac     2529
Pro Ser Asn Thr Lys Val Asp Lys Lys Val Glu Pro Lys Ser Cys Asp
            215                 220                 225

aag acc cat ctgcggaagc ggcgggctcc cgtgaagcag accctgaact             2578
Lys Thr His
        230

ttgacctgct gaagctggct ggcgacgtgg aaagcaaccc cggccccatg tatcggatgc   2638
```

```
agctgctgct gctgattgct ctgagcctgg ctctggtgac caacagc gac att cag     2694
                                                    Asp Ile Gln

ctg acc cag agc ccc agc agc ctg agc gct agc gtg ggc gac cgg gtg     2742
Leu Thr Gln Ser Pro Ser Ser Leu Ser Ala Ser Val Gly Asp Arg Val
    235                 240                 245

acc att acc tgt agc gct agc cag gac att agc aac tat ctg aac tgg     2790
Thr Ile Thr Cys Ser Ala Ser Gln Asp Ile Ser Asn Tyr Leu Asn Trp
250                 255                 260                 265

tat cag cag aag ccc ggc aag gct ccc aag gtg ctg att tat ttt acc     2838
Tyr Gln Gln Lys Pro Gly Lys Ala Pro Lys Val Leu Ile Tyr Phe Thr
                270                 275                 280

agc agc ctg cat agc ggc gtg ccc agc cgg ttt agc ggc agc ggc agc     2886
Ser Ser Leu His Ser Gly Val Pro Ser Arg Phe Ser Gly Ser Gly Ser
            285                 290                 295

ggc acc gac ttt acc ctg acc att agc agc ctg cag ccc gaa gac ttt     2934
Gly Thr Asp Phe Thr Leu Thr Ile Ser Ser Leu Gln Pro Glu Asp Phe
        300                 305                 310

gct acc tat tat tgt cag cag tat agc acc gtg ccc tgg acc ttt ggc     2982
Ala Thr Tyr Tyr Cys Gln Gln Tyr Ser Thr Val Pro Trp Thr Phe Gly
    315                 320                 325

cag ggc acc aag gtg gaa att aag cgg acc gtg gct gct ccc agc gtg     3030
Gln Gly Thr Lys Val Glu Ile Lys Arg Thr Val Ala Ala Pro Ser Val
330                 335                 340                 345

ttt att ttt ccc ccc agc gac gaa cag ctg aag agc ggc acc gct agc     3078
Phe Ile Phe Pro Pro Ser Asp Glu Gln Leu Lys Ser Gly Thr Ala Ser
                350                 355                 360

gtg gtg tgt ctg ctg aac aac ttt tat ccc cgg gaa gct aag gtg cag     3126
Val Val Cys Leu Leu Asn Asn Phe Tyr Pro Arg Glu Ala Lys Val Gln
            365                 370                 375

tgg aag gtg gac aac gct ctg cag agc ggc aac agc cag gaa agc gtg     3174
Trp Lys Val Asp Asn Ala Leu Gln Ser Gly Asn Ser Gln Glu Ser Val
        380                 385                 390

acc gaa cag gac agc aag gac agc acc tat agc ctg agc agc acc ctg     3222
Thr Glu Gln Asp Ser Lys Asp Ser Thr Tyr Ser Leu Ser Ser Thr Leu
    395                 400                 405

acc ctg agc aag gct gac tat gaa aag cat aag gtg tat gct tgt gaa     3270
Thr Leu Ser Lys Ala Asp Tyr Glu Lys His Lys Val Tyr Ala Cys Glu
410                 415                 420                 425

gtg acc cat cag ggc ctg agc agc ccc gtg acc aag agc ttt aac cgg     3318
Val Thr His Gln Gly Leu Ser Ser Pro Val Thr Lys Ser Phe Asn Arg
                430                 435                 440

ggc gaa tgt tgataaagcg gccgcttcga gcagacatga taagatacat            3367
Gly Glu Cys

tgatgagttt ggacaaacca caactagaat gcagtgaaaa aaatgcttta tttgtgaaat   3427

ttgtgatgct attgctttat ttgtaaccat tataagctgc aataaacaag ttaacaacaa   3487

caattgcatt cattttatgt ttcaggttca gggggagatg tgggaggttt tttaaagcaa   3547

gtaaaacctc tacaaatgtg gtaaaatcga taaggatctt cctagagcat ggctacgtag   3607

ataagtagca tggcgggtta atcattaact acaaggaacc cctagtgatg gagttggcca   3667

ctccctctct gcgcgctcgc tcgctcactg aggccgggcg accaaaggtc gcccgacgcc   3727

cgggctttgc ccgggcggcc tcagtgagcg agcgagcgcg cag                     3770
```

<210> SEQ ID NO 10
<211> LENGTH: 123
<212> TYPE: PRT
<213> ORGANISM: Artificial Sequence
<220> FEATURE:

<223> OTHER INFORMATION: Synthetic Construct

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120
```

<210> SEQ ID NO 11
<211> LENGTH: 107
<212> TYPE: PRT
<213> ORGANISM: Artificial Sequence
<220> FEATURE:
<223> OTHER INFORMATION: Synthetic Construct

<400> SEQUENCE: 11

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105
```

<210> SEQ ID NO 12
<211> LENGTH: 107
<212> TYPE: PRT
<213> ORGANISM: Artificial Sequence
<220> FEATURE:
<223> OTHER INFORMATION: Synthetic Construct

<400> SEQUENCE: 12

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
```

-continued

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105


<210> SEQ ID NO 13
<211> LENGTH: 107
<212> TYPE: PRT
<213> ORGANISM: Artificial Sequence
<220> FEATURE:
<223> OTHER INFORMATION: Synthetic Construct

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 14
<211> LENGTH: 3951
<212> TYPE: DNA
<213> ORGANISM: Artificial Sequence
<220> FEATURE:
<223> OTHER INFORMATION: ITR.CB7.CI.aVEGRv3.rBG.ITR
<220> FEATURE:
<221> NAME/KEY: repeat_region
<222> LOCATION: (1)..(130)
<223> OTHER INFORMATION: 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer with 2 mismatches
<220> FEATURE:
<221> NAME/KEY: promoter
<222> LOCATION: (582)..(862)
<223> OTHER INFORMATION: CB promoter
<220> FEATURE:
<221> NAME/KEY: TATA_signal
<222> LOCATION: (836)..(839)
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: 5'UTR
<222> LOCATION: (1940)..(1987)
<220> FEATURE:
<221> NAME/KEY: misc_feature
<222> LOCATION: (1988)..(1993)
<223> OTHER INFORMATION: Kozak
```

<220> FEATURE:
<221> NAME/KEY: misc_feature
<222> LOCATION: (1993)..(2052)
<223> OTHER INFORMATION: leader
<220> FEATURE:
<221> NAME/KEY: CDS
<222> LOCATION: (2053)..(2421)
<223> OTHER INFORMATION: aVEGFv3 VH
<220> FEATURE:
<221> NAME/KEY: CDS
<222> LOCATION: (2422)..(2742)
<223> OTHER INFORMATION: CH1
<220> FEATURE:
<221> NAME/KEY: misc_feature
<222> LOCATION: (2746)..(2757)
<223> OTHER INFORMATION: furin cleavage site
<220> FEATURE:
<221> NAME/KEY: misc_feature
<222> LOCATION: (2758)..(2829)
<223> OTHER INFORMATION: F2a linker
<220> FEATURE:
<221> NAME/KEY: misc_feature
<222> LOCATION: (2830)..(2889)
<223> OTHER INFORMATION: leader
<220> FEATURE:
<221> NAME/KEY: CDS
<222> LOCATION: (2890)..(3210)
<223> OTHER INFORMATION: aVEGFv3 VL
<220> FEATURE:
<221> NAME/KEY: CDS
<222> LOCATION: (3211)..(3531)
<223> OTHER INFORMATION: CL
<220> FEATURE:
<221> NAME/KEY: polyA_signal
<222> LOCATION: (3607)..(3733)
<223> OTHER INFORMATION: rabbit globin polyA
<220> FEATURE:
<221> NAME/KEY: repeat_region
<222> LOCATION: (3822)..(3951)
<223> OTHER INFORMATION: 3' ITR

<400> SEQUENCE: 14
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgggg 180
atcctctaga actatagcta gtcgacattg attattgact agttattaat agtaatcaat 240
tacggggtca ttagttcata gcccatatat ggagttccgc gttacataac ttacggtaaa 300
tggcccgcct ggctgaccgc ccaacgaccc ccgcccattg acgtcaataa tgacgtatgt 360
tcccatagta acgccaatag ggactttcca ttgacgtcaa tgggtggagt atttacggta 420
aactgcccac ttggcagtac atcaagtgta tcatatgcca agtacgcccc ctattgacgt 480
caatgacggt aaatggcccg cctggcatta tgcccagtac atgaccttat gggactttcc 540
tacttggcag tacatctacg tattagtcat cgctattacc atggtcgagg tgagccccac 600
gttctgcttc actctcccca tctccccccc ctccccaccc ccaattttgt atttatttat 660
tttttaatta ttttgtgcag cgatgggggc gggggggggg ggggggcgcg cgccaggcgg 720
ggcggggcgg ggcgaggggc ggggcggggc gaggcggaga ggtgcggcgg cagccaatca 780
gagcggcgcg ctccgaaagt ttccttttat ggcgaggcgg cggcggcggc ggccctataa 840
aaagcgaagc gcgcggcggg cgggagtcgc tgcgcgctgc cttcgccccg tgccccgctc 900
cgccgccgcc tcgcgccgcc cgccccggct ctgactgacc gcgttactcc cacaggtgag 960
cgggcgggac ggcccttctc ctccgggctg taattagcgc ttggtttaat gacggcttgt 1020
ttcttttctg tggctgcgtg aaagccttga ggggctccgg gagggccctt tgtgcggggg 1080

```
gagcggctcg gggggtgcgt gcgtgtgtgt gtgcgtgggg agcgccgcgt gcggctccgc   1140

gctgcccggc ggctgtgagc gctgcgggcg cggcgcgggg ctttgtgcgc tccgcagtgt   1200

gcgcgagggg agcgcggccg ggggcggtgc cccgcggtgc ggggggggct gcgaggggaa   1260

caaaggctgc gtgcggggtg tgtgcgtggg ggggtgagca gggggtgtgg gcgcgtcggt   1320

cgggctgcaa ccccccctgc acccccctcc ccgagttgct gagcacggcc cggcttcggg   1380

tgcggggctc cgtacggggc gtggcgcggg gctcgccgtg ccgggcgggg ggtggcggca   1440

ggtgggggtg ccgggcgggg cggggccgcc tcgggccggg gagggctcgg gggaggggcg   1500

cggcggcccc cggagcgccg gcggctgtcg aggcgcggcg agccgcagcc attgcctttt   1560

atggtaatcg tgcgagaggg cgcagggact tcctttgtcc caaatctgtg cggagccgaa   1620

atctgggagg cgccgccgca ccccctctag cgggcgcggg gcgaagcggt gcggcgccgg   1680

caggaaggaa atgggcgggg agggccttcg tgcgtcgccg cgccgccgtc cccttctccc   1740

tctccagcct cggggctgtc cgcgggggga cggctgcctt cggggggggac ggggcagggc   1800

ggggttcggc ttctggcgtg tgaccggcgg ctctagagcc tctgctaacc atgttcatgc   1860

cttcttcttt ttcctacagc tcctgggcaa cgtgctggtt attgtgctgt ctcatcattt   1920

tggcaaagaa ttcgctagcg ggcactttgc actggaactt acaacacccg agcaaggacg   1980

cgactctcca ccatgtaccg tatgcagctg ctgctgctga tcgcactgtc actggcactg   2040

gttaccaact ca gaa gtt cag ctg gtt gaa tca ggc ggc ggc ctg gtt cag   2091
              Glu Val Gln Leu Val Glu Ser Gly Gly Gly Leu Val Gln
              1               5                   10

ccc ggc ggc tca ctg cgt ctg tca tgt gca gca tca ggc tac gat ttc     2139
Pro Gly Gly Ser Leu Arg Leu Ser Cys Ala Ala Ser Gly Tyr Asp Phe
    15                  20                  25

acc cac tac ggc atg aac tgg gtt cgt cag gca ccc ggc aaa ggc ctg     2187
Thr His Tyr Gly Met Asn Trp Val Arg Gln Ala Pro Gly Lys Gly Leu
30                  35                  40                  45

gaa tgg gtt ggc tgg atc aac acc tac acc ggc gaa ccc acc tac gca     2235
Glu Trp Val Gly Trp Ile Asn Thr Tyr Thr Gly Glu Pro Thr Tyr Ala
                50                  55                  60

gca gat ttc aaa cgt cgt ttc acc ttc tca ctg gat acc tca aaa tca     2283
Ala Asp Phe Lys Arg Arg Phe Thr Phe Ser Leu Asp Thr Ser Lys Ser
            65                  70                  75

acc gca tac ctg cag atg aac tca ctg cgt gca gaa gat acc gca gtt     2331
Thr Ala Tyr Leu Gln Met Asn Ser Leu Arg Ala Glu Asp Thr Ala Val
        80                  85                  90

tac tac tgt gca aaa tac ccc tac tac tac ggc acc tca cac tgg tac     2379
Tyr Tyr Cys Ala Lys Tyr Pro Tyr Tyr Tyr Gly Thr Ser His Trp Tyr
    95                  100                 105

ttc gat gtt tgg ggc cag ggc acc ctg gtt acc gtt tca tca gca tca     2427
Phe Asp Val Trp Gly Gln Gly Thr Leu Val Thr Val Ser Ser Ala Ser
110                 115                 120                 125

acc aaa ggc ccc tca gtt ttc ccc ctg gca ccc tca tca aaa tca acc     2475
Thr Lys Gly Pro Ser Val Phe Pro Leu Ala Pro Ser Ser Lys Ser Thr
                130                 135                 140

tca ggc ggc acc gca gca ctg ggc tgt ctg gtt aaa gat tac ttc ccc     2523
Ser Gly Gly Thr Ala Ala Leu Gly Cys Leu Val Lys Asp Tyr Phe Pro
            145                 150                 155

gaa ccc gtt acc gtt tca tgg aac tca ggc gca ctg acc tca ggc gtt     2571
Glu Pro Val Thr Val Ser Trp Asn Ser Gly Ala Leu Thr Ser Gly Val
        160                 165                 170

cac acc ttc ccc gca gtt ctg cag tca tca ggc ctg tac tca ctg tca     2619
His Thr Phe Pro Ala Val Leu Gln Ser Ser Gly Leu Tyr Ser Leu Ser
    175                 180                 185
```

```
tca gtt gtt acc gtt ccc tca tca tca ctg ggc acc cag acc tac atc     2667
Ser Val Val Thr Val Pro Ser Ser Ser Leu Gly Thr Gln Thr Tyr Ile
190                 195                 200                 205

tgt aac gtt aac cac aaa ccc tca aac acc aaa gtt gat aaa aaa gtt     2715
Cys Asn Val Asn His Lys Pro Ser Asn Thr Lys Val Asp Lys Lys Val
                210                 215                 220

gaa ccc aaa tca tgt gat aaa acc cac ctgcgtaaac gtcgtgcacc           2762
Glu Pro Lys Ser Cys Asp Lys Thr His
            225                 230

cgttaaacag accctgaact tcgatctgct gaaactggca ggcgatgttg aatcaaaccc   2822

cggccccatg taccgtatgc agctgctgct gctgatcgca ctgtcactgg cactggttac   2882

caactca gat atc cag ctg acc cag tca ccc tca tca ctg tca gca tca     2931
        Asp Ile Gln Leu Thr Gln Ser Pro Ser Ser Leu Ser Ala Ser
                        235                 240

gtt ggc gat cgt gtt acc atc acc tgt tca gca tca cag gat atc tca     2979
Val Gly Asp Arg Val Thr Ile Thr Cys Ser Ala Ser Gln Asp Ile Ser
245                 250                 255                 260

aac tac ctg aac tgg tac cag cag aaa ccc ggc aaa gca ccc aaa gtt     3027
Asn Tyr Leu Asn Trp Tyr Gln Gln Lys Pro Gly Lys Ala Pro Lys Val
                265                 270                 275

ctg atc tac ttc acc tca tca ctg cac tca ggc gtt ccc tca cgt ttc     3075
Leu Ile Tyr Phe Thr Ser Ser Leu His Ser Gly Val Pro Ser Arg Phe
            280                 285                 290

tca ggc tca ggc tca ggc acc gat ttc acc ctg acc atc tca tca ctg     3123
Ser Gly Ser Gly Ser Gly Thr Asp Phe Thr Leu Thr Ile Ser Ser Leu
        295                 300                 305

cag ccc gaa gat ttc gca acc tac tac tgt cag cag tac tca acc gtt     3171
Gln Pro Glu Asp Phe Ala Thr Tyr Tyr Cys Gln Gln Tyr Ser Thr Val
    310                 315                 320

ccc tgg acc ttc ggc cag ggc acc aaa gtt gaa atc aaa cgt acc gtt     3219
Pro Trp Thr Phe Gly Gln Gly Thr Lys Val Glu Ile Lys Arg Thr Val
325                 330                 335                 340

gca gca ccc tca gtt ttc atc ttc ccc ccc tca gat gaa cag ctg aaa     3267
Ala Ala Pro Ser Val Phe Ile Phe Pro Pro Ser Asp Glu Gln Leu Lys
                345                 350                 355

tca ggc acc gca tca gtt gtt tgt ctg ctg aac aac ttc tac ccc cgt     3315
Ser Gly Thr Ala Ser Val Val Cys Leu Leu Asn Asn Phe Tyr Pro Arg
            360                 365                 370

gaa gca aaa gtt cag tgg aaa gtt gat aac gca ctg cag tca ggc aac     3363
Glu Ala Lys Val Gln Trp Lys Val Asp Asn Ala Leu Gln Ser Gly Asn
        375                 380                 385

tca cag gaa tca gtt acc gaa cag gat tca aaa gat tca acc tac tca     3411
Ser Gln Glu Ser Val Thr Glu Gln Asp Ser Lys Asp Ser Thr Tyr Ser
    390                 395                 400

ctg tca tca acc ctg acc ctg tca aaa gca gat tac gaa aaa cac aaa     3459
Leu Ser Ser Thr Leu Thr Leu Ser Lys Ala Asp Tyr Glu Lys His Lys
405                 410                 415                 420

gtt tac gca tgt gaa gtt acc cac cag ggc ctg tca tca ccc gtt acc     3507
Val Tyr Ala Cys Glu Val Thr His Gln Gly Leu Ser Ser Pro Val Thr
                425                 430                 435

aaa tca ttc aac cgt ggc gaa tgt tgataaagcg gccgcggtac ctctagagtc    3561
Lys Ser Phe Asn Arg Gly Glu Cys
            440

gacccgggcg gcctcgagga cggggtgaac tacgcctgag gatccgatct tttccctct    3621

gccaaaaatt atggggacat catgaagccc cttgagcatc tgacttctgg ctaataaagg   3681

aaatttattt tcattgcaat agtgtgttgg aatttttgt gtctctcact cggaagcaat    3741
```

-continued

```
tcgttgatct gaatttcgac cacccataat acccattacc ctggtagata agtagcatgg   3801

cgggttaatc attaactaca aggaacccct agtgatggag ttggccactc cctctctgcg   3861

cgctcgctcg ctcactgagg ccgggcgacc aaaggtcgcc cgacgcccgg gctttgcccg   3921

ggcggcctca gtgagcgagc gagcgcgcag                                    3951
```

```
<210> SEQ ID NO 15
<211> LENGTH: 123
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120


<210> SEQ ID NO 16
<211> LENGTH: 107
<212> TYPE: PRT
<213> ORGANISM: Artificial Sequence
<220> FEATURE:
<223> OTHER INFORMATION: Synthetic Construct

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105


<210> SEQ ID NO 17
<211> LENGTH: 107
<212> TYPE: PRT
<213> ORGANISM: Artificial Sequence
<220> FEATURE:
```

<223> OTHER INFORMATION: Synthetic Construct

<400> SEQUENCE: 17

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 18
<211> LENGTH: 107
<212> TYPE: PRT
<213> ORGANISM: Artificial Sequence
<220> FEATURE:
<223> OTHER INFORMATION: Synthetic Construct

<400> SEQUENCE: 18

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 19
<211> LENGTH: 3763
<212> TYPE: DNA
<213> ORGANISM: Artificial Sequence
<220> FEATURE:
<223> OTHER INFORMATION: ITR.UbC.PI.aVEGFv3.SV40.ITR
<220> FEATURE:
<221> NAME/KEY: repeat_region
<222> LOCATION: (17)..(146)
<223> OTHER INFORMATION: AAV2 5' ITR
<220> FEATURE:
<221> NAME/KEY: promoter
<222> LOCATION: (207)..(1434)
<223> OTHER INFORMATION: UbC, with C insert at 289 and G insert at 990
<220> FEATURE:
<221> NAME/KEY: Intron
<222> LOCATION: (1528)..(1660)
<223> OTHER INFORMATION: chimeric intron
<220> FEATURE:
<221> NAME/KEY: 5'UTR
<222> LOCATION: (1729)..(1776)
<223> OTHER INFORMATION: c-myc 5'UTR
<220> FEATURE:
<221> NAME/KEY: misc_feature
<222> LOCATION: (1777)..(1782)
<223> OTHER INFORMATION: kozak
<220> FEATURE:
<221> NAME/KEY: misc_feature
<222> LOCATION: (1782)..(1841)
<223> OTHER INFORMATION: leader
<220> FEATURE:
<221> NAME/KEY: CDS
<222> LOCATION: (1842)..(2210)
<223> OTHER INFORMATION: aVEGFv3 VH
<220> FEATURE:
<221> NAME/KEY: CDS
<222> LOCATION: (2211)..(2531)
<223> OTHER INFORMATION: CH1
<220> FEATURE:
<221> NAME/KEY: misc_feature
<222> LOCATION: (2535)..(2546)
<223> OTHER INFORMATION: furin cleavage site
<220> FEATURE:
<221> NAME/KEY: misc_feature
<222> LOCATION: (2547)..(2618)
<223> OTHER INFORMATION: F2a linker
<220> FEATURE:
<221> NAME/KEY: misc_feature
<222> LOCATION: (2619)..(2678)
<223> OTHER INFORMATION: leader
<220> FEATURE:
<221> NAME/KEY: CDS
<222> LOCATION: (2679)..(2999)
<223> OTHER INFORMATION: aVEGFv3 VL
<220> FEATURE:
<221> NAME/KEY: CDS
<222> LOCATION: (3000)..(3320)
<223> OTHER INFORMATION: CL
<220> FEATURE:
<221> NAME/KEY: polyA_signal
<222> LOCATION: (3338)..(3569)
<223> OTHER INFORMATION: SV40 late polyA
<220> FEATURE:
<221> NAME/KEY: repeat_region
<222> LOCATION: (3634)..(3763)
<223> OTHER INFORMATION: AAV2 3'ITR

<400> SEQUENCE: 19
taaggcctta attaggctgc gcgctcgctc gctcactgag gccgcccggg caaagcccgg 60
gcgtcgggcg acctttggtc gcccggcctc agtgagcgag cgagcgcgca gagagggagt 120
ggccaactcc atcactaggg gttccttgta gttaatgatt aacccgccat gctacttatc 180
tacgtagcca tgctctagga agatctggcc tccgcgccgg gttttggcgc ctcccgcggg 240
cgcccccctc ctcacggcga gcgctgccac gtcagacgaa gggcgcagcg agcgtcctga 300
tccttccgcc cggacgctca ggacagcggc ccgctgctca taagactcgg ccttagaacc 360
ccagtatcag cagaaggaca ttttaggacg ggacttgggt gactctaggg cactggtttt 420
ctttccagag agcggaacag gcgaggaaaa gtagtccctt ctcggcgatt ctgcggaggg 480
atctccgtgg ggcggtgaac gccgatgatt atataaggac gcgccgggtg tggcacagct 540
agttccgtcg cagccgggat ttgggtcgcg gttcttgttt gtggatcgct gtgatcgtca 600
cttggtgagt agcgggctgc tgggctggcc ggggctttcg tggccgccgg gccgctcggt 660
gggacggaag cgtgtggaga gaccgccaag ggctgtagtc tgggtccgcg agcaaggttg 720
ccctgaactg ggggttgggg ggagcgcagc aaaatggcgg ctgttcccga gtcttgaatg 780
gaagacgctt gtgaggcggg ctgtgaggtc gttgaaacaa ggtgggggc atggtgggcg 840 gcaagaaccc aaggtcttga ggccttcgct aatgcgggaa agctcttatt cgggtgagat 900
gggctggggc accatctggg gaccctgacg tgaagtttgt cactgactgg agaactcggt 960

-continued

```
ttgtcgtctg ttgcgggggc ggcagttatg cggtgccgtt gggcagtgca cccgtacctt   1020

tgggagcgcg cgccctcgtc gtgtcgtgac gtcacccgtt ctgttggctt ataatgcagg   1080

gtggggccac ctgccggtag gtgtgcggta ggcttttctc cgtcgcagga cgcagggttc   1140

gggcctaggg taggctctcc tgaatcgaca ggcgccggac ctctggtgag gggagggata   1200

agtgaggcgt cagtttcttt ggtcggtttt atgtacctat cttcttaagt agctgaagct   1260

ccggttttga actatgcgct cggggttggc gagtgtgttt tgtgaagttt tttaggcacc   1320

ttttgaaatg taatcatttg ggtcaatatg taattttcag tgttagacta gtaaattgtc   1380

cgctaaattc tggccgtttt tggctttttt gttagacgaa gctttattgc ggtagtttat   1440

cacagttaaa ttgctaacgc agtcagtgct tctgacacaa cagtctcgaa cttaagctgc   1500

agaagttggt cgtgaggcac tgggcaggta agtatcaagg ttacaagaca ggtttaagga   1560

gaccaataga aactgggctt gtcgagacag agaagactct tgcgtttctg ataggcacct   1620

attggtctta ctgacatcca ctttgccttt ctctccacag gtgtccactc ccagttcaat   1680

tacagctctt aaggctagag tacttaatac gactcactat aggctagcgg gcactttgca   1740

ctggaactta caacacccga gcaaggacgc gactctccac catgtaccgt atgcagctgc   1800

tgctgctgat cgcactgtca ctggcactgg ttaccaactc a gaa gtt cag ctg gtt   1856
                                              Glu Val Gln Leu Val
                                              1               5

gaa tca ggc ggc ggc ctg gtt cag ccc ggc ggc tca ctg cgt ctg tca     1904
Glu Ser Gly Gly Gly Leu Val Gln Pro Gly Gly Ser Leu Arg Leu Ser
                10                  15                  20

tgt gca gca tca ggc tac gat ttc acc cac tac ggc atg aac tgg gtt     1952
Cys Ala Ala Ser Gly Tyr Asp Phe Thr His Tyr Gly Met Asn Trp Val
            25                  30                  35

cgt cag gca ccc ggc aaa ggc ctg gaa tgg gtt ggc tgg atc aac acc     2000
Arg Gln Ala Pro Gly Lys Gly Leu Glu Trp Val Gly Trp Ile Asn Thr
        40                  45                  50

tac acc ggc gaa ccc acc tac gca gca gat ttc aaa cgt cgt ttc acc     2048
Tyr Thr Gly Glu Pro Thr Tyr Ala Ala Asp Phe Lys Arg Arg Phe Thr
    55                  60                  65

ttc tca ctg gat acc tca aaa tca acc gca tac ctg cag atg aac tca     2096
Phe Ser Leu Asp Thr Ser Lys Ser Thr Ala Tyr Leu Gln Met Asn Ser
70                  75                  80                  85

ctg cgt gca gaa gat acc gca gtt tac tac tgt gca aaa tac ccc tac     2144
Leu Arg Ala Glu Asp Thr Ala Val Tyr Tyr Cys Ala Lys Tyr Pro Tyr
                90                  95                  100

tac tac ggc acc tca cac tgg tac ttc gat gtt tgg ggc cag ggc acc     2192
Tyr Tyr Gly Thr Ser His Trp Tyr Phe Asp Val Trp Gly Gln Gly Thr
            105                 110                 115

ctg gtt acc gtt tca tca gca tca acc aaa ggc ccc tca gtt ttc ccc     2240
Leu Val Thr Val Ser Ser Ala Ser Thr Lys Gly Pro Ser Val Phe Pro
        120                 125                 130

ctg gca ccc tca tca aaa tca acc tca ggc ggc acc gca gca ctg ggc     2288
Leu Ala Pro Ser Ser Lys Ser Thr Ser Gly Gly Thr Ala Ala Leu Gly
    135                 140                 145

tgt ctg gtt aaa gat tac ttc ccc gaa ccc gtt acc gtt tca tgg aac     2336
Cys Leu Val Lys Asp Tyr Phe Pro Glu Pro Val Thr Val Ser Trp Asn
150                 155                 160                 165

tca ggc gca ctg acc tca ggc gtt cac acc ttc ccc gca gtt ctg cag     2384
Ser Gly Ala Leu Thr Ser Gly Val His Thr Phe Pro Ala Val Leu Gln
                170                 175                 180

tca tca ggc ctg tac tca ctg tca tca gtt gtt acc gtt ccc tca tca     2432
Ser Ser Gly Leu Tyr Ser Leu Ser Ser Val Val Thr Val Pro Ser Ser
            185                 190                 195
```

-continued

```
tca ctg ggc acc cag acc tac atc tgt aac gtt aac cac aaa ccc tca     2480
Ser Leu Gly Thr Gln Thr Tyr Ile Cys Asn Val Asn His Lys Pro Ser
        200                 205                 210

aac acc aaa gtt gat aaa aaa gtt gaa ccc aaa tca tgt gat aaa acc     2528
Asn Thr Lys Val Asp Lys Lys Val Glu Pro Lys Ser Cys Asp Lys Thr
    215                 220                 225

cac ctgcgtaaac gtcgtgcacc cgttaaacag accctgaact tcgatctgct          2581
His
230

gaaactggca ggcgatgttg aatcaaaccc cggccccatg taccgtatgc agctgctgct   2641

gctgatcgca ctgtcactgg cactggttac caactca gat atc cag ctg acc cag    2696
                                          Asp Ile Gln Leu Thr Gln
                                                          235

tca ccc tca tca ctg tca gca tca gtt ggc gat cgt gtt acc atc acc     2744
Ser Pro Ser Ser Leu Ser Ala Ser Val Gly Asp Arg Val Thr Ile Thr
            240                 245                 250

tgt tca gca tca cag gat atc tca aac tac ctg aac tgg tac cag cag     2792
Cys Ser Ala Ser Gln Asp Ile Ser Asn Tyr Leu Asn Trp Tyr Gln Gln
        255                 260                 265

aaa ccc ggc aaa gca ccc aaa gtt ctg atc tac ttc acc tca tca ctg     2840
Lys Pro Gly Lys Ala Pro Lys Val Leu Ile Tyr Phe Thr Ser Ser Leu
    270                 275                 280

cac tca ggc gtt ccc tca cgt ttc tca ggc tca ggc tca ggc acc gat     2888
His Ser Gly Val Pro Ser Arg Phe Ser Gly Ser Gly Ser Gly Thr Asp
285                 290                 295                 300

ttc acc ctg acc atc tca tca ctg cag ccc gaa gat ttc gca acc tac     2936
Phe Thr Leu Thr Ile Ser Ser Leu Gln Pro Glu Asp Phe Ala Thr Tyr
                305                 310                 315

tac tgt cag cag tac tca acc gtt ccc tgg acc ttc ggc cag ggc acc     2984
Tyr Cys Gln Gln Tyr Ser Thr Val Pro Trp Thr Phe Gly Gln Gly Thr
            320                 325                 330

aaa gtt gaa atc aaa cgt acc gtt gca gca ccc tca gtt ttc atc ttc     3032
Lys Val Glu Ile Lys Arg Thr Val Ala Ala Pro Ser Val Phe Ile Phe
        335                 340                 345

ccc ccc tca gat gaa cag ctg aaa tca ggc acc gca tca gtt gtt tgt     3080
Pro Pro Ser Asp Glu Gln Leu Lys Ser Gly Thr Ala Ser Val Val Cys
    350                 355                 360

ctg ctg aac aac ttc tac ccc cgt gaa gca aaa gtt cag tgg aaa gtt     3128
Leu Leu Asn Asn Phe Tyr Pro Arg Glu Ala Lys Val Gln Trp Lys Val
365                 370                 375                 380

gat aac gca ctg cag tca ggc aac tca cag gaa tca gtt acc gaa cag     3176
Asp Asn Ala Leu Gln Ser Gly Asn Ser Gln Glu Ser Val Thr Glu Gln
                385                 390                 395

gat tca aaa gat tca acc tac tca ctg tca tca acc ctg acc ctg tca     3224
Asp Ser Lys Asp Ser Thr Tyr Ser Leu Ser Ser Thr Leu Thr Leu Ser
            400                 405                 410

aaa gca gat tac gaa aaa cac aaa gtt tac gca tgt gaa gtt acc cac     3272
Lys Ala Asp Tyr Glu Lys His Lys Val Tyr Ala Cys Glu Val Thr His
        415                 420                 425

cag ggc ctg tca tca ccc gtt acc aaa tca ttc aac cgt ggc gaa tgt     3320
Gln Gly Leu Ser Ser Pro Val Thr Lys Ser Phe Asn Arg Gly Glu Cys
    430                 435                 440

tgataaagcg gccgcttcga gcagacatga taagatacat tgatgagttt ggacaaacca   3380

caactagaat gcagtgaaaa aaatgcttta tttgtgaaat ttgtgatgct attgctttat   3440

ttgtaaccat tataagctgc aataaacaag ttaacaacaa caattgcatt cattttatgt   3500

ttcaggttca gggggagatg tgggaggttt tttaaagcaa gtaaaacctc tacaaatgtg   3560
```

-continued gtaaaatcga taaggatctt cctagagcat ggctacgtag ataagtagca tggcgggtta 3620
atcattaact acaaggaacc cctagtgatg gagttggcca ctccctctct gcgcgctcgc 3680
tcgctcactg aggccgggcg accaaaggtc gcccgacgcc cgggctttgc ccgggcggcc 3740
tcagtgagcg agcgagcgcg cag 3763

<210> SEQ ID NO 20
<211> LENGTH: 123
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120

<210> SEQ ID NO 21
<211> LENGTH: 107
<212> TYPE: PRT
<213> ORGANISM: Artificial Sequence
<220> FEATURE:
<223> OTHER INFORMATION: Synthetic Construct

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

<210> SEQ ID NO 22
<211> LENGTH: 107
<212> TYPE: PRT
<213> ORGANISM: Artificial Sequence
<220> FEATURE:

<223> OTHER INFORMATION: Synthetic Construct

<400> SEQUENCE: 22

Asp Ile Gln Leu Thr Gln Ser Pro Ser Ser Leu Ser Ala Ser Val Gly
1 5 10 15

Asp Arg Val Thr Ile Thr Cys Ser Ala Ser Gln Asp Ile Ser Asn Tyr
20 25 30

Leu Asn Trp Tyr Gln Gln Lys Pro Gly Lys Ala Pro Lys Val Leu Ile
35 40 45

Tyr Phe Thr Ser Ser Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Ser Thr Val Pro Trp
85 90 95

Thr Phe Gly Gln Gly Thr Lys Val Glu Ile Lys
100 105

<210> SEQ ID NO 23
<211> LENGTH: 107
<212> TYPE: PRT
<213> ORGANISM: Artificial Sequence
<220> FEATURE:
<223> OTHER INFORMATION: Synthetic Construct

<400> SEQUENCE: 23

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 24
<211> LENGTH: 3764
<212> TYPE: DNA
<213> ORGANISM: Artificial Sequence
<220> FEATURE:
<223> OTHER INFORMATION: ITR.UbC.PI.aVEGFv1.SV40.ITR
<220> FEATURE:
<221> NAME/KEY: repeat_region
<222> LOCATION: (17)..(146)
<223> OTHER INFORMATION: ITR
<220> FEATURE:
<221> NAME/KEY: promoter
<222> LOCATION: (207)..(1435)
<223> OTHER INFORMATION: UbC
<220> FEATURE:
<221> NAME/KEY: Intron
<222> LOCATION: (1529)..(1661)
<223> OTHER INFORMATION: Promoga chimeric intron
<220> FEATURE:
<221> NAME/KEY: 5'UTR
<222> LOCATION: (1730)..(1777)
<223> OTHER INFORMATION: c-myc 5'UTR
<220> FEATURE:
<221> NAME/KEY: misc_feature
<222> LOCATION: (1778)..(1783)
<223> OTHER INFORMATION: kozak
<220> FEATURE:
<221> NAME/KEY: misc_feature
<222> LOCATION: (1783)..(1842)
<223> OTHER INFORMATION: leader
<220> FEATURE:
<221> NAME/KEY: CDS
<222> LOCATION: (1843)..(2211)
<223> OTHER INFORMATION: aVEGFv1 VH
<220> FEATURE:
<221> NAME/KEY: CDS
<222> LOCATION: (2212)..(2532)
<223> OTHER INFORMATION: CH1
<220> FEATURE:
<221> NAME/KEY: misc_feature
<222> LOCATION: (2536)..(2547)
<223> OTHER INFORMATION: furin cleavage site
<220> FEATURE:
<221> NAME/KEY: misc_feature
<222> LOCATION: (2548)..(2619)
<223> OTHER INFORMATION: F2A linker
<220> FEATURE:
<221> NAME/KEY: misc_feature
<222> LOCATION: (2620)..(2679)
<223> OTHER INFORMATION: leader
<220> FEATURE:
<221> NAME/KEY: CDS
<222> LOCATION: (2680)..(3000)
<223> OTHER INFORMATION: aVEGFv1 VL
<220> FEATURE:
<221> NAME/KEY: CDS
<222> LOCATION: (3001)..(3321)
<223> OTHER INFORMATION: CL
<220> FEATURE:
<221> NAME/KEY: polyA_signal
<222> LOCATION: (3339)..(3570)
<223> OTHER INFORMATION: SV40 polyadenylation signal
<220> FEATURE:
<221> NAME/KEY: repeat_region
<222> LOCATION: (3635)..(3764)
<223> OTHER INFORMATION: ITR

<400> SEQUENCE: 24
taaggcctta attaggctgc gcgctcgctc gctcactgag gccgcccggg caaagcccgg 60
gcgtcgggcg acctttggtc gcccggcctc agtgagcgag cgagcgcgca gagagggagt 120
ggccaactcc atcactaggg gttccttgta gttaatgatt aacccgccat gctacttatc 180
tacgtagcca tgctctagga agatctggcc tccgcgccgg gttttggcgc ctcccgcggg 240
cgcccccctc ctcacggcga gcgctgccac gtcagacgaa gggcgcagcg agcgtcctga 300
tccttccgcc cggacgctca ggacagcggc ccgctgctca taagactcgg ccttagaacc 360
ccagtatcag cagaaggaca ttttaggacg ggacttgggt gactctaggg cactggtttt 420
ctttccagag agcggaacag gcgaggaaaa gtagtccctt ctcggcgatt ctgcggaggg 480
atctccgtgg ggcggtgaac gccgatgatt atataaggac gcgccgggtg tggcacagct 540
agttccgtcg cagccgggat ttgggtcgcg gttcttgttt gtggatcgct gtgatcgtca 600
cttggtgagt agcgggctgc tgggctggcc ggggctttcg tggccgccgg gccgctcggt 660
gggacggaag cgtgtggaga gaccgccaag ggctgtagtc tgggtccgcg agcaaggttg 720
ccctgaactg ggggttgggg ggagcgcagc aaaatggcgg ctgttcccga gtcttgaatg 780
gaagacgctt gtgaggcggg ctgtgaggtc gttgaaacaa ggtgggggc atggtgggcg 840 gcaagaaccc aaggtcttga ggccttcgct aatgcgggaa agctcttatt cgggtgagat 900
gggctggggc accatctggg gaccctgacg tgaagtttgt cactgactgg agaactcggt 960

-continued

```
ttgtcgtctg ttgcgggggc ggcagttatg gcggtgccgt tgggcagtgc acccgtacct   1020

ttgggagcgc gcgccctcgt cgtgtcgtga cgtcacccgt tctgttggct tataatgcag   1080

ggtggggcca cctgccggta ggtgtgcggt aggcttttct ccgtcgcagg acgcagggtt   1140

cgggcctagg gtaggctctc ctgaatcgac aggcgccgga cctctggtga ggggagggat   1200

aagtgaggcg tcagtttctt tggtcggttt tatgtaccta tcttcttaag tagctgaagc   1260

tccggttttg aactatgcgc tcggggttgg cgagtgtgtt ttgtgaagtt ttttaggcac   1320

cttttgaaat gtaatcattt gggtcaatat gtaattttca gtgttagact agtaaattgt   1380

ccgctaaatt ctggccgttt ttggcttttt tgttagacga agctttattg cggtagttta   1440

tcacagttaa attgctaacg cagtcagtgc ttctgacaca acagtctcga acttaagctg   1500

cagaagttgg tcgtgaggca ctgggcaggt aagtatcaag gttacaagac aggtttaagg   1560

agaccaatag aaactgggct tgtcgagaca gagaagactc ttgcgtttct gataggcacc   1620

tattggtctt actgacatcc actttgcctt tctctccaca ggtgtccact cccagttcaa   1680

ttacagctct taaggctaga gtacttaata cgactcacta taggctagcg ggcactttgc   1740

actggaactt acaacacccg agcaaggacg cgactctcca ccatgtaccg aatgcagctg   1800

ctgctgctga tcgcactgag cctggcactg gtgaccaaca gc gag gtg cag ctg      1854
                                               Glu Val Gln Leu
                                               1

gtg gag agc gga gga gga ctg gtg cag cca gga gga agc ctg cga ctg     1902
Val Glu Ser Gly Gly Gly Leu Val Gln Pro Gly Gly Ser Leu Arg Leu
5                   10                  15                  20

agc tgt gca gca agc gga tac gac ttc acc cat tac gga atg aac tgg     1950
Ser Cys Ala Ala Ser Gly Tyr Asp Phe Thr His Tyr Gly Met Asn Trp
                25                  30                  35

gtg cga cag gca cca gga aag gga ctg gag tgg gtg gga tgg atc aac     1998
Val Arg Gln Ala Pro Gly Lys Gly Leu Glu Trp Val Gly Trp Ile Asn
            40                  45                  50

acc tac acc gga gag cca acc tac gca gca gac ttc aag cga cga ttc     2046
Thr Tyr Thr Gly Glu Pro Thr Tyr Ala Ala Asp Phe Lys Arg Arg Phe
        55                  60                  65

acc ttc agc ctg gac acc agc aag agc acc gca tac ctg cag atg aac     2094
Thr Phe Ser Leu Asp Thr Ser Lys Ser Thr Ala Tyr Leu Gln Met Asn
    70                  75                  80

agc ctg cga gca gag gac acc gca gtg tac tac tgt gca aag tac cca     2142
Ser Leu Arg Ala Glu Asp Thr Ala Val Tyr Tyr Cys Ala Lys Tyr Pro
85                  90                  95                  100

tac tac tac gga acc agc cat tgg tac ttc gac gtg tgg gga cag gga     2190
Tyr Tyr Tyr Gly Thr Ser His Trp Tyr Phe Asp Val Trp Gly Gln Gly
                105                 110                 115

acc ctg gtg acc gtg agc agc gca agc acc aag gga cca agc gtg ttc     2238
Thr Leu Val Thr Val Ser Ser Ala Ser Thr Lys Gly Pro Ser Val Phe
            120                 125                 130

cca ctg gca cca agc agc aag agc acc agc gga gga acc gca gca ctg     2286
Pro Leu Ala Pro Ser Ser Lys Ser Thr Ser Gly Gly Thr Ala Ala Leu
        135                 140                 145

gga tgt ctg gtg aag gac tac ttc cca gag cca gtg acc gtg agc tgg     2334
Gly Cys Leu Val Lys Asp Tyr Phe Pro Glu Pro Val Thr Val Ser Trp
    150                 155                 160

aac agc gga gca ctg acc agc gga gtg cat acc ttc cca gca gtg ctg     2382
Asn Ser Gly Ala Leu Thr Ser Gly Val His Thr Phe Pro Ala Val Leu
165                 170                 175                 180

cag agc agc gga ctg tac agc ctg agc agc gtg gtg acc gtg cca agc     2430
Gln Ser Ser Gly Leu Tyr Ser Leu Ser Ser Val Val Thr Val Pro Ser
                185                 190                 195
```

-continued

```
agc agc ctg gga acc cag acc tac atc tgt aac gtg aac cat aag cca     2478
Ser Ser Leu Gly Thr Gln Thr Tyr Ile Cys Asn Val Asn His Lys Pro
            200                 205                 210

agc aac acc aag gtg gac aag aag gtg gag cca aag agc tgt gac aag     2526
Ser Asn Thr Lys Val Asp Lys Lys Val Glu Pro Lys Ser Cys Asp Lys
        215                 220                 225

acc cat ctgcgaaagc gacgagcacc agtgaagcag accctgaact tcgacctgct      2582
Thr His
    230

gaagctggca ggagacgtgg agagcaaccc aggaccaatg taccgaatgc agctgctgct   2642

gctgatcgca ctgagcctgg cactggtgac caacagc gac atc cag ctg acc cag    2697
                                         Asp Ile Gln Leu Thr Gln
                                                         235

agc cca agc agc ctg agc gca agc gtg gga gac cga gtg acc atc acc     2745
Ser Pro Ser Ser Leu Ser Ala Ser Val Gly Asp Arg Val Thr Ile Thr
            240                 245                 250

tgt agc gca agc cag gac atc agc aac tac ctg aac tgg tac cag cag     2793
Cys Ser Ala Ser Gln Asp Ile Ser Asn Tyr Leu Asn Trp Tyr Gln Gln
        255                 260                 265

aag cca gga aag gca cca aag gtg ctg atc tac ttc acc agc agc ctg     2841
Lys Pro Gly Lys Ala Pro Lys Val Leu Ile Tyr Phe Thr Ser Ser Leu
    270                 275                 280

cat agc gga gtg cca agc cga ttc agc gga agc gga agc gga acc gac     2889
His Ser Gly Val Pro Ser Arg Phe Ser Gly Ser Gly Ser Gly Thr Asp
285                 290                 295                 300

ttc acc ctg acc atc agc agc ctg cag cca gag gac ttc gca acc tac     2937
Phe Thr Leu Thr Ile Ser Ser Leu Gln Pro Glu Asp Phe Ala Thr Tyr
                305                 310                 315

tac tgt cag cag tac agc acc gtg cca tgg acc ttc gga cag gga acc     2985
Tyr Cys Gln Gln Tyr Ser Thr Val Pro Trp Thr Phe Gly Gln Gly Thr
            320                 325                 330

aag gtg gag atc aag cga acc gtg gca gca cca agc gtg ttc atc ttc     3033
Lys Val Glu Ile Lys Arg Thr Val Ala Ala Pro Ser Val Phe Ile Phe
        335                 340                 345

cca cca agc gac gag cag ctg aag agc gga acc gca agc gtg gtg tgt     3081
Pro Pro Ser Asp Glu Gln Leu Lys Ser Gly Thr Ala Ser Val Val Cys
    350                 355                 360

ctg ctg aac aac ttc tac cca cga gag gca aag gtg cag tgg aag gtg     3129
Leu Leu Asn Asn Phe Tyr Pro Arg Glu Ala Lys Val Gln Trp Lys Val
365                 370                 375                 380

gac aac gca ctg cag agc gga aac agc cag gag agc gtg acc gag cag     3177
Asp Asn Ala Leu Gln Ser Gly Asn Ser Gln Glu Ser Val Thr Glu Gln
                385                 390                 395

gac agc aag gac agc acc tac agc ctg agc agc acc ctg acc ctg agc     3225
Asp Ser Lys Asp Ser Thr Tyr Ser Leu Ser Ser Thr Leu Thr Leu Ser
            400                 405                 410

aag gca gac tac gag aag cat aag gtg tac gca tgt gag gtg acc cat     3273
Lys Ala Asp Tyr Glu Lys His Lys Val Tyr Ala Cys Glu Val Thr His
        415                 420                 425

cag gga ctg agc agc cca gtg acc aag agc ttc aac cga gga gag tgt     3321
Gln Gly Leu Ser Ser Pro Val Thr Lys Ser Phe Asn Arg Gly Glu Cys
    430                 435                 440

tgataaagcg gccgcttcga gcagacatga taagatacat tgatgagttt ggacaaacca   3381

caactagaat gcagtgaaaa aaatgcttta tttgtgaaat ttgtgatgct attgctttat   3441

ttgtaaccat tataagctgc aataaacaag ttaacaacaa caattgcatt cattttatgt   3501

ttcaggttca gggggagatg tgggaggttt tttaaagcaa gtaaaacctc tacaaatgtg   3561
```

-continued

```
gtaaaatcga taaggatctt cctagagcat ggctacgtag ataagtagca tggcgggtta   3621

atcattaact acaaggaacc cctagtgatg gagttggcca ctccctctct gcgcgctcgc   3681

tcgctcactg aggccgggcg accaaaggtc gcccgacgcc cgggctttgc ccgggcggcc   3741

tcagtgagcg agcgagcgcg cag                                           3764
```

<210> SEQ ID NO 25
<211> LENGTH: 123
<212> TYPE: PRT
<213> ORGANISM: Artificial Sequence
<220> FEATURE:
<223> OTHER INFORMATION: Synthetic Construct

<400> SEQUENCE: 25

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120
```

<210> SEQ ID NO 26
<211> LENGTH: 107
<212> TYPE: PRT
<213> ORGANISM: Artificial Sequence
<220> FEATURE:
<223> OTHER INFORMATION: Synthetic Construct

<400> SEQUENCE: 26

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105
```

<210> SEQ ID NO 27
<211> LENGTH: 107
<212> TYPE: PRT
<213> ORGANISM: Artificial Sequence
<220> FEATURE:

<223> OTHER INFORMATION: Synthetic Construct

<400> SEQUENCE: 27

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 28
<211> LENGTH: 107
<212> TYPE: PRT
<213> ORGANISM: Artificial Sequence
<220> FEATURE:
<223> OTHER INFORMATION: Synthetic Construct

<400> SEQUENCE: 28

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 29
<211> LENGTH: 20
<212> TYPE: PRT
<213> ORGANISM: Homo sapiens

<400> SEQUENCE: 29

```
Met Tyr Arg Met Gln Leu Leu Ser Cys Ile Ala Leu Ser Leu Ala Leu
1               5                   10                  15

Val Thr Asn Ser
            20
```

<210> SEQ ID NO 30
<211> LENGTH: 20
<212> TYPE: PRT
<213> ORGANISM: Artificial Sequence
<220> FEATURE:
<223> OTHER INFORMATION: synthetic leader

<400> SEQUENCE: 30

```
Met Tyr Arg Met Gln Leu Leu Leu Leu Ile Ala Leu Ser Leu Ala Leu
1               5                   10                  15

Val Thr Asn Ser
            20


<210> SEQ ID NO 31
<211> LENGTH: 19
<212> TYPE: PRT
<213> ORGANISM: Artificial Sequence
<220> FEATURE:
<223> OTHER INFORMATION: synthetic leader 2

<400> SEQUENCE: 31

Met Arg Met Gln Leu Leu Leu Leu Ile Ala Leu Ser Leu Ala Leu Val
1               5                   10                  15

Thr Asn Ser


<210> SEQ ID NO 32
<211> LENGTH: 355
<212> TYPE: DNA
<213> ORGANISM: Artificial Sequence
<220> FEATURE:
<223> OTHER INFORMATION: derived from encephalomycarditts virus

<400> SEQUENCE: 32

tatgctagta cgtctctcaa ggataagtaa gtaatattaa ggtacgggag gtattggaca      60

ggccgcaata aaatatcttt attttcatta catctgtgtg ttggtttttt gtgtgaatcg     120

atagtactaa catacgctct ccatcaaaac aaaacgaaac aaaacaaact agcaaaatag     180

gctgtcccca gtgcaagtgc aggtgccaga acatttctct ggcctaactg gccggtacct     240

gagctctagt ttcactttcc ctagtttcac tttccctagt ttcactttcc ctagtttcac     300

tttccctagt ttcactttcc cctcgaggat atcaagatct ggcctcggcg gccag          355


<210> SEQ ID NO 33
<211> LENGTH: 513
<212> TYPE: PRT
<213> ORGANISM: Artificial Sequence
<220> FEATURE:
<223> OTHER INFORMATION: aVEGF
<220> FEATURE:
<221> NAME/KEY: MISC_FEATURE
<222> LOCATION: (1)..(20)
<223> OTHER INFORMATION: leader
<220> FEATURE:
<221> NAME/KEY: MISC_FEATURE
<222> LOCATION: (21)..(252)
<223> OTHER INFORMATION: aVEGF Heavy Chain
<220> FEATURE:
<221> NAME/KEY: MISC_FEATURE
<222> LOCATION: (280)..(299)
<223> OTHER INFORMATION: leader
<220> FEATURE:
<221> NAME/KEY: MISC_FEATURE
<222> LOCATION: (300)..(513)
<223> OTHER INFORMATION: aVEGF Light Chain

<400> SEQUENCE: 33

Met Tyr Arg Met Gln Leu Leu Leu Leu Ile Ala Leu Ser Leu Ala Leu
1               5                   10                  15

Val Thr Asn Ser Glu Val Gln Leu Val Glu Ser Gly Gly Gly Leu Val
            20                  25                  30

Gln Pro Gly Gly Ser Leu Arg Leu Ser Cys Ala Ala Ser Gly Tyr Asp
        35                  40                  45
```

-continued

```
Phe Thr His Tyr Gly Met Asn Trp Val Arg Gln Ala Pro Gly Lys Gly
    50                  55                  60

Leu Glu Trp Val Gly Trp Ile Asn Thr Tyr Thr Gly Glu Pro Thr Tyr
65                  70                  75                  80

Ala Ala Asp Phe Lys Arg Arg Phe Thr Phe Ser Leu Asp Thr Ser Lys
                85                  90                  95

Ser Thr Ala Tyr Leu Gln Met Asn Ser Leu Arg Ala Glu Asp Thr Ala
            100                 105                 110

Val Tyr Tyr Cys Ala Lys Tyr Pro Tyr Tyr Tyr Gly Thr Ser His Trp
        115                 120                 125

Tyr Phe Asp Val Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Leu Arg Lys Arg Arg Ala
                245                 250                 255

Pro Val Lys Gln Thr Leu Asn Phe Asp Leu Leu Lys Leu Ala Gly Asp
            260                 265                 270

Val Glu Ser Asn Pro Gly Pro Met Tyr Arg Met Gln Leu Leu Leu Leu
        275                 280                 285

Ile Ala Leu Ser Leu Ala Leu Val Thr Asn Ser Asp Ile Gln Leu Thr
    290                 295                 300

Gln Ser Pro Ser Ser Leu Ser Ala Ser Val Gly Asp Arg Val Thr Ile
305                 310                 315                 320

Thr Cys Ser Ala Ser Gln Asp Ile Ser Asn Tyr Leu Asn Trp Tyr Gln
                325                 330                 335

Gln Lys Pro Gly Lys Ala Pro Lys Val Leu Ile Tyr Phe Thr Ser Ser
            340                 345                 350

Leu His Ser Gly Val Pro Ser Arg Phe Ser Gly Ser Gly Ser Gly Thr
        355                 360                 365

Asp Phe Thr Leu Thr Ile Ser Ser Leu Gln Pro Glu Asp Phe Ala Thr
    370                 375                 380

Tyr Tyr Cys Gln Gln Tyr Ser Thr Val Pro Trp Thr Phe Gly Gln Gly
385                 390                 395                 400

Thr Lys Val Glu Ile Lys Arg Thr Val Ala Ala Pro Ser Val Phe Ile
                405                 410                 415

Phe Pro Pro Ser Asp Glu Gln Leu Lys Ser Gly Thr Ala Ser Val Val
            420                 425                 430

Cys Leu Leu Asn Asn Phe Tyr Pro Arg Glu Ala Lys Val Gln Trp Lys
        435                 440                 445

Val Asp Asn Ala Leu Gln Ser Gly Asn Ser Gln Glu Ser Val Thr Glu
    450                 455                 460

Gln Asp Ser Lys Asp Ser Thr Tyr Ser Leu Ser Ser Thr Leu Thr Leu
```

```
465                 470                 475                 480

Ser Lys Ala Asp Tyr Glu Lys His Lys Val Tyr Ala Cys Glu Val Thr
                485                 490                 495

His Gln Gly Leu Ser Ser Pro Val Thr Lys Ser Phe Asn Arg Gly Glu
            500                 505                 510

Cys


<210> SEQ ID NO 34
<211> LENGTH: 3951
<212> TYPE: DNA
<213> ORGANISM: Artificial Sequence
<220> FEATURE:
<223> OTHER INFORMATION: ITR.CB7.CI.aVEGFv1.rBG.ITR
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (204)..(584)
<223> OTHER INFORMATION: CMV IE promoter
<220> FEATURE:
<221> NAME/KEY: promoter
<222> LOCATION: (585)..(862)
<223> OTHER INFORMATION: CB promoter
<220> FEATURE:
<221> NAME/KEY: TATA_signal
<222> LOCATION: (836)..(839)
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: 5'UTR
<222> LOCATION: (1940)..(1987)
<223> OTHER INFORMATION: c-myc 5'UTR
<220> FEATURE:
<221> NAME/KEY: misc_feature
<222> LOCATION: (1988)..(1993)
<223> OTHER INFORMATION: kozak
<220> FEATURE:
<221> NAME/KEY: misc_feature
<222> LOCATION: (1993)..(2052)
<223> OTHER INFORMATION: leader
<220> FEATURE:
<221> NAME/KEY: misc_feature
<222> LOCATION: (2053)..(2421)
<223> OTHER INFORMATION: aVEGFv1 VH
<220> FEATURE:
<221> NAME/KEY: misc_feature
<222> LOCATION: (2422)..(2742)
<223> OTHER INFORMATION: CH1
<220> FEATURE:
<221> NAME/KEY: misc_feature
<222> LOCATION: (2746)..(2757)
<223> OTHER INFORMATION: furin cleavage site
<220> FEATURE:
<221> NAME/KEY: misc_feature
<222> LOCATION: (2758)..(2829)
<223> OTHER INFORMATION: F2A linker
<220> FEATURE:
<221> NAME/KEY: misc_feature
<222> LOCATION: (2830)..(2889)
<223> OTHER INFORMATION: leader
<220> FEATURE:
<221> NAME/KEY: misc_feature
<222> LOCATION: (2890)..(3210)
<223> OTHER INFORMATION: aVEGFv1 VL
<220> FEATURE:
<221> NAME/KEY: misc_feature
<222> LOCATION: (3211)..(3531)
<223> OTHER INFORMATION: CL
<220> FEATURE:
<221> NAME/KEY: misc_feature
<222> LOCATION: (3532)..(3537)
```

<223> OTHER INFORMATION: stop cassette
<220> FEATURE:
<221> NAME/KEY: polyA_signal
<222> LOCATION: (3607)..(3733)
<223> OTHER INFORMATION: Rabbit globin poly A
<220> FEATURE:
<221> NAME/KEY: misc_feature
<222> LOCATION: (3785)..(3821)
<223> OTHER INFORMATION: part of AAV
<220> FEATURE:
<221> NAME/KEY: repeat_region
<222> LOCATION: (3822)..(3951)
<223> OTHER INFORMATION: 3'ITR

<400> SEQUENCE: 34
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgggg 180
atcctctaga actatagcta gtcgacattg attattgact agttattaat agtaatcaat 240
tacggggtca ttagttcata gcccatatat ggagttccgc gttacataac ttacggtaaa 300
tggcccgcct ggctgaccgc ccaacgaccc ccgcccattg acgtcaataa tgacgtatgt 360
tcccatagta acgccaatag ggactttcca ttgacgtcaa tgggtggagt atttacggta 420
aactgcccac ttggcagtac atcaagtgta tcatatgcca agtacgcccc ctattgacgt 480
caatgacggt aaatggcccg cctggcatta tgcccagtac atgaccttat gggactttcc 540
tacttggcag tacatctacg tattagtcat cgctattacc atggtcgagg tgagccccac 600
gttctgcttc actctcccca tctccccccc ctccccaccc ccaattttgt atttatttat 660
tttttaatta ttttgtgcag cgatgggggc gggggggggg ggggggcgcg cgccaggcgg 720
ggcggggcgg ggcgaggggc ggggcggggc gaggcggaga ggtgcggcgg cagccaatca 780
gagcggcgcg ctccgaaagt ttccttttat ggcgaggcgg cggcggcggc ggccctataa 840
aaagcgaagc gcgcggcggg cgggagtcgc tgcgcgctgc cttcgccccg tgccccgctc 900
cgccgccgcc tcgcgccgcc cgccccggct ctgactgacc gcgttactcc cacaggtgag 960
cgggcgggac ggcccttctc ctccgggctg taattagcgc ttggtttaat gacggcttgt 1020
ttcttttctg tggctgcgtg aaagccttga ggggctccgg gagggccctt tgtgcggggg 1080
gagcggctcg gggggtgcgt gcgtgtgtgt gtgcgtgggg agcgccgcgt gcggctccgc 1140
gctgcccggc ggctgtgagc gctgcgggcg cggcgcgggg ctttgtgcgc tccgcagtgt 1200
gcgcgagggg agcgcggccg gggcggtgc cccgcggtgc ggggggggct gcgaggggaa 1260
caaaggctgc gtgcggggtg tgtgcgtggg ggggtgagca gggggtgtgg gcgcgtcggt 1320
cgggctgcaa ccccccctgc acccccctcc ccgagttgct gagcacggcc cggcttcggg 1380
tgcggggctc cgtacggggc gtggcgcggg gctcgccgtg ccgggcgggg ggtggcggca 1440
ggtgggggtg ccgggcgggg cggggccgcc tcgggccggg gagggctcgg gggaggggcg 1500
cggcggcccc cggagcgccg gcggctgtcg aggcgcggcg agccgcagcc attgcctttt 1560
atggtaatcg tgcgagaggg cgcagggact tcctttgtcc caaatctgtg cggagccgaa 1620
atctgggagg cgccgccgca ccccctctag cgggcgcggg gcgaagcggt gcggcgccgg 1680
caggaaggaa atgggcgggg agggccttcg tgcgtcgccg cgccgccgtc cccttctccc 1740
tctccagcct cggggctgtc cgcgggggga cggctgcctt cgggggggac ggggcagggc 1800
ggggttcggc ttctggcgtg tgaccggcgg ctctagagcc tctgctaacc atgttcatgc 1860
cttcttcttt ttcctacagc tcctgggcaa cgtgctggtt attgtgctgt ctcatcattt 1920

```
tggcaaagaa ttcgctagcg ggcactttgc actggaactt acaacacccg agcaaggacg   1980
cgactctcca ccatgtaccg aatgcagctg ctgctgctga tcgcactgag cctggcactg   2040
gtgaccaaca gcgaggtgca gctggtggag agcggaggag gactggtgca gccaggagga   2100
agcctgcgac tgagctgtgc agcaagcgga tacgacttca cccattacgg aatgaactgg   2160
gtgcgacagg caccaggaaa gggactggag tgggtgggat ggatcaacac ctacaccgga   2220
gagccaacct acgcagcaga cttcaagcga cgattcacct tcagcctgga caccagcaag   2280
agcaccgcat acctgcagat gaacagcctg cgagcagagg acaccgcagt gtactactgt   2340
gcaaagtacc catactacta cggaaccagc cattggtact tcgacgtgtg gggacaggga   2400
accctggtga ccgtgagcag cgcaagcacc aagggaccaa gcgtgttccc actggcacca   2460
agcagcaaga gcaccagcgg aggaaccgca gcactgggat gtctggtgaa ggactacttc   2520
ccagagccag tgaccgtgag ctggaacagc ggagcactga ccagcggagt gcataccttc   2580
ccagcagtgc tgcagagcag cggactgtac agcctgagca gcgtggtgac cgtgccaagc   2640
agcagcctgg gaacccagac ctacatctgt aacgtgaacc ataagccaag caacaccaag   2700
gtggacaaga aggtggagcc aaagagctgt gacaagaccc atctgcgaaa gcgacgagca   2760
ccagtgaagc agaccctgaa cttcgacctg ctgaagctgg caggagacgt ggagagcaac   2820
ccaggaccaa tgtaccgaat gcagctgctg ctgctgatcg cactgagcct ggcactggtg   2880
accaacagcg acatccagct gacccagagc ccaagcagcc tgagcgcaag cgtgggagac   2940
cgagtgacca tcacctgtag cgcaagccag gacatcagca actacctgaa ctggtaccag   3000
cagaagccag gaaaggcacc aaaggtgctg atctacttca ccagcagcct gcatagcgga   3060
gtgccaagcc gattcagcgg aagcggaagc ggaaccgact tcaccctgac catcagcagc   3120
ctgcagccag aggacttcgc aacctactac tgtcagcagt acagcaccgt gccatggacc   3180
ttcggacagg gaaccaaggt ggagatcaag cgaaccgtgg cagcaccaag cgtgttcatc   3240
ttcccaccaa gcgacgagca gctgaagagc ggaaccgcaa gcgtggtgtg tctgctgaac   3300
aacttctacc cacgagaggc aaaggtgcag tggaaggtgg acaacgcact gcagagcgga   3360
aacagccagg agagcgtgac cgagcaggac agcaaggaca gcacctacag cctgagcagc   3420
accctgaccc tgagcaaggc agactacgag aagcataagg tgtacgcatg tgaggtgacc   3480
catcagggac tgagcagccc agtgaccaag agcttcaacc gaggagagtg ttgataaagc   3540
ggccgcggta cctctagagt cgacccgggc ggcctcgagg acggggtgaa ctacgcctga   3600
ggatccgatc tttttccctc tgccaaaaat tatggggaca tcatgaagcc ccttgagcat   3660
ctgacttctg gctaataaag gaaatttatt ttcattgcaa tagtgtgttg gaattttttg   3720
tgtctctcac tcggaagcaa ttcgttgatc tgaatttcga ccacccataa tacccattac   3780
cctggtagat aagtagcatg gcgggttaat cattaactac aaggaacccc tagtgatgga   3840
gttggccact ccctctctgc gcgctcgctc gctcactgag gccgggcgac caaaggtcgc   3900
ccgacgcccg ggctttgccc gggcggcctc agtgagcgag cgagcgcgca g            3951
```

<210> SEQ ID NO 35
<211> LENGTH: 3951
<212> TYPE: DNA
<213> ORGANISM: Artificial Sequence
<220> FEATURE:
<223> OTHER INFORMATION: ITR.CB7.CI.aVEGFv4.rBG.ITR
<220> FEATURE:
<221> NAME/KEY: repeat_region
<222> LOCATION: (1)..(130)

<223> OTHER INFORMATION: 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer
<220> FEATURE:
<221> NAME/KEY: promoter
<222> LOCATION: (582)..(862)
<223> OTHER INFORMATION: CB promoter
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: 5'UTR
<222> LOCATION: (1940)..(1987)
<223> OTHER INFORMATION: c-myc 5'UTR
<220> FEATURE:
<221> NAME/KEY: misc_feature
<222> LOCATION: (1988)..(1993)
<223> OTHER INFORMATION: kozak
<220> FEATURE:
<221> NAME/KEY: misc_feature
<222> LOCATION: (1993)..(2052)
<223> OTHER INFORMATION: leader
<220> FEATURE:
<221> NAME/KEY: misc_feature
<222> LOCATION: (2053)..(2421)
<223> OTHER INFORMATION: aVEGFv4 VH
<220> FEATURE:
<221> NAME/KEY: misc_feature
<222> LOCATION: (2422)..(2742)
<223> OTHER INFORMATION: CH1
<220> FEATURE:
<221> NAME/KEY: misc_feature
<222> LOCATION: (2746)..(2757)
<223> OTHER INFORMATION: furin cleavage site
<220> FEATURE:
<221> NAME/KEY: misc_feature
<222> LOCATION: (2758)..(2829)
<223> OTHER INFORMATION: F2A linker
<220> FEATURE:
<221> NAME/KEY: misc_feature
<222> LOCATION: (2830)..(2889)
<223> OTHER INFORMATION: leader
<220> FEATURE:
<221> NAME/KEY: misc_feature
<222> LOCATION: (2890)..(3210)
<223> OTHER INFORMATION: aVEGFv4 VL
<220> FEATURE:
<221> NAME/KEY: misc_feature
<222> LOCATION: (3211)..(3531)
<223> OTHER INFORMATION: CL
<220> FEATURE:
<221> NAME/KEY: misc_feature
<222> LOCATION: (3532)..(3537)
<223> OTHER INFORMATION: stop cassette
<220> FEATURE:
<221> NAME/KEY: polyA_signal
<222> LOCATION: (3607)..(3733)
<223> OTHER INFORMATION: Rabbit globin poly A
<220> FEATURE:
<221> NAME/KEY: repeat_region
<222> LOCATION: (3822)..(3951)
<223> OTHER INFORMATION: 3'ITR

<400> SEQUENCE: 35
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgggg 180
atcctctaga actatagcta gtcgacattg attattgact agttattaat agtaatcaat 240

```
tacggggtca ttagttcata gcccatatat ggagttccgc gttacataac ttacggtaaa    300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca agtacgcccc ctattgacgt    480
caatgacggt aaatggcccg cctggcatta tgcccagtac atgaccttat gggactttcc    540
tacttggcag tacatctacg tattagtcat cgctattacc atggtcgagg tgagccccac    600
gttctgcttc actctcccca tctccccccc ctccccaccc ccaattttgt atttatttat    660
tttttaatta ttttgtgcag cgatgggggc gggggggggg ggggggcgcg cgccaggcgg    720
ggcggggcgg ggcgaggggc ggggcggggc gaggcggaga ggtgcggcgg cagccaatca    780
gagcggcgcg ctccgaaagt ttccttttat ggcgaggcgg cggcggcggc ggccctataa    840
aaagcgaagc gcgcggcggg cgggagtcgc tgcgcgctgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggccctt tgtgcggggg   1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg gggcggtgc cccgcggtgc ggggggggct gcgaggggaa   1260
caaaggctgc gtgcggggtg tgtgcgtggg ggggtgagca gggggtgtgg gcgcgtcggt   1320
cgggctgcaa ccccccctgc accccccctcc ccgagttgct gagcacggcc cggcttcggg   1380
tgcggggctc cgtacggggc gtggcgcggg gctcgccgtg ccgggcgggg ggtggcggca   1440
ggtgggggtg ccgggcgggg cggggccgcc tcgggccggg gagggctcgg gggaggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca cccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cggggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgctagcg ggcactttgc actggaactt acaacacccg agcaaggacg   1980
cgactctcca ccatgtacag aatgcagctg ctgctgctga tcgccctgag cctggccctg   2040
gtcaccaaca gcgaggtcca gctggtcgag agcggaggag gactggtcca gcccggagga   2100
agcctgagac tgagctgcgc cgccagcgga tacgacttca cccactacgg aatgaactgg   2160
gtcagacagg cccccggaaa gggactggag tgggtcggat ggatcaacac ctacaccgga   2220
gagcccacct acgccgccga cttcaagaga agattcacct tcagcctgga caccagcaag   2280
agcaccgcct acctgcagat gaacagcctg agagccgagg acaccgccgt ctactactgc   2340
gccaagtacc cctactacta cggaaccagc cactggtact tcgacgtctg gggacaggga   2400
accctggtca ccgtcagcag cgccagcacc aagggaccca gcgtcttccc cctggccccc   2460
agcagcaaga gcaccagcgg aggaaccgcc gccctgggat gcctggtcaa ggactacttc   2520
cccgagcccg tcaccgtcag ctggaacagc ggagccctga ccagcggagt ccacaccttc   2580
```

```
cccgccgtcc tgcagagcag cggactgtac agcctgagca gcgtcgtcac cgtccccagc   2640

agcagcctgg gaacccagac ctacatctgc aacgtcaacc acaagcccag caacaccaag   2700

gtcgacaaga aggtcgagcc caagagctgc gacaagaccc acctgagaaa gagaagagcc   2760

cccgtcaagc agaccctgaa cttcgacctg ctgaagctgg ccggagacgt cgagagcaac   2820

cccggaccca tgtacagaat gcagctgctg ctgctgatcg ccctgagcct ggccctggtc   2880

accaacagcg acatccagct gacccagagc cccagcagcc tgagcgccag cgtcggagac   2940

agagtcacca tcacctgcag cgccagccag gacatcagca actacctgaa ctggtaccag   3000

cagaagcccg gaaaggcccc caaggtcctg atctacttca ccagcagcct gcacagcgga   3060

gtccccagca gattcagcgg aagcggaagc ggaaccgact tcaccctgac catcagcagc   3120

ctgcagcccg aggacttcgc cacctactac tgccagcagt acagcaccgt cccctggacc   3180

ttcggacagg gaaccaaggt cgagatcaag agaaccgtcg ccgcccccag cgtcttcatc   3240

ttccccccca gcgacgagca gctgaagagc ggaaccgcca gcgtcgtctg cctgctgaac   3300

aacttctacc ccagagaggc caaggtccag tggaaggtcg acaacgccct gcagagcgga   3360

aacagccagg agagcgtcac cgagcaggac agcaaggaca gcacctacag cctgagcagc   3420

accctgaccc tgagcaaggc cgactacgag aagcacaagg tctacgcctg cgaggtcacc   3480

caccagggac tgagcagccc cgtcaccaag agcttcaaca gaggagagtg ctgataaagc   3540

ggccgcggta cctctagagt cgacccgggc ggcctcgagg acggggtgaa ctacgcctga   3600

ggatccgatc tttttccctc tgccaaaaat tatggggaca tcatgaagcc ccttgagcat   3660

ctgacttctg gctaataaag gaaatttatt ttcattgcaa tagtgtgttg gaattttttg   3720

tgtctctcac tcggaagcaa ttcgttgatc tgaatttcga ccacccataa tacccattac   3780

cctggtagat aagtagcatg gcgggttaat cattaactac aaggaacccc tagtgatgga   3840

gttggccact ccctctctgc gcgctcgctc gctcactgag gccgggcgac caaaggtcgc   3900

ccgacgcccg ggctttgccc gggcggcctc agtgagcgag cgagcgcgca g            3951
```

<210> SEQ ID NO 36
<211> LENGTH: 3951
<212> TYPE: DNA
<213> ORGANISM: Artificial Sequence
<220> FEATURE:
<223> OTHER INFORMATION: ITR.CB7.CI.aVEGFv5.rBG.ITR
<220> FEATURE:
<221> NAME/KEY: repeat_region
<222> LOCATION: (1)..(130)
<223> OTHER INFORMATION: 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer
<220> FEATURE:
<221> NAME/KEY: promoter
<222> LOCATION: (582)..(862)
<223> OTHER INFORMATION: CB promoter
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: 5'UTR
<222> LOCATION: (1940)..(1987)
<223> OTHER INFORMATION: c-myc 5'UTR
<220> FEATURE:
<221> NAME/KEY: misc_feature
<222> LOCATION: (1988)..(1993)
<223> OTHER INFORMATION: kozak
<220> FEATURE:
<221> NAME/KEY: misc_feature
<222> LOCATION: (1993)..(2052)
<223> OTHER INFORMATION: leader
<220> FEATURE:
<221> NAME/KEY: misc_feature
<222> LOCATION: (2053)..(2421)
<223> OTHER INFORMATION: aVEGFv5 VH
<220> FEATURE:
<221> NAME/KEY: misc_feature
<222> LOCATION: (2422)..(2742)
<223> OTHER INFORMATION: CH1
<220> FEATURE:
<221> NAME/KEY: misc_feature
<222> LOCATION: (2746)..(2757)
<223> OTHER INFORMATION: furin cleavage site
<220> FEATURE:
<221> NAME/KEY: misc_feature
<222> LOCATION: (2758)..(2829)
<223> OTHER INFORMATION: F2A linker
<220> FEATURE:
<221> NAME/KEY: misc_feature
<222> LOCATION: (2830)..(2889)
<223> OTHER INFORMATION: leader
<220> FEATURE:
<221> NAME/KEY: misc_feature
<222> LOCATION: (2890)..(3210)
<223> OTHER INFORMATION: aVEGFv5 VL
<220> FEATURE:
<221> NAME/KEY: misc_feature
<222> LOCATION: (3211)..(3531)
<223> OTHER INFORMATION: CL
<220> FEATURE:
<221> NAME/KEY: misc_feature
<222> LOCATION: (3532)..(3537)
<223> OTHER INFORMATION: stop cassette
<220> FEATURE:
<221> NAME/KEY: polyA_signal
<222> LOCATION: (3607)..(3733)
<223> OTHER INFORMATION: rabbit globin poly A
<220> FEATURE:
<221> NAME/KEY: repeat_region
<222> LOCATION: (3822)..(3951)
<223> OTHER INFORMATION: 3'ITR

<400> SEQUENCE: 36
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgggg 180
atcctctaga actatagcta gtcgacattg attattgact agttattaat agtaatcaat 240
tacggggtca ttagttcata gcccatatat ggagttccgc gttacataac ttacggtaaa 300
tggcccgcct ggctgaccgc ccaacgaccc ccgcccattg acgtcaataa tgacgtatgt 360
tcccatagta acgccaatag ggactttcca ttgacgtcaa tgggtggagt atttacggta 420
aactgcccac ttggcagtac atcaagtgta tcatatgcca agtacgcccc ctattgacgt 480
caatgacggt aaatggcccg cctggcatta tgcccagtac atgaccttat gggactttcc 540
tacttggcag tacatctacg tattagtcat cgctattacc atggtcgagg tgagccccac 600
gttctgcttc actctcccca tctcccccc ctccccaccc ccaattttgt atttatttat 660
tttttaatta ttttgtgcag cgatgggggc gggggggggg ggggggcgcg cgccaggcgg 720
ggcggggcgg ggcgaggggc ggggcggggc gaggcggaga ggtgcggcgg cagccaatca 780
gagcggcgcg ctccgaaagt ttccttttat ggcgaggcgg cggcggcggc ggccctataa 840
aaagcgaagc gcgcggcggg cgggagtcgc tgcgcgctgc cttcgccccg tgccccgctc 900

```
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggccctt tgtgcggggg   1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg ggggcggtgc cccgcggtgc ggggggggct gcgaggggaa   1260
caaaggctgc gtgcggggtg tgtgcgtggg ggggtgagca gggggtgtgg gcgcgtcggt   1320
cgggctgcaa ccccccctgc acccccctcc ccgagttgct gagcacggcc cggcttcggg   1380
tgcggggctc cgtacggggc gtggcgcggg gctcgccgtg ccgggcgggg ggtggcggca   1440
ggtgggggtg ccgggcgggg cggggccgcc tcgggccggg gagggctcgg gggaggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cgggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgctagcg ggcactttgc actggaactt acaacacccg agcaaggacg   1980
cgactctcca ccatgtaccg catgcagctt cttcttctta tcgctctttc tcttgctctt   2040
gtgaccaatt ctgaagtgca gcttgtggaa tctggcggcg gccttgtgca gccgggcggc   2100
tctcttcgcc tttcttgcgc tgcttctggc tacgacttta cccattacgg catgaattgg   2160
gtgcgccagg ctccgggcaa gggccttgaa tgggtgggct ggatcaatac ctacaccggc   2220
gaaccgacct acgctgctga ctttaagcgc cgctttacct tttctcttga cacctctaag   2280
tctaccgctt accttcagat gaattctctt cgcgctgaag acaccgctgt gtactactgc   2340
gctaagtacc cgtactacta cggcacctct cattggtact ttgacgtgtg gggccagggc   2400
acccttgtga ccgtgtcttc tgcttctacc aagggcccgt ctgtgtttcc gcttgctccg   2460
tcttctaagt ctacctctgg cggcaccgct gctcttggct gccttgtgaa ggactacttt   2520
ccggaaccgg tgaccgtgtc ttggaattct ggcgctctta cctctggcgt gcataccttt   2580
ccggctgtgc ttcagtcttc tggcctttac tctctttctt ctgtggtgac cgtgccgtct   2640
tcttctcttg gcacccagac ctacatctgc aatgtgaatc ataagccgtc taataccaag   2700
gtggacaaga aggtggaacc gaagtcttgc gacaagaccc atcttcgcaa gcgccgcgct   2760
ccggtgaagc agacccttaa ttttgacctt cttaagcttg ctggcgacgt ggaatctaat   2820
ccgggcccga tgtaccgcat gcagcttctt cttcttatcg ctctttctct tgctcttgtg   2880
accaattctg acatccagct tacccagtct ccgtcttctc tttctgcttc tgtgggcgac   2940
cgcgtgacca tcacctgctc tgcttctcag gacatctcta attaccttaa ttggtaccag   3000
cagaagccgg gcaaggctcc gaaggtgctt atctacttta cctcttctct tcattctggc   3060
gtgccgtctc gcttttctgg ctctggctct ggcaccgact ttacccttac catctcttct   3120
cttcagccgg aagactttgc tacctactac tgccagcagt actctaccgt gccgtggacc   3180
tttggccagg gcaccaaggt ggaaatcaag cgcaccgtgg ctgctccgtc tgtgtttatc   3240
tttccgccgt ctgacgaaca gcttaagtct ggcaccgctt ctgtggtgtg ccttcttaat   3300
```

```
aatttttacc cgcgcgaagc taaggtgcag tggaaggtgg acaatgctct tcagtctggc   3360

aattctcagg aatctgtgac cgaacaggac tctaaggact ctacctactc tctttcttct   3420

acccttaccc tttctaaggc tgactacgaa aagcataagg tgtacgcttg cgaagtgacc   3480

catcagggcc tttcttctcc ggtgaccaag tcttttaatc gcggcgaatg ctgataaagc   3540

ggccgcggta cctctagagt cgacccgggc ggcctcgagg acggggtgaa ctacgcctga   3600

ggatccgatc tttttccctc tgccaaaaat tatggggaca tcatgaagcc ccttgagcat   3660

ctgacttctg gctaataaag gaaatttatt ttcattgcaa tagtgtgttg gaattttttg   3720

tgtctctcac tcggaagcaa ttcgttgatc tgaatttcga ccacccataa tacccattac   3780

cctggtagat aagtagcatg gcgggttaat cattaactac aaggaacccc tagtgatgga   3840

gttggccact ccctctctgc gcgctcgctc gctcactgag gccgggcgac caaaggtcgc   3900

ccgacgcccg ggctttgccc gggcggcctc agtgagcgag cgagcgcgca g            3951
```

<210> SEQ ID NO 37
<211> LENGTH: 3951
<212> TYPE: DNA
<213> ORGANISM: Artificial Sequence
<220> FEATURE:
<223> OTHER INFORMATION: ITR.CB7.CI.aVEGFv6.rBG.ITR
<220> FEATURE:
<221> NAME/KEY: repeat_region
<222> LOCATION: (1)..(130)
<223> OTHER INFORMATION: 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer
<220> FEATURE:
<221> NAME/KEY: promoter
<222> LOCATION: (582)..(862)
<223> OTHER INFORMATION: CB promoter
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: 5'UTR
<222> LOCATION: (1940)..(1987)
<223> OTHER INFORMATION: c-myc 5'UTR
<220> FEATURE:
<221> NAME/KEY: misc_feature
<222> LOCATION: (1993)..(2052)
<223> OTHER INFORMATION: leader
<220> FEATURE:
<221> NAME/KEY: misc_feature
<222> LOCATION: (2053)..(2421)
<223> OTHER INFORMATION: aVEGFv6 VH
<220> FEATURE:
<221> NAME/KEY: misc_feature
<222> LOCATION: (2422)..(2742)
<223> OTHER INFORMATION: CH1
<220> FEATURE:
<221> NAME/KEY: misc_feature
<222> LOCATION: (2746)..(2757)
<223> OTHER INFORMATION: furin cleavage site
<220> FEATURE:
<221> NAME/KEY: misc_feature
<222> LOCATION: (2758)..(2829)
<223> OTHER INFORMATION: F2A linker
<220> FEATURE:
<221> NAME/KEY: misc_feature
<222> LOCATION: (2830)..(2889)
<223> OTHER INFORMATION: leader
<220> FEATURE:

```
<221> NAME/KEY: misc_feature
<222> LOCATION: (2890)..(3210)
<223> OTHER INFORMATION: aVEGFv6 VL
<220> FEATURE:
<221> NAME/KEY: misc_feature
<222> LOCATION: (3211)..(3531)
<223> OTHER INFORMATION: CL
<220> FEATURE:
<221> NAME/KEY: misc_feature
<222> LOCATION: (3532)..(3537)
<223> OTHER INFORMATION: stop cassette
<220> FEATURE:
<221> NAME/KEY: polyA_signal
<222> LOCATION: (3607)..(3733)
<223> OTHER INFORMATION: Rabbit globin poly A
<220> FEATURE:
<221> NAME/KEY: repeat_region
<222> LOCATION: (3822)..(3951)
<223> OTHER INFORMATION: 3'ITR

<400> SEQUENCE: 37

ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctaccag ggtaatgggg    180

atcctctaga actatagcta gtcgacattg attattgact agttattaat agtaatcaat    240

tacggggtca ttagttcata gcccatatat ggagttccgc gttacataac ttacggtaaa    300

tggcccgcct ggctgaccgc ccaacgaccc ccgcccattg acgtcaataa tgacgtatgt    360

tcccatagta acgccaatag ggactttcca ttgacgtcaa tgggtggagt atttacggta    420

aactgcccac ttggcagtac atcaagtgta tcatatgcca agtacgcccc ctattgacgt    480

caatgacggt aaatggcccg cctggcatta tgcccagtac atgaccttat gggactttcc    540

tacttggcag tacatctacg tattagtcat cgctattacc atggtcgagg tgagccccac    600

gttctgcttc actctcccca tctccccccc ctccccaccc ccaattttgt atttatttat    660

tttttaatta ttttgtgcag cgatgggggc gggggggggg ggggggcgcg cgccaggcgg    720

ggcggggcgg ggcgaggggc ggggcggggc gaggcggaga ggtgcggcgg cagccaatca    780

gagcggcgcg ctccgaaagt ttccttttat ggcgaggcgg cggcggcggc ggccctataa    840

aaagcgaagc gcgcggcggg cgggagtcgc tgcgcgctgc cttcgccccg tgccccgctc    900

cgccgccgcc tcgcgccgcc cgccccggct ctgactgacc gcgttactcc cacaggtgag    960

cgggcgggac ggcccttctc ctccgggctg taattagcgc ttggtttaat gacggcttgt   1020

ttcttttctg tggctgcgtg aaagccttga ggggctccgg gagggccctt tgtgcggggg   1080

gagcggctcg gggggtgcgt gcgtgtgtgt gtgcgtgggg agcgccgcgt gcggctccgc   1140

gctgcccggc ggctgtgagc gctgcgggcg cggcgcgggg ctttgtgcgc tccgcagtgt   1200

gcgcgagggg agcgcggccg gggcggtgc cccgcggtgc ggggggggct gcgaggggaa   1260

caaaggctgc gtgcggggtg tgtgcgtggg ggggtgagca gggggtgtgg gcgcgtcggt   1320

cgggctgcaa ccccccctgc acccccctcc ccgagttgct gagcacggcc cggcttcggg   1380

tgcggggctc cgtacggggc gtggcgcggg gctcgccgtg ccgggcgggg ggtggcggca   1440

ggtgggggtg ccgggcgggg cggggccgcc tcgggccggg gagggctcgg gggaggggcg   1500

cggcggcccc cggagcgccg gcggctgtcg aggcgcggcg agccgcagcc attgcctttt   1560

atggtaatcg tgcgagaggg cgcagggact tcctttgtcc caaatctgtg cggagccgaa   1620

atctgggagg cgccgccgca ccccctctag cgggcgcggg gcgaagcggt gcggcgccgg   1680

caggaaggaa atgggcgggg agggccttcg tgcgtcgccg cgccgccgtc cccttctccc   1740
```

```
tctccagcct cggggctgtc cgcgggggga cggctgcctt cggggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgctagcg ggcactttgc actggaactt acaacacccg agcaaggacg   1980
cgactctcca ccatgtaccg gatgcagctg ctgctgctga tcgccctgag cctggccctg   2040
gtgaccaaca gcgaggtgca gctggtggag agcggaggag gactggtgca gccaggagga   2100
agcctgcggc tgagctgcgc cgccagcgga tacgatttca cccactacgg aatgaactgg   2160
gtgcggcagg ccccaggaaa gggactggag tgggtgggat ggatcaacac ctacaccgga   2220
gagccaacct acgccgccga tttcaagcgg cggttcacct tcagcctgga taccagcaag   2280
agcaccgcct acctgcagat gaacagcctg cgggccgagg ataccgccgt gtactactgc   2340
gccaagtacc catactacta cggaaccagc cactggtact tcgatgtgtg gggacaggga   2400
accctggtga ccgtgagcag cgccagcacc aagggaccaa gcgtgttccc actggcccca   2460
agcagcaaga gcaccagcgg aggaaccgcc gccctgggat gcctggtgaa ggattacttc   2520
ccagagccag tgaccgtgag ctggaacagc ggagccctga ccagcggagt gcacaccttc   2580
ccagccgtgc tgcagagcag cggactgtac agcctgagca gcgtggtgac cgtgccaagc   2640
agcagcctgg gaacccagac ctacatctgc aacgtgaacc acaagccaag caacaccaag   2700
gtggataaga aggtggagcc aaagagctgc gataagaccc acctgcggaa gcggcgggcc   2760
ccagtgaagc agaccctgaa cttcgatctg ctgaagctgg ccggagatgt ggagagcaac   2820
ccaggaccaa tgtaccggat gcagctgctg ctgctgatcg ccctgagcct ggccctggtg   2880
accaacagcg atatccagct gacccagagc ccaagcagcc tgagcgccag cgtgggagat   2940
cgggtgacca tcacctgcag cgccagccag gatatcagca actacctgaa ctggtaccag   3000
cagaagccag gaaaggcccc aaaggtgctg atctacttca ccagcagcct gcacagcgga   3060
gtgccaagcc ggttcagcgg aagcggaagc ggaaccgatt tcaccctgac catcagcagc   3120
ctgcagccag aggatttcgc cacctactac tgccagcagt acagcaccgt gccatggacc   3180
ttcggacagg gaaccaaggt ggagatcaag cggaccgtgg ccgccccaag cgtgttcatc   3240
ttcccaccaa gcgatgagca gctgaagagc ggaaccgcca gcgtggtgtg cctgctgaac   3300
aacttctacc cacgggaggc caaggtgcag tggaaggtgg ataacgccct gcagagcgga   3360
aacagccagg agagcgtgac cgagcaggat agcaaggata gcacctacag cctgagcagc   3420
accctgaccc tgagcaaggc cgattacgag aagcacaagg tgtacgcctg cgaggtgacc   3480
caccagggac tgagcagccc agtgaccaag agcttcaacc ggggagagtg ctgataaagc   3540
ggccgcggta cctctagagt cgacccgggc ggcctcgagg acggggtgaa ctacgcctga   3600
ggatccgatc tttttccctc tgccaaaaat tatggggaca tcatgaagcc ccttgagcat   3660
ctgacttctg gctaataaag gaaatttatt ttcattgcaa tagtgtgttg gaattttttg   3720
tgtctctcac tcggaagcaa ttcgttgatc tgaatttcga ccacccataa tacccattac   3780
cctggtagat aagtagcatg gcgggttaat cattaactac aaggaacccc tagtgatgga   3840
gttggccact ccctctctgc gcgctcgctc gctcactgag gccgggcgac caaaggtcgc   3900
ccgacgcccg ggctttgccc gggcggcctc agtgagcgag cgagcgcgca g             3951
```

<210> SEQ ID NO 38
<211> LENGTH: 3951
<212> TYPE: DNA

<213> ORGANISM: Artificial Sequence
<220> FEATURE:
<223> OTHER INFORMATION: ITR.CB7.CI.aVEGFv7.rBG.ITR
<220> FEATURE:
<221> NAME/KEY: repeat_region
<222> LOCATION: (1)..(130)
<223> OTHER INFORMATION: 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer
<220> FEATURE:
<221> NAME/KEY: promoter
<222> LOCATION: (582)..(862)
<223> OTHER INFORMATION: CB promoter
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: 5'UTR
<222> LOCATION: (1940)..(1987)
<223> OTHER INFORMATION: c-myc 5'UTR
<220> FEATURE:
<221> NAME/KEY: misc_feature
<222> LOCATION: (1988)..(1993)
<223> OTHER INFORMATION: kozak
<220> FEATURE:
<221> NAME/KEY: misc_feature
<222> LOCATION: (1993)..(2052)
<223> OTHER INFORMATION: leader
<220> FEATURE:
<221> NAME/KEY: misc_feature
<222> LOCATION: (2053)..(2421)
<223> OTHER INFORMATION: aVEGFv7 VH
<220> FEATURE:
<221> NAME/KEY: misc_feature
<222> LOCATION: (2422)..(2742)
<223> OTHER INFORMATION: CH1
<220> FEATURE:
<221> NAME/KEY: misc_feature
<222> LOCATION: (2746)..(2757)
<223> OTHER INFORMATION: furin cleavage site
<220> FEATURE:
<221> NAME/KEY: misc_feature
<222> LOCATION: (2758)..(2829)
<223> OTHER INFORMATION: F2A linker
<220> FEATURE:
<221> NAME/KEY: misc_feature
<222> LOCATION: (2830)..(2889)
<223> OTHER INFORMATION: leader
<220> FEATURE:
<221> NAME/KEY: misc_feature
<222> LOCATION: (2890)..(3210)
<223> OTHER INFORMATION: aVEGFv7 VL
<220> FEATURE:
<221> NAME/KEY: misc_feature
<222> LOCATION: (3211)..(3531)
<223> OTHER INFORMATION: CL
<220> FEATURE:
<221> NAME/KEY: misc_feature
<222> LOCATION: (3532)..(3537)
<223> OTHER INFORMATION: stop cassette
<220> FEATURE:
<221> NAME/KEY: polyA_signal
<222> LOCATION: (3607)..(3733)
<223> OTHER INFORMATION: rabbit globin poly A
<220> FEATURE:
<221> NAME/KEY: repeat_region
<222> LOCATION: (3822)..(3951)
<223> OTHER INFORMATION: 3'ITR

<400> SEQUENCE: 38
ctgcgcgctc gctcgctcac tgaggccgcc cgggcaaagc ccgggcgtcg ggcgaccttt 60

```
ggtcgcccgg cctcagtgag cgagcgagcg cgcagagagg gagtggccaa ctccatcact    120
aggggttcct tgtagttaat gattaacccg ccatgctact tatctaccag ggtaatgggg    180
atcctctaga actatagcta gtcgacattg attattgact agttattaat agtaatcaat    240
tacggggtca ttagttcata gcccatatat ggagttccgc gttacataac ttacggtaaa    300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca agtacgcccc ctattgacgt    480
caatgacggt aaatggcccg cctggcatta tgcccagtac atgaccttat gggactttcc    540
tacttggcag tacatctacg tattagtcat cgctattacc atggtcgagg tgagccccac    600
gttctgcttc actctcccca tctccccccc ctccccaccc ccaattttgt atttatttat    660
tttttaatta ttttgtgcag cgatgggggc gggggggggg ggggggcgcg cgccaggcgg    720
ggcggggcgg ggcgaggggc ggggcggggc gaggcggaga ggtgcggcgg cagccaatca    780
gagcggcgcg ctccgaaagt ttccttttat ggcgaggcgg cggcggcggc ggccctataa    840
aaagcgaagc gcgcggcggg cgggagtcgc tgcgcgctgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggccctt tgtgcggggg   1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg gggcggtgc cccgcggtgc gggggggggct gcgaggggaa   1260
caaaggctgc gtgcggggtg tgtgcgtggg ggggtgagca gggggtgtgg gcgcgtcggt   1320
cgggctgcaa ccccccctgc acccccctcc ccgagttgct gagcacggcc cggcttcggg   1380
tgcggggctc cgtacggggc gtggcgcggg gctcgccgtg ccgggcgggg ggtggcggca   1440
ggtgggggtg ccgggcgggg cggggccgcc tcgggccggg gagggctcgg gggaggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cgggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgctagcg ggcactttgc actggaactt acaacacccg agcaaggacg   1980
cgactctcca ccatgtaccg gatgcagctg ctgctgctga tcgccctgag cctggccctg   2040
gtgaccaaca gcgaggtgca gctggtggag agcggaggag gactggtgca gccaggagga   2100
agcctgcggc tgagctgcgc cgccagcgga tacgatttca cccactacgg aatgaactgg   2160
gtgcggcagg ccccaggaaa gggactggag tgggtgggat ggatcaacac ctacaccgga   2220
gagccaacct acgccgccga tttcaagcgg cggttcacct tcagcctgga taccagcaag   2280
agcaccgcct acctgcagat gaacagcctg cgggccgagg ataccgccgt gtactactgc   2340
gccaagtacc catactacta cggaaccagc cactggtact tcgatgtgtg ggacagggga   2400
```

```
accctggtga ccgtgagcag cgccagcacc aagggaccaa gcgtgttccc actggcccca   2460

agcagcaaga gcaccagcgg aggaaccgcc gccctgggat gcctggtgaa ggattacttc   2520

ccagagccag tgaccgtgag ctggaacagc ggagccctga ccagcggagt gcacaccttc   2580

ccagccgtgc tgcagagcag cggactgtac agcctgagca gcgtggtgac cgtgccaagc   2640

agcagcctgg gaacccagac ctacatctgc aacgtgaacc acaagccaag caacaccaag   2700

gtggataaga aggtggagcc aaagagctgc gataagaccc acctgcggaa gcggcgggcc   2760

ccagtgaagc agaccctgaa cttcgatctg ctgaagctgg ccggagatgt ggagagcaac   2820

ccaggaccaa tgtaccggat gcagctgctg ctgctgatcg ccctgagcct ggccctggtg   2880

accaacagcg atatccagct gacccagagc ccaagcagcc tgagcgccag cgtgggagat   2940

cgggtgacca tcacctgcag cgccagccag gatatcagca actacctgaa ctggtaccag   3000

cagaagccag gaaaggcccc aaaggtgctg atctacttca ccagcagcct gcacagcgga   3060

gtgccaagcc ggttcagcgg aagcggaagc ggaaccgatt tcaccctgac catcagcagc   3120

ctgcagccag aggatttcgc cacctactac tgccagcagt acagcaccgt gccatggacc   3180

ttcggacagg gaaccaaggt ggagatcaag cggaccgtgg ccgccccaag cgtgttcatc   3240

ttcccaccaa gcgatgagca gctgaagagc ggaaccgcca gcgtggtgtg cctgctgaac   3300

aacttctacc cacgggaggc caaggtgcag tggaaggtgg ataacgccct gcagagcgga   3360

aacagccagg agagcgtgac cgagcaggat agcaaggata gcacctacag cctgagcagc   3420

accctgaccc tgagcaaggc cgattacgag aagcacaagg tgtacgcctg cgaggtgacc   3480

caccagggac tgagcagccc agtgaccaag agcttcaacc ggggagagtg ctgataaagc   3540

ggccgcggta cctctagagt cgacccgggc ggcctcgagg acggggtgaa ctacgcctga   3600

ggatccgatc tttttccctc tgccaaaaat tatggggaca tcatgaagcc ccttgagcat   3660

ctgacttctg gctaataaag gaaatttatt ttcattgcaa tagtgtgttg gaattttttg   3720

tgtctctcac tcggaagcaa ttcgttgatc tgaatttcga ccacccataa tacccattac   3780

cctggtagat aagtagcatg gcgggttaat cattaactac aaggaacccc tagtgatgga   3840

gttggccact ccctctctgc gcgctcgctc gctcactgag gccgggcgac caaaggtcgc   3900

ccgacgcccg ggctttgccc gggcggcctc agtgagcgag cgagcgcgca g            3951
```

```
<210> SEQ ID NO 39
<211> LENGTH: 3951
<212> TYPE: DNA
<213> ORGANISM: Artificial Sequence
<220> FEATURE:
<223> OTHER INFORMATION: ITR.CB7.CI.aVEGFv8.rBG.ITR
<220> FEATURE:
<221> NAME/KEY: repeat_region
<222> LOCATION: (1)..(130)
<223> OTHER INFORMATION: 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer
<220> FEATURE:
<221> NAME/KEY: promoter
<222> LOCATION: (582)..(862)
<223> OTHER INFORMATION: CB promoter
<220> FEATURE:
<221> NAME/KEY: Intron
<222> LOCATION: (956)..(1928)
<223> OTHER INFORMATION: chicken beta-actin intron
```

<220> FEATURE:
<221> NAME/KEY: 5'UTR
<222> LOCATION: (1940)..(1987)
<223> OTHER INFORMATION: c-myc 5'UTR
<220> FEATURE:
<221> NAME/KEY: misc_feature
<222> LOCATION: (1988)..(1993)
<223> OTHER INFORMATION: kozak
<220> FEATURE:
<221> NAME/KEY: misc_feature
<222> LOCATION: (1993)..(2052)
<223> OTHER INFORMATION: leader
<220> FEATURE:
<221> NAME/KEY: misc_feature
<222> LOCATION: (2053)..(2421)
<223> OTHER INFORMATION: aVEGFv8 VH
<220> FEATURE:
<221> NAME/KEY: misc_feature
<222> LOCATION: (2422)..(2742)
<223> OTHER INFORMATION: CH1
<220> FEATURE:
<221> NAME/KEY: misc_feature
<222> LOCATION: (2746)..(2757)
<223> OTHER INFORMATION: furin cleavage site
<220> FEATURE:
<221> NAME/KEY: misc_feature
<222> LOCATION: (2758)..(2829)
<223> OTHER INFORMATION: F2A linker
<220> FEATURE:
<221> NAME/KEY: misc_feature
<222> LOCATION: (2830)..(2889)
<223> OTHER INFORMATION: leader
<220> FEATURE:
<221> NAME/KEY: misc_feature
<222> LOCATION: (2890)..(3210)
<223> OTHER INFORMATION: aVEGFv8 VL
<220> FEATURE:
<221> NAME/KEY: misc_feature
<222> LOCATION: (3211)..(3531)
<223> OTHER INFORMATION: CL
<220> FEATURE:
<221> NAME/KEY: misc_feature
<222> LOCATION: (3532)..(3537)
<223> OTHER INFORMATION: stop cassette
<220> FEATURE:
<221> NAME/KEY: polyA_signal
<222> LOCATION: (3607)..(3733)
<223> OTHER INFORMATION: rabbit globin poly A
<220> FEATURE:
<221> NAME/KEY: repeat_region
<222> LOCATION: (3822)..(3951)
<223> OTHER INFORMATION: 3'ITR

<400> SEQUENCE: 39
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgggg 180
atcctctaga actatagcta gtcgacattg attattgact agttattaat agtaatcaat 240
tacggggtca ttagttcata gcccatatat ggagttccgc gttacataac ttacggtaaa 300
tggcccgcct ggctgaccgc ccaacgaccc ccgcccattg acgtcaataa tgacgtatgt 360
tcccatagta acgccaatag ggactttcca ttgacgtcaa tgggtggagt atttacggta 420
aactgcccac ttggcagtac atcaagtgta tcatatgcca agtacgcccc ctattgacgt 480
caatgacggt aaatggcccg cctggcatta tgcccagtac atgaccttat gggactttcc 540
tacttggcag tacatctacg tattagtcat cgctattacc atggtcgagg tgagccccac 600
gttctgcttc actctcccca tctccccccc ctccccaccc ccaattttgt atttatttat 660
tttttaatta ttttgtgcag cgatgggggc gggggggggg ggggggcgcg cgccaggcgg 720

-continued

```
ggcggggcgg ggcgaggggc ggggcggggc gaggcggaga ggtgcggcgg cagccaatca    780
gagcggcgcg ctccgaaagt ttccttttat ggcgaggcgg cggcggcggc ggccctataa    840
aaagcgaagc gcgcggcggg cgggagtcgc tgcgcgctgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggccctt tgtgcggggg   1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg gggcggtgc cccgcggtgc ggggggggct gcgaggggaa   1260
caaaggctgc gtgcggggtg tgtgcgtggg ggggtgagca gggggtgtgg gcgcgtcggt   1320
cgggctgcaa ccccccctgc acccccctcc ccgagttgct gagcacggcc cggcttcggg   1380
tgcggggctc cgtacggggc gtggcgcggg gctcgccgtg ccgggcgggg ggtggcggca   1440
ggtgggggtg ccgggcgggg cggggccgcc tcgggccggg gagggctcgg gggaggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cgggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgctagcg ggcactttgc actggaactt acaacacccg agcaaggacg   1980
cgactctcca ccatgtaccg catgcagctg ctgctgctga tcgctctgtc actggctctg   2040
gtgaccaatt cagaagtgca gctggtggaa tcaggtggtg gtctggtgca gcccggtggt   2100
tcactgcgcc tgtcatgcgc tgcttcaggt tacgacttta cccattacgg tatgaattgg   2160
gtgcgccagg ctcccggtaa gggtctggaa tgggtgggtt ggatcaatac ctacaccggt   2220
gaacccacct acgctgctga ctttaagcgc cgctttacct tttcactgga cacctcaaag   2280
tcaaccgctt acctgcagat gaattcactg cgcgctgaag acaccgctgt gtactactgc   2340
gctaagtacc cctactacta cggtacctca cattggtact ttgacgtgtg gggtcagggt   2400
accctggtga ccgtgtcatc agcttcaacc aagggtccct cagtgtttcc cctggctccc   2460
tcatcaaagt caacctcagg tggtaccgct gctctgggtt gcctggtgaa ggactacttt   2520
cccgaacccg tgaccgtgtc atggaattca ggtgctctga cctcaggtgt gcataccttt   2580
cccgctgtgc tgcagtcatc aggtctgtac tcactgtcat cagtggtgac cgtgccctca   2640
tcatcactgg gtacccagac ctacatctgc aatgtgaatc ataagccctc aaataccaag   2700
gtggacaaga aggtggaacc caagtcatgc gacaagaccc atctgcgcaa gcgccgcgct   2760
cccgtgaagc agaccctgaa ttttgacctg ctgaagctgg ctggtgacgt ggaatcaaat   2820
cccggtccca tgtaccgcat gcagctgctg ctgctgatcg ctctgtcact ggctctggtg   2880
accaattcag acatccagct gacccagtca ccctcatcac tgtcagcttc agtgggtgac   2940
cgcgtgacca tcacctgctc agcttcacag gacatctcaa attacctgaa ttggtaccag   3000
cagaagcccg gtaaggctcc caaggtgctg atctacttta cctcatcact gcattcaggt   3060
gtgccctcac gcttttcagg ttcaggttca ggtaccgact ttaccctgac catctcatca   3120
```

```
ctgcagcccg aagactttgc tacctactac tgccagcagt actcaaccgt gccctggacc   3180

tttggtcagg gtaccaaggt ggaaatcaag cgcaccgtgg ctgctccctc agtgtttatc   3240

tttcccccct cagacgaaca gctgaagtca ggtaccgctt cagtggtgtg cctgctgaat   3300

aatttttacc cccgcgaagc taaggtgcag tggaaggtgg acaatgctct gcagtcaggt   3360

aattcacagg aatcagtgac cgaacaggac tcaaaggact caacctactc actgtcatca   3420

accctgaccc tgtcaaaggc tgactacgaa aagcataagg tgtacgcttg cgaagtgacc   3480

catcagggtc tgtcatcacc cgtgaccaag tcatttaatc gcggtgaatg ctgataaagc   3540

ggccgcggta cctctagagt cgacccgggc ggcctcgagg acggggtgaa ctacgcctga   3600

ggatccgatc tttttccctc tgccaaaaat tatggggaca tcatgaagcc ccttgagcat   3660

ctgacttctg gctaataaag gaaatttatt ttcattgcaa tagtgtgttg gaattttttg   3720

tgtctctcac tcggaagcaa ttcgttgatc tgaatttcga ccacccataa tacccattac   3780

cctggtagat aagtagcatg gcgggttaat cattaactac aaggaacccc tagtgatgga   3840

gttggccact ccctctctgc gcgctcgctc gctcactgag gccgggcgac caaaggtcgc   3900

ccgacgcccg ggctttgccc gggcggcctc agtgagcgag cgagcgcgca g            3951


<210> SEQ ID NO 40
<211> LENGTH: 3957
<212> TYPE: DNA
<213> ORGANISM: Artificial Sequence
<220> FEATURE:
<223> OTHER INFORMATION: ITR.CB7.CI.aVEGFv9.rBG.ITR
<220> FEATURE:
<221> NAME/KEY: repeat_region
<222> LOCATION: (1)..(130)
<223> OTHER INFORMATION: 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer
<220> FEATURE:
<221> NAME/KEY: promoter
<222> LOCATION: (582)..(862)
<223> OTHER INFORMATION: CB promoter
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: 5'UTR
<222> LOCATION: (1946)..(1993)
<223> OTHER INFORMATION: c-myc 5'UTR
<220> FEATURE:
<221> NAME/KEY: misc_feature
<222> LOCATION: (1994)..(1999)
<223> OTHER INFORMATION: kozak
<220> FEATURE:
<221> NAME/KEY: misc_feature
<222> LOCATION: (1999)..(2058)
<223> OTHER INFORMATION: leader
<220> FEATURE:
<221> NAME/KEY: misc_feature
<222> LOCATION: (2059)..(2427)
<223> OTHER INFORMATION: aVEGFv9 VH
<220> FEATURE:
<221> NAME/KEY: misc_feature
<222> LOCATION: (2428)..(2748)
<223> OTHER INFORMATION: CH1
<220> FEATURE:
<221> NAME/KEY: misc_feature
<222> LOCATION: (2752)..(2763)
```

<223> OTHER INFORMATION: furin cleavage site
<220> FEATURE:
<221> NAME/KEY: misc_feature
<222> LOCATION: (2764)..(2835)
<223> OTHER INFORMATION: F2A linker
<220> FEATURE:
<221> NAME/KEY: misc_feature
<222> LOCATION: (2836)..(2895)
<223> OTHER INFORMATION: leader
<220> FEATURE:
<221> NAME/KEY: misc_feature
<222> LOCATION: (2896)..(3216)
<223> OTHER INFORMATION: aVEGFv9 VL
<220> FEATURE:
<221> NAME/KEY: misc_feature
<222> LOCATION: (3217)..(3537)
<223> OTHER INFORMATION: CL
<220> FEATURE:
<221> NAME/KEY: misc_feature
<222> LOCATION: (3538)..(3543)
<223> OTHER INFORMATION: Stop Cassette
<220> FEATURE:
<221> NAME/KEY: polyA_signal
<222> LOCATION: (3613)..(3739)
<223> OTHER INFORMATION: rabbit globin poly A
<220> FEATURE:
<221> NAME/KEY: repeat_region
<222> LOCATION: (3828)..(3957)
<223> OTHER INFORMATION: 3'ITR

<400> SEQUENCE: 40
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgggg 180
atcctctaga actatagcta gtcgacattg attattgact agttattaat agtaatcaat 240
tacggggtca ttagttcata gcccatatat ggagttccgc gttacataac ttacggtaaa 300
tggcccgcct ggctgaccgc ccaacgaccc ccgcccattg acgtcaataa tgacgtatgt 360
tcccatagta acgccaatag ggactttcca ttgacgtcaa tgggtggagt atttacggta 420
aactgcccac ttggcagtac atcaagtgta tcatatgcca agtacgcccc ctattgacgt 480
caatgacggt aaatggcccg cctggcatta tgcccagtac atgaccttat gggactttcc 540
tacttggcag tacatctacg tattagtcat cgctattacc atggtcgagg tgagccccac 600
gttctgcttc actctcccca tctccccccc ctccccaccc ccaattttgt atttatttat 660
tttttaatta ttttgtgcag cgatgggggc gggggggggg ggggggcgcg cgccaggcgg 720
ggcggggcgg ggcgaggggc ggggcggggc gaggcggaga ggtgcggcgg cagccaatca 780
gagcggcgcg ctccgaaagt ttccttttat ggcgaggcgg cggcggcggc ggccctataa 840
aaagcgaagc gcgcggcggg cgggagtcgc tgcgcgctgc cttcgccccg tgccccgctc 900
cgccgccgcc tcgcgccgcc cgccccggct ctgactgacc gcgttactcc cacaggtgag 960
cgggcgggac ggcccttctc ctccgggctg taattagcgc ttggtttaat gacggcttgt 1020
ttcttttctg tggctgcgtg aaagccttga ggggctccgg gagggccctt tgtgcggggg 1080
gagcggctcg gggggtgcgt gcgtgtgtgt gtgcgtgggg agcgccgcgt gcggctccgc 1140
gctgcccggc ggctgtgagc gctgcgggcg cggcgcgggg ctttgtgcgc tccgcagtgt 1200
gcgcgagggg agcgcggccg gggcggtgc cccgcggtgc ggggggggct gcgaggggaa 1260
caaaggctgc gtgcggggtg tgtgcgtggg ggggtgagca gggggtgtgg gcgcgtcggt 1320
cgggctgcaa cccccccctgc acccccctcc ccgagttgct gagcacggcc cggcttcggg 1380
tgcggggctc cgtacggggc gtggcgcggg gctcgccgtg ccgggcgggg ggtggcggca 1440

-continued

```
ggtgggggtg ccgggcgggg cggggccgcc tcgggccggg gagggctcgg gggaggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cgggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgctagag ctagcgggca ctttgcactg gaacttacaa cacccgagca   1980
aggacgcgac tctccaccat gtatagaatg cagcttcttc ttcttatcgc tcttagcctt   2040
gctcttgtga caaacagcga agtgcagctt gtggaaagcg gggggggct tgtgcagcct   2100
ggggggagcc ttagacttag ctgtgctgct agcgggtatg attttacaca ctatgggatg   2160
aactgggtga gacaggctcc tgggaagggg cttgaatggg tggggtggat caacacatat   2220
acaggggaac ctacatatgc tgctgatttt aagagaagat ttacatttag ccttgataca   2280
agcaagagca cagcttatct tcagatgaac agccttagag ctgaagatac agctgtgtat   2340
tattgtgcta agtatcctta ttattatggg acaagccact ggtattttga tgtgtggggg   2400
caggggacac ttgtgacagt gagcagcgct agcacaaagg ggcctagcgt gtttcctctt   2460
gctcctagca gcaagagcac aagcgggggg acagctgctc ttgggtgtct tgtgaaggat   2520
tattttcctg aacctgtgac agtgagctgg aacagcgggg ctcttacaag cggggtgcac   2580
acatttcctg ctgtgcttca gagcagcggg ctttatagcc ttagcagcgt ggtgacagtg   2640
cctagcagca gccttgggac acagacatat atctgtaacg tgaaccacaa gcctagcaac   2700
acaaaggtgg ataagaaggt ggaacctaag agctgtgata agacacacct tagaaagaga   2760
agagctcctg tgaagcagac acttaacttt gatcttctta agcttgctgg ggatgtggaa   2820
agcaaccctg ggcctatgta tagaatgcag cttcttcttc ttatcgctct tagccttgct   2880
cttgtgacaa acagcgatat ccagcttaca cagagcccta gcagccttag cgctagcgtg   2940
ggggatagag tgacaatcac atgtagcgct agccaggata tcagcaacta tcttaactgg   3000
tatcagcaga agcctgggaa ggctcctaag gtgcttatct attttacaag cagccttcac   3060
agcggggtgc ctagcagatt tagcgggagc gggagcggga cagattttac acttacaatc   3120
agcagccttc agcctgaaga ttttgctaca tattattgtc agcagtatag cacagtgcct   3180
tggacatttg ggcaggggac aaaggtggaa atcaagagaa cagtggctgc tcctagcgtg   3240
tttatctttc ctcctagcga tgaacagctt aagagcggga cagctagcgt ggtgtgtctt   3300
cttaacaact tttatcctag agaagctaag gtgcagtgga aggtggataa cgctcttcag   3360
agcgggaaca gccaggaaag cgtgacagaa caggatagca aggatagcac atatagcctt   3420
agcagcacac ttacacttag caaggctgat tatgaaaagc acaaggtgta tgcttgtgaa   3480
gtgacacacc aggggcttag cagccctgtg acaaagagct ttaacagagg ggaatgttga   3540
taaagcggcc gcggtacctc tagagtcgac ccgggcggcc tcgaggacgg ggtgaactac   3600
gcctgaggat ccgatctttt tccctctgcc aaaaattatg gggacatcat gaagcccctt   3660
gagcatctga cttctggcta ataaaggaaa tttattttca ttgcaatagt gtgttggaat   3720
tttttgtgtc tctcactcgg aagcaattcg ttgatctgaa tttcgaccac ccataatacc   3780
```

cattaccctg gtagataagt agcatggcgg gttaatcatt aactacaagg aacccctagt 3840
gatggagttg gccactccct ctctgcgcgc tcgctcgctc actgaggccg ggcgaccaaa 3900
ggtcgcccga cgcccgggct ttgcccgggc ggcctcagtg agcgagcgag cgcgcag 3957

<210> SEQ ID NO 41
<211> LENGTH: 3951
<212> TYPE: DNA
<213> ORGANISM: Artificial Sequence
<220> FEATURE:
<223> OTHER INFORMATION: ITR.CB7.CI.aVEGFv10.rBG.ITR
<220> FEATURE:
<221> NAME/KEY: repeat_region
<222> LOCATION: (1)..(130)
<223> OTHER INFORMATION: 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer
<220> FEATURE:
<221> NAME/KEY: promoter
<222> LOCATION: (582)..(862)
<223> OTHER INFORMATION: CB promoter
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: 5'UTR
<222> LOCATION: (1940)..(1987)
<223> OTHER INFORMATION: c-myc 5'UTR
<220> FEATURE:
<221> NAME/KEY: misc_feature
<222> LOCATION: (1988)..(1993)
<223> OTHER INFORMATION: kozak
<220> FEATURE:
<221> NAME/KEY: misc_feature
<222> LOCATION: (1993)..(2052)
<223> OTHER INFORMATION: leader
<220> FEATURE:
<221> NAME/KEY: misc_feature
<222> LOCATION: (2053)..(2421)
<223> OTHER INFORMATION: aVEGFv10 VH
<220> FEATURE:
<221> NAME/KEY: misc_feature
<222> LOCATION: (2422)..(2742)
<223> OTHER INFORMATION: CH1
<220> FEATURE:
<221> NAME/KEY: misc_feature
<222> LOCATION: (2746)..(2757)
<223> OTHER INFORMATION: furin cleavage site
<220> FEATURE:
<221> NAME/KEY: misc_feature
<222> LOCATION: (2758)..(2829)
<223> OTHER INFORMATION: F2A linker
<220> FEATURE:
<221> NAME/KEY: misc_feature
<222> LOCATION: (2830)..(2889)
<223> OTHER INFORMATION: leader
<220> FEATURE:
<221> NAME/KEY: misc_feature
<222> LOCATION: (2890)..(3210)
<223> OTHER INFORMATION: aVEGFv10 VL
<220> FEATURE:
<221> NAME/KEY: misc_feature
<222> LOCATION: (3211)..(3531)
<223> OTHER INFORMATION: CL
<220> FEATURE:
<221> NAME/KEY: misc_feature
<222> LOCATION: (3532)..(3537)
<223> OTHER INFORMATION: stop cassette
<220> FEATURE:
<221> NAME/KEY: polyA_signal
<222> LOCATION: (3607)..(3733)
<223> OTHER INFORMATION: rabbit globin poly A
<220> FEATURE:
<221> NAME/KEY: repeat_region
<222> LOCATION: (3822)..(3951)
<223> OTHER INFORMATION: 3'ITR

<400> SEQUENCE: 41
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgggg 180
atcctctaga actatagcta gtcgacattg attattgact agttattaat agtaatcaat 240
tacggggtca ttagttcata gcccatatat ggagttccgc gttacataac ttacggtaaa 300
tggcccgcct ggctgaccgc ccaacgaccc ccgcccattg acgtcaataa tgacgtatgt 360
tcccatagta acgccaatag ggactttcca ttgacgtcaa tgggtggagt atttacggta 420
aactgcccac ttggcagtac atcaagtgta tcatatgcca agtacgcccc ctattgacgt 480
caatgacggt aaatggcccg cctggcatta tgcccagtac atgaccttat gggactttcc 540
tacttggcag tacatctacg tattagtcat cgctattacc atggtcgagg tgagccccac 600
gttctgcttc actctcccca tctccccccc ctccccaccc ccaattttgt atttatttat 660
tttttaatta ttttgtgcag cgatgggggc gggggggggg ggggggcgcg cgccaggcgg 720
ggcggggcgg ggcgaggggc ggggcggggc gaggcggaga ggtgcggcgg cagccaatca 780
gagcggcgcg ctccgaaagt ttccttttat ggcgaggcgg cggcggcggc ggccctataa 840
aaagcgaagc gcgcggcggg cgggagtcgc tgcgcgctgc cttcgccccg tgccccgctc 900
cgccgccgcc tcgcgccgcc cgccccggct ctgactgacc gcgttactcc cacaggtgag 960
cgggcgggac ggcccttctc ctccgggctg taattagcgc ttggtttaat gacggcttgt 1020
ttcttttctg tggctgcgtg aaagccttga ggggctccgg gagggccctt tgtgcggggg 1080
gagcggctcg gggggtgcgt gcgtgtgtgt gtgcgtgggg agcgccgcgt gcggctccgc 1140
gctgcccggc ggctgtgagc gctgcgggcg cggcgcgggg ctttgtgcgc tccgcagtgt 1200
gcgcgagggg agcgcggccg gggcggtgc cccgcggtgc ggggggggct gcgaggggaa 1260
caaaggctgc gtgcggggtg tgtgcgtggg ggggtgagca gggggtgtgg gcgcgtcggt 1320
cgggctgcaa ccccccctgc acccccctcc ccgagttgct gagcacggcc cggcttcggg 1380
tgcggggctc cgtacggggc gtggcgcggg gctcgccgtg ccgggcgggg ggtggcggca 1440
ggtgggggtg ccgggcgggg cggggccgcc tcgggccggg gagggctcgg gggaggggcg 1500
cggcggcccc cggagcgccg gcggctgtcg aggcgcggcg agccgcagcc attgcctttt 1560
atggtaatcg tgcgagaggg cgcagggact tcctttgtcc caaatctgtg cggagccgaa 1620
atctgggagg cgccgccgca ccccctctag cgggcgcggg gcgaagcggt gcggcgccgg 1680
caggaaggaa atgggcgggg agggccttcg tgcgtcgccg cgccgccgtc cccttctccc 1740
tctccagcct cggggctgtc cgcgggggga cggctgcctt cggggggggac ggggcagggc 1800 ggggttcggc ttctggcgtg tgaccggcgg ctctagagcc tctgctaacc atgttcatgc 1860
cttcttcttt ttcctacagc tcctgggcaa cgtgctggtt attgtgctgt ctcatcattt 1920
tggcaaagaa ttcgctagcg ggcactttgc actggaactt acaacacccg agcaaggacg 1980
cgactctcca ccatgtatcg gatgcaactg ctgctgctga ttgccctgag cctggccctg 2040
gttaccaaca gcgaagttca actggttgaa agcggcggcg gcctggttca acccggcggc 2100

```
agcctgcggc tgagctgtgc cgccagcggc tatgacttta cccattatgg catgaactgg   2160
gttcggcaag cccccggcaa gggcctggaa tgggttggct ggattaacac ctataccggc   2220
gaacccacct atgccgccga ctttaagcgg cggtttacct ttagcctgga caccagcaag   2280
agcaccgcct atctgcaaat gaacagcctg cgggccgaag acaccgccgt ttattattgt   2340
gccaagtatc cctattatta tggcaccagc cattggtatt ttgacgtttg gggccaaggc   2400
accctggtta ccgttagcag cgccagcacc aagggcccca gcgtttttcc cctggccccc   2460
agcagcaaga gcaccagcgg cggcaccgcc gccctgggct gtctggttaa ggactatttt   2520
cccgaacccg ttaccgttag ctggaacagc ggcgccctga ccagcggcgt tcatacccttt   2580
cccgccgttc tgcaaagcag cggcctgtat agcctgagca gcgttgttac cgttcccagc   2640
agcagcctgg gcacccaaac ctatatttgt aacgttaacc ataagcccag caacaccaag   2700
gttgacaaga aggttgaacc caagagctgt gacaagaccc atctgcggaa gcggcgggcc   2760
cccgttaagc aaaccctgaa ctttgacctg ctgaagctgg ccggcgacgt tgaaagcaac   2820
cccggcccca tgtatcggat gcaactgctg ctgctgattg ccctgagcct ggccctggtt   2880
accaacagcg acattcaact gacccaaagc cccagcagcc tgagcgccag cgttggcgac   2940
cgggttacca ttacctgtag cgccagccaa gacattagca actatctgaa ctggtatcaa   3000
caaaagcccg gcaaggcccc caaggttctg atttatttta ccagcagcct gcatagcggc   3060
gttcccagcc ggtttagcgg cagcggcagc ggcaccgact ttaccctgac cattagcagc   3120
ctgcaacccg aagactttgc cacctattat tgtcaacaat atagcaccgt tccctggacc   3180
tttggccaag gcaccaaggt tgaaattaag cggaccgttg ccgcccccag cgtttttatt   3240
tttcccccca gcgacgaaca actgaagagc ggcaccgcca gcgttgtttg tctgctgaac   3300
aacttttatc cccgggaagc caaggttcaa tggaaggttg acaacgccct gcaaagcggc   3360
aacagccaag aaagcgttac cgaacaagac agcaaggaca gcacctatag cctgagcagc   3420
accctgaccc tgagcaaggc cgactatgaa aagcataagg tttatgcctg tgaagttacc   3480
catcaaggcc tgagcagccc cgttaccaag agctttaacc ggggcgaatg ttgataaagc   3540
ggccgcggta cctctagagt cgacccgggc ggcctcgagg acggggtgaa ctacgcctga   3600
ggatccgatc tttttccctc tgccaaaaat tatggggaca tcatgaagcc ccttgagcat   3660
ctgacttctg gctaataaag gaaatttatt ttcattgcaa tagtgtgttg gaatttttttg   3720
tgtctctcac tcggaagcaa ttcgttgatc tgaatttcga ccacccataa tacccattac   3780
cctggtagat aagtagcatg gcgggttaat cattaactac aaggaacccc tagtgatgga   3840
gttggccact ccctctctgc gcgctcgctc gctcactgag gccgggcgac caaaggtcgc   3900
ccgacgcccg ggctttgccc gggcggcctc agtgagcgag cgagcgcgca g            3951
```

<210> SEQ ID NO 42
<211> LENGTH: 3951
<212> TYPE: DNA
<213> ORGANISM: Artificial Sequence
<220> FEATURE:
<223> OTHER INFORMATION: ITR.CB7.CI.aVEGFv11.rBG.ITR
<220> FEATURE:
<221> NAME/KEY: repeat_region
<222> LOCATION: (1)..(130)
<223> OTHER INFORMATION: 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer
<220> FEATURE:
<221> NAME/KEY: promoter
<222> LOCATION: (582)..(862)
<223> OTHER INFORMATION: CB promoter
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: 5'UTR
<222> LOCATION: (1940)..(1987)
<223> OTHER INFORMATION: c-myc 5' UTR
<220> FEATURE:
<221> NAME/KEY: misc_feature
<222> LOCATION: (1988)..(1993)
<223> OTHER INFORMATION: kozak
<220> FEATURE:
<221> NAME/KEY: misc_feature
<222> LOCATION: (1993)..(2052)
<223> OTHER INFORMATION: leader
<220> FEATURE:
<221> NAME/KEY: misc_feature
<222> LOCATION: (2053)..(2421)
<223> OTHER INFORMATION: aVEGFv11 VH
<220> FEATURE:
<221> NAME/KEY: misc_feature
<222> LOCATION: (2422)..(2742)
<223> OTHER INFORMATION: CH1
<220> FEATURE:
<221> NAME/KEY: misc_feature
<222> LOCATION: (2746)..(2754)
<223> OTHER INFORMATION: furing cleavage site
<220> FEATURE:
<221> NAME/KEY: misc_feature
<222> LOCATION: (2755)..(2829)
<223> OTHER INFORMATION: F2A linker
<220> FEATURE:
<221> NAME/KEY: misc_feature
<222> LOCATION: (2830)..(2889)
<223> OTHER INFORMATION: leader
<220> FEATURE:
<221> NAME/KEY: misc_feature
<222> LOCATION: (2890)..(3210)
<223> OTHER INFORMATION: aVEGFv11 VL
<220> FEATURE:
<221> NAME/KEY: misc_feature
<222> LOCATION: (3211)..(3531)
<223> OTHER INFORMATION: CL
<220> FEATURE:
<221> NAME/KEY: misc_feature
<222> LOCATION: (3532)..(3537)
<223> OTHER INFORMATION: stop cassette
<220> FEATURE:
<221> NAME/KEY: polyA_signal
<222> LOCATION: (3607)..(3733)
<223> OTHER INFORMATION: rabbit globin poly A
<220> FEATURE:
<221> NAME/KEY: repeat_region
<222> LOCATION: (3822)..(3951)
<223> OTHER INFORMATION: 3' ITR

<400> SEQUENCE: 42
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgggg 180
atcctctaga actatagcta gtcgacattg attattgact agttattaat agtaatcaat 240
tacggggtca ttagttcata gcccatatat ggagttccgc gttacataac ttacggtaaa 300
tggcccgcct ggctgaccgc ccaacgaccc ccgcccattg acgtcaataa tgacgtatgt 360
tcccatagta acgccaatag ggactttcca ttgacgtcaa tgggtggagt atttacggta 420

-continued

```
aactgcccac ttggcagtac atcaagtgta tcatatgcca agtacgcccc ctattgacgt    480
caatgacggt aaatggcccg cctggcatta tgcccagtac atgaccttat gggactttcc    540
tacttggcag tacatctacg tattagtcat cgctattacc atggtcgagg tgagccccac    600
gttctgcttc actctcccca tctccccccc ctccccaccc ccaattttgt atttatttat    660
tttttaatta ttttgtgcag cgatgggggc gggggggggg ggggggcgcg cgccaggcgg    720
ggcggggcgg ggcgaggggc ggggcggggc gaggcggaga ggtgcggcgg cagccaatca    780
gagcggcgcg ctccgaaagt ttccttttat ggcgaggcgg cggcggcggc ggccctataa    840
aaagcgaagc gcgcggcggg cgggagtcgc tgcgcgctgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggccctt tgtgcggggg   1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg gggcggtgc cccgcggtgc ggggggggct gcgaggggaa   1260
caaaggctgc gtgcggggtg tgtgcgtggg ggggtgagca gggggtgtgg gcgcgtcggt   1320
cgggctgcaa ccccccctgc acccccctcc ccgagttgct gagcacggcc cggcttcggg   1380
tgcggggctc cgtacggggc gtggcgcggg gctcgccgtg ccgggcgggg ggtggcggca   1440
ggtgggggtg ccgggcgggg cggggccgcc tcgggccggg gagggctcgg gggaggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cgggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgctagcg ggcactttgc actggaactt acaacacccg agcaaggacg   1980
cgactctcca ccatgtatag aatgcagctg ctgctgctga tcgctctgtc actggctctg   2040
gtgaccaact cagaggtgca gctggtggag tcaggaggag gactggtgca gcccggagga   2100
tcactgagac tgtcatgcgc tgcttcagga tatgatttca cccattatgg aatgaactgg   2160
gtgagacagg ctcccggaaa aggactggag tgggtgggat ggatcaacac ctataccgga   2220
gagcccacct atgctgctga tttcaaaaga agattcacct tctcactgga tacctcaaaa   2280
tcaaccgctt atctgcagat gaactcactg agagctgagg ataccgctgt gtattattgc   2340
gctaaatatc cctattatta tggaacctca cattggtatt tcgatgtgtg gggacaggga   2400
accctggtga ccgtgtcatc agcttcaacc aaaggaccct cagtgttccc cctggctccc   2460
tcatcaaaat caacctcagg aggaaccgct gctctgggat gcctggtgaa agattatttc   2520
cccgagcccg tgaccgtgtc atggaactca ggagctctga cctcaggagt gcataccttc   2580
cccgctgtgc tgcagtcatc aggactgtat tcactgtcat cagtggtgac cgtgccctca   2640
tcatcactgg gaacccagac ctatatctgc aacgtgaacc ataaaccctc aaacaccaaa   2700
gtggataaaa aagtggagcc caaatcatgc gataaaaccc atctgagaaa aagaagagct   2760
cccgtgaaac agaccctgaa cttcgatctg ctgaaactgg ctggagatgt ggagtcaaac   2820
```

```
cccggaccca tgtatagaat gcagctgctg ctgctgatcg ctctgtcact ggctctggtg   2880

accaactcag atatccagct gacccagtca ccctcatcac tgtcagcttc agtgggagat   2940

agagtgacca tcacctgctc agcttcacag gatatctcaa actatctgaa ctggtatcag   3000

cagaaacccg gaaaagctcc caaagtgctg atctatttca cctcatcact gcattcagga   3060

gtgccctcaa gattctcagg atcaggatca ggaaccgatt tcaccctgac catctcatca   3120

ctgcagcccg aggatttcgc tacctattat tgccagcagt attcaaccgt gccctggacc   3180

ttcggacagg gaaccaaagt ggagatcaaa agaaccgtgg ctgctccctc agtgttcatc   3240

ttcccccct cagatgagca gctgaaatca ggaaccgctt cagtggtgtg cctgctgaac   3300

aacttctatc ccagagaggc taaagtgcag tggaaagtgg ataacgctct gcagtcagga   3360

aactcacagg agtcagtgac cgagcaggat tcaaaagatt caacctattc actgtcatca   3420

accctgaccc tgtcaaaagc tgattatgag aaacataaag tgtatgcttg cgaggtgacc   3480

catcagggac tgtcatcacc cgtgaccaaa tcattcaaca gaggagagtg ctgataaagc   3540

ggccgcggta cctctagagt cgacccgggc ggcctcgagg acggggtgaa ctacgcctga   3600

ggatccgatc tttttccctc tgccaaaaat tatggggaca tcatgaagcc ccttgagcat   3660

ctgacttctg gctaataaag gaaatttatt ttcattgcaa tagtgtgttg gaattttttg   3720

tgtctctcac tcggaagcaa ttcgttgatc tgaatttcga ccacccataa tacccattac   3780

cctggtagat aagtagcatg gcgggttaat cattaactac aaggaacccc tagtgatgga   3840

gttggccact ccctctctgc gcgctcgctc gctcactgag gccgggcgac caaaggtcgc   3900

ccgacgcccg ggctttgccc gggcggcctc agtgagcgag cgagcgcgca g            3951
```

<210> SEQ ID NO 43
<211> LENGTH: 3951
<212> TYPE: DNA
<213> ORGANISM: Artificial Sequence
<220> FEATURE:
<223> OTHER INFORMATION: ITR.CB7.CI.aVEGFv12.rBG.ITR
<220> FEATURE:
<221> NAME/KEY: repeat_region
<222> LOCATION: (1)..(130)
<223> OTHER INFORMATION: 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: enhancer
<222> LOCATION: (279)..(538)
<223> OTHER INFORMATION: C4 enhancer
<220> FEATURE:
<221> NAME/KEY: promoter
<222> LOCATION: (582)..(862)
<223> OTHER INFORMATION: CB promoter
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: 5'UTR
<222> LOCATION: (1940)..(1987)
<223> OTHER INFORMATION: c-myc 5'UTR
<220> FEATURE:
<221> NAME/KEY: misc_feature
<222> LOCATION: (1988)..(1993)
<223> OTHER INFORMATION: kozak
<220> FEATURE:
<221> NAME/KEY: misc_feature
<222> LOCATION: (1993)..(2052)
<223> OTHER INFORMATION: leader
<220> FEATURE:

```
<221> NAME/KEY: misc_feature
<222> LOCATION: (2053)..(2421)
<223> OTHER INFORMATION: aVEGFv12 VH
<220> FEATURE:
<221> NAME/KEY: misc_feature
<222> LOCATION: (2422)..(2742)
<223> OTHER INFORMATION: CH1
<220> FEATURE:
<221> NAME/KEY: misc_feature
<222> LOCATION: (2746)..(2757)
<223> OTHER INFORMATION: furing cleavage site
<220> FEATURE:
<221> NAME/KEY: misc_feature
<222> LOCATION: (2758)..(2829)
<223> OTHER INFORMATION: F2A linker
<220> FEATURE:
<221> NAME/KEY: misc_feature
<222> LOCATION: (2830)..(2889)
<223> OTHER INFORMATION: leader
<220> FEATURE:
<221> NAME/KEY: misc_feature
<222> LOCATION: (2890)..(3210)
<223> OTHER INFORMATION: aVEGFv12 VL
<220> FEATURE:
<221> NAME/KEY: misc_feature
<222> LOCATION: (3211)..(3531)
<223> OTHER INFORMATION: CL
<220> FEATURE:
<221> NAME/KEY: misc_feature
<222> LOCATION: (3532)..(3537)
<223> OTHER INFORMATION: stop cassette
<220> FEATURE:
<221> NAME/KEY: polyA_signal
<222> LOCATION: (3607)..(3733)
<223> OTHER INFORMATION: rabbit globin poly A
<220> FEATURE:
<221> NAME/KEY: repeat_region
<222> LOCATION: (3822)..(3951)
<223> OTHER INFORMATION: 3'ITR

<400> SEQUENCE: 43

ctgcgcgctc gctcgctcac tgaggccgcc cgggcaaagc ccgggcgtcg ggcgaccttt      60

ggtcgcccgg cctcagtgag cgagcgagcg cgcagagagg gagtggccaa ctccatcact     120

aggggttcct tgtagttaat gattaacccg ccatgctact tatctaccag ggtaatgggg     180

atcctctaga actatagcta gtcgacattg attattgact agttattaat agtaatcaat     240

tacggggtca ttagttcata gcccatatat ggagttccgc gttacataac ttacggtaaa     300

tggcccgcct ggctgaccgc ccaacgaccc ccgcccattg acgtcaataa tgacgtatgt     360

tcccatagta acgccaatag ggactttcca ttgacgtcaa tgggtggagt atttacggta     420

aactgcccac ttggcagtac atcaagtgta tcatatgcca agtacgcccc ctattgacgt     480

caatgacggt aaatggcccg cctggcatta tgcccagtac atgaccttat gggactttcc     540

tacttggcag tacatctacg tattagtcat cgctattacc atggtcgagg tgagccccac     600

gttctgcttc actctcccca tctccccccc ctccccaccc ccaattttgt atttatttat     660

tttttaatta ttttgtgcag cgatgggggc gggggggggg ggggggcgcg cgccaggcgg     720

ggcggggcgg ggcgaggggc ggggcggggc gaggcggaga ggtgcggcgg cagccaatca     780

gagcggcgcg ctccgaaagt ttccttttat ggcgaggcgg cggcggcggc ggccctataa     840

aaagcgaagc gcgcggcggg cgggagtcgc tgcgcgctgc cttcgccccg tgccccgctc     900

cgccgccgcc tcgcgccgcc cgccccggct ctgactgacc gcgttactcc cacaggtgag     960

cgggcgggac ggcccttctc ctccgggctg taattagcgc ttggtttaat gacggcttgt    1020

ttcttttctg tggctgcgtg aaagccttga ggggctccgg gagggccctt tgtgcggggg    1080

gagcggctcg gggggtgcgt gcgtgtgtgt gtgcgtgggg agcgccgcgt gcggctccgc    1140
```

gctgcccggc ggctgtgagc gctgcgggcg cggcgcgggg ctttgtgcgc tccgcagtgt 1200
gcgcgagggg agcgcggccg ggggcggtgc cccgcggtgc ggggggggct gcgaggggaa 1260
caaaggctgc gtgcggggtg tgtgcgtggg ggggtgagca gggggtgtgg gcgcgtcggt 1320
cgggctgcaa ccccccctgc acccccctcc ccgagttgct gagcacggcc cggcttcggg 1380
tgcggggctc cgtacggggc gtggcgcggg gctcgccgtg ccgggcgggg ggtggcggca 1440
ggtgggggtg ccgggcgggg cggggccgcc tcgggccggg gagggctcgg gggagggggcg 1500
cggcggcccc cggagcgccg gcggctgtcg aggcgcggcg agccgcagcc attgcctttt 1560
atggtaatcg tgcgagaggg cgcagggact tcctttgtcc caaatctgtg cggagccgaa 1620
atctgggagg cgccgccgca ccccctctag cgggcgcggg gcgaagcggt gcggcgccgg 1680
caggaaggaa atgggcgggg agggccttcg tgcgtcgccg cgccgccgtc cccttctccc 1740
tctccagcct cggggctgtc cgcgggggga cggctgcctt cgggggggac ggggcagggc 1800
ggggttcggc ttctggcgtg tgaccggcgg ctctagagcc tctgctaacc atgttcatgc 1860
cttcttcttt ttcctacagc tcctgggcaa cgtgctggtt attgtgctgt ctcatcattt 1920
tggcaaagaa ttcgctagcg ggcactttgc actggaactt acaacacccg agcaaggacg 1980
cgactctcca ccatgtaccg tatgcagctg ctgctgctga tagccctgag cctggccctg 2040
gtgacaaata gcgaggtgca gctggtggag agcggggggg ggctggtgca gcccgggggg 2100
agcctgcgtc tgagctgtgc cgccagcggg tacgacttta cacattacgg gatgaattgg 2160
gtgcgtcagg cccccgggaa agggctggag tgggtggggt ggataaatac atacacaggg 2220
gagcccacat acgccgccga ctttaaacgt cgttttacat ttagcctgga cacaagcaaa 2280
agcacagcct acctgcagat gaatagcctg cgtgccgagg acacagccgt gtactactgt 2340
gccaaatacc cctactacta cggacaagc cattggtact ttgacgtgtg gggcagggg 2400
acactggtga cagtgagcag cgccagcaca aaagggccca gcgtgtttcc cctggccccc 2460
agcagcaaaa gcacaagcgg ggggacagcc gccctggggt gtctggtgaa agactacttt 2520
cccgagcccg tgacagtgag ctggaatagc ggggccctga caagcggggt gcatacattt 2580
cccgccgtgc tgcagagcag cgggctgtac agcctgagca gcgtggtgac agtgcccagc 2640
agcagcctgg ggacacagac atacatatgt aatgtgaatc ataaacccag caatacaaaa 2700
gtggacaaaa aagtggagcc caaaagctgt gacaaaacac atctgcgtaa acgtcgtgcc 2760
cccgtgaaac agacactgaa ttttgacctg ctgaaactgg ccggggacgt ggagagcaat 2820
cccgggccca tgtaccgtat gcagctgctg ctgctgatag ccctgagcct ggccctggtg 2880
acaaatagcg acatacagct gacacagagc cccagcagcc tgagcgccag cgtgggggac 2940
cgtgtgacaa taacatgtag cgccagccag gacataagca attacctgaa ttggtaccag 3000
cagaaacccg ggaaagcccc caaagtgctg atatacttta caagcagcct gcatagcggg 3060
gtgcccagcc gttttagcgg gagcgggagc gggacagact ttacactgac aataagcagc 3120
ctgcagcccg aggactttgc cacatactac tgtcagcagt acagcacagt gccctggaca 3180
tttgggcagg ggacaaaagt ggagataaaa cgtacagtgg ccgcccccag cgtgtttata 3240
tttcccccca gcgacgagca gctgaaaagc gggacagcca gcgtggtgtg tctgctgaat 3300
aatttttacc cccgtgaggc caaagtgcag tggaaagtgg acaatgccct gcagagcggg 3360
aatagccagg agagcgtgac agagcaggac agcaaagaca gcacatacag cctgagcagc 3420
acactgacac tgagcaaagc cgactacgag aaacataaag tgtacgcctg tgaggtgaca 3480

```
catcaggggc tgagcagccc cgtgacaaaa agctttaatc gtggggagtg ttgataaagc   3540

ggccgcggta cctctagagt cgacccgggc ggcctcgagg acggggtgaa ctacgcctga   3600

ggatccgatc tttttccctc tgccaaaaat tatggggaca tcatgaagcc ccttgagcat   3660

ctgacttctg gctaataaag gaaatttatt ttcattgcaa tagtgtgttg gaattttttg   3720

tgtctctcac tcggaagcaa ttcgttgatc tgaatttcga ccacccataa tacccattac   3780

cctggtagat aagtagcatg gcgggttaat cattaactac aaggaacccc tagtgatgga   3840

gttggccact ccctctctgc gcgctcgctc gctcactgag gccgggcgac caaaggtcgc   3900

ccgacgcccg ggctttgccc gggcggcctc agtgagcgag cgagcgcgca g            3951


<210> SEQ ID NO 44
<211> LENGTH: 3951
<212> TYPE: DNA
<213> ORGANISM: Artificial Sequence
<220> FEATURE:
<223> OTHER INFORMATION: ITR.CB7.CI.aVEGFv13.rBG.ITR
<220> FEATURE:
<221> NAME/KEY: repeat_region
<222> LOCATION: (1)..(130)
<223> OTHER INFORMATION: 5'ITR
<220> FEATURE:
<221> NAME/KEY: misc_feature
<222> LOCATION: (131)..(167)
<223> OTHER INFORMATION: part of AAV
<220> FEATURE:
<221> NAME/KEY: promoter
<222> LOCATION: (198)..(579)
<223> OTHER INFORMATION: CME IE promoter
<220> FEATURE:
<221> NAME/KEY: misc_feature
<222> LOCATION: (204)..(233)
<223> OTHER INFORMATION: promoter start
<220> FEATURE:
<221> NAME/KEY: enhancer
<222> LOCATION: (279)..(538)
<223> OTHER INFORMATION: C4 enhancer with 2 mismatches
<220> FEATURE:
<221> NAME/KEY: misc_feature
<222> LOCATION: (561)..(584)
<223> OTHER INFORMATION: CMV promoter end
<220> FEATURE:
<221> NAME/KEY: promoter
<222> LOCATION: (582)..(862)
<223> OTHER INFORMATION: CB promoter
<220> FEATURE:
<221> NAME/KEY: misc_feature
<222> LOCATION: (585)..(615)
<223> OTHER INFORMATION: begin promoter
<220> FEATURE:
<221> NAME/KEY: TATA_signal
<222> LOCATION: (836)..(839)
<220> FEATURE:
<221> NAME/KEY: Intron
<222> LOCATION: (956)..(1928)
<223> OTHER INFORMATION: chichen beta-actin intron
<220> FEATURE:
<221> NAME/KEY: misc_feature
<222> LOCATION: (1814)..(1830)
<223> OTHER INFORMATION: end of intron
<220> FEATURE:
<221> NAME/KEY: 5'UTR
<222> LOCATION: (1940)..(1987)
<223> OTHER INFORMATION: c-myc 5'UTR
<220> FEATURE:
<221> NAME/KEY: misc_feature
<222> LOCATION: (1988)..(1993)
<223> OTHER INFORMATION: kozak
<220> FEATURE:
<221> NAME/KEY: misc_feature
<222> LOCATION: (1993)..(2052)
<223> OTHER INFORMATION: leader
<220> FEATURE:
```

<221> NAME/KEY: misc_feature
<222> LOCATION: (2053)..(2421)
<223> OTHER INFORMATION: aVEGFv13 VH
<220> FEATURE:
<221> NAME/KEY: misc_feature
<222> LOCATION: (2422)..(2742)
<223> OTHER INFORMATION: CH1
<220> FEATURE:
<221> NAME/KEY: misc_feature
<222> LOCATION: (2746)..(2757)
<223> OTHER INFORMATION: furin cleavage site
<220> FEATURE:
<221> NAME/KEY: misc_feature
<222> LOCATION: (2758)..(2829)
<223> OTHER INFORMATION: F2A linker
<220> FEATURE:
<221> NAME/KEY: misc_feature
<222> LOCATION: (2830)..(2889)
<223> OTHER INFORMATION: leader
<220> FEATURE:
<221> NAME/KEY: misc_feature
<222> LOCATION: (2890)..(3210)
<223> OTHER INFORMATION: aVEGFv13 VL
<220> FEATURE:
<221> NAME/KEY: misc_feature
<222> LOCATION: (3211)..(3531)
<223> OTHER INFORMATION: CL
<220> FEATURE:
<221> NAME/KEY: misc_feature
<222> LOCATION: (3532)..(3537)
<223> OTHER INFORMATION: stop cassette
<220> FEATURE:
<221> NAME/KEY: polyA_signal
<222> LOCATION: (3607)..(3733)
<223> OTHER INFORMATION: rabbit globin poly A
<220> FEATURE:
<221> NAME/KEY: misc_feature
<222> LOCATION: (3785)..(3821)
<223> OTHER INFORMATION: part of AAV
<220> FEATURE:
<221> NAME/KEY: repeat_region
<222> LOCATION: (3822)..(3951)
<223> OTHER INFORMATION: 3'ITR

<400> SEQUENCE: 44
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgggg 180
atcctctaga actatagcta gtcgacattg attattgact agttattaat agtaatcaat 240
tacggggtca ttagttcata gcccatatat ggagttccgc gttacataac ttacggtaaa 300
tggcccgcct ggctgaccgc ccaacgaccc ccgcccattg acgtcaataa tgacgtatgt 360
tcccatagta acgccaatag ggactttcca ttgacgtcaa tgggtggagt atttacggta 420
aactgcccac ttggcagtac atcaagtgta tcatatgcca agtacgcccc ctattgacgt 480
caatgacggt aaatggcccg cctggcatta tgcccagtac atgaccttat gggactttcc 540
tacttggcag tacatctacg tattagtcat cgctattacc atggtcgagg tgagccccac 600
gttctgcttc actctcccca tctccccccc ctccccaccc ccaattttgt atttatttat 660
tttttaatta ttttgtgcag cgatgggggc gggggggggg ggggggcgcg cgccaggcgg 720
ggcggggcgg ggcgaggggc ggggcggggc gaggcggaga ggtgcggcgg cagccaatca 780
gagcggcgcg ctccgaaagt ttccttttat ggcgaggcgg cggcggcggc ggccctataa 840
aaagcgaagc gcgcggcggg cgggagtcgc tgcgcgctgc cttcgccccg tgccccgctc 900
cgccgccgcc tcgcgccgcc cgccccggct ctgactgacc gcgttactcc cacaggtgag 960
cgggcgggac ggcccttctc ctccgggctg taattagcgc ttggtttaat gacggcttgt 1020

```
ttcttttctg tggctgcgtg aaagccttga ggggctccgg gagggccctt tgtgcggggg   1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg ggggcggtgc cccgcggtgc ggggggggct gcgaggggaa   1260
caaaggctgc gtgcggggtg tgtgcgtggg ggggtgagca gggggtgtgg gcgcgtcggt   1320
cgggctgcaa ccccccctgc acccccctcc ccgagttgct gagcacggcc cggcttcggg   1380
tgcggggctc cgtacggggc gtggcgcggg gctcgccgtg ccgggcgggg ggtggcggca   1440
ggtgggggtg ccgggcgggg cggggccgcc tcgggccggg gagggctcgg gggagggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cgggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgctagcg ggcactttgc actggaactt acaacacccg agcaaggacg   1980
cgactctcca ccatgtaccg gatgcagctg ctgctgctga tcgccctgag cctggccctg   2040
gtgaccaaca gcgaggtgca gctggtggag agcggggggg ggctggtgca gcccgggggg   2100
agcctgcggc tgagctgcgc cgccagcggg tacgacttca cccactacgg gatgaactgg   2160
gtgcggcagg cccccgggaa ggggctggag tgggtggggt ggatcaacac ctacaccggg   2220
gagcccacct acgccgccga cttcaagcgg cggttcacct tcagcctgga caccagcaag   2280
agcaccgcct acctgcagat gaacagcctg cgggccgagg acaccgccgt gtactactgc   2340
gccaagtacc cctactacta cgggaccagc cactggtact tcgacgtgtg gggcaggggg   2400
accctggtga ccgtgagcag cgccagcacc aaggggccca gcgtgttccc cctggccccc   2460
agcagcaaga gcaccagcgg ggggaccgcc gccctggggt gcctggtgaa ggactacttc   2520
cccgagcccg tgaccgtgag ctggaacagc ggggccctga ccagcggggt gcacaccttc   2580
cccgccgtgc tgcagagcag cgggctgtac agcctgagca gcgtggtgac cgtgcccagc   2640
agcagcctgg ggacccagac ctacatctgc aacgtgaacc acaagcccag caacaccaag   2700
gtggacaaga aggtggagcc caagagctgc gacaagaccc acctgcggaa gcggcgggcc   2760
cccgtgaagc agaccctgaa cttcgacctg ctgaagctgg ccggggacgt ggagagcaac   2820
cccgggccca tgtaccggat gcagctgctg ctgctgatcg ccctgagcct ggccctggtg   2880
accaacagcg acatccagct gacccagagc cccagcagcc tgagcgccag cgtgggggac   2940
cgggtgacca tcacctgcag cgccagccag gacatcagca actacctgaa ctggtaccag   3000
cagaagcccg ggaaggcccc caaggtgctg atctacttca ccagcagcct gcacagcggg   3060
gtgcccagcc ggttcagcgg gagcgggagc gggaccgact tcaccctgac catcagcagc   3120
ctgcagcccg aggacttcgc cacctactac tgccagcagt acagcaccgt gccctggacc   3180
ttcgggcagg ggaccaaggt ggagatcaag cggaccgtgg ccgcccccag cgtgttcatc   3240
ttccccccca gcgacgagca gctgaagagc gggaccgcca gcgtggtgtg cctgctgaac   3300
aacttctacc cccgggaggc caaggtgcag tggaaggtgg acaacgccct gcagagcggg   3360
```

```
aacagccagg agagcgtgac cgagcaggac agcaaggaca gcacctacag cctgagcagc   3420

accctgaccc tgagcaaggc cgactacgag aagcacaagg tgtacgcctg cgaggtgacc   3480

caccaggggc tgagcagccc cgtgaccaag agcttcaacc ggggggagtg ctgataaagc   3540

ggccgcggta cctctagagt cgacccgggc ggcctcgagg acggggtgaa ctacgcctga   3600

ggatccgatc tttttccctc tgccaaaaat tatggggaca tcatgaagcc ccttgagcat   3660

ctgacttctg gctaataaag gaaatttatt ttcattgcaa tagtgtgttg gaattttttg   3720

tgtctctcac tcggaagcaa ttcgttgatc tgaatttcga ccacccataa tacccattac   3780

cctggtagat aagtagcatg gcgggttaat cattaactac aaggaacccc tagtgatgga   3840

gttggccact ccctctctgc gcgctcgctc gctcactgag gccgggcgac caaaggtcgc   3900

ccgacgcccg ggctttgccc gggcggcctc agtgagcgag cgagcgcgca g            3951
```

<210> SEQ ID NO 45
<211> LENGTH: 3809
<212> TYPE: DNA
<213> ORGANISM: Artificial Sequence
<220> FEATURE:
<223> OTHER INFORMATION: ITR.CMV.PI.aVEGFv7.eMCV.IRES.SV40.ITR
<220> FEATURE:
<221> NAME/KEY: repeat_region
<222> LOCATION: (1)..(130)
<223> OTHER INFORMATION: ITR
<220> FEATURE:
<221> NAME/KEY: promoter
<222> LOCATION: (191)..(932)
<223> OTHER INFORMATION: human CMV I.E. enhancer & promoter
<220> FEATURE:
<221> NAME/KEY: Intron
<222> LOCATION: (1047)..(1179)
<223> OTHER INFORMATION: Promega chimeric intron
<220> FEATURE:
<221> NAME/KEY: 5'UTR
<222> LOCATION: (1248)..(1295)
<223> OTHER INFORMATION: c-myc 5'UTR
<220> FEATURE:
<221> NAME/KEY: misc_feature
<222> LOCATION: (1299)..(1307)
<223> OTHER INFORMATION: kozak
<220> FEATURE:
<221> NAME/KEY: misc_feature
<222> LOCATION: (1305)..(1364)
<223> OTHER INFORMATION: leader
<220> FEATURE:
<221> NAME/KEY: misc_feature
<222> LOCATION: (1365)..(1685)
<223> OTHER INFORMATION: aVEGFv7 VL
<220> FEATURE:
<221> NAME/KEY: misc_feature
<222> LOCATION: (1686)..(2006)
<223> OTHER INFORMATION: CL
<220> FEATURE:
<221> NAME/KEY: enhancer
<222> LOCATION: (2018)..(2608)
<223> OTHER INFORMATION: IRES
<220> FEATURE:
<221> NAME/KEY: misc_feature
<222> LOCATION: (2606)..(2665)
<223> OTHER INFORMATION: leader
<220> FEATURE:
<221> NAME/KEY: misc_feature
<222> LOCATION: (2666)..(3034)
<223> OTHER INFORMATION: aVEGFv7 VH
<220> FEATURE:
<221> NAME/KEY: misc_feature
<222> LOCATION: (3035)..(3355)
<223> OTHER INFORMATION: CH1
<220> FEATURE:
<221> NAME/KEY: polyA_signal
<222> LOCATION: (3384)..(3615)
<223> OTHER INFORMATION: SV40 late polyadenylation signal
<220> FEATURE:
<221> NAME/KEY: repeat_region
<222> LOCATION: (3680)..(3809)
<223> OTHER INFORMATION: ITR

<400> SEQUENCE: 45

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatct tcaatattgg ccattagcca tattattcat tggttatata gcataaatca    240
atattggcta ttggccattg catacgttgt atctatatca taatatgtac atttatattg    300
gctcatgtcc aatatgaccg ccatgttggc attgattatt gactagttat taatagtaat    360
caattacggg gtcattagtt catagcccat atatggagtt ccgcgttaca taacttacgg    420
taaatggccc gcctggctga ccgcccaacg acccccgccc attgacgtca ataatgacgt    480
atgttcccat agtaacgcca atagggactt tccattgacg tcaatgggtg gagtatttac    540
ggtaaactgc ccacttggca gtacatcaag tgtatcatat gccaagtccg ccccctattg    600
acgtcaatga cggtaaatgg cccgcctggc attatgccca gtacatgacc ttacgggact    660
ttcctacttg gcagtacatc tacgtattag tcatcgctat taccatggtg atgcggtttt    720
ggcagtacac caatgggcgt ggatagcggt ttgactcacg gggatttcca agtctccacc    780
ccattgacgt caatgggagt ttgttttggc accaaaatca acgggacttt ccaaaatgtc    840
gtaataaccc cgccccgttg acgcaaatgg gcggtaggcg tgtacggtgg gaggtctata    900
taagcagagc tcgtttagtg aaccgtcaga tcactagaag ctttattgcg gtagtttatc    960
acagttaaat tgctaacgca gtcagtgctt ctgacacaac agtctcgaac ttaagctgca   1020
gaagttggtc gtgaggcact gggcaggtaa gtatcaaggt tacaagacag gtttaaggag   1080
accaatagaa actgggcttg tcgagacaga gaagactctt gcgtttctga taggcaccta   1140
ttggtcttac tgacatccac tttgcctttc tctccacagg tgtccactcc cagttcaatt   1200
acagctctta aggctagagt acttaatacg actcactata ggctagcggg gactttgcac   1260
tggaacttac aacacccgag caaggacgcg actctagacc caccatgtac cggatgcagc   1320
tgctgctgct gatcgccctg agcctggccc tggtgaccaa cagcgatatc cagctgaccc   1380
agagcccaag cagcctgagc gccagcgtgg gagatcgggt gaccatcacc tgcagcgcca   1440
gccaggatat cagcaactac ctgaactggt accagcagaa gccaggaaag gccccaaagg   1500
tgctgatcta cttcaccagc agcctgcaca gcggagtgcc aagccggttc agcggaagcg   1560
gaagcggaac cgatttcacc ctgaccatca gcagcctgca gccagaggat ttcgccacct   1620
actactgcca gcagtacagc accgtgccat ggaccttcgg acagggaacc aaggtggaga   1680
tcaagcggac cgtggccgcc ccaagcgtgt tcatcttccc accaagcgat gagcagctga   1740
agagcggaac cgccagcgtg gtgtgcctgc tgaacaactt ctacccacgg gaggccaagg   1800
tgcagtggaa ggtggataac gccctgcaga gcggaaacag ccaggagagc gtgaccgagc   1860
aggatagcaa ggatagcacc tacagcctga gcagcaccct gaccctgagc aaggccgatt   1920
acgagaagca caaggtgtac gcctgcgagg tgacccacca gggactgagc agcccagtga   1980
ccaagagctt caaccgggga gagtgctgat aaggccggcc cctctccctc ccccccccct   2040
aacgttactg gccgaagccg cttggaataa ggccggtgtg cgtttgtcta tatgttattt   2100
tccaccatat tgccgtcttt tggcaatgtg agggcccgga aacctggccc tgtcttcttg   2160
```

-continued

```
acgagcattc ctaggggtct ttcccctctc gccaaaggaa tgcaaggtct gttgaatgtc   2220

gtgaaggaag cagttcctct ggaagcttct tgaagacaaa caacgtctgt agcgaccctt   2280

tgcaggcagc ggaacccccc acctggcgac aggtgcctct gcggccaaaa gccacgtgta   2340

taagatacac ctgcaaaggc ggcacaaccc cagtgccacg ttgtgagttg gatagttgtg   2400

gaaagagtca aatggctctc ctcaagcgta ttcaacaagg ggctgaagga tgcccagaag   2460

gtaccccatt gtatgggatc tgatctgggg cctcggtaca catgctttac atgtgtttag   2520

tcgaggttaa aaaaacgtct aggccccccg aaccacgggg acgtggtttt cctttgaaaa   2580

acacgatgat aatatggcca caaccatgta ccgcatgcag ctgctgctgc tgatcgccct   2640

gagcctggcc ctggtgacca acagcgaggt gcagctggtg gagagcggag gaggactggt   2700

gcagccagga ggaagcctgc ggctgagctg cgccgccagc ggatacgatt tcacccacta   2760

cggaatgaac tgggtgcggc aggccccagg aaagggactg gagtgggtgg gatggatcaa   2820

cacctacacc ggagagccaa cctacgccgc cgatttcaag cggcggttca ccttcagcct   2880

ggataccagc aagagcaccg cctacctgca gatgaacagc ctgcgggccg aggataccgc   2940

cgtgtactac tgcgccaagt acccatacta ctacggaacc agccactggt acttcgatgt   3000

gtggggacag ggaaccctgg tgaccgtgag cagcgccagc accaagggac caagcgtgtt   3060

cccactggcc ccaagcagca agagcaccag cggaggaacc gccgccctgg gatgcctggt   3120

gaaggattac ttcccagagc cagtgaccgt gagctggaac agcggagccc tgaccagcgg   3180

agtgcacacc ttcccagccg tgctgcagag cagcggactg tacagcctga gcagcgtggt   3240

gaccgtgcca agcagcagcc tgggaaccca gacctacatc tgcaacgtga accacaagcc   3300

aagcaacacc aaggtggata agaaggtgga gccaaagagc tgcgataaga cccacctgaa   3360

gtgatgaaag cttgcggccg cttcgagcag acatgataag atacattgat gagtttggac   3420

aaaccacaac tagaatgcag tgaaaaaaat gctttatttg tgaaatttgt gatgctattg   3480

ctttatttgt aaccattata agctgcaata aacaagttaa caacaacaat tgcattcatt   3540

ttatgtttca ggttcagggg gagatgtggg aggtttttta aagcaagtaa aacctctaca   3600

aatgtggtaa aatcgataag gatcttccta gagcatggct acgtagataa gtagcatggc   3660

gggttaatca ttaactacaa ggaaccccta gtgatggagt tggccactcc ctctctgcgc   3720

gctcgctcgc tcactgaggc cgggcgacca aaggtcgccc gacgcccggg ctttgcccgg   3780

gcggcctcag tgagcgagcg agcgcgcag                                     3809
```

<210> SEQ ID NO 46
<211> LENGTH: 3686
<212> TYPE: DNA
<213> ORGANISM: Artificial Sequence
<220> FEATURE:
<223> OTHER INFORMATION: ITR.CMV.PI.aVEGFv7.fmdIRES.SV40.ITR
<220> FEATURE:
<221> NAME/KEY: repeat_region
<222> LOCATION: (1)..(130)
<223> OTHER INFORMATION: ITR
<220> FEATURE:
<221> NAME/KEY: promoter
<222> LOCATION: (191)..(932)
<223> OTHER INFORMATION: human CMV I.E. enhancer and promoter
<220> FEATURE:
<221> NAME/KEY: TATA_signal
<222> LOCATION: (897)..(901)
<220> FEATURE:
<221> NAME/KEY: Intron
<222> LOCATION: (1047)..(1179)
<223> OTHER INFORMATION: Promega chimeric intron
<220> FEATURE:

<221> NAME/KEY: 5'UTR
<222> LOCATION: (1248)..(1295)
<223> OTHER INFORMATION: c-myc 5'UTR
<220> FEATURE:
<221> NAME/KEY: misc_feature
<222> LOCATION: (1299)..(1307)
<223> OTHER INFORMATION: kozak
<220> FEATURE:
<221> NAME/KEY: misc_feature
<222> LOCATION: (1305)..(1313)
<223> OTHER INFORMATION: leader
<220> FEATURE:
<221> NAME/KEY: misc_feature
<222> LOCATION: (1314)..(1364)
<223> OTHER INFORMATION: leader
<220> FEATURE:
<221> NAME/KEY: misc_feature
<222> LOCATION: (1365)..(1685)
<223> OTHER INFORMATION: aVEGFv7 VL
<220> FEATURE:
<221> NAME/KEY: misc_feature
<222> LOCATION: (1686)..(2006)
<223> OTHER INFORMATION: CL
<220> FEATURE:
<221> NAME/KEY: misc_feature
<222> LOCATION: (2021)..(2482)
<223> OTHER INFORMATION: FMDV
<220> FEATURE:
<221> NAME/KEY: misc_feature
<222> LOCATION: (2501)..(2542)
<223> OTHER INFORMATION: leader
<220> FEATURE:
<221> NAME/KEY: misc_feature
<222> LOCATION: (2543)..(2911)
<223> OTHER INFORMATION: aVEGFv7 VH
<220> FEATURE:
<221> NAME/KEY: misc_feature
<222> LOCATION: (2912)..(3232)
<223> OTHER INFORMATION: CH1
<220> FEATURE:
<221> NAME/KEY: polyA_signal
<222> LOCATION: (3261)..(3492)
<223> OTHER INFORMATION: Sv40 late polyadenylation signal
<220> FEATURE:
<221> NAME/KEY: repeat_region
<222> LOCATION: (3557)..(3686)
<223> OTHER INFORMATION: ITR

<400> SEQUENCE: 46
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420
taaatggccc gcctggctga ccgcccaacg acccccgccc attgacgtca ataatgacgt 480
atgttcccat agtaacgcca atagggactt tccattgacg tcaatgggtg gagtatttac 540
ggtaaactgc ccacttggca gtacatcaag tgtatcatat gccaagtccg ccccctattg 600
acgtcaatga cggtaaatgg cccgcctggc attatgccca gtacatgacc ttacgggact 660
ttcctacttg gcagtacatc tacgtattag tcatcgctat taccatggtg atgcggtttt 720
ggcagtacac caatgggcgt ggatagcggt ttgactcacg gggatttcca agtctccacc 780
ccattgacgt caatgggagt ttgttttggc accaaaatca acgggacttt ccaaaatgtc 840
gtaataaccc cgccccgttg acgcaaatgg gcggtaggcg tgtacggtgg gaggtctata 900

-continued

```
taagcagagc tcgtttagtg aaccgtcaga tcactagaag ctttattgcg gtagtttatc    960
acagttaaat tgctaacgca gtcagtgctt ctgacacaac agtctcgaac ttaagctgca   1020
gaagttggtc gtgaggcact gggcaggtaa gtatcaaggt tacaagacag gtttaaggag   1080
accaatagaa actgggcttg tcgagacaga gaagactctt gcgtttctga taggcaccta   1140
ttggtcttac tgacatccac tttgcctttc tctccacagg tgtccactcc cagttcaatt   1200
acagctctta aggctagagt acttaatacg actcactata ggctagcggg gactttgcac   1260
tggaacttac aacacccgag caaggacgcg actctagacc caccatgtac cggatgcagc   1320
tgctgctgct gatcgccctg agcctggccc tggtgaccaa cagcgatatc cagctgaccc   1380
agagcccaag cagcctgagc gccagcgtgg gagatcgggt gaccatcacc tgcagcgcca   1440
gccaggatat cagcaactac ctgaactggt accagcagaa gccaggaaag gccccaaagg   1500
tgctgatcta cttcaccagc agcctgcaca gcggagtgcc aagccggttc agcggaagcg   1560
gaagcggaac cgatttcacc ctgaccatca gcagcctgca gccagaggat ttcgccacct   1620
actactgcca gcagtacagc accgtgccat ggaccttcgg acagggaacc aaggtggaga   1680
tcaagcggac cgtggccgcc ccaagcgtgt tcatcttccc accaagcgat gagcagctga   1740
agagcggaac cgccagcgtg gtgtgcctgc tgaacaactt ctacccacgg gaggccaagg   1800
tgcagtggaa ggtggataac gccctgcaga gcggaaacag ccaggagagc gtgaccgagc   1860
aggatagcaa ggatagcacc tacagcctga gcagcaccct gaccctgagc aaggccgatt   1920
acgagaagca caaggtgtac gcctgcgagg tgacccacca gggactgagc agcccagtga   1980
ccaagagctt caaccgggga gagtgctgat aaggccggcc agcaggtttc cccaactgac   2040
acaaaacgtg caacttgaaa ctccgcctgg tctttccagg tctagagggg taacactttg   2100
tactgcgttt ggctccacgc tcgatccact ggcgagtgtt agtaacagca ctgttgcttc   2160
gtagcggagc atgacggccg tgggaactcc tccttggtaa caaggaccca cggggccaaa   2220
agccacgccc acacgggccc gtcatgtgtg caaccccagc acggcgactt tactgcgaaa   2280
cccactttaa agtgacattg aaactggtac ccacacactg gtgacaggct aaggatgccc   2340
ttcaggtacc ccgaggtaac acgggacact cgggatctga gaaggggact ggggcttcta   2400
taaaagcgct cggtttaaaa agcttctatg cctgaatagg tgaccggagg tcggcacctt   2460
tcctttacaa ttaatgaccc taatgtaccg catgcagctg ctgctgctga tcgccctgag   2520
cctggccctg gtgaccaaca gcgaggtgca gctggtggag agcggaggag gactggtgca   2580
gccaggagga agcctgcggc tgagctgcgc cgccagcgga tacgatttca cccactacgg   2640
aatgaactgg gtgcggcagg ccccaggaaa gggactggag tgggtgggat ggatcaacac   2700
ctacaccgga gagccaacct acgccgccga tttcaagcgg cggttcacct tcagcctgga   2760
taccagcaag agcaccgcct acctgcagat gaacagcctg cgggccgagg ataccgccgt   2820
gtactactgc gccaagtacc catactacta cggaaccagc cactggtact tcgatgtgtg   2880
gggacaggga accctggtga ccgtgagcag cgccagcacc aagggaccaa gcgtgttccc   2940
actggcccca agcagcaaga gcaccagcgg aggaaccgcc gccctgggat gcctggtgaa   3000
ggattacttc ccagagccag tgaccgtgag ctggaacagc ggagccctga ccagcggagt   3060
gcacaccttc ccagccgtgc tgcagagcag cggactgtac agcctgagca gcgtggtgac   3120
cgtgccaagc agcagcctgg gaacccagac ctacatctgc aacgtgaacc acaagccaag   3180
caacaccaag gtggataaga aggtggagcc aaagagctgc gataagaccc acctgaagtg   3240
```

-continued

```
atgaaagctt gcggccgctt cgagcagaca tgataagata cattgatgag tttggacaaa   3300

ccacaactag aatgcagtga aaaaaatgct ttatttgtga aatttgtgat gctattgctt   3360

tatttgtaac cattataagc tgcaataaac aagttaacaa caacaattgc attcatttta   3420

tgtttcaggt tcagggggag atgtgggagg ttttttaaag caagtaaaac ctctacaaat   3480

gtggtaaaat cgataaggat cttcctagag catggctacg tagataagta gcatggcggg   3540

ttaatcatta actacaagga acccctagtg atggagttgg ccactccctc tctgcgcgct   3600

cgctcgctca ctgaggccgg gcgaccaaag gtcgcccgac gcccgggctt tgcccgggcg   3660

gcctcagtga gcgagcgagc gcgcag                                         3686
```

<210> SEQ ID NO 47
<211> LENGTH: 3619
<212> TYPE: DNA
<213> ORGANISM: Artificial Sequence
<220> FEATURE:
<223> OTHER INFORMATION: ITR.CMV.PI.aVEGFv7.cMycIRES.SV40.ITR
<220> FEATURE:
<221> NAME/KEY: repeat_region
<222> LOCATION: (1)..(130)
<223> OTHER INFORMATION: ITR
<220> FEATURE:
<221> NAME/KEY: promoter
<222> LOCATION: (191)..(932)
<223> OTHER INFORMATION: human CMV I.E. enhancer and promoter
<220> FEATURE:
<221> NAME/KEY: TATA_signal
<222> LOCATION: (897)..(901)
<220> FEATURE:
<221> NAME/KEY: Intron
<222> LOCATION: (1047)..(1179)
<223> OTHER INFORMATION: Promega chimeric intron
<220> FEATURE:
<221> NAME/KEY: 5'UTR
<222> LOCATION: (1248)..(1295)
<223> OTHER INFORMATION: c-myc 5'UTR
<220> FEATURE:
<221> NAME/KEY: misc_feature
<222> LOCATION: (1299)..(1307)
<223> OTHER INFORMATION: kozak
<220> FEATURE:
<221> NAME/KEY: misc_feature
<222> LOCATION: (1305)..(1313)
<223> OTHER INFORMATION: leader
<220> FEATURE:
<221> NAME/KEY: misc_feature
<222> LOCATION: (1314)..(1364)
<223> OTHER INFORMATION: leader
<220> FEATURE:
<221> NAME/KEY: misc_feature
<222> LOCATION: (1365)..(1685)
<223> OTHER INFORMATION: aVEGFv7 VL
<220> FEATURE:
<221> NAME/KEY: misc_feature
<222> LOCATION: (1686)..(2006)
<223> OTHER INFORMATION: CL
<220> FEATURE:
<221> NAME/KEY: misc_feature
<222> LOCATION: (2021)..(2415)
<223> OTHER INFORMATION: IRES c-myc
<220> FEATURE:
<221> NAME/KEY: misc_feature
<222> LOCATION: (2226)..(2273)
<223> OTHER INFORMATION: mini c-myc IRES
<220> FEATURE:
<221> NAME/KEY: misc_feature
<222> LOCATION: (2275)..(2275)
<223> OTHER INFORMATION: this C to T mutaion increases expression
<220> FEATURE:
<221> NAME/KEY: misc_feature
<222> LOCATION: (2434)..(2475)
<223> OTHER INFORMATION: leader
<220> FEATURE:

<221> NAME/KEY: misc_feature
<222> LOCATION: (2476)..(2844)
<223> OTHER INFORMATION: aVEGFv7 VH
<220> FEATURE:
<221> NAME/KEY: misc_feature
<222> LOCATION: (2845)..(3165)
<223> OTHER INFORMATION: CH1
<220> FEATURE:
<221> NAME/KEY: polyA_signal
<222> LOCATION: (3194)..(3425)
<223> OTHER INFORMATION: SV40 late polyadenylation signal
<220> FEATURE:
<221> NAME/KEY: repeat_region
<222> LOCATION: (3490)..(3619)
<223> OTHER INFORMATION: ITR

<400> SEQUENCE: 47

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

aggaagatct tcaatattgg ccattagcca tattattcat tggttatata gcataaatca    240

atattggcta ttggccattg catacgttgt atctatatca taatatgtac atttatattg    300

gctcatgtcc aatatgaccg ccatgttggc attgattatt gactagttat taatagtaat    360

caattacggg gtcattagtt catagcccat atatggagtt ccgcgttaca taacttacgg    420

taaatggccc gcctggctga ccgcccaacg acccccgccc attgacgtca ataatgacgt    480

atgttcccat agtaacgcca atagggactt tccattgacg tcaatgggtg gagtatttac    540

ggtaaactgc ccacttggca gtacatcaag tgtatcatat gccaagtccg ccccctattg    600

acgtcaatga cggtaaatgg cccgcctggc attatgccca gtacatgacc ttacgggact    660

ttcctacttg gcagtacatc tacgtattag tcatcgctat taccatggtg atgcggtttt    720

ggcagtacac caatgggcgt ggatagcggt ttgactcacg gggatttcca agtctccacc    780

ccattgacgt caatgggagt ttgttttggc accaaaatca acgggacttt ccaaaatgtc    840

gtaataaccc cgccccgttg acgcaaatgg gcggtaggcg tgtacggtgg gaggtctata    900

taagcagagc tcgtttagtg aaccgtcaga tcactagaag ctttattgcg gtagtttatc    960

acagttaaat tgctaacgca gtcagtgctt ctgacacaac agtctcgaac ttaagctgca   1020

gaagttggtc gtgaggcact gggcaggtaa gtatcaaggt tacaagacag gtttaaggag   1080

accaatagaa actgggcttg tcgagacaga gaagactctt gcgtttctga taggcaccta   1140

ttggtcttac tgacatccac tttgcctttc tctccacagg tgtccactcc cagttcaatt   1200

acagctctta aggctagagt acttaatacg actcactata ggctagcggg gactttgcac   1260

tggaacttac aacacccgag caaggacgcg actctagacc caccatgtac cggatgcagc   1320

tgctgctgct gatcgccctg agcctggccc tggtgaccaa cagcgatatc cagctgaccc   1380

agagcccaag cagcctgagc gccagcgtgg gagatcgggt gaccatcacc tgcagcgcca   1440

gccaggatat cagcaactac ctgaactggt accagcagaa gccaggaaag gccccaaagg   1500

tgctgatcta cttcaccagc agcctgcaca gcggagtgcc aagccggttc agcggaagcg   1560

gaagcggaac cgatttcacc ctgaccatca gcagcctgca gccagaggat ttcgccacct   1620

actactgcca gcagtacagc accgtgccat ggaccttcgg acagggaacc aaggtggaga   1680

tcaagcggac cgtggccgcc ccaagcgtgt tcatcttccc accaagcgat gagcagctga   1740

agagcggaac cgccagcgtg gtgtgcctgc tgaacaactt ctacccacgg gaggccaagg   1800

tgcagtggaa ggtggataac gccctgcaga gcggaaacag ccaggagagc gtgaccgagc   1860
```

```
aggatagcaa ggatagcacc tacagcctga gcagcaccct gaccctgagc aaggccgatt   1920

acgagaagca caaggtgtac gcctgcgagg tgacccacca gggactgagc agcccagtga   1980

ccaagagctt caaccgggga gagtgctgat aaggccggcc aattccagcg agaggcagag   2040

ggagcgagcg ggcggccggc tagggtggaa gagccgggcg agcagagctg cgctgcgggc   2100

gtcctgggaa gggagatccg gagcgaatag gggcttcgc ctctggccca gccctcccgc   2160

tgatccccca gccagcggtc cgcaaccctt gccgcatcca cgaaactttg cccatagcag   2220

cgggcgggca ctttgcactg gaacttacaa cacccgagca aggacgcgac tctcccgacg   2280

cggggaggct attctgccca tttggggaca cttccccgcc gctgccagga cccgcttctc   2340

tgaaaggctc tccttgcagc tgcttagacg ctggattttt ttcgggtagt ggaaaaccag   2400

cagcctcccg cgacgatgta ccgcatgcag ctgctgctgc tgatcgccct gagcctggcc   2460

ctggtgacca acagcgaggt gcagctggtg gagagcggag gaggactggt gcagccagga   2520

ggaagcctgc ggctgagctg cgccgccagc ggatacgatt tcacccacta cggaatgaac   2580

tgggtgcggc aggccccagg aaagggactg gagtgggtgg gatggatcaa cacctacacc   2640

ggagagccaa cctacgccgc cgatttcaag cggcggttca ccttcagcct ggataccagc   2700

aagagcaccg cctacctgca gatgaacagc ctgcgggccg aggataccgc cgtgtactac   2760

tgcgccaagt acccatacta ctacggaacc agccactggt acttcgatgt gtggggacag   2820

ggaaccctgg tgaccgtgag cagcgccagc accaagggac caagcgtgtt cccactggcc   2880

ccaagcagca agagcaccag cggaggaacc gccgccctgg gatgcctggt gaaggattac   2940

ttcccagagc cagtgaccgt gagctggaac agcggagccc tgaccagcgg agtgcacacc   3000

ttcccagccg tgctgcagag cagcggactg tacagcctga gcagcgtggt gaccgtgcca   3060

agcagcagcc tgggaaccca gacctacatc tgcaacgtga accacaagcc aagcaacacc   3120

aaggtggata agaaggtgga gccaaagagc tgcgataaga cccacctgaa gtgatgaaag   3180

cttgcggccg cttcgagcag acatgataag atacattgat gagtttggac aaaccacaac   3240

tagaatgcag tgaaaaaaat gctttatttg tgaaatttgt gatgctattg ctttatttgt   3300

aaccattata agctgcaata aacaagttaa caacaacaat tgcattcatt ttatgtttca   3360

ggttcagggg gagatgtggg aggtttttta aagcaagtaa aacctctaca aatgtggtaa   3420

aatcgataag gatcttccta gagcatggct acgtagataa gtagcatggc gggttaatca   3480

ttaactacaa ggaaccccta gtgatggagt tggccactcc ctctctgcgc gctcgctcgc   3540

tcactgaggc cgggcgacca aaggtcgccc gacgcccggg ctttgcccgg gcggcctcag   3600

tgagcgagcg agcgcgcag                                                3619
```

```
<210> SEQ ID NO 48
<211> LENGTH: 738
<212> TYPE: PRT
<213> ORGANISM: Unknown
<220> FEATURE:
<223> OTHER INFORMATION: AAV8 capsid

<400> SEQUENCE: 48

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45
```

-continued

```
Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460
```

```
Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 49
<211> LENGTH: 2217
<212> TYPE: DNA
<213> ORGANISM: Unknown
<220> FEATURE:
<223> OTHER INFORMATION: Nucleic acid sequence of AAV8 capsid

<400> SEQUENCE: 49

```
atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctgc aggcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480
```

-continued

```
ggcaagaaag gccaacagcc cgccagaaaa agactcaatt ttggtcagac tggcgactca    540
gagtcagttc cagaccctca acctctcgga gaacctccag cagcgccctc tggtgtggga    600
cctaatacaa tggctgcagg cggtggcgca ccaatggcag acaataacga aggcgccgac    660
ggagtgggta gttcctcggg aaattggcat tgcgattcca catggctggg cgacagagtc    720
atcaccacca gcacccgaac ctgggccctg cccacctaca acaaccacct ctacaagcaa    780
atctccaacg ggacatcggg aggagccacc aacgacaaca cctacttcgg ctacagcacc    840
ccctgggggt attttgactt taacagattc cactgccact tttcaccacg tgactggcag    900
cgactcatca acaacaactg gggattccgg cccaagagac tcagcttcaa gctcttcaac    960
atccaggtca aggaggtcac gcagaatgaa ggcaccaaga ccatcgccaa taacctcacc   1020
agcaccatcc aggtgtttac ggactcggag taccagctgc cgtacgttct cggctctgcc   1080
caccagggct gcctgcctcc gttcccggcg gacgtgttca tgattcccca gtacggctac   1140
ctaacactca acaacggtag tcaggccgtg ggacgctcct ccttctactg cctggaatac   1200
tttccttcgc agatgctgag aaccggcaac aacttccagt ttacttacac cttcgaggac   1260
gtgcctttcc acagcagcta cgcccacagc cagagcttgg accggctgat gaatcctctg   1320
attgaccagt acctgtacta cttgtctcgg actcaaacaa caggaggcac ggcaaatacg   1380
cagactctgg gcttcagcca aggtgggcct aatacaatgg ccaatcaggc aaagaactgg   1440
ctgccaggac cctgttaccg ccaacaacgc gtctcaacga caaccgggca aaacaacaat   1500
agcaactttg cctggactgc tgggaccaaa taccatctga atggaagaaa ttcattggct   1560
aatcctggca tcgctatggc aacacacaaa gacgacgagg agcgtttttt tcccagtaac   1620
gggatcctga tttttggcaa acaaaatgct gccagagaca atgcggatta cagcgatgtc   1680
atgctcacca gcgaggaaga aatcaaaacc actaaccctg tggctacaga ggaatacggt   1740
atcgtggcag ataacttgca gcagcaaaac acggctcctc aaattggaac tgtcaacagc   1800
caggggggcct tacccggtat ggtctggcag aaccgggacg tgtacctgca gggtcccatc   1860
tgggccaaga ttcctcacac ggacggcaac ttccacccgt ctccgctgat gggcggcttt   1920
ggcctgaaac atcctccgcc tcagatcctg atcaagaaca cgcctgtacc tgcggatcct   1980
ccgaccacct tcaaccagtc aaagctgaac tctttcatca cgcaatacag caccggacag   2040
gtcagcgtgg aaattgaatg ggagctgcag aaggaaaaca gcaagcgctg gaaccccgag   2100
atccagtaca cctccaacta ctacaaatct acaagtgtgg actttgctgt taatacagaa   2160
ggcgtgtact ctgaaccccg ccccattggc acccgttacc tcacccgtaa tctgtaa      2217
```